US011788065B2

(12) United States Patent
Mostoslavsky et al.

(10) Patent No.: US 11,788,065 B2
(45) Date of Patent: Oct. 17, 2023

(54) HUMAN IPSC-BASED DERIVATION OF NK AND T-CELLS USING EARLY NOTCH INDUCTION

(71) Applicant: BOSTON MEDICAL CENTER CORPORATION, Boston, MA (US)

(72) Inventors: Gustavo Mostoslavsky, Boston, MA (US); Dar Heinze, Chelmsford, MA (US)

(73) Assignee: BOSTON MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 17/131,887

(22) Filed: Dec. 23, 2020

(65) Prior Publication Data

US 2021/0207100 A1 Jul. 8, 2021

Related U.S. Application Data

(60) Provisional application No. 62/952,715, filed on Dec. 23, 2019.

(51) Int. Cl.
*C12N 5/074* (2010.01)
*C12N 5/0783* (2010.01)

(52) U.S. Cl.
CPC ......... *C12N 5/0696* (2013.01); *C12N 5/0636* (2013.01); *C12N 5/0646* (2013.01); *C12N 2506/45* (2013.01); *C12N 2510/00* (2013.01)

(58) Field of Classification Search
CPC .......................... C12N 5/0696; C12N 2506/45
See application file for complete search history.

(56) References Cited

U.S. PATENT DOCUMENTS

| | | | |
|---|---|---|---|
| 2015/0352180 A1 | 12/2015 | Hankenson et al. |
| 2018/0072988 A1 | 3/2018 | Sun et al. |

FOREIGN PATENT DOCUMENTS

| | | |
|---|---|---|
| WO | 2016/123100 A1 | 8/2016 |
| WO | 2017/219062 A1 | 12/2017 |

OTHER PUBLICATIONS

Yu (Cell Stem Cell. May 8, 2008; 2(5): 461-471).*
Mallon (Stem Cell Res, 2013, 10:57-66).*
Oh (2019, Mol. Cells, 42:200-209).*
Ebrahimi (2020, Stem Cell Research and Therapy, 11:483, pp. 1-13).*
Fujita (2019, Stem Cells, 37:992-1002).*
Podkalicka (2020, Biomolecules, 10:1614, pp. 1-30).*
Awong et al., "Human CD8 T cells generated in vitro from hematopoietic stem cells are functionally mature." BMC Immunol 12, 22 (2011).
Choi et al., "Identification of the hemogenic endothelial progenitor and its direct precursor in human pluripotent stem cell differentiation cultures." Cell reports 2, 553-567 (2012).
Clements et al., "A somitic Wnt16/Notch pathway specifies haematopoietic stem cells." Nature, 474, 220-224 (2011).
D'souza et al., "GSK3beta Inhibition Promotes Efficient Myeloid and Lymphoid Hematopoiesis from Non-human Primate-Induced Pluripotent Stem Cells." Stem Cell Reports 6, 243-256 (2016).
Ditadi et al., "Directed differentiation of definitive hemogenic endothelium and hematopoietic progenitors from human pluripotent stem cells." Methods 101, 65-72 (2016).
Fraser et al., "Definitive hematopoietic commitment within the embryonic vascular endothelial-cadherin(+) population." Experimental hematology 30, 1070-1078 (2002).
Galat et al., "Application of small molecule CHIR99021 leads to the loss of hemangioblast progenitor and increased hematopoiesis of human pluripotent stem cells." Experimental hematology 65, 38-48 e31 (2018).
Gordon et al. "Mechanical Allostery: Evidence for a Force Requirement in the Proteolytic Activation of Notch." Dev Cell 33, 729-736 (2015).
Kumano et al., "Notch1 but not Notch2 is essential for generating hematopoietic stem cells from endothelial ceils." Immunity 18, 699-711 (2003).
Leung et al. "Notch and Aryl Hydrocarbon Receptor Signaling Impact Definitive Hematopoiesis from Human Pluripotent Stem Cells." Stem Cells 36, 1004-1019 (2018).
Matsuno et al., "Notch signaling regulates cell density-dependent apoptosis of NIH 3T3 through an IL-6/STAT3 dependent mechanism." Eur J Cell Biol., 97, 512-522 (2018).
Minagawa et al., "Enhancing T Cell Receptor Stability in Rejuvenated iPSC-Derived T Cells Improves Their Use in Cancer Immunotherapy." Cell Stem Cell, 23, 850-858 e854 (2018).
Montel-Hagen et al. "Organoid-Induced Differentiation of Conventional T Cells from Human Pluripotent Stem Cells." Cell Stem Cell 24, 376-389 e378 (2019).
Robert-Moreno et al., "Impaired embryonic haematopoiesis yet normal arterial development in the absence of the Notch ligand Jagged1." EMBO J 27, 1886-1895 (2008).
Schmitt et al., "Induction of T cell development and establishment of T cell competence from embryonic stem cells differentiated in vitro." Nat Immunol 5, 410-417 (2004).
Schmitt et al., "Induction of T cell development from hematopoietic progenitor cells by delta-like-1 in vitro." Immunity 17, 749-756 (2002).
Souilhol et al., "Developing HSCs become Notch independent by the end of maturation in the AGM region." Blood 128, 1567-1577 (2016).
Sturgeon et al.,Wnt signaling controls the specification of definitive and primitive hematopoiesis from human pluripotent stem cells. Nature biotechnology 32, 554-561 (2014).
Tan et al., "Efficient derivation of lateral plate and paraxial mesoderm subtypes from human embryonic stem cells through GSKi-mediated differentiation." Stem Ceils Dev 22, 1893-1906 (2013).

(Continued)

*Primary Examiner* — Valarie E Bertoglio
(74) *Attorney, Agent, or Firm* — Nixon Peabody LLP; Ronald I. Eisenstein; Susanna C. Benn

(57) ABSTRACT

The technology described herein relates to compositions and methods for the generation of a primordial NK/T cell, where the produced NK/T primordial cell can subsequently differentiate into T cells or NK cells at an extremely high efficiency and reproducibility. Other aspects relate to genetically modified iPSC cell lines, and method of their use to generate iPSC-derived NK/T primordial cells with a very high yield and high efficiency.

15 Claims, 34 Drawing Sheets

Specification includes a Sequence Listing.

(56) References Cited

OTHER PUBLICATIONS

Themeli et al., Generation of tumor-targeted human T lymphocytes from induced pluripotent stem cells for cancer therapy. Nature biotechnology 31, 928-933 (2013).
Uenishi et al., "Notch signaling specifies arterial-type definitive hemogenic endothelium from human pluripotent stem cells." Nat Commun 9, 1828 (2018).
Vizcardo et al., "Generation of Tumor Antigen-Specific iPSC-Derived Thymic Emigrants Using a 3D Thymic Culture System." Cell reports 22, 3175-3190 (2018).

* cited by examiner

Protocol A

| Day: 0 | 2 | 3 | 4 | 6 | 15 (passage every 7 days) |
|---|---|---|---|---|---|
| RPMI+KSR | StemPro34 | | | StemPro34 | OP9 media (aMEM, 20%FBS) |
| BMP4 | BMP4 | BMP4 | VEGF | D6 HSPC media | IL-7 | IL-7 |
| VEGF | VEGF | VEGF | bFGF | | FLT3L | FLT3L |
| Wnt3a | bFGF | bFGF | CH22319 | | SCF | |
| | Chir | | | | | |

VEGF, bFGF, SCF, FLT3L, TPO, IL-6

Protocol B

| Day: 0 | 2 | 3 | 4 | 6 | 15 (passage every 7 days) |
|---|---|---|---|---|---|
| RPMI+KSR | StemPro34 | | | StemPro34 | OP9 media (aMEM, 20%FBS) |
| BMP4 | BMP4 | BMP4 | VEGF | D6 HE media | IL-7 | IL-7 |
| VEGF | VEGF | VEGF | bFGF | | FLT3L | FLT3L |
| Wnt3a | bFGF | bFGF | CH223191 | | SCF | |
| | Chir | | | | | |

BMP4, VEGF, bFGF, SCF, FLT3L, TPO, EPO, IL-3, IL-6, IL-11, IGF-1, SHH, angiotensin II, Losartan, transferrin

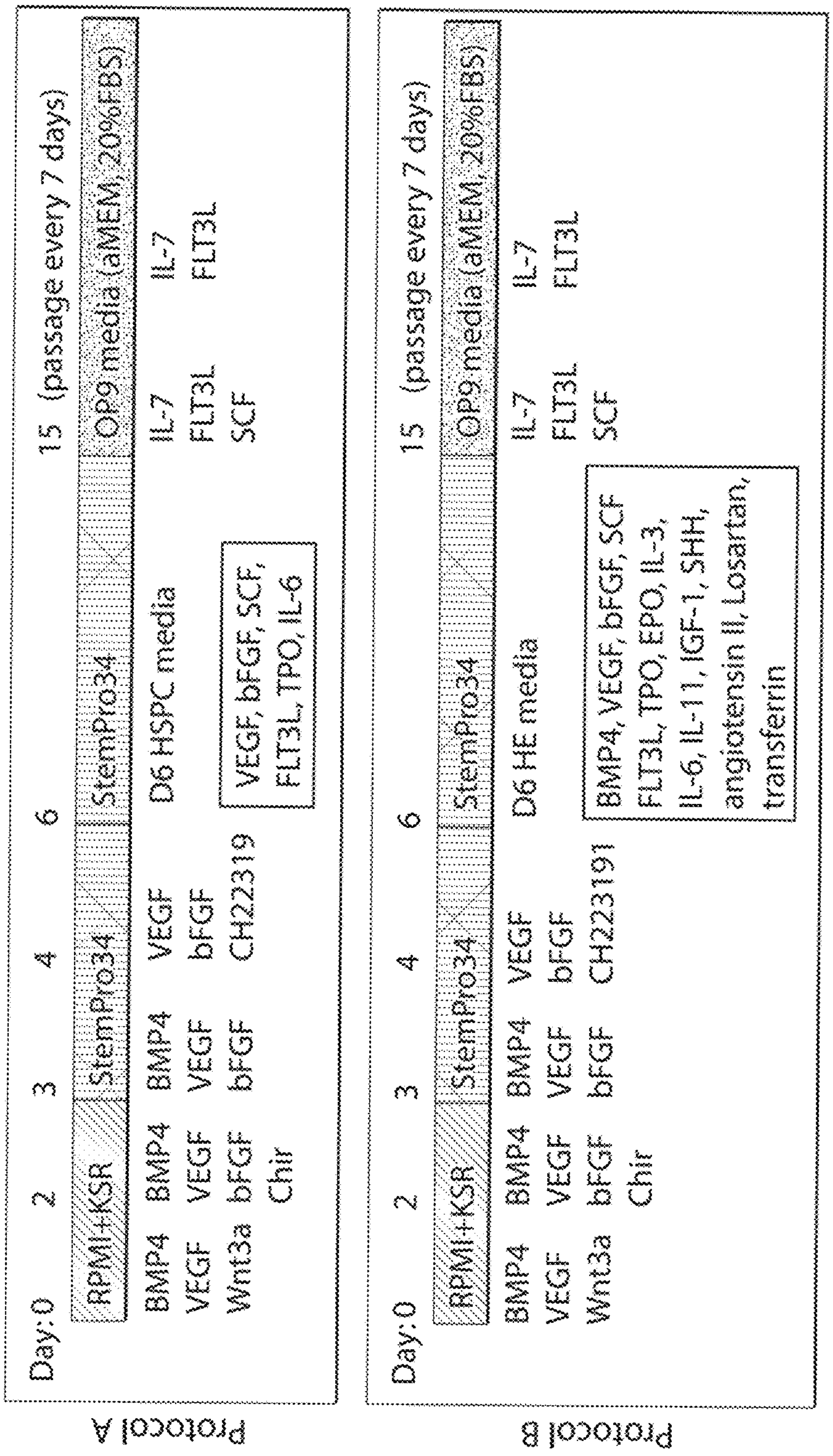

FIG. 1A

HUMAN IPSC-BASED DERIVATION OF NK AND T-CELLS USING EARLY NOTCH INDUCTION

CROSS-REFERENCE TO RELATED APPLICATIONS

This invention claims benefit under 35 U.S.C. § 119(e) of U.S. Provisional Application 62/952,715 filed on Dec. 23, 2019, the contents of each are incorporated herein in their entirety by reference.

FIELD OF THE INVENTION

The technology described herein relates to human stem cell-derived T and NK cells, and iPSC lines for the derivation of iPSC-derived T and NK cells.

SEQUENCE LISTING

The instant application contains a Sequence Listing which has been submitted electronically in ASCII format, and is hereby incorporated by reference in its entirety. Said ASCII copy, created on Dec. 21, 2020 is named 701586-096650US-PT_SL.txt and is 80,201 bytes in size.

BACKGROUND OF THE DISCLOSURE

The seminal discovery that ectopic expression of a notch ligand on mouse bone marrow stromal cells allowed the differentiation of mouse and human hematopoietic progenitors into T cells opened the door for exploration of in vitro T cell development (Schmitt and Zuniga-Pflucker, 2002). However, the production of T cells from induced Pluripotent Stem Cells (iPSCs) has suffered from the difficulty of producing hematopoietic progenitors capable of accessing the T cell lineage and the ability to mature these early T cells into naïve T cells, especially of the CD4 lineage. Significant progress in the production of T-capable progenitors was achieved using strong activation of the WNT signaling pathway with a GSK3β inhibitor (Chir 99021) at day 2 of differentiation (Sturgeon, 2014). In addition, the same GSK3β inhibitor has been shown to be sufficient for the differentiation of iPSCs into hemogenic endothelium (D'Souza et al., 2016; Galat et al., 2018). Some incremental improvements have been reported using various methods of Notch activation such as a dll4-Fc fusion at day 4 (Uenishi et al., 2018) or a stromal-cell layer expressing dll4 (M55-dll4, OP9-dll1/4) (Montel-Hagen et al., 2019). This early activation of the Notch pathway increased the T cell potential of the resulting progenitors however these models did not define the optimal timing and dosage of Notch signaling for T cell emergence. Subsequent analysis of these iPSC-derived T cells showed a strong bias toward CD8+ T cells (Awong et al., 2011) and the production of cells with an abnormal CD8 alpha-alpha phenotype (Themeli et al., 2013). These results suggest limitations of in vitro positive/negative selection that is more profound for the CD4 lineage. Several approaches to improve the output of CD8αβ T cells have been reported, which include T cell production from 3-D organoids either with ex vivo human thymus (Vizcardo et al., 2018) or MS5-dll4 stromal cells (Montel-Hagen et al., 2019) and the use of carefully timed CD3 stimulation in the presence of dexamethasone (Minagawa et al., 2018). The majority of T cells produced in these methods express the desired CD8αβ heterodimer. However, CD4+ T cell production remains very low.

Notch is an important pathway in many developmental decisions. The Notch1 receptor is required for the production of definitive Hematopoietic Stem Cells (HSCs) with full lineage potential in vivo, but is dispensable for primitive hematopoiesis (Kumano et al., 2003). The shared developmental origin of arterial and hemogenic endothelial cells capable of endothelial to hematopoietic transition partly explains this. Even in vitro, stimulation of the notch pathway using a dll4-fc fusion protein at day 4 of hematopoietic differentiation improved the output and lineage potential of the progenitors produced by enhancing the arterial phenotype of the hemogenic endothelium (Uenishi et al., 2018). However, there are differences in Notch utilization between arterial and hemogenic endothelial cells. In jag1−/− mice, arterial endothelial cells are produced but there is a failure of definitive hematopoiesis (Robert-Moreno et al., 2008). In zebrafish, notch ligands delta C and delta D function downstream of WNT16 in a signaling pathway required for HSC formation but not the vasculature (Clements et al., 2011). Finally, developing HSCs become independent of Notch stimulation as they mature (Souilhol et al., 2016). This suggests an early dependence on notch in both arterial and hemogenic endothelial cell development that then bifurcates with arterial endothelium maintaining notch and developing HSCs eventually turning it off. Notch receptors are activated by the mechanical force of ligand endocytosis (Gordon et al., 2015), making it challenging to control in vitro. Even the benefit of immobilized dll4-fc fusion proteins is limited to cells expressing the correct Notch receptor. Due to the artificial nature of iPSC hematopoietic differentiation, there is no guarantee the required receptor will be expressed at the correct time.

The ability to generate T cells from self-renewing pluripotent stem cells (PSC) has the potential to transform the current practice of autologous T cell immunotherapy into universal off-the-shelf products. Engineered T cell therapies hold promise for the effective treatment of cancer and chronic viral infections. The ability to generate T cells on demand from self-renewing human pluripotent stem cells (PSC) may substantially advance the field by allowing the production of universal-donor T cells from stably gene-modified PSC lines (Themeli et al., 2015). However, differentiation of human PSCs into mature, conventional T cells has been challenging with existing methods. Although protocols to differentiate PSC into essentially any non-hematopoietic or hematopoietic lineage have been extensively reported, generation of fully functional mature cells that resemble their adult counterparts has been more problematic. Differentiation of mature T cells from human PSCs has been limited on two fronts: the ability to specify hematopoietic progenitor cells with T-lineage potential (Dravid et al., 2011; Kennedy et al., 2012), and the capacity of existing methods to support maturation of T-lineage committed precursors to conventional, naïve T cells (Themeli et al., 2013; Vizcardo et al., 2013). Improved PSC-to-T cell differentiation strategies must therefore integrate T-competent hematopoietic specification with the full span of conventional, thymic-like T cell differentiation.

If realized, iPSCs are an ideal starting source for T cells for therapeutic purposes. They offer a tractable platform for careful introduction of germline modifications including chimeric antigen receptors, safety features (e.g., inducible death genes), and reducing immunogenicity. These modifications can be pre-validated, making them potentially safer than alternative methods of T cell production. Potential clinical applications include oncology, autoimmunity, or even tolerance induction in transplantation depending on the subset of T cells in question. For these reasons, a robust method of T-cell differentiation from iPSCs is of great clinical interest.

SUMMARY OF THE DISCLOSURE

The present disclosure relates to methods, compositions and kits for producing a multi-lineage hemogenic endothelium (HE) progenitor which has both T cell and Natural killer (NK) cell linage potential (referred to herein as a "T/NK progenitor") from pluripotent stem cells, including iPSC, where the T/NK progenitor can be subsequently directed to differentiate into either mature T cells or NK cells. Some aspects of the technology described herein relates to a modified pluripotent stem cell (PSC) line or modified iPSC line that can be used to generate the T/NK cell progenitors, where the modified PSC line comprises a nucleic acid encoding a NICD protein under an inducible promoter. Additional aspects of the technology described herein relate to a composition comprising a modified iPSC line that is further modified to be a "universal iPSC line", and their use in the methods disclosed herein generating of a population of universal T/NK cell progenitors.

The ability to generate T cells from self-renewing pluripotent stem cells (PSC) has the potential to transform the current practice of autologous T cell immunotherapy into universal off-the-shelf products. However, differentiation of human PSCs into mature, conventional T cells has been highly challenging with existing methods, where the methods are both unreliable and have a very low yield and/or efficiency of producing T cells. In particular, differentiation of mature T cells from human PSCs has been limited on two fronts: the ability to specify hematopoietic progenitor cells with T-lineage potential, and the capacity of existing methods to support maturation of T-lineage committed precursors to conventional, naïve T cells.

Herein, the inventors address both of these issues and teach (i) a method that has a very high efficiency of directing iPSC into hematopoietic progenitor cells with both T cell and NK cell linage potential, can produce a population comprising about 90% CD7+ T/NK cell progenitor, and (ii) a method for maturation of the CD7+ T/NK cell progenitor into either mature T cells or NK cells, based on plating densities, thereby significantly providing advantages over prior methods by providing a robust method for producing a high yield of T cells and NK cells that does not require complex cell selection (i.e., negative and/or positive cell selection methods) or cell sorting.

In particular, the inventors discovered a robust method of producing T/NK cell capable progenitors from pluripotent stem cells that is highly consistent and robust, and has a very high efficiency and high yield of production of T/NK cell progenitors from a pluripotent stem cell source, such as, but not limited to induced pluripotent stem cells (iPSCs). In particular, in all aspects of the methods and compositions herein relate to activating Notch signaling in a pluripotent stem cell (PSC), such as a human PSC or a hiPSC at a very early developmental time period which is before the normal Notch signaling is activated. That is, the inventors have taught that specific activation of the Notch signaling pathway in the iPSC at a time period before endogenous Notch signaling occurs has a surprising and significant effect on inducing the PSC to become T/NK cell progenitors. The inventors show that temporal expression of the Notch Signal Intracellular Domain (NICD) from day 0 to day 2 (day 0-2) in pluripotent stem cells, which is at a very early stage in hiPSC development and before endogenous Notch signaling occurs in the cell, increases the yield of CD7+ T/NK cell progenitors to about 60% at day 19, as compared to the yield of about 10% at day 19 without the early expression of NICD. (see, for example, FIG. 5E which shows CD7+ cells in 4 different iPSC-NICD1 cell lines at day 19, with Dox+ (i.e., induced NICD1 expression at d0-d2) resulting in 65.1%, 61.5%, 67% and 44.4% of the cells are CD7+ cells, as compared to only 13.2%, 4.39%, 35.6% and 3.25% of the cells being CD7+ cells in the No Dox treated cells).

Accordingly, the inventors have discovered that artificial notch signaling in iPSC during a narrow 48- to 72-time period, i.e., between day 0 and day 2 of iPSC differentiation and early mesoderm induction, and importantly, at a developmental time period prior to onset of endogenous notch signaling, can significantly increase the yield of T/NK cell progenitors.

Another aspect relates to a method of further expanding the T/NK progenitor cells by co-culture on an engineered stroma cell layer expressing a human notch ligand (e.g., DDL1-DLL4), and optionally can also express MHC class II, to generate a population containing more than 90% CD7+ T/NK progenitors. Unlike previously reported protocols that require cell sorting, because of the high homogeneity of the population comprising 90% CD7+ T/NK progenitors, these cells can be harvested without cell sorting (or other negative and/or positive cell selection methods) and be further co-cultured on an engineered stroma cell layer expressing a human notch ligand (e.g., DDL1-DLL4) at a defined density to either differentiate into T cells or NK cells. In particular, the inventors have also discovered that co-culturing CD7+ T/NK progenitors at a cell density of about 50,000 cells/10 cm plate (or alternatively, 5,000 cells/ml) or less, results in maturation of the CD7+ T/NK progenitors into mature T cells, whereas co-culturing CD7+ T/NK progenitors at a cell density of about 200,000 cells/10 cm plate (or alternatively, 20,000 cells/ml) or greater, results in maturation of the CD7+ T/NK progenitors into NK cells. Therefore, the inventors have taught a robust protocol for inducing iPSC into T/NK CD7+ progenitors that are capable of deriving both types of populations (T-cells and NK cells) without having to perform complex, time consuming and expensive cell sorting (or negative and/or positive cell selection) procedures. Accordingly, not only do the methods and compositions described herein provide a high yield of T cells and NK cells to be produced, it is a highly robust and efficient methodology that does not require cell sorting or other negative and/or positive cell selection methods.

Importantly and in contrast to the present invention, previous methods for the generation of T cells and NK cells from iPSC depended on strong Notch stimulation in the later stages of differentiation, and in particular such methods used exogenous notch agonists and ligands such as dll1-dll4 to activate Notch signaling—that is, such methods relied upon on the presence of endogenous notch receptors (Notch1-4) expressed on the surface of the iPSC. However, the yields of differentiation using such methods activating endogenously expressed notch receptors were poor and highly biased towards CD8+ T cells. Stated differently—prior methods for generation of T cells and NK cells resulted in low yield and poor reproducibility and required exogenously supplied Notch agonists, therefore relying on the iPSC to have exogenously expressed Notch receptors on the surface of the iPSC cells, which are not expressed until at least after day 3. Herein, the inventors have surprisingly discovered that, in direct contrast to existing methods, the generation of T/NK progenitors can be produced with a significantly high yield and high reproducibility by inducing notch signaling between day 0 and day 2 (d0-d2) in iPSC, which before the onset of endogenous notch signaling (or notch receptor expression). These T/NK progenitors can be reliably and robustly differentiated into substantially homogenous populations of T-cells or homogenous populations of NK cells accordingly, as disclosed herein.

Another advantage of the methods and compositions disclosed herein is that the inventors have taught a robust method for derivation of hemogenic endothelium that have more definitive T/NK properties which is a feeder-free system and therefore can more robustly generate a highly enriched population of Hematopoietic Stem Progenitor Cells (HSPCs).

Methods to generate T cells from mouse ESC previously relied on the use of a stromal feeder layer (OP9 cells) overexpressing mouse DLL1 (Schmitt et al, Nat. Immunol. 2004), which was then adapted for human cells, both ESC and iPSC (Kennedy et al, Cell Reports 2012). However, in both cases they were highly variable and inconsistent and generated a relatively low yield of T cells. Since then, other protocols have been reported which describe the manipulation of the TCR by engineering the expression of a specific chimeric antigen receptor (CAR) that improved on the specificity of the obtained T cells, that were all CD8 (no CD4 cells) (Minagawa et al, Cell Stem Cell 2018). A method using a 3D organoid approach has also been reported that while it appears more robust in terms of cell numbers, the method still generates mostly CD8 cells (Montel-Hagen et al, Cell Stem Cell 2019). In contrast, the methods described herein of induction of notch signaling before the onset of endogenous notch signaling improves these methods by (1) focuses on the generation and expansion of a more definitive HSPC (by manipulating Notch signaling very early during differentiation) and (2) generates both T cells or NK cells.

Another aspect of the technology described herein relates to the generation of novel induced pluripotent stem cell (iPSC) lines that contain Notch Intracellular Domain (NICD) under an inducible promoter, enabling NICD expression to occur (i.e., be induced or turned on) at a very early stage in hPSC development before the onset of endogenous Notch signaling. More specifically, herein the inventors teach, using a doxycycline inducible Notch NICD1 signaling gene knock in, the production of T/NK capable progenitors with very high efficiency and yield. Using these modified iPSC-NICD cell lines, the inventors have developed a protocol for the robust generation of hematopoietic stem/progenitor cells (HSPCs) capable of differentiating into T and NK cells.

In another aspect, the disclosure provides a method of enhancing production of hemogenic endothelium progenitors, the method comprising: (a) introducing a nucleic acid encoding a NICD protein, operatively linked to an inducible promoter into a pluripotent stem cell; and (b) culturing the pluripotent stem cells for 0-2 days in the presence of an agent which induces expression of the NICD protein from the inducible promoter within the pluripotent stem cell. In some embodiments, the method further comprises culturing the cells for 0-9 days in iT media to obtain a population of CD7+ cells, where the population of cells at 9 days comprises between 30-50% CD7+ cells, or 50-60%, or at least 65%, or at least 70%, or at least 75%, or at least 80%, or at least 85%, or at least 90%, or at least 95%, or more than 95% CD7+ T/NK progenitor cells. In some embodiments, after culturing the cells for 0-9 days in iT media to obtain a population of CD7+ cells, the cell population is collected at day 9 without the need for cell sorting, wherein the collected population of cells comprises between 30-50% CD7+ cells, or 50-60%, or at least 65%, or at least 70%, or at least 75%, or at least 80%, or at least 85%, or at least 90%, or at least 95%, or more than 95% CD7+ T/NK progenitor cells. In some embodiments, the method further comprises harvesting or collecting the CD7+ T/NK progenitor cells, for example, where cell sorting or cell selection such as FACS is not necessary. In some embodiments, the method further comprises co-culturing the population of the collected CD7+ T/NK progenitors on an engineered stromal cell layer, such as for example, OP9 cells expressing a notch ligand such as dll1, dll2, dll3, dll4 at a cell density of about 50,000 cells/10 cm plate or less, or a cell density of about 200,000 cells/10 cm plate or greater, and collecting the cells after a period of time, for example, for at least 3 weeks, or at least 4 weeks or at least 5 weeks or at least 6 weeks or any time period between 3-6 weeks, or more than 6 weeks, where the T/NK CD7+ progenitor cells cultured at a density of about 50,000 cells/10 cm plate (i.e., about 5,000 cells/ml) or less differentiate into mature T cells, or there the T/NK CD7+ progenitor cells co-cultured at a density of about 200,000 cells/10 cm plate (i.e., about 20,000 cells/ml) or greater differentiate into NK cells.

Through the methods and compositions described herein, an unlimited number of engineered NK cells or T cells can be generated. Accordingly, the method and compositions described herein which can be used to efficiently and robustly produce high yields T/NK progenitors and subsequently mature T cells and NK cells will have a major impact in the field of cancer immunotherapy, autoimmunity and organ transplantation.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 1A-1C show use of a modified "HE" media used at day 6 outperforms HSPC media for mesodermal to hematopoietic transition for inducing T competence of iPSC-derived hematopoietic progenitors. FIG. 1A shows two protocols (protocol A, upper panel and Protocol B, lower panel) for inducing T competence of iPSC-derived hematopoietic progenitors. Protocol A and B differ in the composition of growth factors in the StemPro34 media used at day 6, with Protocol A using a D6 HSPC media comprising: VEGF, bFGF, SCF, FLT3L, TPO and IL-6, and Protocol B using a D6 HE media comprising: BMP4, VEGF, bFGF, SCF, FLT3L, TPO, IL-3, IL-6, IL-11, IGF-1, SHH, angiotensin II, losartan and transferrin. FIG. 1B shows representative flow of protocol A (top row) and B (bottom row) (n>3 in each case) of Day 15 progenitors and after 9 days and 15-days in a co-culture in OP9 cells, showing T/NK lineage cells are produced only with protocol B. More specifically, Protocol B produces more CD7+ cells after 9 days of co-culture (day 24 from the beginning of the protocol), and that these cells are able to continue to develop into CD4/CD8 DP cells by 15 days in co-culture (day 30 overall, or from the beginning of the protocol). FIG. 1C shows the iT media, where erythropoietin (EPO) is absent or removed from "HE media" in protocol B which results in a reduction of CD235a+ cells (putative erythrocytes) and similar population of CD34/45 double positive cells (n=2 with two different iPSC cell lines).

FIG. 2A is a schematic Protocol B with the HE media and changes only in the first 5 days. FIG. 2B shows a schematic of the "iT" protocol, which uses an alternative day 0-5 differentiation with earlier GSK-3B inhibition and hypoxia. FIG. 2C shows the iT Protocol yields higher CD34+/CD45+ double positive cells negative for CD235a ($CD34^+$/$CD45^+$/$CD235a^-$) hematopoietic progenitors at day 12, (n=2 for each cell line). FIG. 2D shows day 4 flow cytometry demonstrating a 4-fold increase in the $KDR^{high}$/$CD34^+$/VE-$Cadherin^+$ population with the "iT" protocol as compared to the B protocol (representative flow, n=4). FIG. 2E shows results of FACs sorted Day 4 cells sorted into 3 populations: $KDR^-$, $KDR^{low}$, and $KDR^{high}CD34^+VEcadherin^+$. Only the $KDR^{high}CD34^+$VE $cadherin^+$ population produced CD34+/CD45+ double positive progenitors at day 12 as shown by FACS. (n=2 separate sorts). FIG. 2F shows cell counts of CD34+/45+ double positive cells at day 12 from each population sorted at day 4 ($KDR^-$; $KDR^{low}$; $KDR^{high}$/$CD34^+$/VE-$Cadherin^+$ population) from FIG. 2E.

FIG. 3A shows dose responses of notch target genes HES5 and HEY1 in 4 TetOn:NICD1 iPSC lines (bBU1c2N1, BU2 N1, BU3 N1, BU8 N1) in response to 72 hrs of doxycycline treatment. For bBU1c2 N1, doxycycline concentrations were 0, 100, 200, and 500 ng/ml. For BU2, BU3, and BU8 N1 doxycycline concentrations were 0, 250, 500, and 1000 ng/ml. For each time point, 3 biological replicates were used; *=p<0.05 by standard T test, error bars are standard deviation. FIG. 3B shows a schematic of the constructs used for the creation of OP9-hdll4:hMCHII using lentiviral transduction, including flow of the final sorted cell line. For the hMHCII lentivirus, HLA DP alpha, beta, and CD74 were amplified from a cDNA pool from iPSC-derived dendritic cells. Two polycistronic constructs were created by using overlapping PCR to insert 2A sequences and cloned into a PHAGE2 lentivirus construct on either side of an IRES element to produce an expression cassette to express all 4 transcripts. For the hDLL4 lentivirus, human DLL4 was amplified from cDNA from iPSC-derived hemogenic endothelium and cloned into a PHAGE2 lentiviral construct. These lentiviral constructs were then packaged by 5-plasmid transfection of 293T cells. Resulting concentrated viral supernatants were used to simultaneously infect OP9 cells. OP9 cells expressing both hDLL4 and hMHCII were FACS sorted and >95% purity confirmed by flow cytometry after resulting cells were expanded.

FIG. 4A is a schematic of Protocol B and the iT protocol which were used during the titration of dox treatment, which were then assessed by flow cytometry staining of progenitors (CD235 negative CD34/CD45 positive), as well as early T/NK lineage cells (CD7 positive) after one week of co-culture with OP9-DLL4:MHCII feeder cells. (FIGS. 4B-4C used protocol B, while FIG. 4D used the iT protocol). FIG. 4B shows results of FACs sorting of cells after Protocol B treatment and shows that early Dox administration (Dox 2-5, second row) (resulting in early Notch induction) is better than later treatment (Dox d3-6 or d4-7, rows 3 and 4 respectively) as measured by CD7+ cell output after 1 week of co-culture. FIG. 4C shows FACS sorting of cells after Protocol B showing dox treatment for a single day at day 2 (Dox d2) provides most of the improvement in CD7 percentages as compared to administration at d2-5, d2-d4, d2-d3. Longer treatment times appeared to reduce the number of progenitors produced. FIG. 4D shows FACS sorting of cells after the iT protocol, showing dox treatment before day 2 is optimal, especially from day 0-2 (Dox d0-d2 or Dox d0-d1) (n>5). bBU1c2:N1 was used with a doxycycline concentration of 100 ng/ml for all these experiments.

FIG. 5A show an exemplary construct for an inducible system using Tet-On promoter operatively linked to the NICD1 gene (i.e., the Tet-On:NICD1 nucleic acid construct) which is used to simulate autonomous early control of Notch activation, which was inserted into the AAVS1 locus of 4 iPSC lines. The cHS4 insulators reduce silencing and the T2A:puro is used for selection. FIG. 5B shows the results of PCR screening of positive iPSC clones with a representative 1 kb PCR screening band for positive clones showing successful targeting. Primers Z-AV-4 (binds outside of the AAVS1 L arm) and T2A R were used to confirm correct targeting. FIG. 5C shows dose-response curve for notch targets genes HES5 and HEY1 after doxycycline (0-500 ng/ml) treatment for 72 hrs for bBU1c2-TetON:NICD1. The parental (non-targeted) line is also included and was treated with doxycycline at 500 ng/ml. Three biological replicates of each condition were used, error bars are standard deviation, data shown is fold change calculated by delta-deltaCt method with BACT as control gene, *=P<0.05 from two-tailed T test compared with untreated control. (iPSCs, n=3, 1 representative line shown). FIG. 5D is a schematic of the iT differentiation protocol outlining cytokines, media changes, and time. FIG. 5E shows flow cytometry of day 12 progenitors (labeled with CD235a, CD34 and CD45), and day 19 after one week of co-culture (labeled with CD7), and shows a robust increase in CD7+ population at day 19 in all 4 iPSC lines when doxycycline is used to activate the Notch pathway from day 0-2 of differentiation All 4 TetOn:NICD1 lines are shown with and without doxycycline treatment from day 0-2 (doxycycline concentrations were 100 ng/ml for bBU1c2, 350 ng/ml for BU3, and 500 ng/ml for BU2 and BU8). This representative flow cytometry shows increase in CD7+ cells at day 19 in dox treated cultures is consistent across 4 independent iPSC lines. N=5 for bBU1c2, N=2 for the other 3.

FIG. 6A shows gene expression analysis of Notch target and early hematopoietic genes comparing all 4 TetON:NICD1 lines and their parental (non-targeted lines) all treated with doxycycline (100 ng/ml for bBU1c2 and 250 ng/ml for the others). Comparisons are day 1 treated versus day 1 parental, day 2 treated to day 2 parental and so forth, and the ΔΔCt (fold change) is shown. This showed an early peak of notch target genes followed by the parental lines "catching up" as endogenous Notch signaling begins. A significant increase in KDR is also seen. FIG. 6B shows the expression of notch target genes and KDR in the 4 TetOn:NICD1 lines treated with doxycycline (day 0-2, and showed a marked drop in HES5 after dox removal that immediately rebounds as endogenous signaling begins. Comparisons were day 2 to day 1, day 3 to day 1, and so forth. N=4 for each condition, data shown is fold change calculated by ΔΔCt method with BACT as control gene. *=P<0.05 by two-tailed T test from untreated iPSCs. FIG. 6C shows representative staining for NICD1 (AF488-green) and nuclei (Hoescht-blue) in BU2-TetOn:NICD1 in dox-treated (day 0-2) and untreated differentiations on days 1-4. Similar results were obtained in 3 separate TetOn:NICD1 iPSC lines (not shown). Images shown taken with 20× objective; scale bars=30 uM. FIG. 6D shows two-second exposure of NICD1 (AF488-green) channel showing weak nuclear staining in both treated and untreated cultures at day 4 compared with iPSCs. FIG. 6E shows representative CD7 flow cytometry of day 19 cells (1 week of co-culture) showing doxycycline can rescue T/NK capacity in DAPT (1 uM) inhibited cultures. N=2 for 4 individual TetOn:NICD1 iPSC lines.

FIG. 7A shows representative flow cytometry showing percentage of CD7+ cells at day 19 and day 27 of differentiation and CD4+/CD5+ cells at day 34 when co-cultures were initiated at three different densities at day 12 (50,000 top, 100,000 middle and 250,000 bottom). A marked loss of CD7+ and/or CD5+ cells is present at higher density (the 250K group), where NK cells lysed the stroma and no T cells were noted (n=3. The best CD7+/CD5_double positive population was noted in the 50K group). N=4, representative flow cytometry shown. The progenitors co-cultured on OP9:dll4-MHCII co-culture using 50, 100, and 250K progenitors. FIG. 7B shows flow cytometry showing percentage of NK cells expressing NK markers CD56 and NKp44, NKG2D, or NKp46 at day 35 of differentiation in the co-culture plated with 250,000 cells at day 12. For this staining, N=2. FIG. 7C shows Day 26 20× objective brightfield images of low (left) and high (right) density cultures showing loss of OP9 stroma and increase in debris (scale bar=60 uM). Inset: Staining for live vs dead cells shows the significant increase in the percentage of dead cells under conditions that promote emergence of NK cells in the culture. N=5.

FIG. 8A shows representative flow cytometry evaluating expression of CD4, CD8, and CD3 from day 30 to day 63 of differentiation, showing the progression of maturation of iPSC-derived T cells to CD8SP cells. The strong CD8 bias is present despite human MHCII expressed on the feeder cells. FIG. 8B shows gene expression of a panel of T-cell related transcripts of day 45 CD7+ FACS sorted cells and human thymocytes compared to iPSCs. Four separate differentiations were sorted at day 45 (N=2 for 2 separate cell lines). Fold change is calculated by the delta-deltaCt method with BACT as control gene and log 2-transformed. Error bars are standard deviation. FIGS. 8C-8E show day 40 cells were stimulated with CD3/CD28 tetramers or PMA/Ionomycin (25 ng/ml and 250 ng/ml respectively) and activation assessed by surface markers (FIG. 8C), proliferation using Cell Trace Violet (FIG. 8D), and increase in absolute number (FIG. 8E). N=2.

FIGS. 9A and 9B shows violin plots showing top 5 up and downregulated genes between dox-treated (red) and untreated (blue) day 12 progenitors. Top five up (FIG. 9A) and down (FIG. 9B) differentially expressed genes are shown. FIGS. 9C-9G show spring plots of the day 12 progenitors are shown highlighting upregulated genes. The day 12 dox-treated (left) and untreated (right) cells were manually separated to aid in visualization of differences. FIG. 9C shows composite expression signature of a list of hematopoietic progenitor genes is shown. Higher expression was visualized as yellow/red, low expression is black. Expression of CD34 (FIG. 9D), Serglycin (SRGN) (FIG. 9E), GATA1 (FIG. 9D) and GYPA (CD235a) (FIG. 9G) are shown, with increased expression were visualized as green. FIG. 9H shows Full Spring plot of day 12 progenitors showing main clusters annotated for progenitor, myeloid, and Meg/Ery groups.

FIG. 10A shows violin plots showing expression of key T cell (top row) and hematopoietic progenitor (bottom row) transcripts across time from progenitors (left) to day 42 T cells (right) compared with human thymus (far right column). This shows a gradual increase in T cell transcripts and loss of progenitor transcripts over time. FIG. 10B shows full annotated Spring plot showing Louvain clustering at 0.25 resolution. Clusters and direction of differentiation are annotated. FIG. 10C show full spring plot showing all cells at each timepoint analyzed, showing progression of differentiation by time of cell harvest. FIG. 10D shows a full spring plot showing positive cells for a composite expression signature of gene lists for hematopoietic progenitors, T cells, and NK cells increased expression appears red/yellow. FIG. 10E shows expression of individual key transcripts for progenitors, myeloid, erythroid, T/NK, and maturing T cells. Increased expression is visualized in green. Gene ontology and top 10 gene lists for each cluster are in Table 3 and 4 respectively.

DETAILED DESCRIPTION OF THE DISCLOSURE

I. In General

Figure 1B:
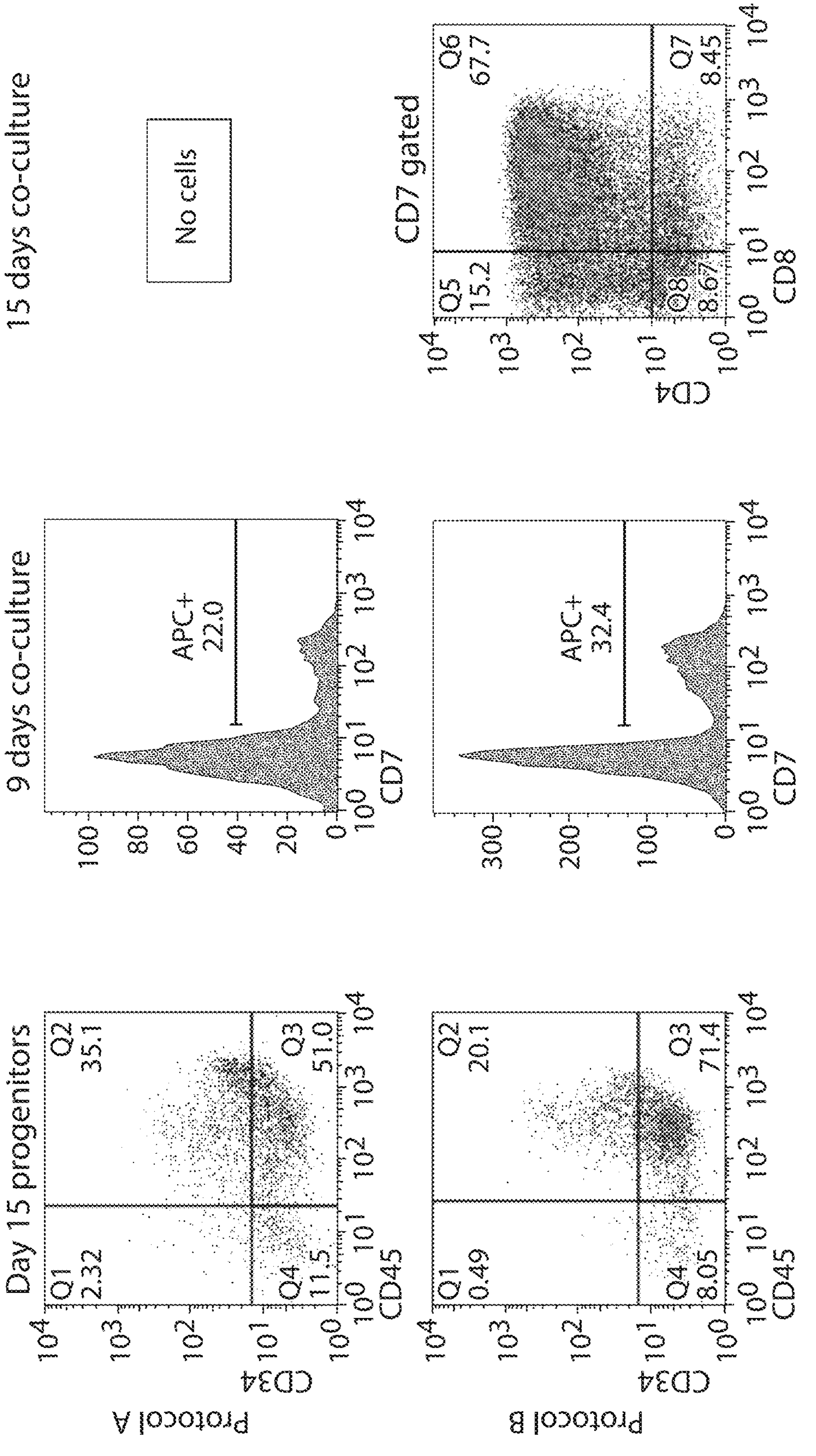

In all aspects of the technology as described herein generally relates to methods, compositions and kits for inducing pluripotent stem cells and iPSC into T/NK progenitors with high efficiency, yield and reproducibility. The technology disclosed herein also generally relates to methods, compositions and kits for co-culturing the T/NK CD7+ progenitors on an engineered stroma cell layer expressing a human notch ligand (e.g., DDL1-DLL4), to generate a population containing more than 90% CD7+ T/NK progenitors, which develop into mature T cells and NK cells by co-culture the CD7+ T/NK progenitors on a stromal cell layer at specific cell densities. In some embodiments, the methods, compositions and kits can be used according to the technology described herein to generate a population containing between 30-40%, 40-50%, 50-60%, or 60-70%, or 70-80%, or 90-95% or 90-98% CD7+ T/NK progenitors, which can then develop into mature T cells and NK cells by co-culture the CD7+ T/NK progenitors on a stromal cell layer at specific cell densities, as described herein. Therefore, the inventors teach herein a robust protocol for inducing iPSC into T/NK CD7+ progenitors that are capable of deriving both types of populations (e.g., a substantially homogenous population of T-cells or a substantially homogenous population of NK cells) from a single cell source.

Accordingly, the inventors discovered and teach an efficient, highly robust 2-D hematopoietic progenitor differentiation protocol that requires induction of notch activation before endogenous Notch signaling typically occurs, specifies robust access to the T/NK cell lineage in iPSC-derived hematopoietic progenitor cells. Moreover, the inventors teach that these T/NK cell progenitors can differentiate into T or NK cells based on the density of progenitors co-cultured on a layer of stromal cells expressing a Notch, such as dll1-dll4 (i.e., a OP9-dll4 co-culture system). Single-cell sequencing at several time points across the commitment to T cells revealed early notch activation produced a population of progenitors with less prior lineage commitment. These iPSC-derived T cells matured into mostly CD8 single positive (CD8+) T cells that could be activated in the presence of CD3/CD28 tetramers or PMA/Ionomycin. In addition, an OP9 stromal layer engineered to express both human dll4 and human MHC II (DPα, DPβ, and CD74) still supported a strong CD8+ bias in resulting T cells, suggesting the presence/absence of hMHCII is not the primary driver of CD4+ T cell failure.

The methods of the present application allow the generation of large numbers of T/NK progenitor cells. These T/NK progenitor cells exhibit, or have the potential to differentiate into cells that exhibit morphological, physiological, functional, and/or immunological features of T cells and NK cells. The generation of large numbers of T/NK progenitor cells with the ability to form mature T cells or NK cells makes them highly useful in cell therapy.

II. Notch Signaling in General and the Prior Methods to Generate Stem-Cell Derived T Cells Notch is the name derived from a gene that induces the excessive growth of the wings of *Drosophila* during mutation to make Notches in the wings. It is a signaling pathway that plays a crucial role in fast cell-to-cell signaling and amplification in multicellular animals. Notch transduces a signal by cell-to-cell contact through a Delta or Serrate ligand present in the adjacent cell. In the present invention, in order to activate the Notch signaling pathway, a gene that is involved in the Notch signaling pathway is inserted into pluripotent stem cells.

The Notch family of receptors includes Notch-1, -2, -3, and -4 are highly conserved proteins with a wide range of physiological roles including regulating cell fate, proliferation, angiogenesis, cell survival, and the immune response. Like many other proteins associated with these processes, aberrant Notch activity is reported to have complex and context-dependent effects on tumorigenesis. Upon translation, Notch undergoes several pre-processing steps during its transport to the membrane. These include the addition of O-fucose by O-fucosyltransferase 1 (POFUT1) in the endoplasmic reticulum and, in the Golgi, the addition of N-acetylglucosamine by any of three N-acetylglucosaminetransferases that in vertebrates include Lunatic Fringe (LFNG), Manic Fringe (MFNG), and Radical Fringe (RFNG). Also in the Golgi, Notch is cleaved by Furin to produce a heterodimer consisting of the Notch intracellular domain (NICD) and the Notch extracellular domain (NECD). The heterodimer is then transported to the membrane where it exists as a single pass transmembrane protein. Notch is thought to be in a cycling state that includes endocytosis and re-insertion into the membrane or it may be targeted for lysosomal degradation.

Notch is activated by a unique process that includes ligand binding and multistep proteolytic processing. In invertebrates, Notch ligands include Delta, Serrate, and Lag2 (DSL), while their DSL counterparts in mammals include Delta-like (DLL)-1, -3, -4, Jagged 1, and Jagged 2. Like Notch, DSL ligands are single pass transmembrane receptors and typical Notch activation includes direct cell-cell interaction (trans-activation). Subsequent to binding Notch, the intracellular domain of the Notch ligand is ubiquitinated via the E3 ligase Mind Bomb-1. This initiates endocytosis of the Notch ligand/NECD complex into the ligand-expressing cell. Common endocytic factors have been implicated in this process including Clathrin, Dynamin, Epsin, and Picalm. The mechanical forces generated by these endocytosis-related events may be important for the next steps in the Notch pathway that include sequential proteolytic cleavage of Notch. Notch is first cleaved by TACE/ADAM17 and then the gamma-Secretase complex that includes Presenilin, PSENEN/PEN-2, APH1, and Nicastrin. Whether gamma-Secretase cleavage occurs at the membrane or the endosomal compartment is still a matter of investigation. After its cleavage, the NICD is released into the cytosol and translocated to the nucleus.

Notch activity is primarily dependent on its ability to regulate gene transcription. Recombination Signal Binding Protein for Immunoglobulin Kappa J Region (RBPj) plays a crucial role in Notch-mediated gene transcription. RBPj is also known as CBF-1, or CSL based on its mammalian (CBF-1), *Drosophila* (Suppressor of Hairless), and *C. elegans* (Lag-2) orthologs. In the absence of Notch activation, CSL/RBPj acts as a transcriptional repressor in complex with a growing list of co-repressors, linker proteins, and enzymes such as histone deacetylases (HDACs). In the nucleus the NICD displaces transcriptional repressors and forms a complex with CSL/RBPj and Mastermind-like (MAML). MAML recruits transcriptional co-activators, such as the histone acetyltransferase p300, forming a Notch activator complex that culminates in the transcription of Notch target genes. The number of proteins associated with regulating the activator complex continues to grow. There are kinases that can directly phosphorylate and positively or negatively regulate the NICD. In addition, a range of DNA-binding factors and proteins that directly interact with the NICD exists that can either promote or inhibit transcription depending on the context. Turnover of the NICD is high and phosphorylation by CDK8 promotes recognition by the E3 ligase FBW7, resulting in NICD ubiquitination and proteasomal degradation. There appears to be a complex equilibrium in place, and the balance between of the opposing regulators that dictate the overall level of Notch activity.

Binding of Notch by DSL ligands and transcriptional activation involving CSL/RBPj is considered the canonical Notch pathway. However, descriptions of non-canonical signaling continue to be described. Several non-canonical Notch ligands have been identified that have varied effects including the inhibition or activation of the Notch pathways. In addition, it is evident that there is crosstalk between Notch and other signaling pathways, including Akt/mTOR, NF kappa B, Wnt/beta-Catenin, and others.

A Notch ligand is selected that promotes and maintains differentiation and proliferation of cells of the T cell lineage. A Notch ligand may be human in origin, or may be derived from other species, including mammalian species such as rodent, dog, cat, pig, sheep, cow, goat, and primates. Particular examples of Notch Ligands include the Delta family. The Delta family includes Delta-1 (Genbank Accession No. AF003522, *Homo sapiens*), Delta-3 (Genbank Accession No. AF084576, *Rattus norvegicus*), Delta-like 1 (Genbank Accession No. NM_005618 and NP_005609, *Homo sapiens*; Genbank Accession No. X80903, 148324, *M. musculus*), Delta-like 3 (Genbank Accession No. NM_053666, N_446118, *Rattus norvegicus*), Delta-4 (Genbank Accession No. AF273454, BAB18580, *Mus musculus*; Genbank Accession No. AF279305, AAF81912, *Homo sapiens*), and Delta-like 4 (Genbank Accession. No. Q9NR61, AAF76427, AF253468, NM_019074, *Homo sapiens*; Genbank Accession No. NM_019454, *Mus musculus*). Notch ligands are commercially available or can be produced by recombinant DNA techniques and purified to various degrees.

HSCs express multiple Notch receptors (Milner et al., 1996; Milner et al., 1994) but the expression patterns of the various Notch ligands have been reported to be distinct between bone marrow stromal cells (Jones et al., 1998; Karanu et al., 2001; Li et al., 1998; Varnum-Finney et al., 1998; Walker et al., 1999) and thymic epithelial cells (Anderson et al., 2001) Taken together, these results suggest that different Notch receptors and ligands may control different aspects of hematopoiesis depending on the microenvironment: allowing for self-renewal in the bone marrow and influencing cell fate decisions in the thymus (Varnum-Finney et al., 1998). This led to the use of bone marrow stromal lines, such as OP9 cells (Cho et al., 1999; Kim et al., 2003; Kodama et al., 1994), which support B cell differentiation and provide an appropriate Notch ligand to induce T cell commitment. It was reported that OP9 cells, which do not express Dll1, when retrovirally-transduced to express Dll-1 (OP9-DL1) inhibited the development of B cells and favored the development of T cells from fetal liver-derived HSCs (Schmitt and Zúñiga-Pflücker, 2002) or mouse ESCs (Schmitt et al., 2004). Given the high level of homology (90%) between mouse and human Dll-1 molecules, and that mouse stromal lines can support the differentiation of human HSCs (Bennaceur-Griscelli et al., 2001; Jaleco et al., 2001; Karanu et al., 2001; Rawlings et al., 1995), HSCs cultured on OP9-DL1 cells were used to initiate and support T cell differentiation in vitro.

T-cells develop within the thymus from bone marrow-derived hematopoietic progenitors, and follow a series of stage-specific differentiation events, which are broadly characterized by the developmentally-coordinated expression of CD4 and CD8 (Blom and Spits, 2006; Spits, 2002). The initial stages of human T-cell development include precursors that express the stem cell marker CD34 (Haddad et al., 2006; Hao et al., 2001), which is also present on hematopoietic stem cells (HSCs) and on multipotent or lineage-specified progenitor cells. Furthermore, several groups have established that the most primitive cells in the human thymus possess multi-lineage potential (Blom et al, 1997; Res et al., 1996; Weerkamp et al., 2006a) as they give rise to T-lineage, as well as, natural killer (NK), dendritic cells (DCs) and to some extent myeloid-lineage cells (Blom et al., 1997; La Motte-Mohs et al., 2007). Within the known hierarchy of T-cell development, the earliest precursor subset is further defined by their lack of CD3, CD4, CD8 and CD1a expression (Galy et al., 1993; Vanhecke et al., 1995).

While immature stages of T-cell development are typically delineated as CD34+CD1a− (most immature) and CD34+CD1a+ cells, these populations remain heterogeneous. Of note, CD7 expression is one of the earliest cell surface markers known to appear during T-lymphopoiesis (Haddad et al., 2006; Haynes et al., 1988). Importantly, the transition from CD34+CD7+CD1a− to CD34+CD7+CD1a+ by early thymocytes is associated with T-cell commitment, as a small percentage (~10%) of these cells bear rearrangement at the T-cell receptor β-chain (TCRβ) locus (Blom et al., 1999; Dik et al., 2005). In addition, CD34+CD7+CD1a+ cells appear to be T-lineage restricted, as these cells show low precursor activity towards non-T-cell lineages (Spits, 2002). Following this stage, thymocytes progress to a CD4 immature single positive (CD4iSP) stage, at which point CD4 is expressed in the absence of CD8. Thereafter, a subset of CD4iSP cells are thought to complete TCRβ rearrangement leading to β-selection and differentiation to the CD4+ CD8+ double positive (DP) stage. Finally, following TCRα rearrangement, TCRαβ-expressing DP thymocytes undergo positive and negative selection, and yield CD4+CD8− and CD4−CD8+ single positive (SP) T-cells, which emigrate to the periphery (Vanhecke et al., 1997).

Current understanding of the above-outlined stages has been obtained from analyses of human fetal or adult thymocyte subsets, and by analyzing T-cell development in vitro using xenogeneic engraftment of mouse fetal thymus organ cultures (FTOCs) (Fisher et al., 1990; La Motte-Mohs et al., 2007). While these systems have provided important insight into T-cell development, the capacity to evaluate specific progenitor populations has remained difficult to assess given the requirement of human thymus tissue, and the limited number of progenitor T-cells that can be readily analyzed.

Previous work for T-cell production has been reported from umbilical cord-blood (UCB)-derived HSCs cocultured with OP9-DL1 cells (La Motte-Mohs et al., 2005), however, it was unclear whether functional T-cells could be generated. Moreover, as DL1 was expressed from OP9 cells, any activation of Notch receptors (Notch1-4) and notch signaling was after the onset of endogenous notch signaling, because the dll1 ligand is required to activate its receptor for its functional effect.

III. Method for Activating Notch Signaling Before Onset of Endogenous Notch Signaling One aspect herein relates to a method for promoting arterial hemogenic endothelium (AHE) cell differentiation for human pluripotent stem cell populations in vitro. In one aspect, the method provides a method of promoting AHE differentiation by overexpression of a Notch Intracellular domain (NICD) during hPSCs differentiation at the mesoderm cell population stage, and before the onset of endogenous Notch signaling, which enhances arterial HE (AHE) formation. In one aspect, the overexpression of a NICD protein, e.g., NICD1, NICD2, NICD3, NICD4, between day 0 and day 2 of differentiation promotes HE formation with T cell and NK cell lineage capable progenitors being produced with very high efficiency and reproducibility.

In the Examples an exemplary iPSC cell line was generated, which was a modified human iPSC line comprising a nucleic acid sequence encoding NICD1 under the control of an inducible promoter, enabling controlled temporal expression of the NICD1 protein in the presence of doxycycline (Dox) from day 0 to day 2. In the examples, such a Tet-ON inducible expression of NICD1 also enabled a dose-dependent expression of NICD1, as it was surprisingly discovered that too high an expression of NICD1 or too little expression of NICD1 during this critical d0-d2 window abrogated the effect of the NICD1 overexpression and resulted in lower yields of CD7+ T/NK progenitors.

Also encompassed herein, is a pluripotent stem cell line, such as an embryonic stem (ES) cell line, such as a human ES cell line, or a human iPSC line comprising an exogenous vector comprising the nucleic acid sequence encoding a NICD1 protein under the control of, or operatively linked to an inducible promoter. Such a cell population, in the presence of an agent which induces expression of the NICD protein from the inducible promoter between from day 0 to day 2, is capable of differentiating into hemogenic endothelium cells that are CD7+ T/NK progenitors as described herein. Any exogenous vector can be used, including but not limited to expression vectors, viral vectors and non-viral vectors, such as doggybone DNA the like.

A T/NK progenitor cell is preferably human and derived from a stem cell or progenitor cell. Stem or progenitor cells may be obtained from any suitable source, including, without limitation, umbilical cord, blood, embryos, embryonic tissue, fetal tissue, bone marrow and blood. In one embodiment, the stem or progenitor cell is an induced pluripotent stem cell (iPSC). In another embodiment, the stem cell is an embryonic stem (ES) cell. For therapeutic applications, the stem cells or progenitor cells used to generate the progenitor T cells may be preferably obtained from the patient to be treated. Progenitor T cells may be isolated from the stem or progenitor cells by techniques known in the art. Typically, a sample containing the cells is first depleted with non-stem cells or mature cells.

In an alternative embodiment, the temporal activation of notch signaling between d0-d2 of differentiation in pluripotent stem cells can be achieved by any means known to one of ordinary skill in the art. For example, one can culture the pluripotent stem cells in the presence of modified RNA (modRNA) encoding a NICD protein for 0-2 days. In alternative embodiments, one can culture the pluripotent stem cells in the presence of exogenous nucleic acid sequence encoding a NICD protein, e.g., using naked DNA, synthetic plasmids such as Doggybone DNA (dbDNA) (see U.S. Pat. No. 9,109,250, which is incorporated herein in its entirety), and other closed-ended DNA vectors, including but not limited to dumbbell DNA, ceDNA (us application 2019/0032083a1 and wo 2019/051255 which are incorporated herein in their entirety), and the like.

In the Examples the inventors demonstrate production of CD7+ T/NK cells from iPSC by activating notch signaling by overexpression of NICD1 during d0-d2 differentiation of the pluripotent stem cells, and that this time period is before onset of endogenous notch signaling. Accordingly, in some embodiments, activation of notch signaling by the methods disclosed herein is in a pluripotent stem cell that does not express any one or more of: a Notch receptor (Notch 1, Notch2, Notch 3, Notch 4), notch ligands (dll1, dll2, dll3, dll4). In some embodiments, activation of notch signaling by the methods disclosed herein is in a pluripotent stem cell that does not express (e.g., is negative for the expression of) any one or more of: a Notch receptor (Notch 1, Notch2, Notch 3, Notch 4), notch ligands (dll1, dll2, dll3, dll4). In some embodiments, activation of notch signaling by the methods disclosed herein is in a pluripotent stem cell at developmental time period before the cell expresses a notch target gene, e.g., any one or more of: LM02, T (brachyury) or TAL1. In some embodiments, activation of notch signaling by the methods disclosed herein is in a pluripotent stem cell that does not express (e.g., is negative for the expression of): LM02, T (brachyury) or TAL1.

In the Examples the inventors demonstrate production of CD7+ T/NK cells from iPSC by activating notch signaling by overexpression of NICD1 during d0-d2 differentiation of the pluripotent stem cells, and that at d4, the cells have a phenotype of $KDR^{high}$, CD34+ and VE-cadherin+. This time period is before onset of endogenous notch signaling. Accordingly, in some embodiments, activation of notch signaling by the methods disclosed herein is in a pluripotent stem cell at developmental time period where the pluripotent stem cell is $KDR^{low}$, CD34− and VE-cadherin. In some embodiments, activation of notch signaling by the methods disclosed herein is in a pluripotent stem cell that does not express (e.g., is negative for the expression of): CD34− and/or VE-cadherin− and/or is $KDR^{-}$ and/or has $KDR^{low}$ expression. By way of explanation only, KDR expression in cells is relative to the whole population of cells can be classified as $KDR^{-}$, $KDR^{low}$ and $KDR^{high}$. In a population of cells, the lowest ⅓ of the population of cells with the least amount of KDR expression are categorized as $KDR^{-}$, the $2^{nd}$ third of the population of cells with the next amount of KDR expression are categorized as $KDR^{low}$, and the ⅓ of the population of cells with the highest amount of KDR expression are categorized as $KDR^{high}$ (see FIG. 2D).

In some embodiments, activation of notch signaling by the methods disclosed herein is by transient transfection with a nucleic acid expressing a NICD. Methods for transient transfection are known by persons of ordinary skill in the art. In some embodiments, activation of notch signaling by the methods disclosed herein is by expression of a NICD protein from a vector, such as an expression vector or viral vector or non-viral vector. In all aspects of the technology described herein, the nucleic acid encoding the NICD protein is operatively linked to an inducible promoter.

Transfection of pluripotent stem cells with a gene that activates Notch signaling means introducing a nucleic acid encoding the gene in the pluripotent stem cells. In all aspects of the methods and compositions as disclosed herein, any gene that activates Notch signaling before endogenous Notch signaling occurs in the transfected cell may be used without limitation. That is – any gene that functions downstream of Notch ligand-mediated cleavage of Notch receptors. Stated differently, any gene that activates notch signaling that is Notch receptor (e.g., Notch receptor 1-4) independent and/or Notch ligand independent (e.g., does not depend on ligands such as Delta-like (DLL)-1, -3, -4, Jagged 1, and Jagged 2 to bind to the notch receptor).

Preferably, in exemplary embodiments, the NICD gene may be expressed in a pluripotent stem cell as disclosed herein. As a nucleic acid encoding the NICD, any nucleotide sequence encoding a NICD known in the art, may be used without limitation, for example, a nucleotide sequence encoding NICD1, NICD2, NICD3, or NICD4 or functional variants thereof.

In some embodiments, the gene that activates Notch signaling may have an NICD1-encoding sequence comprising a DNA sequence set forth in SEQ ID NO: 1 and may have an amino acid sequence set forth in SEQ ID NO: 5, but the scope of the present invention is not limited thereto. Namely, it may have a nucleotide sequence encoding a protein that is the functional equivalent of the protein of NICD1 corresponding to SEQ ID NO:5 is encompassed for use in the methods and compositions as disclosed herein. In some embodiments, a nucleic acid sequence having at least 80% sequence identity to SEQ ID NO: 1 is encompassed for use in the methods and compositions as disclosed herein.

In some embodiments, the gene that activates Notch signaling may have an NICD2-encoding sequence comprising a DNA sequence set forth in SEQ ID NO: 2 and may have an amino acid sequence set forth in SEQ ID NO: 6, but the scope of the present invention is not limited thereto. Namely, it may have a nucleotide sequence encoding a protein that is the functional equivalent of the protein of NICD2 corresponding to SEQ ID NO:6 is encompassed for use in the methods and compositions as disclosed herein. In some embodiments, a nucleic acid sequence having at least 80% sequence identity to SEQ ID NO: 2 is encompassed for use in the methods and compositions as disclosed herein.

In some embodiments, the gene that activates Notch signaling may have an NICD3-encoding sequence comprising a DNA sequence set forth in SEQ ID NO: 3 and may have an amino acid sequence set forth in SEQ ID NO: 7, but the scope of the present invention is not limited thereto. Namely, it may have a nucleotide sequence encoding a protein that is the functional equivalent of the protein of NICD3 corresponding to SEQ ID NO:7 is encompassed for use in the methods and compositions as disclosed herein. In some embodiments, a nucleic acid sequence having at least 80% sequence identity to SEQ ID NO: 3 is encompassed for use in the methods and compositions as disclosed herein.

In some embodiments, the gene that activates Notch signaling may have an NICD4-encoding sequence comprising a DNA sequence set forth in SEQ ID NO: 4 and may have an amino acid sequence set forth in SEQ ID NO: 8, but the scope of the present invention is not limited thereto. Namely, it may have a nucleotide sequence encoding a protein that is the functional equivalent of the protein of NICD4 corresponding to SEQ ID NO:8 is encompassed for use in the methods and compositions as disclosed herein. In some embodiments, a nucleic acid sequence having at least 80% sequence identity to SEQ ID NO: 4 is encompassed for use in the methods and compositions as disclosed herein.

As used herein, the term "functional equivalent" refers to a polypeptide having substantially the same physiological activity as the NICD protein it is an equivalent of By way of an example only, a functional equivalent of NICD1 has a sequence identity of at least 70%, preferably at least 80%, and more preferably at least 90%, with an amino acid sequence set forth in SEQ ID NO: 5, as a results of the addition, substitution or deletion of amino acids. For example, the polypeptide has a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% with the amino acid sequence set forth in SEQ ID NO: 5. As used herein, the term "substantially the same physiological activity" as the NICD1 refers to activity that activates the Notch signaling pathway. Also, the nucleic acid encoding the NICD1 may be prepared by a gene recombination method known in the art.

In some embodiments, a nucleic acid sequence having at least 80% sequence identity to SEQ ID NO: 1 is encompassed for use in the methods and compositions as disclosed herein.

In some embodiments, a nucleic acid sequence that activates Notch signaling before the onset of endogenous notch signaling, for example, a NICD1, NICD2, NICD3 or NICD4 gene or a functional equivalent or variant thereof with at least 80% sequence identity thereto, results in the expression of Notch targets, for example, induces the expression of any one or more of: LM02, T (brachyury), TAL1, HES5, HEY1. That is, a nucleic acid sequence that activates Notch signaling before the onset of endogenous notch signaling, for example, a NICD1, NICD2, NICD3 or NICD4 gene or a functional equivalent or variant thereof with at least 80% sequence identity thereto, results in the increase in expression by at least 10%, or 20% or 30% of one or more Notch targets genes selected from any one or more of: LM02, T (brachyury), TAL1, HES5, HEY1 as compared to a control stem cell, when notch is not activated prior to the onset of endogenous notch signaling.

In another embodiment, the gene that activates Notch signaling, for example, an NICD1-encoding nucleic acid, may be operably linked to an inducible promoter or other expression control sequence and may be inserted into an expression vector. As used herein, the term "expression control sequence" refers to a DNA sequence that regulates the expression of the operably linked nucleic acid in a specific host cell. Such an expression control sequence includes a promoter for initiating transcription, an optional operator sequence for controlling transcription, and a sequence controlling termination of transcription or translation. As used herein, the term "expression vector" refers to a plasmid, vector, or viral vector or other vehicles known in the art, into which a nucleic acid encoding the structural gene can be inserted and which can express in the nucleic acid in a host cell. In some embodiments, the expression vector is a plasmid comprising homology arms to allow targeted insertion of the NICD gene into the genome of the pluripotent stem cell genome at a specific insertion site, such as a genomic safe harbor site as described herein.

In some embodiments, the pluripotent stem cells or iPSC are transduced with an exogenous vector encoding for the NICD gene, for example a recombinant vector (recombinant expression vector) such as a plasmid or viral vector. The exogenous vector allows for the expression of the NICD protein factor within the cell, in some examples, the exogenous vector is an inducible vector allowing for the controlled expression of the NICD protein within the pluripotent stem cells during d0-d2 of differentiation. In another embodiment, the PCSs or iPSC are transduced with an exogenous modified mRNA of the NICD protein. In yet another embodiment, the PSCs or iPSCs are transduced with the NICD protein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." The vector can optionally include exogenous genetic material that allow for the expression of the transgene, for example, can comprise homology arms that allow insertion of the transgene, e.g., NICD gene into a specific loci, such as the AAVS1, of the host cell genome.

While in preferred embodiments, the expression vector is a targeting vector containing arms of homology that recognize the integration site of AAV, named AAVS1 locus, to induce DNA homology repair and knock-in of the nucleic acid sequence that contains the NICD gene operatively linked to an inducible promoter, in alternative embodiments, the expression vector is a viral vector. Suitable viral vectors are known in the art and include, but are not limited to, for example, an adenovirus vector; an adeno-associated virus vector; a pox virus vector, such as a fowlpox virus vector; an alpha virus vector; a baculoviral vector; a herpes virus vector; a retrovirus vector, such as a lentivirus vector; a Modified Vaccinia virus Ankara vector; a Ross River virus vector; a Sindbis virus vector; a Semliki Forest virus vector; and a Venezuelan Equine Encephalitis virus vector. In a preferred embodiment, the viral vector is a lentiviral vector, an adenovirus vector or an adeno-associated virus vector. Examples of the expression vector include, but are not limited to, a retroviral vector, an adenoviral vector, adeno-associated virus (AAV), a herpes-viral vector, an avipox viral vector, an Epstein-Barr viral vector, a lentiviral vector, etc. In one embodiment of the present invention, an AAV or lentiviral vector is used.

A method of preparing an AAV or lentivirus using a recombinant expression vector according to the present invention may be carried out using a method known in the art. The expression vector comprising the nucleic acid according to the present invention may be introduced into a population of pluripotent stem cells by any method known in the art, such as transient transfection, microinjection, transduction, cell fusion, calcium phosphate precipitation, liposome-mediated transfection, DEAE dextran-mediated transfection, polybrene-mediated transfection, electroporation, gene gun or other methods for introducing DNA into cells.

In some embodiments, the nucleic acid sequence encodes NICD1 protein. In some embodiments, the nucleic acid sequence is SEQ ID NO: 1 or a nucleic acid sequence having at least 60%, 70%, 80%, 85%, 90%, 95%, 98% or 99% sequence identity to SEQ ID NO: 1. In some embodiments, the nucleic acid sequence encodes the NICD1 protein comprising SEQ ID NO: 5, or a nucleic acid sequence encodes the NICD1 protein comprising having at least 60%, 70%, 80%, 85%, 90%, 95%, 98% or 99% sequence identity to SEQ ID NO: 5.

In some embodiments, the nucleic acid sequence encodes NICD2 protein. In some embodiments, the nucleic acid sequence is SEQ ID NO: 2 or a nucleic acid sequence having at least 60%, 70%, 80%, 85%, 90%, 95%, 98% or 99% sequence identity to SEQ ID NO: 2. In some embodiments, the nucleic acid sequence encodes the NICD2 protein comprising SEQ ID NO: 6, or a nucleic acid sequence encodes a NICD2 protein comprising having at least 60%, 70%, 80%, 85%, 90%, 95%, 98% or 99% sequence identity to SEQ ID NO: 6.

In some embodiments, the nucleic acid sequence encodes NICD3 protein. In some embodiments, the nucleic acid sequence is SEQ ID NO: 3 or a nucleic acid sequence having at least 60%, 70%, 80%, 85%, 90%, 95%, 98% or 99% sequence identity to SEQ ID NO: 3. In some embodiments, the nucleic acid sequence encodes a NICD3 protein comprising is SEQ ID NO: 7, or a nucleic acid sequence encodes the NICD3 protein comprising having at least 60%, 70%, 80%, 85%, 90%, 95%, 98% or 99% sequence identity to SEQ ID NO: 7.

In some embodiments, the nucleic acid sequence encodes NICD4 protein. In some embodiments, the nucleic acid sequence is SEQ ID NO: 4 or a nucleic acid sequence having at least 60%, 70%, 80%, 85%, 90%, 95%, 98% or 99% sequence identity to SEQ ID NO: 4. In some embodiments, the nucleic acid sequence encodes a NICD4 protein comprising is SEQ ID NO:8, or a nucleic acid sequence encoding a NICD4 protein comprising having at least 60%, 70%, 80%, 85%, 90%, 95%, 98% or 99% sequence identity to SEQ ID NO: 8.

In some embodiments, the NICD1 gene expressed by the pluripotent stem cell or iPSC is encoded by the nucleic acid of SEQ ID NO: 1, or a nucleic acid sequence of at least 80% sequence identity to SEQ ID NO: 1. In some embodiments, the NICD1-encoding sequence comprising a DNA sequence set forth in SEQ ID NO: 1 may encode a protein having an amino acid sequence set forth in SEQ ID NO: 5, but the scope of the present invention is not limited thereto. Namely, it may have a nucleotide sequence encoding a protein that is the functional equivalent of the protein of NICD1 corresponding to SEQ ID NO:5 is encompassed for use in the methods and compositions as disclosed herein. In some embodiments, a nucleic acid sequence having at least 80% sequence identity to SEQ ID NO: 1 is encompassed for use in generating an iPSC-NICD1 line.

In some embodiments, the NICD2 gene expressed by the pluripotent stem cell or iPSC is encoded by the nucleic acid of SEQ ID NO: 2, or a nucleic acid sequence of at least 80% sequence identity to SEQ ID NO: 2. In some embodiments, the NICD2-encoding sequence comprising a DNA sequence set forth in SEQ ID NO: 2 may encode a protein having an amino acid sequence set forth in SEQ ID NO: 6, but the scope of the present invention is not limited thereto. Namely, it may have a nucleotide sequence encoding a protein that is the functional equivalent of the protein of NICD2 corresponding to SEQ ID NO:6 is encompassed for use in the methods and compositions as disclosed herein. In some embodiments, a nucleic acid sequence having at least 80% sequence identity to SEQ ID NO: 2 is encompassed for use in generating an iPSC-NICD2 line.

In some embodiments, the NICD3 gene expressed by the pluripotent stem cell or iPSC is encoded by the nucleic acid of SEQ ID NO: 3, or a nucleic acid sequence of at least 80% sequence identity to SEQ ID NO: 3. In some embodiments, the NICD3-encoding sequence comprising a DNA sequence set forth in SEQ ID NO: 3 may encode a protein having an amino acid sequence set forth in SEQ ID NO: 7, but the scope of the present invention is not limited thereto. Namely, it may have a nucleotide sequence encoding a protein that is the functional equivalent of the protein of NICD3 corresponding to SEQ ID NO:7 is encompassed for use in the methods and compositions as disclosed herein. In some embodiments, a nucleic acid sequence having at least 80% sequence identity to SEQ ID NO: 3 is encompassed for use in generating an iPSC-NICD3 line.

In some embodiments, the NICD4 gene expressed by the pluripotent stem cell or iPSC is encoded by the nucleic acid of SEQ ID NO: 4, or a nucleic acid sequence of at least 80% sequence identity to SEQ ID NO: 4. In some embodiments, the NICD4-encoding sequence comprising a DNA sequence set forth in SEQ ID NO: 4 may encode a protein having an amino acid sequence set forth in SEQ ID NO: 8, but the scope of the present invention is not limited thereto. Namely, it may have a nucleotide sequence encoding a protein that is the functional equivalent of the protein of NICD4 corresponding to SEQ ID NO:8 is encompassed for use in the methods and compositions as disclosed herein. In some embodiments, a nucleic acid sequence having at least 80% sequence identity to SEQ ID NO: 4 is encompassed for use in generating an iPSC-NICD4 line.

Other non-human NICD genes are also encompassed for use, e.g., nucleic acid sequences and protein sequence encoding mouse NICD1 or NICD2, for example, as disclosed in US application 2015/0352180 or disclosed as SEQ ID NO: 10-13 herein.

In some embodiments, a pluripotent stem cell, e.g., a human ES cell or iPSC is contacted between d0-d2 with a NICD protein and an agent that allows the NICD protein to enter the cell.

IV. The Generation of Pluripotent Stem Cell or iPSC-Derived T/NK CD7+ Progenitors (iT/NK Progenitors)

In all aspects of the methods and compositions as disclosed herein, the pluripotent stem cells in which notch signaling is activated before onset of endogenous notch signaling in the iPSC, the cells are cultured during and after induction of NICD1 expression in a iT media (also referred to herein as a modified HE media, or "mod-HE media"). By way of example only, hemogenic endothelium media (HE media) or HSPC-HE media typically comprises erythropoietin (EPO) and angiotensin. In some embodiments, the pluripotent stem cells are cultured for 12 days (d0-d12) according to the iT protocol, which is outlined in Table 1 below, where the cells are cultured in the absence of EPO and/or angiotensin between d6-d12 significantly reduced the CD235+ cell population without sacrificing overall cell yield (see also FIG. 1C).

Figure 2A:
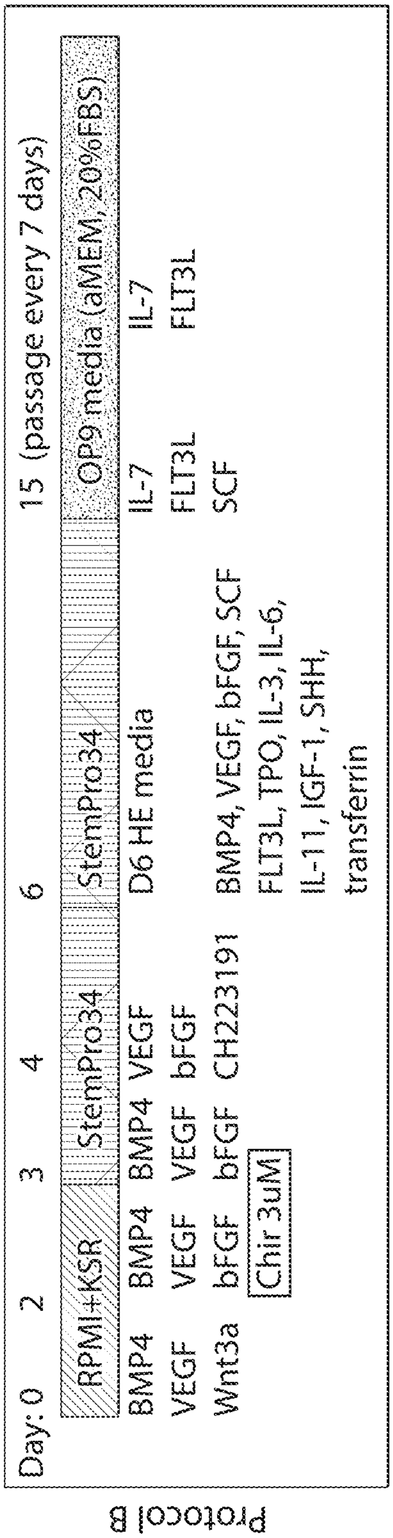
FIGS. 2A-2F show that early GSK-3β inhibition (GSK-3β inhibitor (Chir)) combined with hypoxia robustly increases the efficiency of putative hemogenic endothelium differentiation and increases the hematopoietic progenitor population ($KDR^{high}$, $CD34^+$, VE-$Cadherin^+$ population) at day 4.
Figure 2B:
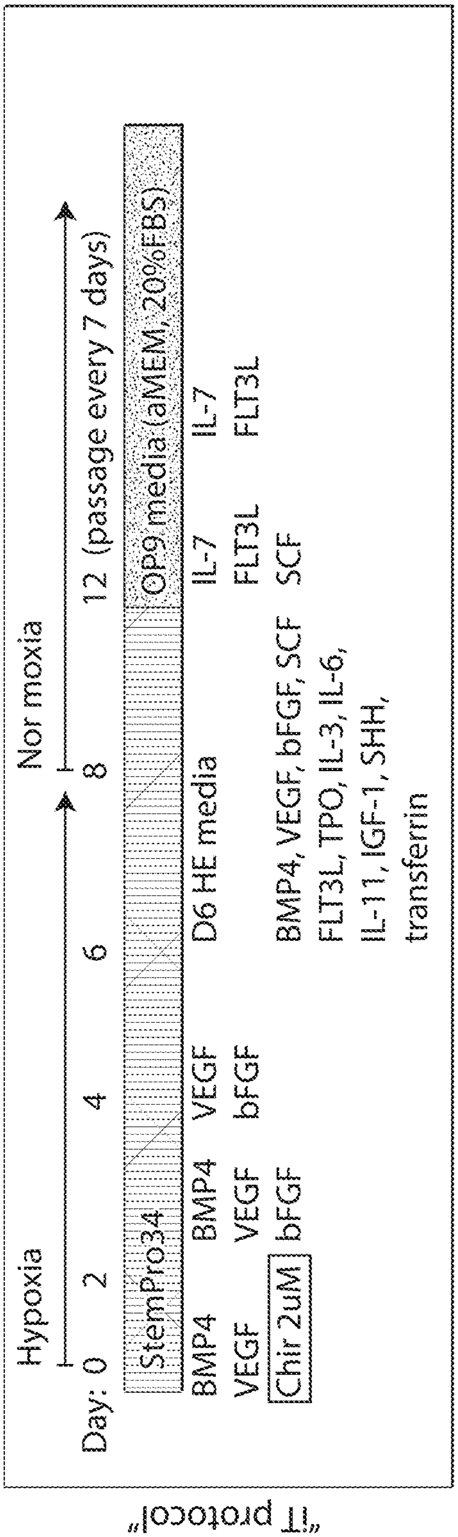

In particular, an exemplary method for generating iPSC-derived T/NK progenitors is using an iT protocol, which is summarized in FIGS. 2A and 2B, and can comprise, for example, comprising the steps of:

(a) inducing NICD1 expression in the pluripotent stem cells from d0-d2. In some embodiments, where the pluripotent stem cell is a modified iPSC comprising a NICD1 gene as disclosed herein, the induction of NICD1 expression comprises contacting the iPSC with an agent that induces expression of NICD1 from the inducible promoter (e.g. contacting the iPSC with DOX between 100-500 ng/ml).

(b) optionally culturing the pluripotent stem cells from d0-d1 or d0-d2 in a media BMP4 5 ng/mL; VEGF 50 ng/mL; CHIR99021 2 uM (d0-d1), where the CHIR99021 is for inhibition of GSK-3β. Any inhibitor of GSK-3β known to one of ordinary skill in the art can be used in place of CHIR99021.

(c) optionally culturing the pluripotent stem cells from d2-d3 in a media comprising BMP4 5 ng/mL; VEGF 50 ng/mL; bFGF 20 ng/mL (d2-d3), and (d) optionally culturing the pluripotent stem cells from d4-d5 in a media comprising VEGF 15 ng/mL; bFGF 5 ng/mL, and not comprising BMP4 (d4-d5), and (e) optionally culturing the pluripotent stem cells in iT media from d6-d12, where iT media comprises BMP4 10 ng/ml; VEGF 5 ng/ml; bFGF 5 ng/ml; SCF 100 ng/ml; FLT3L 10 ng/ml; TPO 30 ng/ml; IL3 30 ng/ml; IL6 10 ng/ml; IL11 5 ng/ml; IFG1 25 ng/ml; SHH 20 ng/ml; Transferrin 150 ug/ml, and where the iT media does not comprise EPO and/or angiotensin.

(f) optionally maintaining the pluripotent stem cells from d0-d7 in a hypoxic conditions (5% $O_2$), and then maintaining in normal oxygen conditions (normoxia) from d8-d12.

TABLE 1 iT protocol.

| Day 0 | 1 | 2 | 3 | 4 | 5 | 6 | 7 | 8 | 9 | 10 | 11 | 12 |
|---|---|---|---|---|---|---|---|---|---|---|---|---|
| NCID1 induction (DOX 100-500 ng/ml) (do-d2) | | | | | | | | | | | | |
| | StemPro 34 + glutamax + primocin + aMTG + Ascorbic Acid (d1-d12) iT media (d1-d12) | | | | | | | | | | | |
| BMP4 5 ng/mL; VEGF 50 ng/mL; CHIR99021 2 uM (d0-d0) | | | | | | | | | | | | |
| Hypoxia (5% O2) (d0-d7) | | | | | | | | D8-d12 (normoxia) | | | | |
| | | BMP4 5 ng/mL; VEGF 50 ng/mL; bFGF 20 ng/mL (d2-d3) | | | | | | | | | | |
| | | | | VEGF 15 ng/mL; bFGF 5 ng/mL (d4-d5) | | | | | | | | |
| | | | | | | iT Media (also referred to as "mod-HE media"): BMP4 10 ng/ml; VEGF 5 ng/ml; bFGF 5 ng/ml; SCF 100 ng/ml; FLT3L 10 ng/ml; TPO 30 ng/ml; IL3 30 ng/ml; IL6 10 ng/ml; IL11 5 ng/ml; IFG1 25 ng/ml; SHH 20 ng/ml; Transferrin 150 ug/ml. 2 ml/well 6 well plate on day 6, spin cells down to replace media every 2 days. (d6-d12) | | | | | | |

Figure 2C:
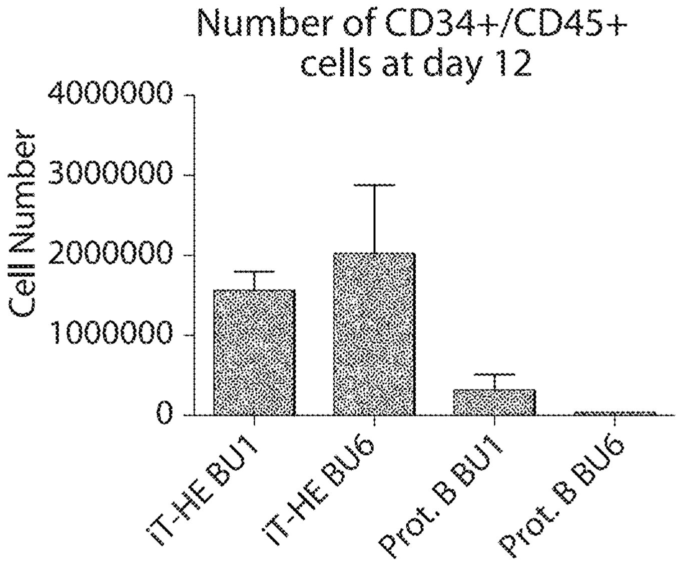
Figure 2D:
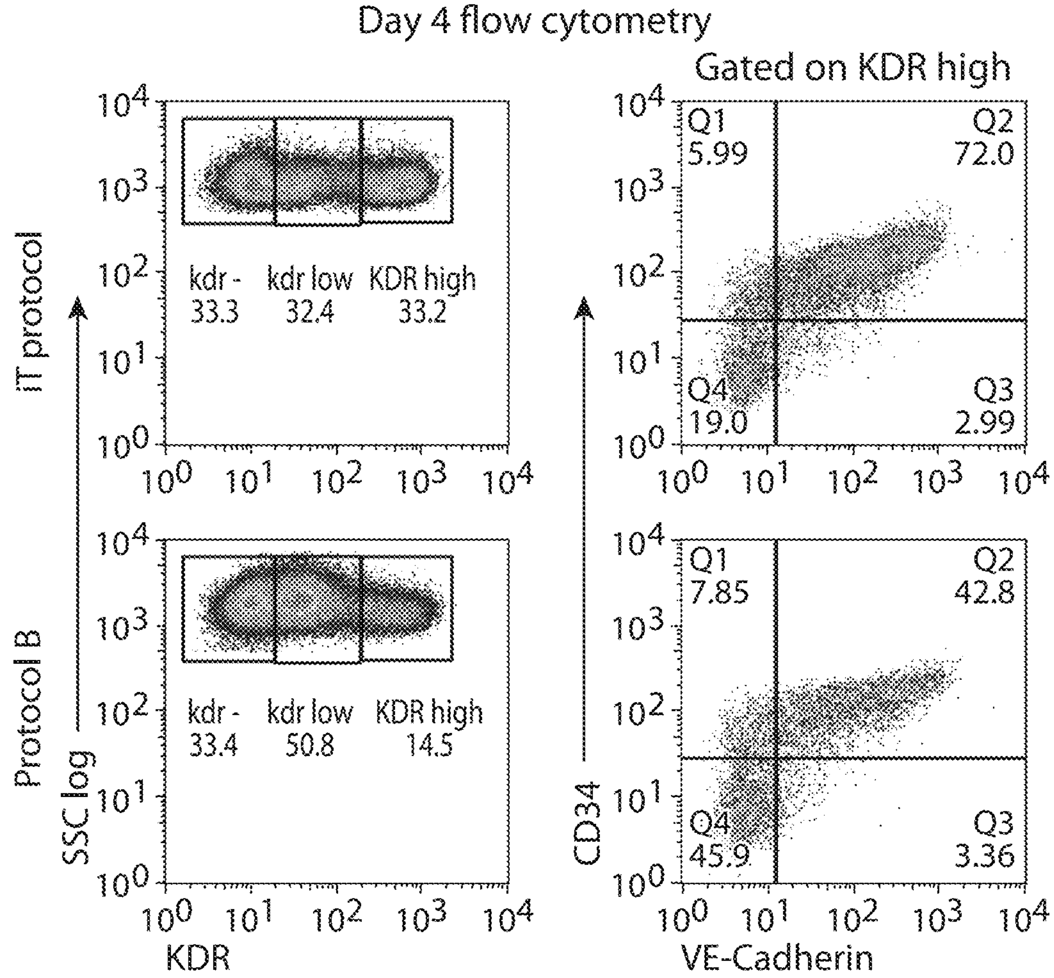

Using such an iT protocol as disclosed in Table 1, there is increased $KDR^{high}/CD34^{+}$/VE-cadherin$^{+}$ population of cells at day 4 (d4) as compared to normal HE media (see FIG. 2D, which shows even without having NICD1 induction at d0-d2, a 4-fold increase in $KDR^{high}/CD34^{+}$/VE-cadherin$^{+}$ cells a day 4 with the iT protocol (72% of the $KDR^{high}$ cells at day 4 are $KDR^{high}/CD34^{+}$/VE-cadherin$^{+}$ with the iT protocol, whereas only 42.8.5% of the $KDR^{high}$ cells are $KDR^{high}/CD34^{+}$/VE-cadherin$^{+}$ with the HCPC-HE media). When these day 4 $KDR^{high}/CD34^{+}$/VE-cadherin$^{+}$ cells (generated with the iT protocol without d0-d2 NICD1 induction) are further cultured to d12, 86% of the population at day 12 are $CD34^{+}/CD45^{+}/CD235a^{-}$.

Figure 5A:
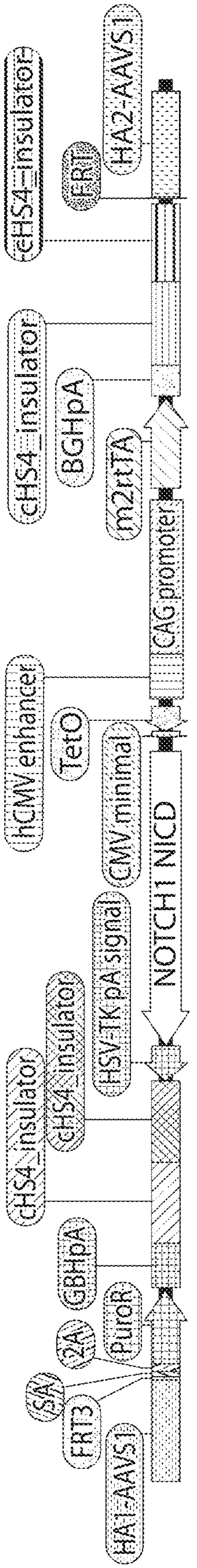
FIGS. 5A-5E show that notch activation at d0-d2 during mesoderm induction robustly improves access to the T/NK cell lineage by stimulating notch target genes prior to the onset of endogenous notch signaling.
Figure 5B:
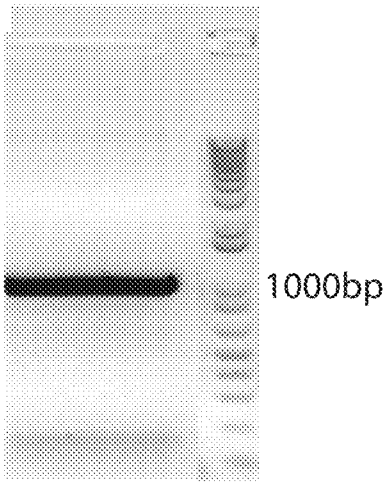
Figure 5C:
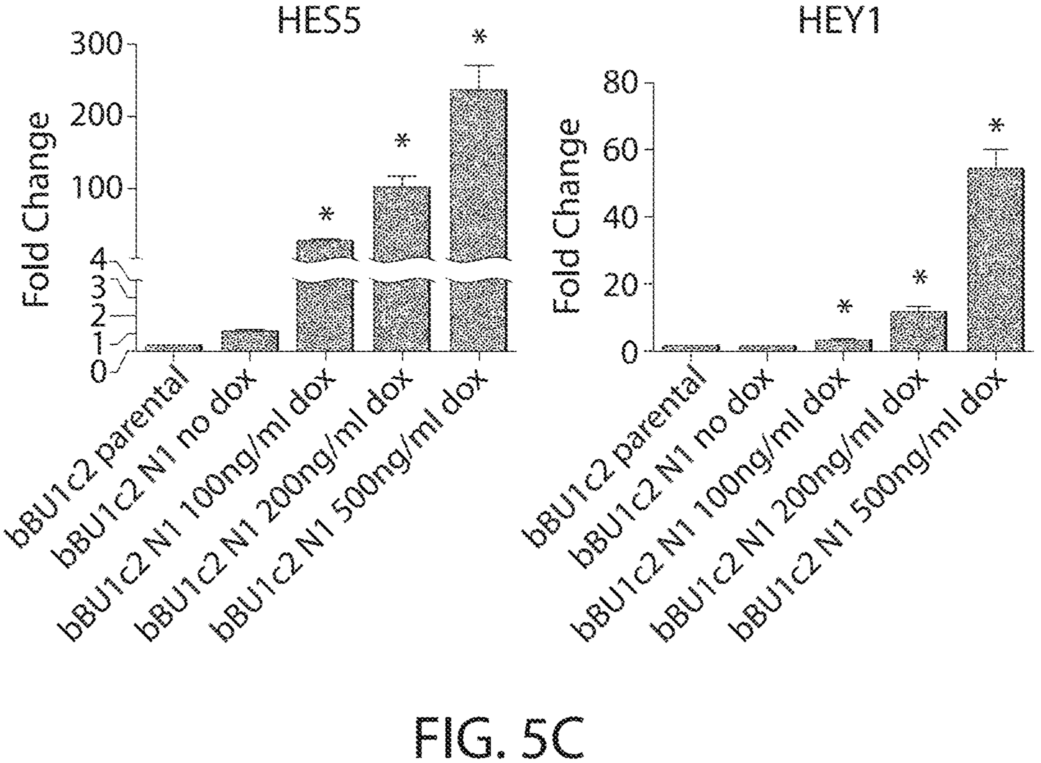
Figure 5D:
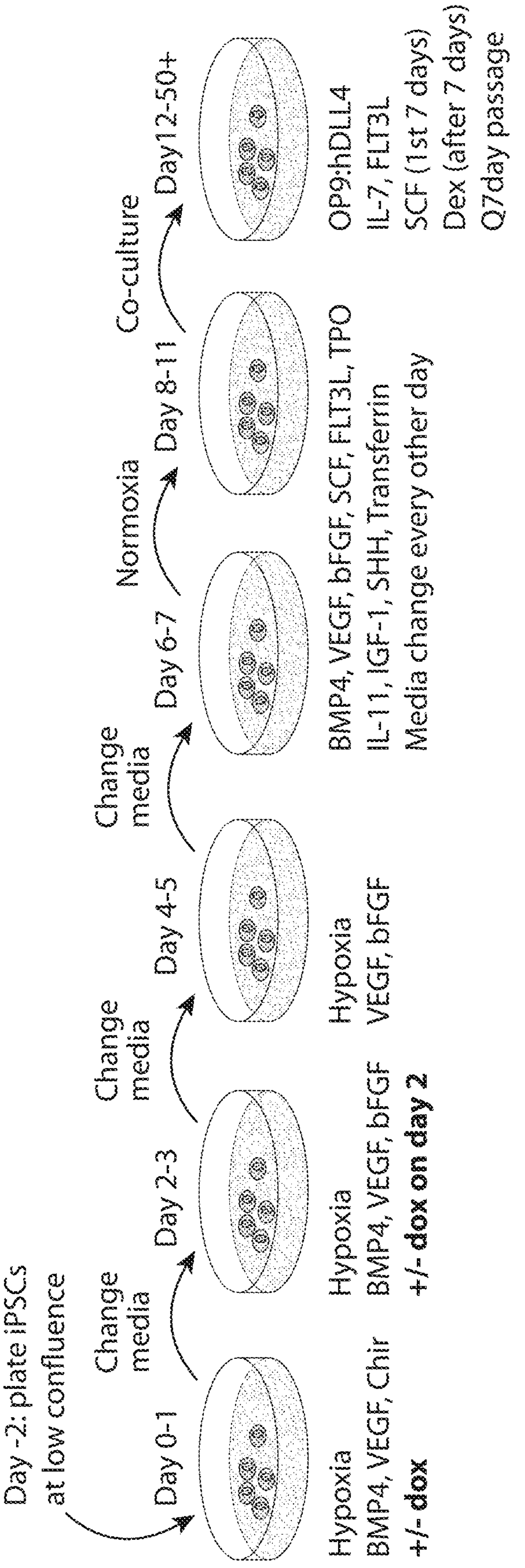
Figure 5E:
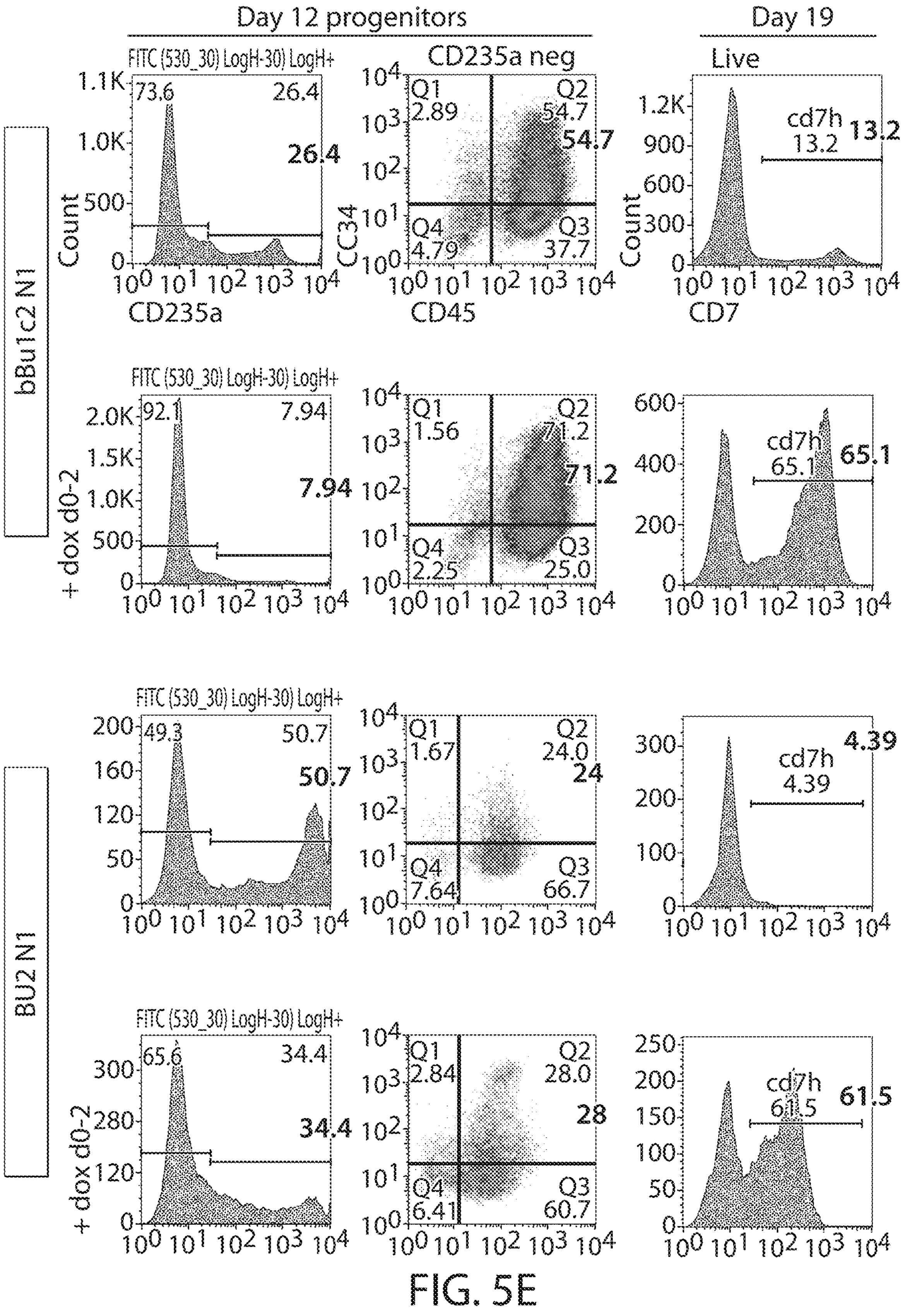
Figure 5E:
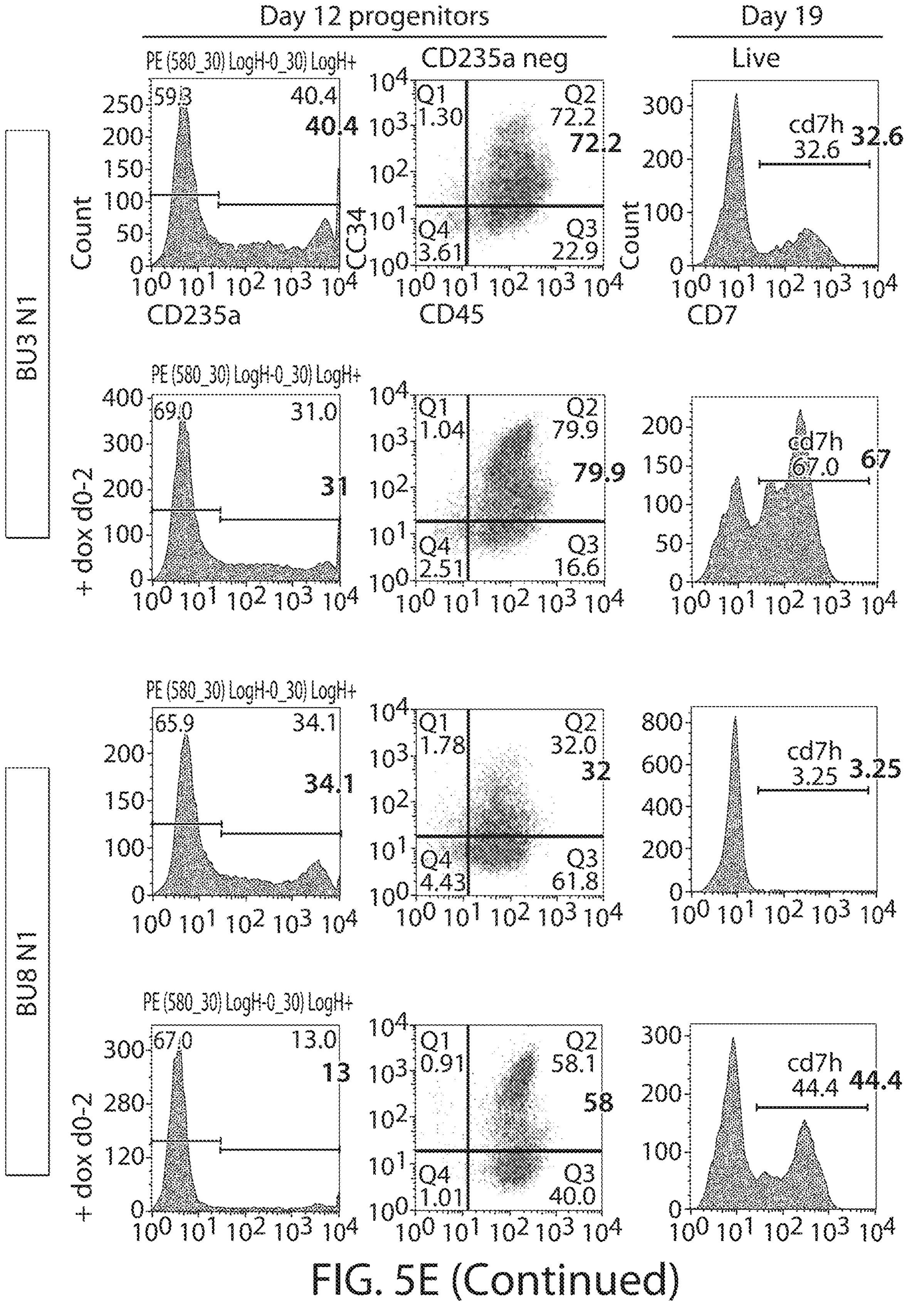

Furthermore, when the full iT protocol disclosed in Table 1 is used, which includes induction of notch signaling from d0-d2 by transient expression of NICD1, it produces a robust increase in CD7+ population at day 19 (See FIG. 5E, showing greater than 60% CD7+ cells at day 19 as compared to 13.2%, 4.39%, 32.6% and 3.25% when the iT protocol was used without NICD1 induction between d0-d2).

As the CD7+ population of cells at day 19 (d19) are free-floating pluripotent stem cell-derived or iPSC-derived T/NK progenitor cells, the method further comprises collecting (or harvesting) the cell population. In some embodiments, as the population of cells at day 19 is a substantially homogenous population of iPSC-derived T/NK progenitor cells comprising at least 20%, or 30%, or 40%, or 50%, or 60%, or 70%, or 80% or 85%, or 90%, or 95% or greater than 95% CD7+ T/NK progenitors, the cells are collected without the need for cell-sorting or FACS.

In some embodiments, the pluripotent stem cell-derived or iPSC-derived T/NK progenitor cells are CD7+ at day 19.

In all aspects as disclosed herein, the methods and compositions as disclosed herein, to activate notch signaling at d0-d2 and at a time period before onset of endogenous notch signaling, are used to generate a population of pluripotent stem cell-derived T/NK progenitor cells, or a population of iPSC-derived T/NK progenitor cells, where at day 12 (d12) the cell population comprises at least 20%, or 30%, or 40%, or 50%, or 60%, or 70%, or 80% or 85%, or 90%, or 95% or greater than 95% of the cells are T-NK progenitors that have a phenotype of CD34+/CD 45+/CD235a−. In some embodiments, at day 12, the population comprises more than 50%, or more than 60%, or more than 65%, or more than 70%, or more than 75% $CD34^+/CD45^+/CD235a-$ T/NK progenitors.

Accordingly, in some embodiments the technology relates to a composition comprising a population of T-NK progenitor cells, where at day 12, the population comprises at least 50% or at least 60% or more than 60% of cells that have a phenotype of CD34+/CD45+/CD235a−.

In all aspects as disclosed herein, the methods and compositions as disclosed herein, to activate notch signaling at d0-d2 and at a time period before onset of endogenous notch signaling, are used to generate a population of pluripotent stem cell-derived T/NK progenitor cells, or a population of iPSC-derived T/NK progenitor cells (referred to herein as "iT/NK progenitors"), where at day 19 (d19) the population of T-NK progenitors comprise at least 20%, or 30%, or 40%, or 50%, or 60%, or 70%, or 80% or 85%, or 90%, or 95% or greater than 95% CD7+ T/NK progenitors. In some embodiments, the population comprises more than 50%, or more than 60%, or more than 65%, or more than 70%, or more than 75% CD7+ T/NK progenitors.

Accordingly, in some embodiments the technology relates to a composition comprising a population of T-NK progenitor cells, where at day 19, the population comprises at least 50% or at least 60% or more than 60% cells that are CD7+.

V. Differentiation of iT/NK CD7+ Progenitor Population into Mature T-Cells and NK Cells In all aspects as disclosed herein, the methods and compositions as disclosed herein also relate to methods of maturing the iT/NK progenitors, i.e., the population of pluripotent stem cell-derived T/NK progenitor cells, or a population of iPSC-derived T/NK progenitor cells (i.e., the CD7+iT/NK progenitors) generated using the compositions and methods as disclosed herein.

Unlike previously reported protocols that require cell sorting, because of the generation of a highly homogeneous population of cells comprising 90% CD7+ T/NK progenitors, these cells can be harvested without cell sorting (or other negative and/or positive cell selection methods) and be further co-cultured on an engineered stroma cell layer expressing a human notch ligand (e.g., DDL1-DLL4) at a defined density to either differentiate into T cells or NK cells. In particular, the inventors have also discovered that co-culturing CD7+ T/NK progenitors at a cell density of about 50,000 cells/10 cm plate or less on a confluent stromal cell layer expressing a notch ligand, results in maturation of the CD7+ T/NK progenitors into mature T cells, whereas co-culturing CD7+ T/NK progenitors at a cell density of about 200,000 cells/10 cm plate or greater on a confluent stroma cell layer expressing a notch ligand, results in maturation of the CD7+ T/NK progenitors into NK cells. Therefore, the inventors teach a robust protocol for inducing iPSC into T/NK CD7+ progenitors that are capable of deriving both types of populations (T-cells and NK cells) without having to perform complex, time consuming and expensive cell sorting (or negative and/or positive cell selection) procedures. Accordingly, not only do the methods and compositions described herein provide a high yield of T cells and NK cells to be produced, it is a highly robust and efficient methodology that does not require cell sorting or other negative and/or positive cell selection methods.

Accordingly, in some embodiments, the iT/NK CD7+ progenitors are collected (without the need for cell-sorting or positive and/or negative selection methods) and co-cultured on a stromal cell feeder layer expressing a notch ligand.

In some embodiments, the iT/NK CD7+ progenitors generated herein are cultured at specific densities in the presence of cells expressing Notch ligand as disclosed in detail in US2004/0171148 and US2017/0121684, which are incorporated herein in their entirety by reference.

In some embodiments, the iT/NK CD7+ progenitors are cultured under suitable conditions to generate mature T cells and NK cells. Preferably, the iT/NK CD7+ progenitors produced using the methods and compositions as disclosed herein are cultured in the presence of one or more Notch ligand for a sufficient time to form iT cells or iNK cells as disclosed herein. More preferably, the stem cells are cultured in the presence cells expressing a Notch ligand, for example, as described in detail in US2004/0171148 and US2017/0121684 which are both incorporated herein in their entirety by reference.

In some embodiments, the iT/NK CD7+ progenitors are cultured in a 6 cm or 10 cm tissue culture-treated dish with a Notch Ligand Cell Preparation, e.g., a confluent layer of a stromal cell line expressing a Notch ligand as described herein.

In particular, the inventors have surprisingly discovered that the plating density of the iT/NK CD7+ progenitors on the co-culture of cells expressing a notch ligand is important to direct their differentiation and maturation into either a substantially homogenous population of mature T-cells or substantially homogenous population of NK cells.

1. Maturation of T/NK CD7+ Progenitor Cells into Mature T-Cells

In some embodiments, the method comprises harvesting or collecting the CD7+ T/NK progenitor cells, for example, without the need for cell sorting or positive or negative cell selection methods, and co-culturing the population of the collected CD7+ T/NK progenitors on a confluent or about 80% confluent engineered stromal cell layer, such as for example, OP9 cells which have been modified to express a notch ligand such as dll1, dll2, dll3, dll4, where the CD7+ T/NK progenitors are plated at a cell density of about 50,000 cells/10 cm plate or less, or a cell density of about 200,000 cells/10 cm plate or greater, and collecting the cells after a selected period of time, for example, between about 3-6 weeks, where the cells cultured at a density of about, or less than 50,000 cells/10 ml (e.g., <5,000 cells/ml) or less are mature T cells, and the cells co-cultured at a density of about, or greater than 200,000 cells/ml (or about >20,000 cells/ml) or greater are NK cells.

Accordingly, in some embodiments, the T/NK CD7+ progenitors generated using the methods disclosed herein are plated at a cell density optimal for their maturation into T-cells, where the cells are plated at a density of about 500 cells/ml, at about 1,000 cells/ml, or about 2,000 cells/ml, or about 3,000 cells/ml, or about 4,000 cells/ml, or about 5,000 cells/ml on a co-culture feeder layer of a stromal cells (e.g., OP9 cells) which express a notch ligand such as dll1, dll2, dll3, dll4, and the cells cultured for a sufficient amount of time for the T/NK CD7+ progenitors to differentiate into mature T-cells, which are harvested and collected. As the T cells are floating cells in the co-culture, the supernatant comprising the T cells is collected. In some embodiments, cell sorting of the T cells collected from the supernatant is not required. In some embodiments, the collected T cells are a substantially homogenous population of T cells derived from CD7+ T/NK progenitors as disclosed herein.

Figure 7A:
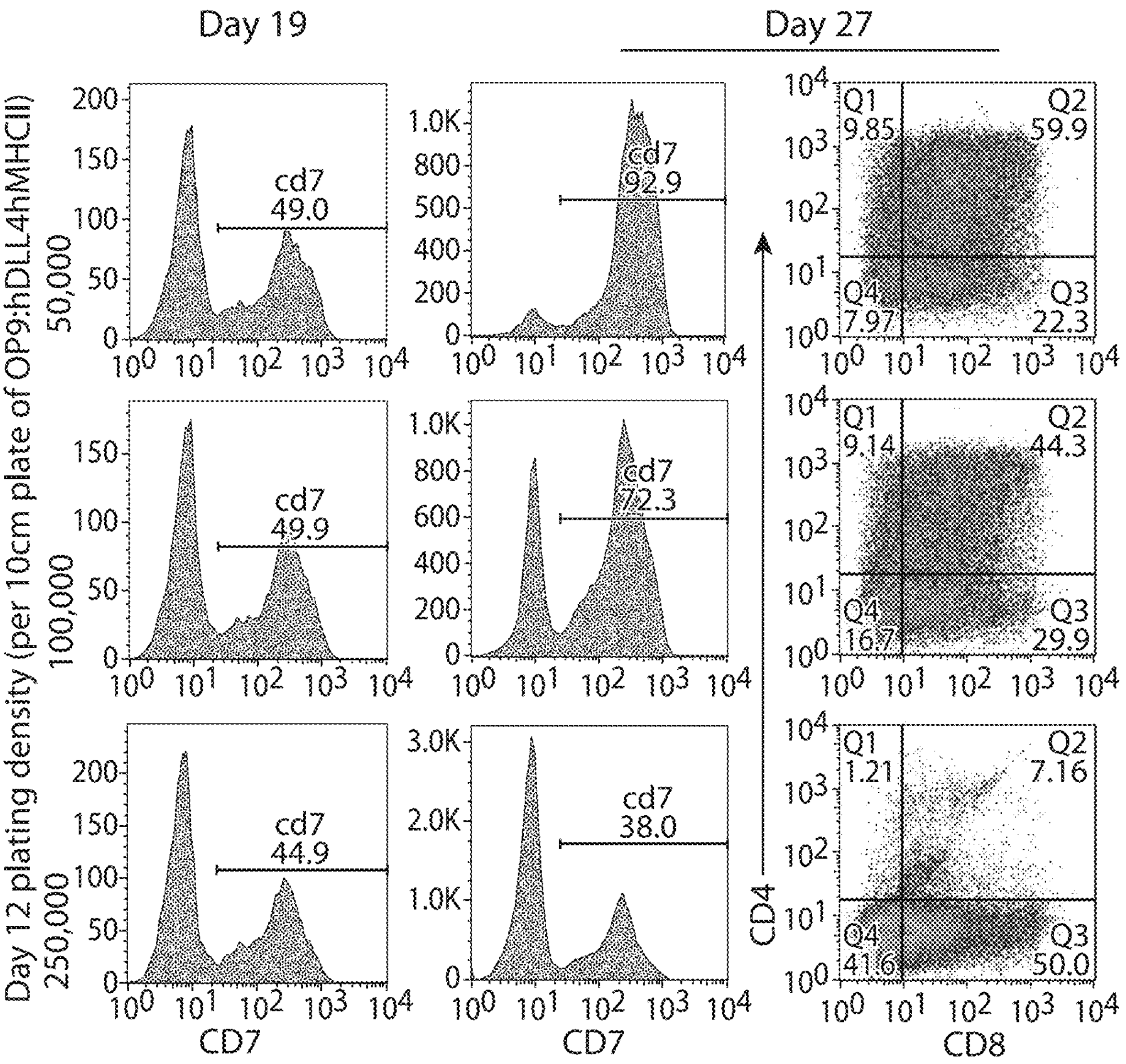
FIG. 7A-7C shows T vs NK lineage specification is determined by co-plating density (the co-plating density of progenitors at the initiation of OP9:dll4-MHCII co-culture and iPSC-derived T cells mature into CD3/CD8 SP cells despite hMHCII expressed on OP9:dll4 feeder cells).
Figure 8A:
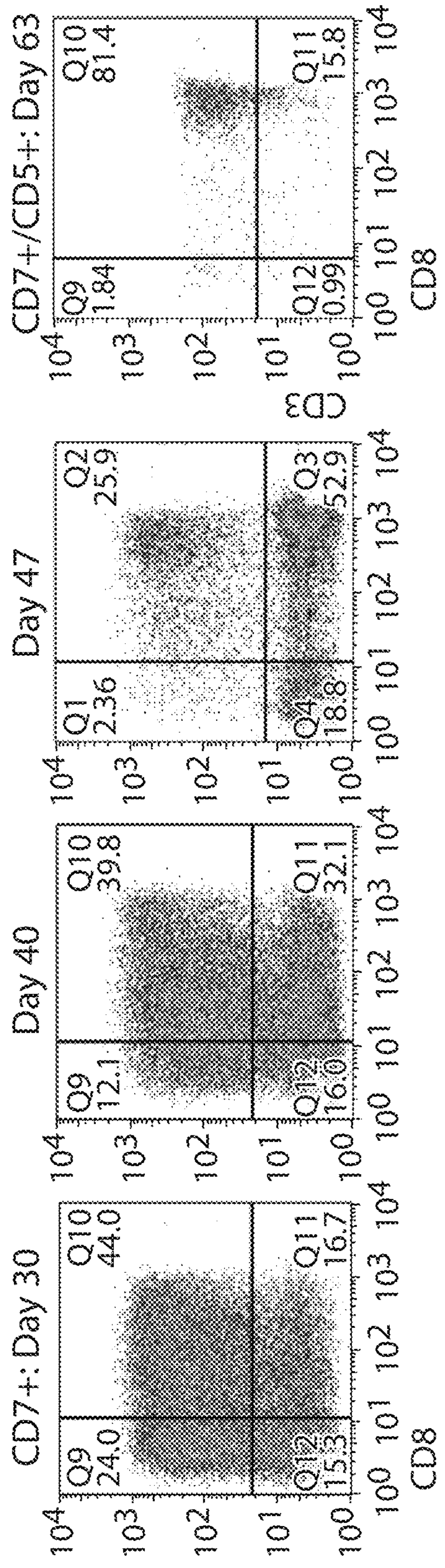
FIGS. 8A-8E show iPSC-derived T cells Mature into functional $CD3^{+}CD8^{+}$ T cells.

As shown in FIG. 7A and FIG. 8A, the T cells generated by the methods and compositions as disclosed herein go through a CD7+ progenitor stage (e.g., at day 19), that eventually transitions to into CD8+/CD4+ double positive stage (at day 27) and are CD4+/CD5+ (at day 34), and CD4+CD8+ (at day 35, day 48) and can be CD8+ T cells (at day 55). In some embodiments, the T cells generated are CD8+/CD4+ double positive cells, that can differentiate into CD4+ or CD8+ T cells. In some embodiments, the T cells generated are a CD8+/CD4+ T cell population that is at least about 60% pure, or at least about 70% pure, or at least about 80% pure, or at least about 90% pure or more than 90% pure. In some embodiments, the methods provide a population of T cells derived from pluripotent stem cells or iPSC that is at least 90% positive for CD4+ and CD8+. In some embodiments, the T cells generated are a CD8+ single positive T cell population that is at least about 60% pure, or at least about 70% pure, or at least about 80% pure, or at least about 90% pure or more than 90% pure. In some embodiments, the methods provide a population of T cells derived from pluripotent stem cells or iPSC that is at least 90% positive for CD4+ or CD8+ or CD4+ and CD8+.

In an aspect, the present disclosure provides a method for producing mature T cell by culturing the T/NK CD7+ progenitor cells in the presence of a notch ligand, e.g., DLL4:Fc notch chimera or cell line expressing a notch ligand. In some embodiments, the method can optionally also includes culturing the cells in a medium, wherein the medium includes an effective amount of a notch ligand and one or more cytokines selected from the group consisting of IL-7, IL-11, SCF, Flt-3 and IL-3. In some particular embodiments, the medium can further include IL-6. In some embodiments, the notch ligand is delta4 notch ligand (DLL4), such as DLL4: Fc chimera. For example, the maturing T/NK CD7+ progenitor cells may be monitored by flow cytometry for the development of T cells by staining the cells with anti-CD3 antibodies. The cells may be analyzed for the presence of T and NK cells using the cell surface markers CD4, CD8, CD3, CD94 and CD56. For example, cells which are CD8+/CD3+ would be indicative of differentiated T cells while NK cells would be CD3−/CD56+ and NK/T cells would be CD3+/CD56+.

2. Maturation of T/NK CD7+ Progenitor Cells into NK Cells

Alternatively, in some embodiments, the T/NK CD7+ progenitors generated using the methods disclosed herein are plated at a cell density optimal for their maturation into NK cells, where the cells are plated at a density of greater than about 20,000 cells/ml, at about 25,000 cells/ml, or about 30,000 cells/ml, or about 40,000 cells/ml, or about 50,000 cells/ml, or more than 50,000 cells/ml on a confluent or about 80% confluent co-culture feeder layer of a stromal cells (e.g., OP9 cells) which express a notch ligand such as dll1, dll2, dll3, dll4, and the T/NK CD7+ progenitors cells are cultured for a sufficient amount of time for the T/NK CD7+ progenitors to differentiate into NK cells, which are harvested and collected. As the NK cells are floating cells in the co-culture, the supernatant comprising the NK cells is collected. In some embodiments, cell sorting of the cells in the supernatant is not required. In some embodiments, the collected NK cells are a substantially homogenous population of NK cells derived from CD7+ T/NK progenitors as disclosed herein.

Figure 7B:
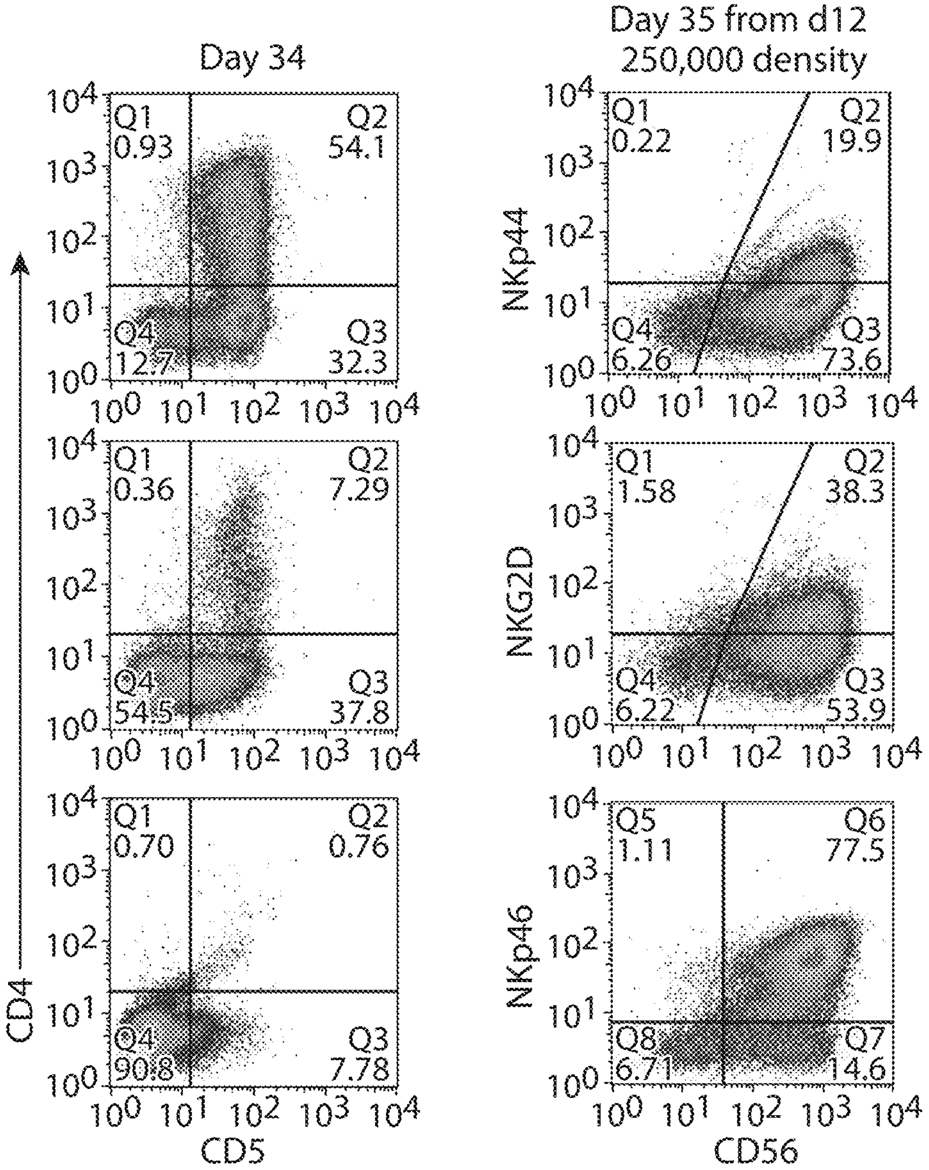
Figure 7C:
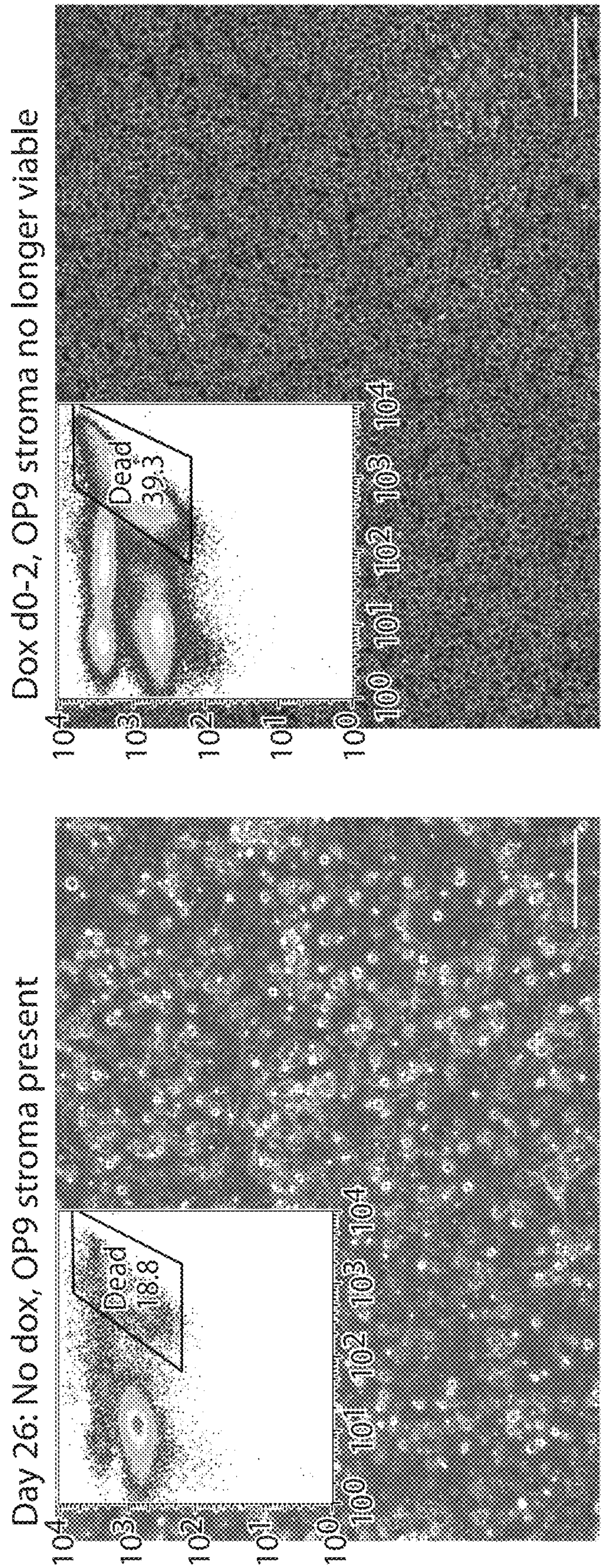

As shown in FIG. 7A and FIG. 7B, the NK cells generated by the methods and compositions as disclosed herein go through a CD7+ progenitor stage (e.g., at day 19), that eventually transitions to into a CD56+ NK cell population that is also positive for any one or more of NKp44+, NKG2D+ and NKp46+ (at day 35) (see FIG. 7B). In some embodiments, the NK cells generated are a CD56+NK cell population that is at least about 60% pure, or at least about 70% pure, or at least about 80% pure, or at least about 90% pure or more than 90% pure. In some embodiments, the methods provide a population of NK cells derived from pluripotent stem cells or iPSC that is at least 90% positive for NK56+.

In general, the determination of the maturation of the T/NK CD7+ cells into mature NK cells and/or their state of differentiation is assessed using conventional methods known to those of ordinary skill in the art. For example, the maturation of the T/NK CD7+ cells may be monitored by flow cytometry for the development of NK cells by staining the cells with anti-CD56 and anti-CD3 antibodies. Cells which are CD56+/CD3− would be indicative of differentiated NK cells.

In alternative embodiments, the T/NK CD7+ progenitors generated using the methods disclosed herein can be cultured on other surfaces or stromal cell lines or other cell lines that activate notch signaling. Examples of suitable factors that activate NOTCH signaling include, but are not limited to, for example, NOTCH ligands, feeder or stromal cells expressing NOTCH ligands (e.g. OP9 cells expressing DLL1 or DLL4) and solid surfaces with immobilized NOTCH ligands (e.g. plates coated with NOTCH ligands). Suitable NOTCH ligands include, for example, DLL1-Fc (which has been described in other papers as Delta1ext-IgG), Jag1 ligand, and DLL4. Other examples of suitable factors that activate NOTCH signaling include an immobilized synthetic molecule that can bind to NOTCH and sufficiently activate the NOTCH receptor and the ectopic expression of the active, intracellular domain of NOTCH1 (Notch-ICD).

Accordingly, the T/NK CD7+ progenitors generated using the methods disclosed herein can be plated at the optimal density for maturation into either T cells or NK cells (e.g., <50K cells/10 cm plate for T-cell maturation, or >200K cells/10 cm plate for NK cell maturation) on a plate comprising a NOTCH activation agent, such as immobilized Notch ligands, to activate NOTCH signaling (Hadland et al., 2015; Ohishi et al., 2002). Activation of NOTCH signaling by any means is suitable, for example, overexpression of the active form of NOTCH receptor or NOTCH ligands. See, e.g., Bigas, A. et al., (2012). The Notch pathway in hematopoietic stem cells. Curr Top Microbiol Immunol 360, 1-18; Bigas, A., and Espinosa, L. (2012). Hematopoietic stem cells: to be or Notch to be. Blood 119, 3226-3235; Butko, E., Pouget, C., and Traver, D. (2016). Complex regulation of HSC emergence by the Notch signaling pathway. Dev Biol 409, 129-138; Lu, Y F., Callan, P., Ross, S., Sahalie, J., Sousa, P M., Hadland, B. K., Cai, W., Serrao, E., Engelman, A N., Bernstein, I D., Daley, G Q. (2016) Engineered Murine HSCs Reconstitute Multi-lineage Hematopoiesis and Adaptive Immunity. Cell Report 17, 3178-3192, the contents of each are incorporated by reference in their entirety.

In some embodiments, the stromal cell is OP9 cells. In some embodiments, the factor capable of activating NOTCH signaling is selected from the group consisting of DLL4, DLL1-Fc, DLL1-expressing feeder or stromal cells (e.g. DLL1-expressing OP9 cells), DLL4-expressing feeder or stromal cells (e.g. DLL4-expressing OP9 cells), plates coated with DLL4-Fc, and plates coated with DLL1-Fc.

Methods for co-culturing cells with OP-9 cells are well known in the art. In some embodiments, the methods disclosed herein provides a method of differentiating the T/NK progenitors produced using the methods disclosed herein into CD8+CD4+ T cell population by culturing the T/NK CD7+ progenitors in the presence of OP9-hDLL4 cells. By way of an exemplary embodiment only, OP9-hDLL4 cells were maintained in a-MEM media containing 20% FBS on 0.1% gelatin—in distilled water coated 10 cm cell culture dish. Cells were passaged every 4 days. For lymphoid differentiation, OP9-hDLL4 cells were cultured in the gelatin coated 10- or 6 well plates. When OP9-hDLL4 cells formed a confluent monolayered (4 days old cells), the harvested T/NK CD7+ progenitors were plated at either a density of <50K cells/10 cm plate for T-cell maturation, or >200K cells/10 cm plate for NK cell maturation and co-cultured on OP9-DLL4 in a-MEM, 20% FBS, IL-7 (5 ng/ml), Flt3L (5 ng/ml) and SCF (10 ng/ml) at 37° C. and 5% $CO_2$ for 3-4 weeks with weekly passage. In some embodiments, every 6-7 days co-cultures were transferred onto fresh OP9-DLL4 cells by vigorous pipetting and passaging through a 40 μm cell strainer.

One or more positive cytokines that promote commitment and differentiation of iT/NK CD7+ progenitors into T cells or NK cells may also be added to the culture. The cytokines may be human in origin, or may be derived from other species. The concentration of a cytokine in a culture is typically about 1-10 ng/ml. The following are representative examples of cytokines that may be employed in the present application: all members of the fibroblast growth factor (FGF) family including FGF-4 and FGF-2, Flt-3-ligand, and interleukin-7 (IL-7). Preferably the cytokines used herein are Flt-3-ligand and IL-7. The cytokines may be used in combination with equal molar or greater amounts of a glycosaminoglycan such as heparin sulfate. The cytokines are commercially available or can be produced by recombinant DNA techniques and purified to various degrees. Some of the cytokines may be purified from culture media of cell lines by standard biochemical techniques.

The iT/NK CD7+ progenitors may be cultured in culture medium comprising conditioned medium, non-conditioned medium, or embryonic stem cell medium. Examples of suitable conditioned medium include IMDM, DMEM, or αMEM, conditioned with embryonic fibroblast cells (e.g. human embryonic fibroblast cells or mouse embryonic fibroblast cells), or equivalent medium. Examples of suitable non-conditioned medium include Iscove's Modified Delbecco's Medium (IMDM), DMEM, or αMEM, or equivalent medium. The culture medium may comprise serum (e.g. bovine serum, fetal bovine serum, calf bovine serum, horse serum, human serum, or an artificial serum substitute) or it may be serum free.

The culture conditions entail culturing the iT/NK CD7+ progenitors for a sufficient period of time so that cells in the preparation form mature T cells or NK cells. The cells are maintained in culture generally for 4-50 days, preferably 5 to 20 days. It will be appreciated that the cells may be maintained for the appropriate amount of time required to achieve the desired cellular composition.

Accordingly, the present application provides a method of generating a mature T cells or NK cells comprising (a) culturing a sample comprising iT/NK CD7+ progenitors with cells that express a Notch ligand at defined plating densities and (b) isolating either T cells or NK cells. The cells expressing a Notch ligand are preferably OP9 cells expressing DL1 or DL4. The mature T cells may be characterized by the phenotype CD3+/CD8+. Moreover, the mature T cells are differentiated into CD4+/CD8+ cells. The mature NK cells may be characterized by the phenotype of expressing any one or more of: CD56+, NKp44, NKp46 or NKG2D.

In another embodiment, a mature T-cell or NK cells is obtained by co-culturing iT/NK CD7+ progenitors produced using the methods and compositions as disclosed herein with OP9-DL1 cells or OP9-DL4 cells, and collecting the cells of a desired phenotype. There is no need for a fractionation step to collect the cells, rather the cells can be collected without cell sorting (i.e., positive or negative selection steps) or other cell separation technique known in the art such as (density gradient, ferromagnetic beads cytometry and fluorescence activated call sorting.) In some embodiments, bioreactors (matrices) can be used for co-culture of the iT/NK CD7+ progenitors and the OP9-DL1 or OP9-DL4 cells.

In another embodiment, the iT/NK CD7+ progenitors may be used to generate NK cells when cultured under appropriate conditions. Appropriate conditions to generate NK cells include culturing the iT/NK CD7+ progenitors in a co-culture of stromal cells, such as OP-9 expressing DL1 or DL4, and optionally in the presence of additional cytokines such as IL-15 or IL-2. Accordingly, the present application provides a method of generating natural killer (NK) cells comprising a) culturing an isolated iT/NK CD7+ progenitor on a stromal cell line expressing a notch ligand at a density of greater than 20,000 cells/ml (or 200 Kcells/10 ml) and b) isolating NK cells. The NK cells may be characterized by the phenotype CD56+.

Accordingly, the methods described herein produce a highly enriched population of CD7+ T/NK progenitors from pluripotent stem cells that are definitive for T cell and NK cell lineages, where the highly enriched population can comprise as many as 90% CD7+ T/NK progenitors. In addition, without the need for cell sorting or cell-selection methods, the CD7+ T/NK progenitors can be co-cultured at distinct densities on stromal cells expressing a notch ligand for further differentiation into NK cells and mature T cells. Accordingly, the technology provides improved methods for T/NK progenitor production, and is suitable for scalable T cell or NK cell production which is essential for to advance the translation of pluripotent stem cell, and iPSC-based immunotherapies into the clinic.

In some embodiments, the technology disclosed herein provides a method of creating a cell population, comprising (a) obtaining a population of pluripotent stem cells, (b)

inducing the expression of a NICD gene in the pluripotent stem cells between d0-d2 of differentiation, (c) culturing the cells using an iT protocol as disclosed herein and differentiating the cells into at least 50% of the cells are a CD7+ T/NK progenitor population. The method can optionally further comprise (d) culturing the cell population comprising at least 50% T/NK CD7+ progenitor cells in a co-culture of stromal cells expressing a notch ligand (e.g., DLL4, or others (DDL1, DLL2, DLL3, JAG1 or JAG2) (e.g., OP9-Dll4 cells) wherein the T/NK CD7+ progenitor cells are plated at a density of <50K cells/10 cm plate (i.e., <5,000 cells/ml) for T-cell maturation, or >200K cells/10 cm plate (i.e., >20,000 cells/ml) for NK cell maturation, and (e) culturing the cells in a suitable medium for an effective amount of time for differentiation of the T/NK CD7+ progenitor cells into T cells or NK cells, respectively.

VI. Modified iPSCs for Derivation of T/NK Cell Progenitors

Another aspect of the present invention relates to a composition comprising a modified iPSC comprising a NICD gene, which can be used in the methods for generating iPSC-derived T/NK progenitors disclosed herein. Another aspect of the present invention relates to a composition comprising a modified iPSC, which can serve as a universal iPSC for use in the methods for generating iPSC-derived T/NK progenitors disclosed herein, where the universal iPSC comprises a NICD gene and a knock-out of the beta-2 microglobulin (b2m) gene and/or CD47 knock-in and/or CIITA knock-out and/or HLA-E knock-in.

1. Modified iPSC Comprising Inducible NICD Gene

As disclosed herein, the inventors have generated an exemplary engineered iPSC cell line which is a modified human iPSC line comprising a nucleic acid sequence encoding NICD1 under the control of an inducible promoter, enabling controlled temporal expression of the NICD1 protein in the presence of doxycycline (Dox). In the examples, such a Tet-ON inducible expression of NICD1 also enabled both temporal expression of NICD1 from d0-d2 as well as dose-dependent expression of NICD1, as it was surprisingly discovered that too high an expression of NICD1 or too little expression of NICD1 during this critical d0-d2 window abrogated the effect of the NICD1 overexpression and resulted in lower yields of CD7+ T/NK progenitors.

As shown in FIG. 5A and described in the Examples, to gain autonomous control of Notch1 activation, a Tet-On: NICD1 construct was generated and it was inserted into the AAVS1 locus of four iPSC lines using zinc-finger nucleases and an optimized targeting vector for the AAVS1 locus. Using this tet-on:NICD1 system, it allowed activation of the Notch pathway prior to the onset of the expression of endogenous Notch receptors and without disturbance of the developing cell layer in completely defined media. This is in contrast to the prior use of feeder cells expressing notch ligands or the use of dll4-fc fusion proteins (Schmitt et al., 2004; Uenishi et al., 2018). Such early induction of notch signaling before the onset of endogenous notch signaling in iPSC provides a significantly more robust and consistent access of differentiation of the iPSC towards the lymphoid lineage.

In one embodiment, an engineered iPSC-NIDC1 cell line is generated which involves introducing into the genome of the iPSC a NICD transgene (e.g. NICD1, NICD2, NICD3 or NICD4 transgene), preferably operatively linked to an inducible promoter. In a preferred embodiment, the NICD transgene is an NICD1 transgene. In another embodiment, the NICD transgene is a selected from the group consisting NICD1, NICD2, NICD3 or NICD4 transgenes.

The transgene can be inserted into the iPSC via any suitable method, for example by transfection or transduction.

Figure 11:
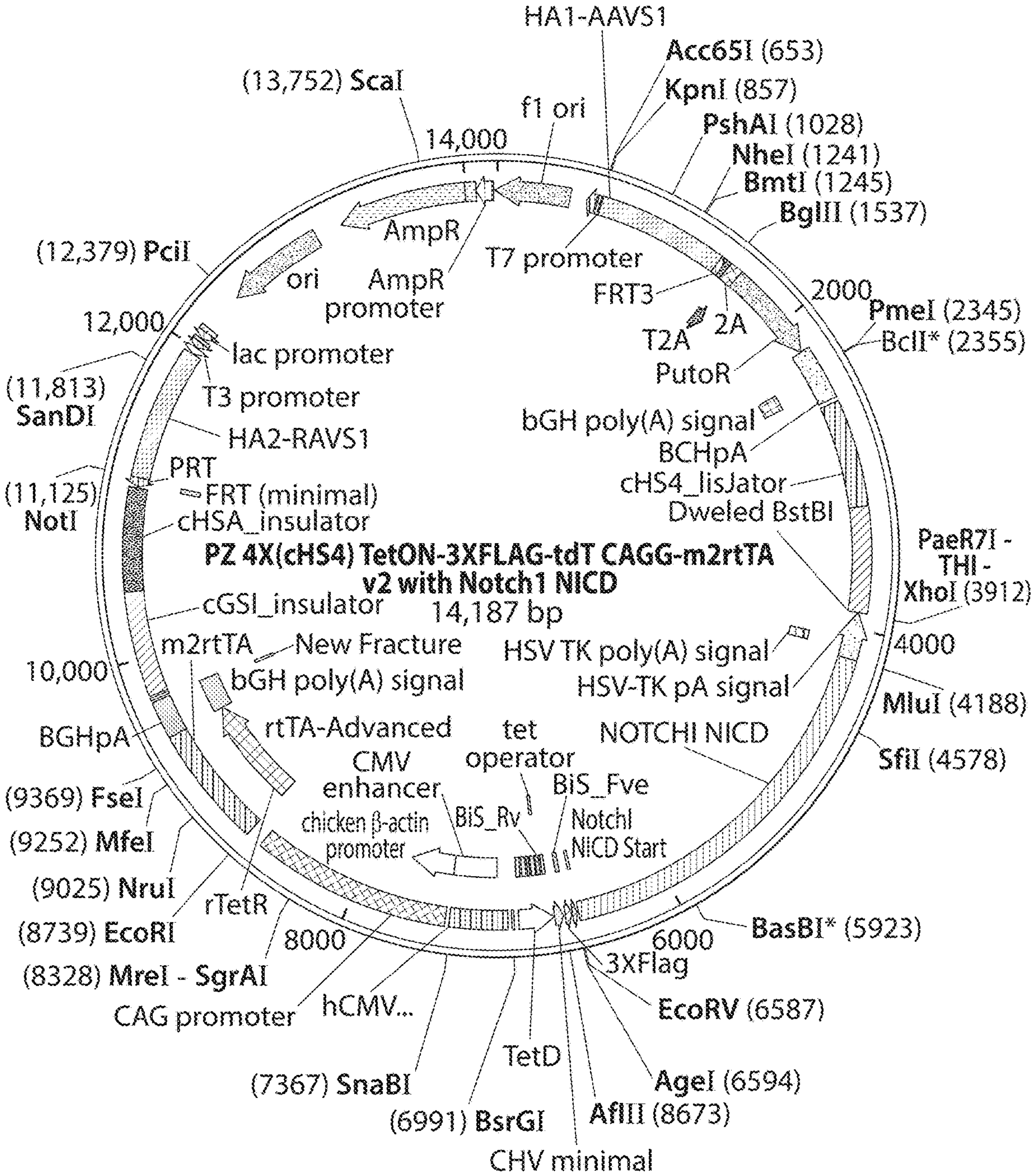
FIG. 11 is a schematic of an exemplary AAVS1 targeting vector construct for inducible expression of a NICD gene. The NICD1 is operatively linked to a Tet:ON promoter (TetON:NICD1 expression cassette), and is flanked by homology arms for insertion of the construct into a genomic safe harbor gene (the AAVS1 safe harbor gene). One of ordinary skill in the art can readily modify this exemplary construct to replace the NICD1 gene with any other NICD gene disclosed herein, and/or modify the promoter to be any inducible promoter or regulatory switch as disclosed herein. In some embodiments, one can also modify the homology arms for insertion into a specific gene or insertion into a different genomic safe harbor loci, e.g., albumin gene, hROSA26, CCR5 gene, AAVS1.

An exemplary construct to generate an engineered iPSC-NICD cell line is shown in FIG. 5A and FIG. 11. Any NICD gene may be expressed in the iPSC, and in some embodiments, any nucleotide sequence encoding a NICD known in the art, may be used without limitation, for example, a nucleotide sequence encoding NICD1, NICD2, NICD3, or NICD4 or functional variants thereof.

In some embodiments, the NICD1 gene inserted into a iPSC genome is encoded by the nucleic acid of SEQ ID NO: 1, or a nucleic acid sequence of at least 80% sequence identity to SEQ ID NO: 1. In some embodiments, the NICD1-encoding sequence comprising a DNA sequence set forth in SEQ ID NO: 1 may encode a protein having an amino acid sequence set forth in SEQ ID NO: 5, but the scope of the present invention is not limited thereto. Namely, it may have a nucleotide sequence encoding a protein that is the functional equivalent of the protein of NICD1 corresponding to SEQ ID NO:5 is encompassed for use in the methods and compositions as disclosed herein. In some embodiments, a nucleic acid sequence having at least 80% sequence identity to SEQ ID NO: 1 is encompassed for use in generating an iPSC-NICD1 line.

In some embodiments, the NICD2 gene inserted into a iPSC genome is encoded by the nucleic acid of SEQ ID NO: 2, or a nucleic acid sequence of at least 80% sequence identity to SEQ ID NO: 2. In some embodiments, the NICD2-encoding sequence comprising a DNA sequence set forth in SEQ ID NO: 2 may encode a protein having an amino acid sequence set forth in SEQ ID NO: 6, but the scope of the present invention is not limited thereto. Namely, it may have a nucleotide sequence encoding a protein that is the functional equivalent of the protein of NICD2 corresponding to SEQ ID NO:6 is encompassed for use in the methods and compositions as disclosed herein. In some embodiments, a nucleic acid sequence having at least 80% sequence identity to SEQ ID NO: 2 is encompassed for use in generating an iPSC-NICD2 line.

In some embodiments, the NICD3 gene inserted into a iPSC genome is encoded by the nucleic acid of SEQ ID NO: 3, or a nucleic acid sequence of at least 80% sequence identity to SEQ ID NO: 3. In some embodiments, the NICD3-encoding sequence comprising a DNA sequence set forth in SEQ ID NO: 3 may encode a protein having an amino acid sequence set forth in SEQ ID NO: 7, but the scope of the present invention is not limited thereto. Namely, it may have a nucleotide sequence encoding a protein that is the functional equivalent of the protein of NICD3 corresponding to SEQ ID NO:7 is encompassed for use in the methods and compositions as disclosed herein. In some embodiments, a nucleic acid sequence having at least 80% sequence identity to SEQ ID NO: 3 is encompassed for use in generating an iPSC-NICD3 line.

In some embodiments, the NICD4 gene inserted into a iPSC genome is encoded by the nucleic acid of SEQ ID NO: 4, or a nucleic acid sequence of at least 80% sequence identity to SEQ ID NO: 4. In some embodiments, the NICD4-encoding sequence comprising a DNA sequence set forth in SEQ ID NO: 4 may encode a protein having an amino acid sequence set forth in SEQ ID NO: 8, but the scope of the present invention is not limited thereto. Namely, it may have a nucleotide sequence encoding a protein that is the functional equivalent of the protein of NICD4 corresponding to SEQ ID NO:8 is encompassed for use in the methods and compositions as disclosed herein. In some embodiments, a nucleic acid sequence having at least 80% sequence identity to SEQ ID NO: 4 is encompassed for use in generating an iPSC-NICD4 line.

The nucleic acid sequences for human NICD1-NICD2, and nucleic acid sequences for NICD1-NICD4 are disclosed in US applications US20030119771A1 (e.g., see FIGS. 14A-14F) and 2015/0352180, which are each incorporated herein in their entirety, and encompassed for use in the methods and compositions herein, e.g., for generation of an iPSC line expressing an inducible NICD gene, and/or for induction of notch signaling before the onset of endogenous notch signaling in a pluripotent stem cell according to the methods disclosed herein. Other non-human NICD genes are also encompassed for use, e.g., nucleic acid sequences and protein sequence encoding mouse NICD1 or NICD2, for example, as disclosed in US application 2015/0352180 or disclosed as SEQ ID NO: 10-13 herein.

2. Modified iPSC for a Universal iPSC

In addition to the generation of an engineered iPSC comprising a NICD gene for use in the methods for generating iPSC-derived T/NK progenitors disclosed herein, another aspect of the present invention relates to a composition comprising an engineered iPSC, which can serve as a universal iPSC for use in the methods for generating iPSC-derived T/NK progenitors disclosed herein, where the universal iPSC is engineered to comprise both a NICD gene and also a knock-out of the beta-2 microglobulin (b2m) gene and/or CD47 knock-in and/or CIITA knock-out and/or HLA-E knock-in.

A) Knock-Out of MHC I

In some embodiments, an engineered iPSC for generation of a universal iPSC has a knock-out of MHC class I expression. In some embodiments, knock-out of MHC class I expression is achieved by removing native expression of beta-2 microglobulin (β2M) (i.e., generation of a β2M knock-out) which abrogates the expression of MHC class I alleles, making it difficult for the immune system to recognize these cells as allogeneic. In some embodiments, to achieve knock-out of endogenous expression of beta-2 microglobulin (referred to as a "B2M-KO"), one can insert a beta-2 microglobulin_HLA-E fusion protein into the beta-2 microglobulin locus, effectively blocking MHC I expression and instead over-expressing HLA-E, and inhibitory MHC I molecule to block NK cell recognition.

By way of an example only, in some embodiments, a cDNA corresponding to beta-2 microglobulin_(G4S)4_HLA-E*103_bGH poly(A) will be synthesized with 400 bp homology arms targeting the first exon of beta-2 microglobulin. This synthesized donor will be cloned into the pJET1.2 vector. CRISPR guides for the beginning of the first exon of beta-2 microglobulin will be designed using Broad Institute GPP and ChopChop using SpCas9 PAM NGG. Three guides will be selected and cloned into add gene plasmid 48138 (SpCas9_2A_GFP). IPSCs will be nucleofected with individual guides and the donor plasmid with 1 ug each plasmid/106 cells. After 48 hrs, they will be sorted for GFP positive cells and plated at low density on 10 cm plates to allow grow-out of clonal populations. Individual clones will be screened for bi-allelic insertion of the donor template using PCR.

In alternative embodiments, a modified iPSC line is achieved by generating a (32M knock-out, where a stop codon of beta-2 microglobulin is targeted and a donor nucleic acid sequence inserted comprising a (G4S)4 linker_HLA-E*103_stop. Such a construct would result in the cell still expressing the beta-2 microglobulin, but it would be a fusion with HLA-E. Such a strategy is useful, as it enables the donor sequence to be considerably shorter as it avoid having to require the beta-2 microglobulin cDNA sequence.

Any method to knock-out beta-2 microglobulin in an iPSC is envisioned for use in the methods as disclosed herein. In alternative embodiments, any modification of the iPSC to render the iPSC incapable of expressing endogenous beta-2 microglobulin is also envisioned for use in the methods and compositions as disclosed herein. In some embodiments, an engineered iPSC for use on the compositions and methods disclosed herein is an iPSC that cannot express endogenous beta-2-myoglobin and is generated by the methods disclosed in US applications US2018/0179496, US2019/0175651, which is incorporated herein in its entirety by reference.

"Beta-2 microglobulin", also known as "B2M", is the light chain of MHC class I molecules, and as such an integral part of the major histocompatibility complex. In humans, B2M is encoded by the b2m gene which is located on chromosome 15, opposed to the other MHC genes which are located as gene cluster on chromosome 6. The human protein is composed of 119 amino acids and has a molecular weight of 11.8 Kilodaltons. Mice models deficient for beta-2 microglobulin have shown that B2M is necessary for cell surface expression of MHC class I and stability of the peptide binding groove. It was further shown that haemopoietic transplants from mice that are deficient for normal cell-surface MHC I expression are rejected by NK1.1+ cells in normal mice because of a targeted mutation in the beta-2 microglobulin gene, suggesting that deficient expression of MHC I molecules renders marrow cells susceptible to rejection by the host immune system (Bix M. et al (1991). "Rejection of class I MHC-deficient haemopoietic cells by irradiated MHC-matched mice." Nature 349(6307):329-31).

B) Knock-Out of MHC II

In some embodiments, a modified iPSC for generation of a universal iPSC also optionally comprises a knock-out of MHC class II expression. Removing expression of MHC II from the surface of the cell would reduce recognition of these cells as allogeneic by the immune system. CIITA is the master-regulator transcription factor for MHC II expression, and creating CIITA −/− iPSCs (i.e., a "CIITA-KO") would block all MHC II expression. CD47 is a molecule expressed by many cell types to block phagocytosis by macrophages.

In some embodiments, knock-out of MHC class II expression is achieved by interrupting the expression of CIITA (i.e., generation of a CIITA knock-out).

By way of an example only, in some embodiments, to block expression of MHC II, interruption of the expression of CIITA is achieved by inserting into the CIIA locus a DNA construct for the expression of CD47. In some embodiments, is endogenous expression of CIITA is low, and the DNA construct can further comprise a promoter, e.g., an inducible or high expression promoter, that is operatively linked to the nucleic acid sequence encoding CD47, therefore increasing the capacity of the expression of CD47 to improve immune-evasion. In some embodiments, a cDNA construct comprising a human EF1-alpha promoter, operatively linked to a nucleic acid encoding CD47, followed by a 3' bGH poly(A) tail is inserted into the CIITA locus. In some embodiments, the construct also comprises 5' and 3' homology arms (e.g., about 400 bp homology arms) that flank the hEF1α-CD47-polyA construct, where the 5' and 3' homology arms target the first exon of CIITA. Such a construct can be cloned into a suitable vector, for example, a pJET1.2 vector. In some embodiments, CRISPR guides for the beginning of the first exon of CIITA can be used (e.g., they can be readily designed by persons of ordinary skill in the art and organization such as the Broad Institute GPP and ChopChop using SpCas9 PAM NGG). Three CRISPR guides will be selected and cloned into add gene plasmid 48138 (SpCas9_2A_GFP). For generation of the modified iPSC line comprising the CIIA knock-out/CD47 knock-in, iPSCs are nucleofected with a composition comprising the individual guides and the donor plasmid with 1 ug each plasmid/$10^6$ cells. After 48 hrs, the transfected iPSC are sorted for GFP positive cells and plated at low density on 10 cm plates to allow grow-out of clonal populations. Individual iPSC clones will be screened for bi-allelic insertion of the donor template using PCR.

3. Regulatory Elements.

In some embodiments, the nucleic acid construct disclosed herein, e.g., for inducible expression of a NICD gene, or for expression of CD47 at the CIITA locus (for MHCII knockout), or HLA-E gene at the B2M locus (for MHC I knockout) can further comprise a specific combination of cis-regulatory elements which are disclosed herein. The cis-regulatory elements include, but are not limited to, a promoter, a riboswitch, an insulator, a mir-regulatable element, a post-transcriptional regulatory element, a tissue- and cell type-specific promoter and an enhancer. In some embodiments, the NICD gene is operatively linked to any inducible promoter commonly known to persons of ordinary skill in the art, or alternatively, a tissue-specific promoter. In some embodiments, the NICD gene is operatively linked to a regulatory element that is part of a genetic circuit, such as, for example, a genetic circuit disclosed in US applications 2017/0183654A1, 2017/0183654, US20170255857A1 and U.S. Pat. No. 9,697,460, which are each incorporated herein in their entirety by reference. In some embodiments, the nucleic acid construct comprising the NICD gene operatively linked to a inducible promoter comprises additional components to regulate expression of the transgene, for example, regulatory switches as described herein, to regulate the expression of the transgene, or a kill switch, which can kill a cell comprising the nucleic acid construct.

Regulatory Switches

A molecular regulatory switch is one which generates a measurable change in state in response to a signal. Such regulatory switches can be usefully combined with the nucleic acid constructs described herein to control the output of the nucleic acid construct. In some embodiments, the nucleic acid construct comprises a regulatory switch that serves to fine tune expression of the transgene. For example, it can serve as a biocontainment function of the nucleic acid construct. In some embodiments, the switch is an "ON/OFF" switch that is designed to start or stop (i.e., shut down) expression of the gene of interest in a controllable and regulatable fashion. In some embodiments, the switch can include a "kill switch" that can instruct the cell comprising the nucleic acid construct to undergo cell programmed death once the switch is activated.

A. Binary Regulatory Switches

In some embodiments, the nucleic acid construct comprises a regulatory switch that can serve to controllably modulate expression of the transgene. In such an embodiment, the expression cassette may additionally comprise a regulatory region, e.g., a promoter, cis-element, repressor, enhancer etc., that is operatively linked to the gene of interest, where the regulatory region is regulated by one or more cofactors or exogenous agents. Accordingly, in one embodiment, only when the one or more cofactor(s) or exogenous agents are present in the cell will transcription and expression of the gene of interest from the nucleic acid construct occur. In another embodiment, one or more cofactor(s) or exogenous agents may be used to de-repress the transcription and expression of the gene of interest.

Any nucleic acid regulatory regions known by a person of ordinary skill in the art can be employed in a nucleic acid construct designed to include a regulatory switch. By way of example only, regulatory regions can be modulated by small molecule switches or inducible or repressible promoters. Nonlimiting examples of inducible promoters are hormone-inducible or metal-inducible promoters. Other exemplary inducible promoters/enhancer elements include, but are not limited to, an RU486-inducible promoter, an ecdysone-inducible promoter, a rapamycin-inducible promoter, and a metallothionein promoter. Classic tetracycline-based or other antibiotic-based switches are encompassed for use, including those disclosed in (Fussenegger et al., Nature Biotechnol. 18: 1203-1208 (2000)).

B. Small Molecule Regulatory Switches

A variety of art-known small-molecule based regulatory switches are known in the art and can be combined with the nucleic acid constructs disclosed herein to form a regulatory-switch controlled nucleic acid construct. In some embodiments, the regulatory switch can be selected from any one or a combination of: an orthogonal ligand/nuclear receptor pair, for example retinoid receptor variant/LG335 and GRQCIMFI, along with an artificial promoter controlling expression of the operatively linked transgene, such as that as disclosed in Taylor, et al. BMC Biotechnology 10 (2010): 15; engineered steroid receptors, e.g., modified progesterone receptor with a C-terminal truncation that cannot bind progesterone but binds RU486 (mifepristone) (U.S. Pat. No. 5,364,791); an ecdysone receptor from *Drosophila* and their ecdysteroid ligands (Saez, et al., PNAS, 97(26)(2000), 14512-14517; or a switch controlled by the antibiotic trimethoprim (TMP), as disclosed in Sando R 3rd; Nat Methods. 2013, 10(11):1085-8.

Other small molecule based regulatory switches known by an ordinarily skilled artisan are also envisioned for use to control transgene expression of the NICD gene and include, but are not limited to, those disclosed in Buskirk et al., Cell; Chem and Biol., 2005; 12(2); 151-161; an abscisic acid sensitive ON-switch; such as that disclosed in Liang, F.-S., et al., (2011) Science Signaling, 4(164); exogenous L-arginine sensitive ON-switches such as those disclosed in Hartenbach, et al. *Nucleic Acids Research,* 35(20), 2007, synthetic bile-acid sensitive ON-switches such as those disclosed in Rössger et al., Metab Eng. 2014, 21: 81-90; biotin sensitive ON-switches such as those disclosed in Weber et al., Metab. Eng. 2009 March; 11(2): 117-124; dual input food additive benzoate/vanillin sensitive regulatory switches such as those disclosed in Xie et al., Nucleic Acids Research, 2014; 42(14); e116; 4-hydroxytamoxifen sensitive switches such as those disclosed in Giuseppe et al., Molecular Therapy, 6(5), 653-663; and flavinoid (phloretin) sensitive regulatory switches such as those disclosed in Gitzinger et al., Proc. Natl. Acad. Sci. USA. 2009 Jun. 30; 106(26): 10638-10643.

In some embodiments, the regulatory switch to control the transgene or expressed by the nucleic acid construct is a pro-drug activation switch, such as that disclosed in U.S. Pat. Nos. 8,771,679, and 6,339,070.

Exemplary regulatory switches for use in the nucleic acid constructs include, but are not limited to those in Table 2.

TABLE 2

Exemplary regulatory switches

| no. | name | ON switch[b] | OFF switch[c] | origin | effectord | references[e] |
|---|---|---|---|---|---|---|
| | | | | Transcriptional Switches | | |
| 1 | ABA | yes | no | *Arabidopsis thaliana*, yeast | abscisic acid | [19] |
| 2 | AIR | yes | no | *Aspergillus nidulans* | acetaldehyde | [20] |
| 3 | ART | yes | no | *Chlamydia pneumoniae* | l-arginine | [21] |
| 4 | BEARON, BEAROFF | yes | yes | *Campylobacter jejuni* | bile acid | [22] |
| 5 | BirA-tTA | no | yes | *Escherichia coli* | biotin (vitamin H) | [23] |
| 6 | BIT | yes | no | *Escherichia coli* | biotin (vitamin H) | [24] |
| 7 | Cry2-CIB1 | yes | no | *Arabidopsis thaliana*, yeast | blue light | [25] |
| 8 | CTA, CTS | yes | yes | *Comamonas testosteroni*, *Homo sapiens* | food additives (benzoate, vanillate) | [26] |
| 9 | cTA, rcTA | yes | yes | *Pseudomonas putida* | cumate | [27] |
| 10 | Ecdysone | yes | no | *Homo sapiens*, *Drosophila melanogaster* | Ecdysone | [28] |
| 11 | EcR:RXR | yes | no | *Homo sapiens*, *Locusta migratoria* | ecdysone | [29] |
| 12 | electro-genetic | yes | no | *Aspergillus nidulans* | electricity, acetaldehyde | [30] |
| 13 | ER-p65-ZF | yes | no | *Homo sapiens*, yeast | 4,4'-dyhydroxybenzil | [31] |
| 14 | E.REX | yes | yes | *Escherichia coli* | erythromycin | [32] |
| 15 | EthR | no | yes | *Mycobacterium tuberculosis* | 2-phenylethyl-butyrate | [33] |
| 16 | GAL4-ER | yes | yes | yeast, *Homo sapiens* | oestrogen, 4-hydroxytamoxifen | [34] |
| 17 | GAL4-hPR | yes | yes | yeast, *Homo sapiens* | mifepristone | [35, 36] |
| 18 | GAL4-Raps | yes | yes | yeast, *Homo sapiens* | rapamycin and rapamycin derivatives | [37] |
| 19 | GAL4-TR | yes | no | yeast, *Homo sapiens* | thyroid hormone | [38] |
| 20 | GyrB | yes | yes | *Escherichia coli* | coumermycin, novobiocin | [39] |
| 21 | HEA-3 | yes | no | *Homo sapiens* | 4-hydroxytamoxifen | [40] |
| 22 | Intramer | no | yes | synthetic SELEX-derived aptamers | theophylline | [41] |
| 23 | LacI | yes | no | *Escherichia coli* | IPTG | [42-46] |
| 24 | LAD | yes | no | *Arabidopsis thaliana*, yeast | blue light | [47] |
| 25 | LightOn | yes | no | *Neurospora crassa*, yeast | blue light | [48] |
| 26 | NICE | yes | yes | *Arthrobacter nicotinovorans* | 6-hydroxynicotine | [49] |
| 27 | PPAR* | yes | no | *Homo sapiens* | rosiglitazone | [50] |
| 28 | PEACE | no | yes | *Pseudomonas putida* | flavonoids (e.g. phloretin) | [51] |
| 29 | PIT | yes | yes | *Streptomyces coelicolor* | pristinamycin I, virginiamycin | [12] |
| 30 | REDOX | no | yes | *Streptomyces coelicolor* | NADH | [52] |
| 31 | QuoRex | yes | yes | *Streptomyces coelicolor*, *Streptomyces pristinaespiralis* | butyrolactones (e.g. SCB1) | [53] |
| 32 | ST-TA | yes | yes | *Streptomyces coelicolor*, *Escherichia coli*, Herpes simplex | γ-butyrolactone, tetracycline | [54] |
| 33 | TIGR | no | yes | *Streptomyces albus* | temperature | [55] |
| 34 | TraR | yes | no | *Agrobacterium tumefaciens* | N-(3-oxo-octanoyl)homoserine lactone | [56] |

TABLE 2-continued

| no. | name | ON switch[b] | OFF switch[c] | origin | effectord | references[e] |
|---|---|---|---|---|---|---|
| | **Exemplary regulatory switches** | | | | | |
| 35 | TET-OFF, TET-ON | yes | yes | *Escherichia coli*, Herpes simplex | tetracycline, doxycycline | [11, 57] |
| 36 | TRT | yes | no | *Chlamydia trachomatis* | 1-tryptophan | [58] |
| 37 | UREX | yes | no | *Deinococcus radiodurans* | uric acid | [59] |
| 38 | VAC | yes | yes | *Caulobacter crescentus* | vanillic acid | [60] |
| 39 | ZF-ER, ZF-RXR/EcR | yes | yes | *Mus musculus*, *Homo sapiens*, *Drosophila melanogaster* | 4-hydroxytamoxifen, ponasterone-A | [61] |
| 40 | ZF-Raps | yes | no | *Homo sapiens* | rapamycin | [62] |
| 41 | ZF switches | yes | no | *Mus musculus*, *Homo sapiens*, *Drosophila melanogaster* | 4-hydroxytamoxifen, mifepristone | [63] |
| 42 | ZF(TF)s | yes | no | *Xenopus laevis*, *Homo sapiens* | ethyl-4-hydroxybenzoate, propyl-4-hydroxybenzoate | [64] |
| | **post-transcriptional switches** | | | | | |
| 1 | aptamer RNAi | yes | no | synthetic SELEX-derived aptamer | theophylline | [65] |
| 2 | aptamer RNAi | no | yes | synthetic SELEX-derived aptamer | theophylline | [66] |
| 3 | aptamer RNAi miRNA | yes | no | synthetic SELEX-derived aptamer | theophylline, tetracycline, hypoxanthine | [67] |
| 4 | aptamer Splicing | yes | yes | *Homo sapiens*, MS2 bacteriophage | MS2, p65, p50, b-catenin | [68] |
| 5 | aptazyme | no | yes | synthetic SELEX-derived aptamer, *Schistosoma mansoni* | theophylline | [69] |
| 6 | replicon CytTS | yes | no | Sindbis virus | temperature | [70] |
| 7 | TET-OFF-shRNA, TET-ON-shRNA | yes | yes | *Escherichia coli*, Herpes simplex, *Homo sapiens* | doxycycline | [71] |
| 8 | theo aptamer | no | yes | synthetic SELEX-derived aptamer | theophylline | [72] |
| 9 | 3'UTR aptazyme | yes | no | synthetic SELEX-derived aptamers, tobacco ringspot virus | theophylline, tetracycline | [73] |
| 10 | 5'UTR aptazyme | no | yes | synthetic SELEX-derived aptamer, *Schistosoma mansoni* | theophylline | [74] |
| | **translational switches** | | | | | |
| 1 | Hoechst aptamer | no | yes | synthetic RNA sequence | Hoechst dyes | [75] |
| 2 | H23 aptamer | no | yes | *Archaeoglobus fulgidus* | L7Ae, L7KK | [76] |
| 3 | L7Ae aptamer | yes | yes | *Archaeoglobus fulgidus* | L7Ae | [77] |
| 4 | MS2 aptamer | no | yes | MS2 bacteriophage | MS2 | [78] |

TABLE 2-continued

| Exemplary regulatory switches | | | | | | |
|---|---|---|---|---|---|---|
| no. | name | ON switch[b] | OFF switch[c] | origin | effector[d] | references[e] |
| post-translational switches | | | | | | |
| 1 | AID | no | yes | *Arabidopsis thaliana*, *Oryza sativa*, *Gossypium hirsutum* | auxins (e.g. IAA) | [79] |
| 2 | ER DD | no | yes | *Homo sapiens* | CMP8, 4-hydroxytamoxifen | [80] |
| 3 | FM | yes | no | *Homo sapiens* | AP21998 | [81] |
| 4 | HaloTag | no | yes | *Rhodococcus* sp. RHA1 | HyT13 | [82, 83] |
| 5 | HDV-aptazyme | no | yes | hepatitis delta virus | theophylline, guanine | [84] |
| 6 | PROTAC | no | yes | *Homo sapiens* | proteolysis targeting chimeric molecules (PROTACS) | [85] |
| 7 | shield DD | yes | no | *Homo sapiens* | shields (e.g. Shld1) | [86] |
| 8 | shield LID | no | yes | *Homo sapiens* | shields (e.g. Shld1) | [87] |
| 9 | TMP DD | yes | no | *Escherichia coli* | trimethoprim (TMP) | [88] |

[b]ON switchability by an effector; other than removing the effector which confers the OFF state.
[c]OFF switchability by an effector; other than removing the effector which confers the ON state.
[d]A ligand or other physical stimuli (e.g. temperature, electromagnetic radiation, electricity) which stabilizes the switch either in its ON or OFF state.
[e]refers to the reference number cited in Kis et al., *J R Soc Interface*. 12:20141000 (2015), where both the article and the references cited therein are hereby incorporated by reference herein.

C. "Passcode" Regulatory Switches

In some embodiments the regulatory switch can be a "passcode switch" or "passcode circuit". Passcode switches allow fine tuning of the control of the expression of the transgene from the nucleic acid construct when specific conditions occur—that is, a combination of conditions need to be present for transgene expression and/or repression to occur. For example, for expression of a transgene to occur at least conditions A and B must occur. A passcode regulatory switch can be any number of conditions, e.g., at least 2, or at least 3, or at least 4, or at least 5, or at least 6 or at least 7 or more conditions to be present for transgene expression to occur. In some embodiments, at least 2 conditions (e.g., A, B conditions) need to occur, and in some embodiments, at least 3 conditions need to occur (e.g., A, B and C, or A, B and D). By way of an example only, for gene expression from NICD to occur that has a passcode "ABC" regulatory switch, conditions A, B and C must be present. Conditions A, B and C could be as follows; condition A is the presence of a condition or disease, condition B is a hormonal response, and condition C is a response to the transgene expression. As an exemplary example only, if the transgene is insulin, Condition A occurs if the subject has diabetes, Condition B is if the sugar level in the blood is high and Condition C is the level of endogenous insulin not being expressed at required amounts. Once the sugar level declines or the desired level of insulin is reached, the transgene (e.g. insulin), turns off again until the 3 conditions occur, turning it back on. In another exemplary example, if the transgene is EPO, Condition A is the presence of Chronic Kidney Disease (CKD), Condition B occurs if the subject has hypoxic conditions in the kidney, Condition C is that Erythropoietin-producing cells (EPC) recruitment in the kidney is impaired; or alternatively, HIF-2 activation is impaired. Once the oxygen levels increase or the desired level of EPO is reached, the transgene (e.g., EPO) turns off again until 3 conditions occur, turning it back on.

Passcode regulatory switches are useful to fine tune the expression of the transgene from the nucleic acid construct. In some embodiments, a passcode regulatory switch encompassed for use in the nucleic acid construct is disclosed in WO2017/059245, which describes a switch referred to as a "Passcode switch" or a "Passcode circuit" or "Passcode kill switch" which is a synthetic biological circuit that uses hybrid transcription factors (TFs) to construct complex environmental requirements for cell survival. The Passcode regulatory switches described in WO2017/059245 are particularly useful for use in the nucleic acid constructs, as they are modular and customizable, both in terms of the environmental conditions that control circuit activation and in the output modules that control cell fate. In addition, the Passcode circuit has particular utility to be used in nucleic acid constructs, since without the appropriate "passcode" molecules it will allow transgene expression only in the presence of the required predetermined conditions. If something goes wrong with a cell or no further transgene expression is desired for any reason, then the related kill switch (i.e. deadman switch) can be triggered.

In some embodiments, a passcode regulatory switch or "Passcode circuit" encompassed for use in the nucleic acid construct comprises hybrid transcription factors (TFs) to expand the range and complexity of environmental signals used to define biocontainment conditions. As opposed to the deadman switch which triggers cell death on in the presence of a predetermined condition, the "passcode circuit" allows cell survival or transgene expression in the presence of a particular "passcode", and can be easily reprogrammed to allow transgene expression and/or cell survival only when the predetermined environmental condition or passcode is present.

Accordingly, a nucleic acid construct can comprise a "Passcode regulatory circuit" that requires the presence and/or absence of specific molecules to activate the output module. In some embodiments, where genes that encode for cellular toxins are placed in the output module, this passcode regulatory circuit can not only be used to regulate transgene expression, but also can be used to create a kill switch mechanism in which the circuit kills the cell if the cell behaves in an undesired fashion (e.g., it leaves the specific environment defined by the sensor domains, or differentiates into a different cell type). In one nonlimiting example, the modularity of the hybrid transcription factors, the circuit architecture, and the output module allows the circuit to be reconfigured to sense other environmental signals, to react to the environmental signals in other ways, and to control other functions in the cell in addition to induced cell death, as is understood in the art.

Any and all combinations of regulatory switches disclosed herein, e.g., small molecule switches, nucleic acid-based switches, small molecule-nucleic acid hybrid switches, post-transcriptional transgene regulation switches, post-translational regulation, radiation-controlled switches, hypoxia-mediated switches and other regulatory switches known by persons of ordinary skill in the art as disclosed herein can be used in a passcode regulatory switch as disclosed herein. Regulatory switches encompassed for use are also discussed in the review article Kis et al., J R Soc Interface. 12: 20141000 (2015), and summarized in Table 1 of Kis. In some embodiments, a regulatory switch for use in a passcode system can be selected from any or a combination of the switches in Table 2.

D. Nucleic Acid-Based Regulatory Switches to Control Transgene Expression

In some embodiments, the regulatory switch to control the transgene expressed by the nucleic acid construct can be based on a nucleic-acid based control mechanism. Exemplary nucleic acid control mechanisms are known in the art and are envisioned for use. For example, such mechanisms include riboswiches, such as those disclosed in, e.g., US2009/0305253, US2008/0269258, US2017/0204477, WO2018026762A1, U.S. Pat. No. 9,222,093 and EP application EP288071, and also disclosed in the review by Villa J K et al., Microbiol Spectr. 2018 May; 6(3). Also included are metabolite-responsive transcription biosensors, such as those disclosed in WO2018/075486 and WO2017/147585. Other art-known mechanisms envisioned for use include silencing of the transgene with an siRNA or RNAi molecule (e.g., miR, shRNA). For example, the nucleic acid construct can comprise a regulatory switch that encodes a RNAi molecule that is complementary to the transgene expressed by the nucleic acid construct. When such RNAi is expressed even if the transgene is expressed by the nucleic acid construct, it will be silenced by the complementary RNAi molecule, and when the RNAi is not expressed when the transgene is expressed by the nucleic acid construct the transgene is not silenced by the RNAi. Such an example of a RNAi molecule controlling gene expression, or as a regulatory switch is disclosed in US2017/0183664. In some embodiments, the regulatory switch comprises a repressor that blocks expression of the transgene from the nucleic acid construct. In some embodiments, the on/off switch is a Small transcription activating RNA (STAR)-based switch, for example, such as the one disclosed in Chappell J. et al., Nat Chem Biol. 2015 March; 11(3):214-20; and Chappell et al., Microbiol Spectr. 2018 May; 6(3. In some embodiments, the regulatory switch is a toehold switch, such as that disclosed in US2009/0191546, US2016/0076083, WO2017/087530, US2017/0204477, WO2017/075486 and in Green et al, Cell, 2014; 159(4); 925-939.

In some embodiments, the regulatory switch is a tissue-specific self-inactivating regulatory switch, for example as disclosed in US2002/0022018, whereby the regulatory switch deliberately switches transgene expression off at a site where transgene expression might otherwise be disadvantageous. In some embodiments, the regulatory switch is a recombinase reversible gene expression system, for example as disclosed in US2014/0127162 and U.S. Pat. No. 8,324,436.

In some embodiments, the regulatory switch to control the transgene or gene of interest expressed by the nucleic acid construct is a hybrid of a nucleic acid-based control mechanism and a small molecule regulator system. Such systems are well known to persons of ordinary skill in the art and are envisioned for use herein. Examples of such regulatory switches include, but are not limited to, an LTRi system or "Lac-Tet-RNAi" system, e.g., as disclosed in US2010/0175141 and in Deans T. et al., Cell., 2007, 130(2); 363-372, WO2008/051854 and U.S. Pat. No. 9,388,425.

In some embodiments, the regulatory switch to control the transgene or gene of interest expressed by the nucleic acid construct involves circular permutation, as disclosed in U.S. Pat. No. 8,338,138. In such an embodiment, the molecular switch is multistable, i.e., able to switch between at least two states, or alternatively, bistable, i.e., a state is either "ON" or "OFF," for example, able to emit light or not, able to bind or not, able to catalyze or not, able to transfer electrons or not, and so forth. In another aspect, the molecular switch uses a fusion molecule, therefore the switch is able to switch between more than two states. For example, in response to a particular threshold state exhibited by an insertion sequence or acceptor sequence, the respective other sequence of the fusion may exhibit a range of states (e.g., a range of binding activity, a range of enzyme catalysis, etc.). Thus, rather than switching from "ON" or "OFF," the fusion molecule can exhibit a graded response to a stimulus.

In some embodiments, a nucleic acid based regulatory switch can be selected from any or a combination of the switches in Table 2.

E. Post-Transcriptional and Post-Translational Regulatory Switches.

In some embodiments, the regulatory switch to control the transgene or gene of interest expressed by the nucleic acid construct is a post-transcriptional modification system. For example, such a regulatory switch can be an aptazyme riboswitch that is sensitive to tetracycline or theophylline, as disclosed in US2018/0119156, GB201107768, WO2001/064956A3, EP Patent 2707487 and Beilstein et al., ACS Synth. Biol., 2015, 4 (5), pp 526-534; Zhong et al., Elife. 2016 Nov. 2; 5. pii: e18858. In some embodiments, it is envisioned that a person of ordinary skill in the art could encode both the transgene and an inhibitory siRNA which contains a ligand sensitive (OFF-switch) aptamer, the net result being a ligand sensitive ON-switch.

In some embodiments, the regulatory switch to control the transgene or gene of interest expressed by the nucleic acid construct is a post-translational modification system. In alternative embodiments, the gene of interest or protein is expressed as pro-protein or pre-proprotein, or has a signal response element (SRE) or a destabilizing domain (DD) attached to the expressed protein, thereby preventing correct protein folding and/or activity until post-translation modification has occurred. In the case of a destabilizing domain (DD) or SRE, the de-stabilization domain is post-translationally cleaved in the presence of an exogenous agent or small molecule. One of ordinary skill in the art can utilize such control methods as disclosed in U.S. Pat. No. 8,173,792 and PCT application WO2017180587. Other post-transcriptional control switches envisioned for use in the nucleic acid construct for controlling functional transgene activity are disclosed in Rakhit et al., Chem Biol. 2014; 21(9):1238-52 and Navarro et al., ACS Chem Biol. 2016; 19; 11(8): 2101-2104A.

In some embodiments, a regulatory switch to control the transgene or gene of interest expressed by the nucleic acid construct is a post-translational modification system that incorporates ligand sensitive inteins into the transgene coding sequence, such that the transgene or expressed protein is inhibited prior to splicing. For example, this has been demonstrated using both 4-hydroxytamoxifen and thyroid hormone (see, e.g., U.S. Pat. Nos. 7,541,450, 9,200,045; 7,192,739, Buskirk, et al, Proc Natl Acad Sci USA. 2004 Jul. 20; 101(29): 10505-10510; ACS Synth Biol. 2016 Dec. 16; 5(12): 1475-1484; and 2005 February; 14(2): 523-532. In some embodiments, a post-transcriptional based regulatory switch can be selected from any or a combination of the switches in Table 2.

F. Other Exemplary Regulatory Switches

Any known regulatory switch can be used in the nucleic acid construct to control the gene expression of the transgene expressed by the nucleic acid construct, including those triggered by environmental changes. Additional examples include, but are not limited to; the BOC method of Suzuki et al., Scientific Reports 8; 10051 (2018); genetic code expansion and a non-physiologic amino acid; radiation-controlled or ultra-sound controlled on/off switches (see, e.g., Scott S et al., Gene Ther. 2000 July; 7(13):1121-5; U.S. Pat. Nos. 5,612,318; 5,571,797; 5,770,581; 5,817,636; and WO1999/025385A1. In some embodiments, the regulatory switch is controlled by an implantable system, e.g., as disclosed in U.S. Pat. No. 7,840,263; US2007/0190028A1 where gene expression is controlled by one or more forms of energy, including electromagnetic energy, that activates promoters operatively linked to the transgene in the nucleic acid construct.

In some embodiments, a regulatory switch envisioned for use in the nucleic acid construct is a hypoxia-mediated or stress-activated switch, e.g., such as those disclosed in WO1999060142A2, U.S. Pat. Nos. 5,834,306; 6,218,179; 6,709,858; US2015/0322410; Greco et al., (2004) Targeted Cancer Therapies 9, S368, as well as FROG, TOAD and NRSE elements and conditionally inducible silence elements, including hypoxia response elements (HREs), inflammatory response elements (IREs) and shear-stress activated elements (SSAEs), e.g., as disclosed in U.S. Pat. No. 9,394,526. Such an embodiment is useful for turning on expression of the transgene from the nucleic acid construct after ischemia or in ischemic tissues, and/or tumors.

In some embodiments, a regulatory switch envisioned for use in the nucleic acid construct is an optogenetic (e.g., light controlled) regulatory switch, e.g., such as one of the switches reviewed in Polesskaya et al., BMC Neurosci. 2018; 19(Suppl 1): 12, and are also envisioned for use herein. In such embodiments, a nucleic acid construct can comprise genetic elements are light sensitive and can regulate transgene expression in response to visible wavelengths (e.g. blue, near IR). nucleic acid constructs comprising optogenetic regulatory switches are useful when expressing the transgene in locations of the body that can receive such light sources, e.g., the skin, eye, muscle etc., and can also be used when nucleic acid constructs are expressing transgenes in internal organs and tissues, where the light signal can be provided by a suitable means (e.g., implantable device as disclosed herein). Such optogenetic regulatory switches include use of the light responsive elements, or light-inducible transcriptional effector (LITE) (e.g., disclosed in 2014/0287938), a Light-On system (e.g., disclosed in Wang et al., Nat Methods. 2012 Feb. 12; 9(3):266-9; which has reported to enable in vivo control of expression of an insulin transgene, the Cry2/CIB1 system (e.g., disclosed on Kennedy et al., Nature Methods; 7, 973-975 (2010); and the FKF1/GIGANTEA system (e.g., disclosed in Yazawa et al., Nat Biotechnol. 2009 October; 27(10):941-5).

G. Kill Switches

Other embodiments of the invention relate to a nucleic acid construct comprising a kill switch. A kill switch as disclosed herein enables a cell comprising the nucleic acid construct to be killed or undergo programmed cell death as a means to permanently remove an introduced nucleic acid construct from the subject's system. It will be appreciated by one of ordinary skill in the art that use of kill switches in the nucleic acid constructs of the invention would be typically coupled with targeting of the nucleic acid construct to a limited number of cells that the subject can acceptably lose or to a cell type where apoptosis is desirable (e.g., cancer cells). In all aspects, a "kill switch" as disclosed herein is designed to provide rapid and robust cell killing of the cell comprising the nucleic acid construct in the absence of an input survival signal or other specified condition. Stated another way, a kill switch encoded by a nucleic acid construct herein can restrict cell survival of a cell comprising a nucleic acid construct to an environment defined by specific input signals. Such kill switches serve as a biological biocontainment function should it be desirable to remove the nucleic acid construct from a subject or to ensure that it will not express the encoded transgene. Accordingly, kill switches are synthetic biological circuits in the nucleic acid construct that couple environmental signals with conditional survival of the cell comprising the nucleic acid construct. In some embodiments different nucleic acid constructs can be designed to have different kill switches. This permits one to be able to control which transgene expressing cells are killed if cocktails of nucleic acid constructs are used.

In some embodiments, a nucleic acid construct can comprise a kill switch which is a modular biological containment circuit. In some embodiments, a kill switch encompassed for use in the nucleic acid construct is disclosed in WO2017/059245, which describes a switch referred to as a "Deadman kill switch" that comprises a mutually inhibitory arrangement of at least two repressible sequences, such that an environmental signal represses the activity of a second molecule in the construct (e.g., a small molecule-binding transcription factor is used to produce a 'survival' state due to repression of toxin production). In cells comprising a nucleic acid construct comprising a deadman kill switch, upon loss of the environmental signal, the circuit switches permanently to the 'death' state, where the toxin is now derepressed, resulting in toxin production which kills the cell. In another embodiment, a synthetic biological circuit referred to as a "Passcode circuit" or "Passcode kill switch" that uses hybrid transcription factors (TFs) to construct complex environmental requirements for cell survival, is provided. The Deadman and Passcode kill switches described in WO2017/059245 are particularly useful for use in nucleic acid constructs, as they are modular and customizable, both in terms of the environmental conditions that control circuit activation and in the output modules that control cell fate. With the proper choice of toxins, including, but not limited to an endonuclease, e.g., a EcoRI, Passcode circuits present in the nucleic acid construct can be used to not only kill the host cell comprising the nucleic acid construct, but also to degrade its genome and accompanying plasmids.

Other kill switches known to a person of ordinary skill in the art are encompassed for use in the nucleic acid construct as disclosed herein, e.g., as disclosed in US2010/0175141; US2013/0009799; US2011/0172826; US2013/0109568, as well as kill switches disclosed in Jusiak et al, Reviews in Cell Biology and molecular Medicine; 2014; 1-56; Kobayashi et al., PNAS, 2004; 101; 8419-9; Marchisio et al., Int. Journal of Biochem and Cell Biol., 2011; 43; 310-319; and in Reinshagen et al., Science Translational Medicine, 2018, 11.

Accordingly, in some embodiments, the nucleic acid construct can comprise a kill switch nucleic acid construct, which comprises the nucleic acid encoding an effector toxin or reporter protein, where the expression of the effector toxin (e.g., a death protein) or reporter protein is controlled by a predetermined condition. For example, a predetermined condition can be the presence of an environmental agent, such as, e.g., an exogenous agent, without which the cell will default to expression of the effector toxin (e.g., a death protein) and be killed. In alternative embodiments, a predetermined condition is the presence of two or more environmental agents, e.g., the cell will only survive when two or more necessary exogenous agents are supplied, and without either of which, the cell comprising the nucleic acid construct is killed.

In some embodiments, the nucleic acid construct is modified to incorporate a kill-switch to destroy the cells comprising the nucleic acid construct to effectively terminate the in vivo expression of the transgene being expressed by the nucleic acid construct (e.g., therapeutic gene, protein or peptide etc.). Specifically, the nucleic acid construct is further genetically engineered to express a switch-protein that is not functional in mammalian cells under normal physiological conditions. Only upon administration of a drug or environmental condition that specifically targets this switch-protein, the cells expressing the switch-protein will be destroyed thereby terminating the expression of the therapeutic protein or peptide. For instance, it was reported that cells expressing HSV-thymidine kinase can be killed upon administration of drugs, such as ganciclovir and cytosine deaminase. See, for example, Dey and Evans, Suicide Gene Therapy by Herpes Simplex Virus-1 Thymidine Kinase (HSV-TK), in Targets in Gene Therapy, edited by You (2011); and Beltinger et al., Proc. Natl. Acad. Sci. USA 96(15):8699-8704 (1999). In some embodiments the nucleic acid construct can comprise a siRNA kill switch referred to as DISE (Death Induced by Survival geneElimination) (Murmann et al., Oncotarget. 2017; 8:84643-84658. Induction of DISE in ovarian cancer cells in vivo).

In some aspects, a deadman kill switch is a biological circuit or system rendering a cellular response sensitive to a predetermined condition, such as the lack of an agent in the cell growth environment, e.g., an exogenous agent. Such a circuit or system can comprise a nucleic acid construct comprising expression modules that form a deadman regulatory circuit sensitive to the predetermined condition, the construct comprising expression modules that form a regulatory circuit, the construct including:

i) a first repressor protein expression module, wherein the first repressor protein binds a first repressor protein nucleic acid binding element and represses transcription from a coding sequence comprising the first repressor protein binding element, and wherein repression activity of the first repressor protein is sensitive to inhibition by a first exogenous agent, the presence or absence of the first exogenous agent establishing a predetermined condition;

ii) a second repressor protein expression module, wherein the second repressor protein binds a second repressor protein nucleic acid binding element and represses transcription from a coding sequence comprising the second repressor protein binding element, wherein the second repressor protein is different from the first repressor protein; and iii) an effector expression module, comprising a nucleic acid sequence encoding an effector protein, operably linked to a genetic element comprising a binding element for the second repressor protein, such that expression of the second repressor protein causes repression of effector expression from the effector expression module, wherein the second expression module comprises a first repressor protein nucleic acid binding element that permits repression of transcription of the second repressor protein when the element is bound by the first repressor protein, the respective modules forming a regulatory circuit such that in the absence of the first exogenous agent, the first repressor protein is produced from the first repressor protein expression module and represses transcription from the second repressor protein expression module, such that repression of effector expression by the second repressor protein is relieved, resulting in expression of the effector protein, but in the presence of the first exogenous agent, the activity of the first repressor protein is inhibited, permitting expression of the second repressor protein, which maintains expression of effector protein expression in the "off" state, such that the first exogenous agent is required by the circuit to maintain effector protein expression in the "off" state, and removal or absence of the first exogenous agent defaults to expression of the effector protein.

In some embodiments, the effector is a toxin or a protein that induces a cell death program. Any protein that is toxic to the host cell can be used. In some embodiments the toxin only kills those cells in which it is expressed. In other embodiments, the toxin kills other cells of the same host organism. Any of a large number of products that will lead to cell death can be employed in a deadman kill switch. Agents that inhibit DNA replication, protein translation or other processes or, e.g., that degrade the host cell's nucleic acid, are of particular usefulness. To identify an efficient mechanism to kill the host cells upon circuit activation, several toxin genes were tested that directly damage the host cell's DNA or RNA. The endonuclease ecoRI[21], the DNA gyrase inhibitor ccdB[22] and the ribonuclease-type toxin mazF[23] were tested because they are well-characterized, are native to *E. coli*, and provide a range of killing mechanisms. To increase the robustness of the circuit and provide an independent method of circuit-dependent cell death, the system can be further adapted to express, e.g., a targeted protease or nuclease that further interferes with the repressor that maintains the death gene in the "off" state. Upon loss or withdrawal of the survival signal, death gene repression is even more efficiently removed by, e.g., active degradation of the repressor protein or its message. As non-limiting examples, mf-Lon protease was used to not only degrade Lad but also target essential proteins for degradation. The mf-Lon degradation tag pdt #1 can be attached to the 3' end of five essential genes whose protein products are particularly sensitive to mf-Lon degradation[20], and cell viability was measured following removal of ATc. Among the tested essential gene targets, the peptidoglycan biosynthesis gene murC provided the strongest and fastest cell death phenotype (survival ratio$<1\times10^{-4}$ within 6 hours).

As used herein, the term "predetermined input" refers to an agent or condition that influences the activity of a transcription factor polypeptide in a known manner. Generally, such agents can bind to and/or change the conformation of the transcription factor polypeptide to thereby modify the activity of the transcription factor polypeptide. Examples of predetermined inputs include, but are not limited to, environmental input agents that are not required for the survival of a given host organism (i.e., in the absence of a synthetic biological circuit as described herein). Conditions that can provide a predetermined input include, for example temperature, e.g., where the activity of one or more factors is temperature-sensitive, the presence or absence of light, including light of a given spectrum of wavelengths, and the concentration of a gas, salt, metal or mineral. Environmental input agents include, for example, a small molecule, biological agents such as pheromones, hormones, growth factors, metabolites, nutrients, and the like and analogs thereof; concentrations of chemicals, environmental byproducts, metal ions, and other such molecules or agents; light levels; temperature; mechanical stress or pressure; or electrical signals, such as currents and voltages.

In some embodiments, reporters are used to quantify the strength or activity of the signal received by the modules or programmable synthetic biological circuits of the invention. In some embodiments, reporters can be fused in-frame to other protein coding sequences to identify where a protein is located in a cell or organism. Luciferases can be used as effector proteins for various embodiments described herein, for example, measuring low levels of gene expression, because cells tend to have little to no background luminescence in the absence of a luciferase. In other embodiments, enzymes that produce colored substrates can be quantified using spectrophotometers or other instruments that can take absorbance measurements including plate readers. Like luciferases, enzymes like β-galactosidase can be used for measuring low levels of gene expression because they tend to amplify low signals. In some embodiments, an effector protein can be an enzyme that can degrade or otherwise destroy a given toxin. In some embodiments, an effector protein can be an odorant enzyme that converts a substrate to an odorant product. In some embodiments, an effector protein can be an enzyme that phosphorylates or dephosphorylates either small molecules or other proteins, or an enzyme that methylates or demethylates other proteins or DNA.

In some embodiments, an effector protein can be a receptor, ligand, or lytic protein. Receptors tend to have three domains: an extracellular domain for binding ligands such as proteins, peptides or small molecules, a transmembrane domain, and an intracellular or cytoplasmic domain which frequently can participate in some sort of signal transduction event such as phosphorylation. In some embodiments, transporter, channel, or pump gene sequences are used as effector proteins. Non-limiting examples and sequences of effector proteins for use with the kill switches as described herein can be found at the Registry of Standard Biological Parts on the world wide web at parts.igem.org.

As used herein, a "modulator protein" is a protein that modulates the expression from a target nucleic acid sequence. Modulator proteins include, for example, transcription factors, including transcriptional activators and repressors, among others, and proteins that bind to or modify a transcription factor and influence its activity. In some embodiments, a modulator protein includes, for example, a protease that degrades a protein factor involved in the regulation of expression from a target nucleic acid sequence. Preferred modulator proteins include modular proteins in which, for example, DNA-binding and input agent-binding or responsive elements or domains are separable and transferrable, such that, for example, the fusion of the DNA binding domain of a first modulator protein to the input agent-responsive domain of a second results in a new protein that binds the DNA sequence recognized by the first protein, yet is sensitive to the input agent to which the second protein normally responds. Accordingly, as used herein, the term "modulator polypeptide," and the more specific "repressor polypeptide" include, in addition to the specified polypeptides, e.g., "a Lad (repressor) polypeptide," variants, or derivatives of such polypeptides that responds to a different or variant input agent. Thus, for a Lad polypeptide, included are Lad mutants or variants that bind to agents other than lactose or IPTG. A wide range of such agents are known in the art.

Polyadenylation Sequences: A sequence encoding a polyadenylation sequence can be included in the nucleic acid construct to stabilize the mRNA expressed from the nucleic acid construct, and to aid in nuclear export and translation. In one embodiment, the nucleic acid construct does not include a polyadenylation sequence. In other embodiments, the vector includes at least 1, at least 2, at least 3, at least 4, at least 5, at least 10, at least 15, at least 20, at least 25, at least 30, at least 40, least 45, at least 50 or more adenine dinucleotides. In some embodiments, the polyadenylation sequence comprises about 43 nucleotides, about 40-50 nucleotides, about 40-55 nucleotides, about 45-50 nucleotides, about 35-50 nucleotides, or any range there between.

The expression cassettes can include a poly-adenylation sequence known in the art or a variation thereof, such as a naturally occurring sequence isolated from bovine BGHpA or a virus SV40 pA or a synthetic poly A sequence. Some expression cassettes can also include SV40 late polyA signal upstream enhancer (USE) sequence. In some embodiments, the, USE can be used in combination with SV40 pA or heterologous poly-A signal.

The expression cassettes can also include a post-transcriptional element to increase the expression of a transgene. In some embodiments, Woodchuck Hepatitis Virus (WHP) posttranscriptional regulatory element (WPRE) is used to increase the expression of a transgene. Other posttranscriptional processing elements such as the post-transcriptional element from the thymidine kinase gene of herpes simplex virus, or hepatitis B virus (HBV) can be used. Secretory sequences can be linked to the transgenes, e.g., VH-02 and VK-A26 sequences.

4. General Methods for Generating an Engineered iPSC:

In certain aspects, B2M and/or CIITA gene expression, activity or function is disrupted in cells, such as PSCs (e.g., ESCs or iPSCs). In some embodiments, the gene disruption is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. For example, the disruption can be effected be sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the B2M and/or CIITA gene or a portion thereof.

In some embodiments, the disruption of the expression, activity, and/or function of the gene is carried out by disrupting the gene. In some aspects, the gene is disrupted so that its expression is reduced by at least at or about 20, 30, or 40%, generally at least at or about 50, 60, 70, 80, 90, or 95% as compared to the expression in the absence of the gene disruption or in the absence of the components introduced to effect the disruption.

In some embodiments, the disruption is transient or reversible, such that expression of the gene is restored at a later time. In other embodiments, the disruption is not reversible or transient, e.g., is permanent.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g., an endonuclease, such as a gene-targeted nuclease. In some aspects, the breaks are induced in the coding region of the gene, e.g., in an exon. For example, in some embodiments, the induction occurs near the N-terminal portion of the coding region, e.g., in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene.

In some embodiments, gene disruption is achieved using antisense techniques, such as by RNA interference (RNAi), short interfering RNA (siRNA), short hairpin (shRNA), and/or ribozymes are used to selectively suppress or repress expression of the gene. siRNA technology is RNAi which employs a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions. In some aspects, the siRNA is comprised in a polycistronic construct. In particular aspects, the siRNA suppresses both wild-type and mutant B2M and/or CIITA translation from endogenous mRNA.

In some aspects, the gene disruption is carried out by the administration of a pharmacological drug or small molecule inhibitor of B2M and/or CIITA. There is a link between DNA methylation and the deacetylation of chromatin. There are both histone deacetylase (HDAC)-dependent and HDAC-independent modes of transcriptional repression by B2M and/or CIITA. Thus, HDAC inhibitors such as trichostatin A (TSA) or Valproic acid can be used to disrupt B2M and/or CIITA. In addition, protein inhibitors, DNA binding proteins that inhibit transcription, and proteins that bind to B2M and/or CIITA protein and inhibit function may be used. Further, in differentiated female mouse embryonic stem cells, a PDPK1 inhibitor decreased Xist levels and increased B2M and/or CIITA mRNA levels compared with vehicle (Bhatnagar et al., 2014).

A. Endonucleases

In some embodiments, the disruption is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 2011/0301073.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 2005/0064474; 2006/0188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone nonhomologous end joining (NHEJ) and homology-directed repair (HDR). In some embodiments the nuclease is an endonuclease, such as a zinc finger nuclease (ZFN), TALE nuclease (TALEN), and RNA-guided endonuclease (RGEN), such as a CRISPR-associated (Cas) protein, or a meganuclease.

In some embodiments, a donor nucleic acid, e.g., a donor plasmid or nucleic acid encoding the genetically engineered antigen receptor, is provided and is inserted by HDR at the site of gene editing following the introduction of the DSBs. Thus, in some embodiments, the disruption of the gene and the introduction of the antigen receptor, e.g., CAR, are carried out simultaneously, whereby the gene is disrupted in part by knock-in or insertion of the CAR-encoding nucleic acid.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

1. ZFPs and ZFNs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al, 2013.

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al., 2002; Pabo et al., 2001; Isalan et al., 2001; Segal et al., 2001; Choo et al., 2000; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In some aspects, disruption of B2M and/or CIITA is carried out by contacting a first target site in the gene with a first ZFP, thereby disrupting the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains.

In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type liS restriction enzyme and one or more zinc finger binding domains, which may or may not be engineered. In some embodiments, the cleavage domain is from the Type liS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al., 1992; Li et al., 1993; Kim et al., 1994a; Kim et al., 1994b. 269:31, 978-31, 982.]

In some embodiments, ZFNs target a gene present in the engineered cell. In some aspects, the ZFNs efficiently generate a double strand break (DSB), for example at a predetermined site in the coding region of the gene. Typical regions targeted include exons, regions encoding N terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins (Gaj et al., Trends in Biotechnology, 2013, 31(7), 397-405). In some embodiments, commercially available zinc fingers are used or are custom designed. (See, for example, Sigma-Aldrich catalog numbers CSTZFND, CSTZFN, CTil-1KT, and PZD0020).

2. TALs, TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. See, U.S. Patent Publication No. 2011/0301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, 1998) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3). Exemplary molecules are described, e.g., in U.S. Patent Publication Nos. US 2014/0120622, and 2013/0315884.

In some embodiments the TALEN s are introduced as trans genes encoded by one or more plasmid vectors. In some aspects, the plasmid vector can contain a selection marker which provides for identification and/or selection of cells which received said vector.

3. RGENs (CRISPR/Cas Systems)

In some embodiments, the disruption is carried out using one or more DNA-binding nucleic acids, such as disruption via an RNA-guided endonuclease (RGEN). For example, the disruption can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

B. Delivery of Nucleic Acids

In some aspects, a nucleic acid encoding the DNA-targeting molecule, complex, or combination, is administered or introduced to the cell. The nucleic acid typically is administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding the disruption molecule or complex, such as the DNA-targeting molecule, is delivered to the cell. In some aspects, the delivery is by delivery of one or more vectors, one or more transcripts thereof, and/or one or more proteins transcribed therefrom, is delivered to the cell.

In some embodiments, the polypeptides are synthesized in situ in the cell as a result of the introduction of polynucleotides encoding the polypeptides into the cell. In some aspects, the polypeptides could be produced outside the cell and then introduced thereto. Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, 1992; Nabel & Feigner, 1993; Mitani & Caskey, 1993; Dillon, 1993; Miller, 1992; Van Brunt, 1988; Vigne, 1995; Kremer & Perricaudet, 1995; Haddada et al., 1995; and Yu et al., 1994.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase.

In certain embodiments, the transgene cassette is integrated through the use of transposase systems. A transposable element (TE or transposon) is a DNA sequence that can change its position within the genome, sometimes creating or reversing mutations and altering the cell's genome size. Transposons can be used in genetic research and recombinant genetic engineering for insertional mutagenesis. Insertional mutagenesis is when transposons function as vectors to help remove and integrate genetic sequences. Given their relatively simple design and inherent ability to move DNA sequences, transposons are highly compatible at transducing genetic material, making them ideal genetic tools. Generally, transposase systems include Sleeping Beauty, miniTol2 and PiggyBac.

A miniTol2 plasmid system (Balciunas et al., 2006) may be used for integration of the transgene. In the two-plasmid system, one plasmid contains the terminal Tol2 sequences flanking the promoter driving the reporter gene and the other plasmid (pTrans) contains the transposase sequence under the control of another promoter. Promoters for use in the miniTol2 plasmid system can be the pCAGGS promoter, the CMV IE promoter. In this system, the miniTol-reporter gene sequence is incorporated into the target genomic DNA while the pTrans sequence will not be incorporated.

The PiggyBac transposon which is a mobile genetic element that efficiently transposes between vectors and chromosomes via a "cut and paste" mechanism may be used. During transposition, the Super PB transposase recognizes transposon-specific inverted terminal repeat sequences (ITRs) located on both ends of the transposon vector and moves the contents from the original sites and efficiently integrates them into TTAA chromosomal sites. The powerful activity of the PiggyBac transposon system enables genes of interest between the two ITRs in the PB vector to be easily mobilized into target genomes

VII. Sources of Pluripotent Stem Cells for Generation of Stem-Cell Derived T/NK Cell Progenitors Cells In certain embodiments of the present disclosure, there are disclosed methods and compositions for generating T/NK progenitors from pluripotent stem cells (PSCs). The PSCs may be stem cells including but are not limited to, iPSCs and embryonic stem cells (ESCs).

The PSCs used in the present method to produce T/NK progenitors according to the methods disclosed herein are characterized by the ability to renew themselves through mitotic cell division and the ability to differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin or intestinal tissues.

In particular aspects, the PSCs used herein are human ESCs or iPSCs which are capable of long-term proliferation in vitro, while retaining the potential to differentiate into all cell types of the body, including the T/NK progenitors of the present disclosure. Thus, these cells could potentially provide an unlimited supply of patient-specific functional cells for both drug development and therapeutic uses.

A. Embryonic Stem Cells

In some embodiments, the T/NK progenitor cells as described herein can be derived from human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein in their entireties by reference.

In certain aspects, the PSCs are embryonic stem cells (ESCs). ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson and Marshall, 1998; Thomson et al., 1995; Thomson and Odorico, 2000; U.S. Pat. No. 5,843,780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

Human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used. Stem cells are maintained in culture in a pluripotent state by routine passage until it is desired that they be differentiated into definitive endoderm then ultimately to endocrine precursor cells and/or pancreatic islet hormone-expressing cells.

In some embodiments, the T/NK progenitor cells generated according to the methods as described herein can be derived from reprogrammed cells, e.g., induced pluripotent stem cells (iPS cells), which can be derived from differentiated or somatic cells. In some embodiments, the iPSC are derived from fibroblasts, or from a subject with cancer or an immune disease. In some embodiments, the iPS cells can be derived from, for example, but not limited to, neoplastic cells, tumor cells and cancer cells. Such an embodiment is useful in identifying and/or isolating and/or studying cancerous cells and tumor cells. In some embodiments, the de-differentiated cells are from a subject, and in some embodiments, the de-differentiated stem cells are obtained from a biopsy, e.g., a patient with cancer.

B. Induced Pluripotent Stem Cells

In some embodiments, an iPS cell used for generation of a T/NK progenitor cell according to the methods disclosed herein, can be produced by any method known in the art can be used, for example virally-induced or chemically induced generation of iPS cells are described in Mauritz et al., Circulation. 2008; 118:507-517, and disclosed in International Application WO2008/088882, EP1970446, US2009/0047263, 052009/0068742, and 2009/0227032, which are incorporated herein in their entirety by reference.

iPS cells can also be generated using other methods commonly known in the art, such as, including but not limited to uses of non-viral methods, polycistronic vectors, mRNA species, miRNA, and proteins, including International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/0112693, US2010/07542, US2009/0246875, US2009/0203141, US2010/00625343, US2009/0269763, which are incorporated herein in their entirety by reference.

In other aspects, the PSCs used herein are induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648; U.S. Publication No. 2015/0191697). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. iPS cells can be grown under conditions that are known to differentiate human ES cells into specific cell types, and express human ES cell markers including: SSEA-1, SSEA-3, SSEA-4, TRA-1-60, and TRA-1-81.

Somatic cells can be reprogrammed to produce iPS cells using methods known to one of skill in the art. One of skill in the art can readily produce iPS cells, see for example, Published U.S. Patent Application No. 2009/0246875, Published U.S. Patent Application No. 2010/0210014; Published U.S. Patent Application No. 2012/0276636; U.S. Pat. Nos. 8,058,065; 8,129,187; PCT Publication NO. WO 2007/069666 A1, U.S. Pat. Nos. 8,268,620; 8,546,140; 9,175,268; 8,741,648; U.S. Patent Application No. 2011/0104125, and U.S. Pat. No. 8,691,574, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which are both incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the methods disclosed herein.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments, plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. In particular aspects, the plasmids do not comprise a tyrosinase enhancer or promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, and U.S. application Ser. No. 12/478,154 which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911, PCT/JP2011/069588).

C. Embryonic Stem Cells Derived by Somatic Cell Nuclear Transfer

PSCs for producing the T/NK progenitor cells according to the methods disclosed herein can also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

In some embodiments, a T/NK progenitor cell generated according to the methods as disclosed herein can also be generated from stem cells, preferably adult stem cells, more preferably adult stem cells expressing Lgr5 (Barker et al., Cell Stem Cell 7, 656 2010, WO2010/090513, WO2012/168930 and Sato et al., GASTROENTEROLOGY 2011; 141:1762-1772).

In another embodiment, a iPSC for generation of a T/NK progenitor cell according to the methods disclosed herein can be derived from a cell isolated from tissue including solid tissues (the exception to solid tissue is whole blood, including blood, plasma and bone marrow) which were previously unidentified in the literature as sources of stem cells. In some embodiments, the tissue is lung tissue. In other embodiments, the tissue is for example but not limited to, umbilical cord blood, placenta, bone marrow, or chondral villi.

VIII. Uses of the iT Cells or iNK Cells for Treatment or Personalized Medicine As disclosed in the Examples, the ability to generate pluripotent stem cell-derived T/NK progenitor allows for the unlimited ability to generate a population of T cells (i.e., iT cells) and NK cells (i.e. iNK cells). The ability to produce large populations of T cells can be used in combination with the ability to transduce the T cells and express an engineered chimeric antigen receptor (CAR) within these cell populations. These engineered T cells can further be used for treatment of cancer as a form of cancer therapy. Accordingly, T-cells generated using the methods and compositions as disclosed herein can be transduced with an exogenous CAR, e.g., CD19. These engineered CAR-expressing iT cells can be used to kill tumor cells according to known methods (see, e.g., Raji cells, cultured cell line of lymphoblastoid cells derived from a Burkitt lymphoma).

In one embodiment, derived T/NK progenitors can be used to produce iT cells which are modified to be CAR expressing T cells for use to kill tumor cells. The tumor cells are contacted with the CAR expressing T cells in an effective amount in order to kill the tumor cells.

In another embodiment, the CAR expressing iT cells generated using the methods and compositions as disclosed herein can be used to treat a subject having cancer. The CAR expressing iT cells can be administered in an effective amount to treat the cancer. The CAR expressing iT cells can be adoptively transferred to the patient. Suitable engineered CAR-expressing iT cells for use in treating a subject having cancer are known in the art and include, CAR that are specific to a tumor-associated antigen. For example, in one embodiment, the CAR is a CD19 chimeric antigen receptor.

Design and methods of making CARS are known in the art and include, but are not limited to the first, second, third and fourth generation of CARs. Genetically engineered CARs are contemplated herein. These genetically engineered receptors, CARs, comprise an antigen-specific recognition domain that binds to specific target antigen or cell and a transmembrane domain linking the extracellular domain to an intracellular signaling domain. Design and methods of making CAR are known in the art. In one embodiment, the antigen-specific recognition domain in the extracellular domain redirects cytotoxicity of the effector cell toward tumor cells. By way of an exemplary embodiment, a CAR expressing CD19, which is expressed on certain kinds of leukemia or lymphoma, can be expressed by the iT cells derived by these methods and used to kill tumor cells (Riji cells, which are a cell line derived from Burkitt Lymphoma patient).

The iT cells produced by the methods herein can be engineered to express CAR specific for tumor or cancer cells, and used in the treatment of such cancers. As is known in the art, a cancer is generally considered as uncontrolled cell growth. Suitable cancers that can be treated using the T cells expressing the engineered CAR receptors include, but are not limited to, hematologic malignancies and solid tumors. Suitable hematologic malignancies are forms of cancer that begin in the cells of blood-forming tissue, such as the bone marrow, or in the cells of the immune system. Examples of hematologic cancer include, but are not limited, to, for example, acute and chronic leukemias, lymphomas, multiple myeloma and myelodysplastic syndromes. The methods of the present invention can be used to treat any cancer, any metastases thereof, including, but not limited to, carcinoma, lymphoma, blastoma, sarcoma, and leukemia. Suitable cancers able to be treated by the compositions, methods and kits described herein include, but are not limited to, for example, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, and peripheral neuroepithelioma. In one embodiment, the cancer is selected from leukemia, lymphoma, melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

The term "treating" can be characterized by one or more of the following: (a) the reducing, slowing or inhibiting the growth of tumor cells; (b) preventing the further growth of tumor cells; (c) reducing or preventing the metastasis of tumor cells within a patient, and (d) reducing or ameliorating at least one symptom of the tumor or cancer. In some embodiments, the optimum effective amounts can be readily determined by one of ordinary skill in the art using routine experimentation. As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

As used herein "subject" or "patient" refers to mammals and non-mammals. The term "subject" does not denote a particular age or sex. In one specific embodiment, a subject is a mammal, preferably a human. In some embodiments, the subject suffers from a cancer, particularly a hemotologic malignancy.

1. Pharmaceutical Compositions

In another aspect, the present application provides a pharmaceutical composition comprising isolated T/NK progenitors, or iT cells or iNK cells, and a pharmaceutically acceptable diluent or carrier.

Suitable diluents and carriers are described, for example, in Remington's Pharmaceutical Sciences. On this basis, the compositions include, albeit not exclusively, solutions of the iT cells or iNK cells as disclosed herein, in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain anti-oxidants, buffers, bacteriostats and solutes that render the compositions substantially compatible with the tissues or the blood of an intended recipient. Other components that may be present in such compositions include water, surfactants (such as Tween™), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and non-toxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions of the application can be administered for example, by parenteral, intra-venous, subcutaneous, intramuscular, intracranial, intraorbital, ophthalmic, intraventricu-lar, intracapsular, intraspinal, intracisternal, intraperitoneal, intranasal, aerosol or oral ad-ministration. For parenteral administration, solutions of the iT cells or iNK cells as disclosed herein, can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

Preferably the iT cells or iNK cells, as disclosed herein, are present in an amount effective for treating a disease state in a mammalian need thereof. In one embodiment the iT cells or iNK cells as disclosed herein. is present in an amount effective to enhance hematopoietic progenitor cell engraftment in a mammal in need thereof. Optionally, the composition further comprises iT cells or iNK cells, as disclosed herein, or tissue for transplantation. In one embodiment the tissue comprises a thymus. In another embodiment the tissue comprises an organ.

2. Applications

The present application includes the use of the generated iT cells or iNK cells, as disclosed herein in any and all applications.

A. Genetic Modification iT cells or iNK cells, as disclosed herein that are generated using the methods of the application may be genetically modified (transduced or transfected) either in nature or by genetic engineering techniques in vivo or in vitro. Cells can be modified by introducing mutations into genes in the cells or by introducing transgenes into the cells. Insertion or deletion mutations may be introduced in a cell using standard techniques. A gene encoding a selectable marker may also be integrated into the cells.

An aspect of the present application relates to iT cells or iNK cells as disclosed herein, that are genetically engineered in such a manner that the cells or cells derived therefrom produce, in vitro or in vivo, polypeptides, hormones and proteins not normally produced in the cells in biologically significant amounts, or produced in small amounts but in situations in which regulatory expression would lead to a therapeutic benefit. For example, the cells could be engineered with a gene that expresses insulin at levels compatible with normal injected doses, or with a gene that can make up for a deficiency or abnormality of a gene causing a disease. Alternatively, the cells could be modified such that a protein normally expressed will be expressed at much lower levels. These products would then be secreted into the surrounding media or purified from the cells. The cells formed in this way can serve as continuous short term or long term production systems of the expressed substance.

Thus, in accordance with this aspect of the application, iT cells or iNK cells as disclosed herein generated using the methods of the application can be modified with genetic material of interest. The modified cells can be cultured in vitro under suitable conditions so that they are able to express the product of the gene expression or secrete the expression product. These modified cells can be administered so that the expressed product will have a beneficial effect.

In a further embodiment, transduced T/NK progenitor cells (with the potential to form mature T cells) can be induced in vivo to differentiate into T cells that will express the gene product. For example, the transduced cells may be administered to induce production of T cells having the transduced gene. The cells may be administered in a mixture with other cells or separately and may be delivered to a targeted area. The cells can be introduced intravenously and home to a targeted area. Alternatively, the cells may be used alone and caused to differentiate in vivo.

Thus, genes can be introduced into cells that are then injected into a recipient where the expression of the gene will have a therapeutic effect. For example, an insulin gene may be introduced into the cells to provide a constant therapeutic dose of insulin in the bone mar-row and peripheral blood.

The technology may be used to produce additional copies of essential genes to allow augmented expression by T cells of certain gene products in vivo. These genes can be, for example, hormones, matrix proteins, cell membrane proteins, and cytokines.

In a specific embodiment, the iT cells or iNK cells as disclosed herein, are engineered to recognize an antigen such as a tumor antigen, a viral antigen or a bacterial antigen. As such the immune response to the target antigen will be augmented by administering antigen specific progenitor T cells.

B. Therapeutic Applications

The ability to generate in vitro-derived human progenitor T cells and to test their safety in human/mouse immune engraftment models, opens avenues for cellular based approaches for treating immune-related disorders of the T lineage (Legrand et al., 2006; van den Brink et al., 2004). T cells are the major effector arm of the adaptive immune system in recognizing and eliminating viral and bacterial pathogens. In certain rare blood cancers such as T cell acute lymphoblastic leukemia (T-ALL), T cells proliferate crowding out healthy immune cells and perturbing normal immune function (Ferrando et al., 2002; Weng et al., 2004). Although chemotherapy can often impart therapeutic benefits in cancer patients, it often can lead to immuno-deficiency and susceptibility to opportunistic infections. Opportunistic infections also pose a serious concern in AIDS patients whose CD4+ T cells have been depleted following infection with HIV. While immunodeficiency remains a serious concern in HIV/AIDS and cancer, immune-hyperactivity is equally problematic in autoimmune disease where T cells that lack proper regulatory control, make immune responses to self-tissue.

Accordingly, the present application includes a method of treating an animal having a condition requiring an increase in the number of T cells comprising administering an effective amount of a progenitor T cell to an animal in need thereof.

As used herein, the phrase "effective amount" or "therapeutically effective amount" means an amount effective, at dosages and for periods of time necessary to achieve the desired result. Effective amounts may vary according to factors such as the disease state, age, sex, weight of the animal. The amount of a given cell preparation that will correspond to such an amount will vary depending upon various factors. Such as the pharmaceutical formulation, the route of administration, the type of disease or disorder, the identity of the subject or host being treated, and the like, but can nevertheless be routinely determined by one skilled in the art. An "effective amount" will preferably be an amount effective for the progenitor T cells to engraft the subject being treated.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment.

The term "animal" as used herein means any member of the animal kingdom and is preferably a human.

A "condition requiring an increase in number of T cells" includes any condition wherein T cell levels are reduced as compared to a healthy animal, including, without limitation, immunodeficiency, cancer, genetic diseases, infectious diseases and autoimmunity, some of which are described in detail below.

(i) Cancer

In 2005, nearly 128,000 individuals were diagnosed with myeloma, lymphoma and leukemia in North America (US & Canada). Following aggressive myeloablative-chemo/radiotherapy of these blood cancers, these individuals may become immunodeficient and require stem cell transplantation to replace or restore their immune system. In-deed, every year in North America 9,000 individuals undergo stem cell transplantation. Although, HSCs may be obtained from bone marrow, GM-CSF-mobilized peripheral blood, or cord blood, several clinical challenges present themselves in most stem cell transplantations: from finding a suitably major-histocompatible matched donor, to pre-venting GvHD, to successful engraftment of a donor immune system onto the host (So-cie, 2005). Most immune cells recover quickly following transplantation, but T cells take the most time (~C2 years) to recover in terms of cell numbers and function (Petropoulos and Chan, 2005). This is perhaps dictated by the broad repertoire of TCRs required to cover the range of environmental and pathogenic antigens that an individual will be exposed to. Until that broad repertoire is re-established, gaps may exist that permit the emergence of opportunistic infections.

Accordingly, the present application provides a method of treating or preventing cancer comprising administering an effective amount of a progenitor T cell to an animal in need thereof.

In one embodiment, the iT cells or iNK cells as disclosed herein, have been genetically engineered to recognize tumor specific antigens. For example, progenitor T cells could be manufactured to recognize tumor-specific antigens found in certain breast cancers as well as Burkitt's lymphoma, neuroblastoma, malignant melanoma, osteosarcoma, and renal cell carcinoma (Renkvist et al., 2001). One example of this genetic approach utilizing CD8+ Wilms' tumor (WT1) gene-specific cytotoxic T-lymphocyte clones for the treatment of Chronic Myeloid Leukemia (CML) or Acute Lymphoblastic Leukemia (ALL). Thus, progenitor T cell transplantation could be used as an adjuvant therapy with stem cell transplantation to quickly reconstitute the T cell compartment in patients with terminal illness or specifically target cancer cells for destruction (van den Brink et al., 2004).

In certain aspects, the invention includes a method of using the T/NK progenitors for making iT cells for the production of engineered CAR-T cells using an expression vector containing a DNA construct encoding the CAR.

In another aspect, this invention is a method of stably transfecting the iT cells generated using the methods disclosed herein by electroporation, or other non-viral gene transfer (such as, but not limited to sonoporation) using naked DNA. Most investigators have used viral vectors to carry heterologous genes into T cells. By using naked DNA, the time required to produce redirected T cells can be reduced. "Naked DNA" means DNA encoding a chimeric T-cell receptor (cTCR) contained in an expression cassette or vector in proper orientation for expression. The electroporation method of this invention produces stable transfectants that express and carry on their surfaces the chimeric TCR (cTCR).

"Chimeric TCR" means a receptor that is expressed by T cells and that comprises intracellular signaling, transmembrane, and extracellular domains, where the extracellular domain is capable of specifically binding in an MHC unrestricted manner an antigen that is not normally bound by a T-cell receptor in that manner. Stimulation of the T cells by the antigen under proper conditions results in proliferation (expansion) of the cells. However, the method is applicable to transfection with chimeric TCRs that are specific for other target antigens, such as chimeric TCRs that are specific for HER2/Neu, ERBB2, folate binding protein, renal cell carcinoma, and HIV-1 envelope glycoproteins gp20 and gp41. Other cell-surface target antigens include, but are not limited to, CD20, carcinoembryonic antigen, mesothelin, c-Met, CD56, HERV-K, GD2, GD3, aiphafetoprotein, CD23, CD30, CD123, IL-11Ralpha, kappa chain, lambda chain, CD70, CA-125, MUC-1, EGFR and variants, epithelial tumor antigen, and so forth.

In certain aspects, iT cells generated using the methods disclosed herein can be used for generation of CAR-T cells (i.e., CAR-iT cells). Conditions include the use of mRNA and DNA and electroporation. Following transfection, the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric receptor is expanded ex vivo. The recombinant iT cells may be expanded by stimulation with IL-2, or other cytokines that bind the common gamma-chain (e.g., IL-7, IL-15, IL-21, and others). In a further aspect, the genetically modified cells may be cryopreserved.

iT cells propagation (survival) after infusion may be assessed by: (i) q-PCR using primers specific for the CAR; and/or (ii) flow cytometry using an antibody specific for the CAR.

This invention also represents the targeting of a cancer, using the iT cells. Malignant B cells are an excellent target for iT cells, as B cells can serve as immunostimulatory antigen-presenting cells for T cells. In certain embodiments of the invention, CAR-iT cells of the invention are delivered to an individual in need thereof, such as an individual that has cancer or an infection. The CAR-iT cells then enhance the individual's immune system to attack the respective cancer or pathogenic cells. In some cases, the individual is provided with one or more doses of the antigen-specific CAR-iT cells. In cases where the individual is provided with two or more doses of the antigen-specific CAR-iT cells, the duration between the administrations should be sufficient to allow time for propagation in the individual, and in specific embodiments the duration between doses is 1, 2, 3, 4, 5, 6, 7, or more days.

The source of the iT cells that are modified to include both a chimeric antigen receptor may be of any kind, but in specific embodiments the cells are obtained from a bank of umbilical cord blood, peripheral blood, human embryonic stem cells, or induced pluripotent stem cells, for example. The different banks will not share the same HLAs, so multiple banks may be employed.

Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

In some embodiments, a pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

In some embodiments, a composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the engineered iT cells is present in the composition and introduced into the subject such that long-term, specific, antitumor responses are established to reduce the size of a tumor or eliminate tumor growth or regrowth than would otherwise result in the absence of such treatment. Desirably, the amount of the engineered iT cells reintroduced into the subject causes a 10%, 20%, 30%, 40%, 50%, 60%, 70%, 80%, 90%, 95%, 98%, or 100% decrease in tumor size when compared to otherwise same conditions wherein the engineered immortalized T cells are not present. Accordingly, the amount of the iT cells administered should take into account the route of administration and should be such that a sufficient number of the iT cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of the iT cells desirably should be sufficient to provide in the subject being treated at least from about $1\times10^6$ to about $1\times10^9$ iT cells, even more desirably, from about $1\times10^7$ to about $5\times10^8$ iT cells, although any suitable amount can be utilized either above, e.g., greater than 5×10' cells, or below, e.g., less than $1\times10^7$ cells. The dosing schedule can be based on well-established cell-based therapies (see, e.g., Topalian and Rosenberg, Ada Haematol, 78 Suppl 1:75-76, 1987; U.S. Pat. No. 4,690,915), or an alternate continuous infusion strategy can be employed.

These values provide general guidance of the range of the iT cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

(ii) HIV/AIDS:

Acquired Immunodeficiency Syndrome (AIDS), which follows the infection with the Human Immunodeficiency Virus (HIV), is characterized by a chronic decline in the number of CD4 helper T cells. The CD4 T cell is a critical immune or white-blood cell that helps to maintain the function of "killer" CD8 cytotoxic T cells, which lyse virus-infected cells (Grossman et al., 2006). AIDS has become a global pandemic with an estimated 38 million people living with the disease worldwide and 1.6 million cases in North America alone. Current treatment regimens including the highly active anti-retroviral therapy (HAART), a combination of several anti-HIV drugs [i.e.: VIRAMUNE™ (nevirapine), RESCRIPTOR™ (delavirdine), INVIRASE™ (saquinavir), and NORVIR™ (ritonavir)], have been effective in reducing viral load and extending the life-span of HIV-infected individuals but have proven difficult to implement/achieve/maintain over long-periods of times for a variety of reasons (i.e.: toxicity, financial burden, government apathy, and evolving resistance of HIV to these drugs). Indeed, HAART is often given in cycles with 'vacations'/break periods to allow the patient to recover from anti-viral drug induced toxicity. As a result there is continued interest to find more efficacious drugs and/or cellular based therapies (i.e. vaccines or stem cell approaches) that keep pace with the evolving resistance of HIV and would augment or replace current treatment regimens to restore or maintain T cell numbers.

In the case of HIV/AIDS, the value of the present application may be the ability to create large numbers of in vitro-generated progenitor T cells that would offer therapeutic bene-fits to individuals that HAART has failed or that have gone off HAART due to drug toxicity. One advantage of a progenitor T cell based therapy would be minimal toxicity and side-effects of these cells compared to antiretrovirals. Given, that few treatment options are available to this subpopulation of individuals that have failed HAART, the use of progenitor T cells could be a viable option. Although these progenitor T cells and their CD4+ progeny would again be subject to HIV infection in vivo and require multiple treatments, the capacity to expand non-infected cells in vitro and restore T cell numbers in vivo may help to restore immune function and limit the emergence of opportunistic infections for some time during periods of planned HAART 'vacation' or failure. This presents two future extensions of this technology for therapeutic potential. First, the OP9-DL1 co-culture system may have therapeutic potential as an adjuvant therapy in combination with HAART, or as a stand-alone therapy when HAART is periodically discontinued. As with the case of cancer, the OP9-DL1 coculture system lends itself towards emerging genetic approaches to create designer T cells resistant to HIV infection. One example of such an innovative approach would be the expression of the mutant form of the chemokine co-receptor CCR5 that blocks viral infection (Markovic, 2006; Samson et al., 1996) in progenitor T cells. Such an approach would offer a novel means to treat HIV/AIDS by pre-venting HIV infection and thus maintaining T cell numbers and T cell function and is no longer far-fetched as several clinical trials have been approved for the treatment of HIV/AIDS using genetically modified mature-CD4+ T cells and CD34+ HSCs, but not-progenitor T cells.

Accordingly, the present application provides a method of treating or preventing an immunodeficiency comprising administering an effective amount of a progenitor T cell to an animal in need thereof. In one embodiment, the immunodeficiency is HIV/AIDS.

(iii) Autoimmunity

Traditionally, tolerance was thought to be established centrally in the thymus to self-antigen presented by thymic cells and blood-borne self-antigens, while T cells with specificity towards tissue-specific antigens underwent tolerance induction in the periphery (Kyewski and Derbinski, 2004). The recent observation that thymic epithelial cells that express the AIRE gene can promote the promiscuous expression of tissue-restricted anti-gens has yielded new insights for how self-tolerance is maintained and broken (Kyewski and Derbinski, 2004). Autoimmune diseases result from the dysregulation or breakdown of the processes that maintain self-tolerance in the periphery. Many investigators have reported that a population of T cells with regulatory activity (TReg) can suppress pathological immune responses in murine models of autoimmune disease, transplantation and GvHD (Chatenoud et al., 2001) suggesting that these cells could be utilized therapeutically to treat human autoimmune disease (Bluestone, 2005). TReg cells express CD4 and CD25 as wells as the forkhead transcription factor boxP3 (Foxp3) (Sakaguchi, 2005), which serves as a master regulator for TReg development and function (Fontenot et al., 2003; Hori et al., 2003). Indeed, Foxp3-mutant mice have a deficiency in TReg cells and develop severe lymphoproliferative autoimmune syndrome. Similarly, humans with the rare recessive disorder: Immunodysregulation, Polyendocrinopathy and Enteropathy X-linked (IPEX) syndrome exhibit aggressive autoimmunity and early (Walker et al., 2003).

TReg cells can be generated both in the thymus and in the periphery and appear phenotypically and functionally similar. Studies with TCR-transgenic systems indicate that relatively high-affinity interactions of αβTCR with self-peptide agonists presented on thymic epithelial cells are required to efficiently generate TReg cells in a CD28-dependent manner (Apostolou et al., 2002; Jordan et al., 2001; Tai et al., 2005; Walker et al., 2003). As a result, intrathymic TReg cells utilize a diverse TCR repertoire (Bluestone and Abbas, 2003) skewed toward autoantigen recognition. Recently, it was reported Hassall's corpuscles express thymic stromal lymphopoietin (TSLP), which activates thymic dendritic cells to induce the proliferation of TReg cells (Watanabe et al., 2005). Alternatively, TReg cells can be expanded extra-thymically through differences in self-peptide exposure and cytokine milieu (i.e.: transforming growth factor-β (TGF-β) and IL-10) (Apostolou and von Boehmer, 2004; Belghith et al., 2003; Roncarolo et al., 2001; Weiner, 2001).

The observation that TReg cells are deficient in patients with multiple sclerosis, type 1 diabetes, rheumatoid arthritis (Ehrenstein et al., 2004; Lindley et al., 2005; Viglietta et al., 2004) has raised hope that treatment of these and other autoimmune diseases may rest with the restoration of TReg cells (Bluestone, 2005). In contrast, the elimination of TReg cells may play a significant role in enhancing cancer immunotherapeutic approaches by releasing the breaks on antitumor T cell responses and inducing limited local autoimmunity (Sakaguchi et al., 2001). Finally, TReg cells may play a critical role in the establishment of tolerance following allogenic organ transplant thereby minimizing rejection mediated by GvHD (Gregori et al., 2005; Hoffmann and Edinger, 2006; Touraine et al., 2005).

As with most cellular based therapies, the major obstacle for the utilization of TReg cells in the treatment of autoimmunity is the ability to generate them in large numbers to realize therapeutic effectiveness. Currently, the OP9-DL1 coculture system does not support the generation of large numbers of TReg cells from progenitor T cells. Given the role of TSLP in the generation of TReg cells (Watanabe et al., 2005), it is unclear whether the absence of TReg cells in the OP9-DL1 coculture system is due to a deficiency of OP9 cells to produce TSLP.

Regardless, stem cell transplantation for the treatment of severe autoimmunity is gaining momentum (Bluestone, 2005; Gregori et al., 2005; Sykes and Nikolic, 2005) with the development of human/immunodeficient mouse models of alloreaction (Thomsen et al., 2005), methods to expand regulatory T cell populations (Kretschmer et al., 2005) and to engineer stem cells and progenitor T cells to express self-antigen (Alderuccio et al., 2003).

Accordingly, the present application provides a method of treating or preventing an autoimmune disease comprising administering an effective amount of a progenitor T cell to an animal thereof.

(iv) Genetic Diseases

As mentioned previously, the iT cells or iNK cells as disclosed herein, may be transfected with a desired gene. Such cells can be used for treatment of genetic diseases. Hematopoietic cell-related genetic diseases can be treated by grafting the cellular composition with cells transfected with a gene that can make up for the deficiency or the abnormality of the gene causing the diseases. For example, a normal wild type gene that causes a disease such as β-thalassemia (Mediterranean anemia), sickle cell anemia, ADA deficiency, recombinase deficiency, recombinase regulatory gene deficiency and the like, can be transferred into the iT cells or iNK cells as disclosed herein, by homologous or random recombination and the cells can be grafted into a patient. Further, a cellular composition comprising normal T cells free from abnormalities of genes (from a suitable donor) can be used for treatment.

Another application of gene therapy permits the use of a drug in a high concentration, which is normally considered to be dangerous, by providing drug resistance to normal T cells by transferring a drug resistant gene into the cells. In particular, it is possible to carry out the treatment using an anticancer drug in high concentration by transferring a gene having drug resistance against the anticancer drug, e.g., a multiple drug resistant gene, into iT cells or iNK cells as disclosed herein, in a cellular composition of the application.

Diseases other than those relating to the hematopoietic system can be treated by using the cellular compositions comprising iT cells or iNK cells as disclosed herein, in so far as the diseases relate to a deficiency of secretory proteins such as hormones, enzymes, cytokines, growth factors and the like. A deficient protein can be induced and expressed by transferring a gene encoding a target protein into the iT cells or iNK cells as disclosed herein, under the control of a suitable promoter. The expression of the protein can be controlled to obtain the same activity as that obtained by the natural expression in vivo.

It is also possible to insert a gene encoding a ribozyme, an antisense nucleic acid or the like (e.g., short-interfering RNA) or another suitable gene into iT cells or iNK cells as disclosed herein, to control expression of a specific gene product in the cells or to inhibit susceptibility to diseases. For example, the iT cells or iNK cells as disclosed herein, can be subjected to gene modification to express an antisense nucleic acid, siRNA, or a ribozyme, which can prevent growth of hematic pathogens such as HIV, HTLV-I, HTLV-II and the like in iT cells or iNK cells as disclosed herein. In an embodiment, iT cells or iNK cells as disclosed herein, of a cellular composition of the application are created which express known inhibitory genes of HIV replication, such as RNA decoys or the Tat- or Rev-responsive elements, or a dominant negative mutant of the Rev trans-activator protein. IT cells or iNK cells as disclosed herein, derived from hematopoietic progenitor cells or ES carrying these genes would provide a potentially limitless and defined source of HIV-resistant lymphocyte progenitors.

C. Screening

The cellular compositions comprising iT cells or iNK cells as disclosed herein, may be used to screen for potential modulators or therapeutics that modulate development or activity of iT cells or iNK cells as disclosed herein, or cells differentiated therefrom. In particular, the cellular compositions may be subjected to a test substance, and the effect of the test substance may be compared to a control (e.g. in the absence of the substance) to determine if the test substance modulates development or activity of iT cells or iNK cells as disclosed herein, or cells differentiated therefrom.

In an aspect of the application a method is provided for using a cellular composition of the application comprising iT cells or iNK cells as disclosed herein, or cells differentiated therefrom to assay the activity of a test substance comprising the steps of:

(a) generating iT cells or iNK cells as disclosed herein, with a system or method of the application in the presence of a test substance, or culturing iT cells or iNK cells as disclosed herein, compositions generated using a system or method of the application in the presence of a test substance; and (b) detecting the presence or absence of an effect of the test substance on the survival of the cells or on a morphological, functional, or physiological characteristic and/or molecular biological property of said cells, whereby an effect altering cell survival, a morphological, functional, or physiological characteristic and/or a molecular biological property of the cells indicates the activity of the test substance.

In another aspect a method is provided for using iT cells or iNK cells as disclosed herein, or cells differentiated therefrom generated in accordance with the application, to screen a potential new drug to treat a disorder involving T cells comprising the steps of:

(a) generating iT cells or iNK cells as disclosed herein, with a system or method of the application in the presence of a potential new drug, or culturing iT cells or iNK cells as disclosed herein, preparations generated using a system or method of the application in the presence of a potential new drug; and (b) detecting the presence or absence of an effect of the potential new drug on the survival of the cells in vitro or on a morphological, functional or physiological characteristic and/or molecular biological property of said cells, whereby an effect altering cell survival, a morphological, functional, or physiological characteristic and/or a molecular biological property of the cells in vitro indicates the activity of the potential new drug.

The cellular compositions of the application may be used to prepare model systems of disease. The cellular compositions of the application can also be used to produce growth factors, hormones, etc.

The cellular compositions of the application can be used to screen for genes expressed in or essential for differentiation of T cells. Screening methods that can be used include Representational Difference Analysis (RDA) or gene trapping with for example SA-lacZ (D. P. Hill and W. Wurst, Methods in Enzymology, 225: 664, 1993). Gene trapping can be used to induce dominant mutations (e.g. by deleting particular domains of the gene product) that affect differentiation or activity of T cells and allow the identification of genes expressed in or essential for differentiation of these cells.

(i) Use of the Assay in Personalized Medicine

In some embodiments, the invention provides an assay wherein the iT cells or iNK cells are patient derived and comprises stimulation of the cells with one or more drugs, for example for use in personalized medicine, e.g., use in personalized medicine, for example to test individual patient response to drugs for the disease or affliction of interest.

Accordingly, the present invention relates to an in vitro assay to predict in vivo drug-responsiveness of individual patients. Another aspect of the invention relates use of the population of human the iT cells or iNK cells as described herein to screen for agents, for example molecules and genes involved in biological events. In such an embodiment, the biological event is an event that affects the function of the iT cells or iNK cells.

In another embodiment, a population of human the iT cells or iNK cells as described herein can be used to assess the effect of genetic variation (e.g. ethnicity, human mutations or gene variants or polymorphism) on lung function. For example, the effect of different environmental factors, such as, for example, pollen, pollution, high fat diet, lack of exercise, can be assessed in human lung tissue as described herein, generated from populations of human pluripotent stem cells as described herein from different genetic and socio-economic backgrounds. In an alternative embodiment, the effect (e.g. efficacy and/or safety profile) of different therapeutic agents, including blood or cancer related drugs, can be assessed in vivo in an animal model comprising a population of human the iT cells or iNK cells as described herein from different genetic backgrounds. Accordingly, in some embodiments, a population of the iT cells or iNK cells as described herein which are a variant human the iT cells or iNK cells, for example but not limited to a genetic variant and/or a genetically modified the iT cells or iNK cells.

In another embodiment, a population of human T/NK CD7+ progenitor cells as described herein can be used in an assay for studying the differentiation pathways of T cells and NK cells. In some embodiments, the human T/NK CD7+ progenitor cells can be genetically engineered to comprise markers operatively linked to promoters that are expressed in one or more of the lineages being studied.

In alternative embodiments, the human T/NK CD7+ progenitor cells used to generate a population of iT cells or iNK cells as described herein can comprise a mutation and/or polymorphism that relates to the disease phenotype, and in other embodiments, a population of T/NK CD7+ progenitor cells as described herein been genetically engineered to carry a mutation and/or polymorphism.

Any suitable animal can be used for implanting a population of human T/NK CD7+ progenitor cells as described herein, for example, rodents (such as mice, rats), monkeys, pigs and the like. In some embodiments, the subject animal is a transgenic or knockout animal, e.g., a transgenic mice or knock out mice. In some embodiments, the subject animal is a humanized mouse, such as the SCID mouse.

In some embodiments, a population of T/NK CD7+ progenitor cells as described herein is useful as an in vivo assays and screening method to detect agents for the effect of the agent assessed by monitoring output parameters, such as expression of markers, cell viability, differentiation characteristics, multipotency capacity and the like.

In some embodiments, the in vivo humanized model of disease can be produced by implanting a population of T/NK CD7+ progenitor cells or iT cells or iNK cells as described herein into an immunodeficient animal (such as nude mice, such as SCID mice, or animals rendered immunodeficient chemically or by irradiation).

In some embodiments, a population of iT cells or iNK cells as described herein administered to the subject can express a detectable label (such as green fluorescent protein, or beta-galactosidase); that have been prelabeled (for example, with BrdU or [3H]thymidine), or by subsequent detection of a constitutive cell marker (for example, using human-specific antibody). The presence and phenotype of the administered human iT cells or iNK cells as described herein can be assessed by immunohistochemistry or ELISA using human-specific antibody, or by RT-PCR analysis using primers and hybridization conditions that cause amplification to be specific for human polynucleotides, according to published sequence data.

A population of T/NK CD7+ progenitor cells, or iT cells or iNK cells for use in an assay or for therapeutic use as described herein may be freshly isolated, cultured, or frozen and thawed, or genetically engineered as described above, or the like. A population of human T/NK CD7+ progenitor cells, or iT cells or iNK cells as described herein may be environmentally induced variants of clonal cultures: e.g. split into independent cultures and grown under distinct conditions, for example with or without virus; in the presence or absence of other cytokines or combinations thereof. Alternatively, a population of human T/NK CD7+ progenitor cells, or iT cells or iNK cells as described herein may be variants with a desired pathological characteristic. For example, the desired pathological characteristic includes a mutation and/or polymorphism which contribute to disease pathology.

In such an embodiment, a population of T/NK CD7+ progenitor cells, or iT cells or iNK cells as described herein can be used to screen for agents which alleviate the pathology. In alternative embodiments, a population of human T/NK CD7+ progenitor cells, or iT cells or iNK cells as described herein can be assessed to screen for agents in which some T/NK CD7+ progenitor cells, or iT cells or iNK cells comprising a particular mutation and/or polymorphism respond differently compared with T/NK CD7+ progenitor cells, or iT cells or iNK cells without the mutation and/or polymorphism, therefore the methods can be used for example, to assess an effect of a particular drug and/or agent on human T/NK CD7+ progenitor cells, or iT cells or iNK cells from a defined subpopulation of people and/or cells, therefore acting as a high-throughput screen for personalized medicine and/or pharmacogenetics. The manner in which a population of human T/NK CD7+ progenitor cells, or iT cells or iNK cells as described herein respond to an agent, particularly a pharmacologic agent, including the timing of responses, is an important reflection of the physiologic state of the T/NK CD7+ progenitor cells, or iT cells or iNK cells.

In some embodiments, an agent administered in an assay comprising a population of human T/NK CD7+ progenitor cells, or iT cells or iNK cells as disclosed herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising: nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising: mutated proteins, genetically engineered proteins, peptides, synthetic peptides, recombinant proteins, chimeric proteins, antibodies, humanized proteins, humanized antibodies, chimeric antibodies, modified proteins and fragments thereof.

In some embodiment, at least one agent is administered to a population of human T/NK CD7+ progenitor cells, or iT cells or iNK cells as described herein by any suitable means known to one of ordinary skill in the art. In some embodiments, administration occurs more than once, for example at multiple different time points. In some embodiments, the administration of an agent to a population of human T/NK CD7+ progenitor or iT cells or iNK cells as described herein is continuous, for example via means of an infusion pump or cather or the like, or via a slow-release formulation of the agent.

In some embodiments, where the population of human T/NK CD7+ progenitor cells, or iT cells or iNK cells as described herein is implanted into an animal model, i.e., an in vivo assay, an agent can be administered via any or a combination of the following administration methods; systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

The term "agent" refers to any chemical, entity or moiety, including without limitation synthetic and naturally-occurring non-proteinaceous entities. In certain embodiments the compound of interest is a small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

In some embodiments, a population of human T/NK CD7+ progenitor cells, or iT cells or iNK cells as described herein for use in an in vitro or in vivo assay can be genetically modified to express markers, e.g. bioluminescence markers, such as luciferase and the like and other bioluminescent markers commonly known in the art for real-time imaging of the function, and/or growth of a population of human T cells as described herein in vivo in real time. The is advantageous as it allows the continuous and/or time-point analysis of the effect of an agent on the population of T cells or NK cells in the same animal over a period of time, as well as allows one to compare the effect of multiple different agents (administered to the subject at different timepoints) in the same in vivo subject without sacrificing the in vivo animal model.

While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

A plurality of assays as disclosed herein may be run in parallel (e.g. different subjects used to derive the populations of human T/NK CD7+ progenitor cells, or iT cells or iNK cells as described herein) with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, a population of human T/NK CD7+ progenitor cells, or iT cells or iNK cells as described herein used in the screen can be manipulated to express desired gene products. Gene therapy can be used to either modify a cell to replace a gene product or add or knockdown a gene product. In some embodiments the genetic engineering is done to facilitate regeneration of tissue, to treat disease, or to improve survival of the cells following implantation into a subject.

A skilled artisan could envision a multitude of genes which would convey beneficial properties to a population of human T/NK CD7+ progenitor cells, or iT cells or iNK cells as described herein to be used in implantation (discussed in more detail below). The added gene may ultimately remain in the recipient human T/NK CD7+ progenitor cells, or iT cells or iNK cells as described herein and all its progeny, or may only remain transiently, depending on the embodiment. The desired gene can be transfected into a population of human T/NK CD7+ progenitor cells, or iT cells or iNK cells as described herein using a variety of techniques. Preferably, the gene is transfected into a population of human T/NK CD7+ progenitor cells, or iT cells or iNK cells as described herein using an expression vector. Suitable expression vectors are disclosed herein and include plasmid vectors (such as those available from Stratagene, Madison Wis.), viral vectors (such as replication defective retroviral vectors, herpes virus, adenovirus, adeno-virus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used to generate "knockout" or modified ES cells, which can be applied to human or marine ES cells (U.S. Pat. Nos. 5,616,491; 5,614,396, which are incorporated herein in their entirety by reference). These techniques take advantage of the ability of embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the present invention can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

IX. Kits

Another aspect of the present disclosure relates to kits or pharmaceutical packages comprising the iT cells or iNK cells produced using the methods and compositions as disclosed herein. In some embodiments, another aspect of the technology is a kit for producing T/NK progenitor cells from a subject, e.g., for personalized medicine. In some embodiments, the kit also comprises reagents and/or materials for maturation of the T/NK progenitor cells into mature T cells or NK cells, according to the methods as disclosed herein. In some embodiments, such a kit comprises OP9 cells that express a notch ligand (e.g. dll1. Dll2, dll3, dll4), Another aspect relates to a kit comprising the nucleic acid constructs for generating an iPSC that expresses a NICD gene, e.g., NICD1 under an inducible promoter, for example, for the generation of an iPSC-NICD1 cell line for a specific patient. Thus, an iPSC-NICD1 cell line can be generated from a subject in need to T-cell therapy or requiring NK cells. Accordingly, in some embodiments, the kit can comprise a nucleic acid constructs for inducible expression of a NICD gene as discussed herein in Section VI (1) entitled "modified iPSC comprising inducible iPSC".

In some embodiments, the kit can further optionally comprise nucleic acid constructs for MHC I KO and/or MHC II KO as discussed herein in Section VI (2) entitled "modified iPSC for a universal iPSC".

In some embodiments, the kit can also comprise reagents and/or culture media and/or growth factors for carrying out the iT protocol as disclosed in Table 1 herein.

X. Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

The term "isolated" as used herein means that the progenitor cell has been separated or purified from cellular or biological material found with the cells in their native environment. It thus distinguishes the cells from how they exist in nature.

The term "a cell" or "the cell" includes a plurality of cells.

The term "T/NK progenitor cell" as used herein means a T cell that is capable of maturing into a mature T cell or lymphocyte. A mature T cell includes CD4+ and CD8+ T cells. A lymphocyte includes CD56+ NK cells.

Negative and positive selection methods known in the art may be used for enrichment of the progenitor cells. For example, cells can be sorted based on cell surface antigens using a fluorescence activated cell sorter, or magnetic beads which bind cells with certain cell surface antigens. Negative selection columns can be used to remove cells expressing lineage specific surface antigens.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Bel3, CCRF-CEM, CML-T, DND-41, DU.528, EU-9, HD-Mar, HPB-ALL, H-SB2, HT-1, JK-TI, Jurkat, Karpas 45, KE-37, KOPT-Ki, K-TI, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-TI to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (see world wide web at address: atcc.org/) and the German Collection of Microorganisms and Cell Cultures (see world wide web at address: dsmz.de/).

The term "chimeric antigen receptors (CARs)" as used herein may be referred to as artificial T-cell receptors, chimeric T-cell receptors, or chimeric immune-receptors, for example, and encompass engineered receptors that graft an artificial specificity onto a particular immune effector cell. The CARs may be employed to impart the specificity of a monoclonal antibody onto a T cell, thereby allowing a large number of specific T cells to be generated, for example, in use for adoptive cell therapy. In specific embodiments, the CARS direct specificity of the cell to a tumor associated antigen, for example. In some embodiments, the CARS comprise an intracellular activation domain, a transmembrane domain and an extracellular domain comprising a tumor associated antigen binding region. In particular aspects, CARs comprise fusions of single-chain variable fragments (scFv) derived from monoclonal antibodies, fused to CD3-zeta transmembrane and endodomain. In other aspects, CARs comprise fusions of fibronectin type III domains, fused to CD3-zeta transmembrane and endodomain. The specificity of other CARS designs may be derived from ligands of receptors (e.g., peptides) or from Dectins. In particular embodiments, one can target malignant B cells by redirecting the specificity of T cells using a chimeric immunoreceptor specific for the B-lineage molecule, BCMA. In certain cases, the CARs comprise domains for additional co-stimulatory signaling, such as CD3-zeta, FcR, CD27, CD28, CD137, DAP 10, and/or OX40. In some cases molecules can be co-expressed with the CAR.

As used herein, the term "gene" includes a segment of DNA that contains all the information for the regulated biosynthesis of an RNA product, including promoters, exons, introns, and other untranslated regions that control expression. Those in the art will readily recognize that nucleic acid molecules can be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference can be made to either strand and still comprise the same polymorphic site and an oligonucleotide can be designed to hybridize to either strand. Throughout this specification, in identifying a polymorphic site, reference is made to the sense strand, only for the purpose of convenience. As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyedenosine, deoxycytidine, deoxyguanosine, and deoxythymidine. For purposes of clarity, when referring herein to a nucleotide of a nucleic acid, which can be DNA or RNA, the terms "adenosine", "cytosine", "guanosine", and "thymidine" are used. It is understood that if the nucleic acid is RNA, a nucleotide having a uracil base is uridine. The term "nucleotide" or nucleic acid as used herein is intended to refer to ribonucleotides, deoxyribonucleotides, acrylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that can be formed into a polynucleotide that retains the ability to hybridize in a sequence specific manner to a target polynucleotide. As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "variant", "variance", "mutation" or "polymorphism" are used interchangeably herein and as used herein with respect to nucleic acid sequence refers to a difference in nucleic acid sequence in the population. Polymorphisms are sometimes referred to as "single nucleotide polymorphism" or "SNP" can be synonymous or non-synonymous. Synonymous polymorphisms when present in the coding region typically do not result in an amino acid change. Non-synonymous polymorphism when present in the coding region alter one or more codons resulting in an amino acid replacement in the amino acid chain. Such mutations and polymorphisms can be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members can have an altered sequence (e.g., the variant or, mutant "allele"). In the simplest case, only one mutated variant of the sequence can exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished "+" or "−". Using these symbols, homozygous individuals are +/+, or −/− or two of the same symbol, for example A/A, G/G, T/T and C/C. Heterozygous individuals are +/− or two different symbols, for example A/G, A/T. A/C, G/T etc. The occurrence of alternative mutations can give rise to tri-allelic and tetra-allelic polymorphisms, etc. An allele can be referred to by the nucleotide(s) that comprise the mutation. In some instances a "silent mutation" is a synonymous codon change, or silent SNP is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide.

The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom.

The term "endogenously expressed" or "endogenous expression" refers to the expression of a gene product at normal levels and under normal regulation for that cell type.

The term "entity" refers to any structural molecule or combination of molecules.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising: chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising: nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising: mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct or indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The terms "patient", "subject" and "individual" are used interchangeably herein, and refer to an animal, particularly a human, to whom treatment including prophylaxis treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "tissue" refers to a group or layer of similarly specialized cells which together perform certain special functions. The term "tissue-specific" refers to a source or defining characteristic of cells from a specific tissue.

As used herein, the term "donor" refers to a subject to which an organ, tissue or cell to be transplanted is harvested from.

As used herein, the term "recipient" refers to a subject which will receive a transplanted organ, tissue or cell.

The term "allograft" refers to a transplanted cell, tissue, or organ derived from a different animal of the same species.

The term "effective amount" includes within its meaning a sufficient amount of a pharmacological composition to provide the desired effect. For example, an effective amount using the methods as disclosed herein would be considered as the amount sufficient to reduce a symptom of cancer or an autoimmune disease by at least 10%. Further, an effective amount as used herein would also include an amount sufficient to prevent or delay the development of a symptom experienced by a subject, or alter the course of a symptom disease (for example but not limited to, slow the progression or development of at least one symptom experienced by a subject with the disease), or reverse at least one symptom experienced by a subject with the disease of interest.

As used herein, the term "treating" includes administering a population of iT cells and/or iNK cells as disclosed herein to a subject to reduce at least one symptom experienced by a subject with a disease of interest. In some embodiments, a reduction in at least one symptom at least one symptom experienced by a subject in need treatment would also be considered as affective treatments by the methods as disclosed herein.

The term "polynucleotide" as used herein, refers to single- or double-stranded polymer of deoxyribonucleotide, ribonucleotide bases or known analogies of natural nucleotides, or mixtures thereof. The term includes reference to the specified sequence as well as to the sequence complementary thereto, unless otherwise indicated.

The term "polypeptide" means a polymer made up of amino acids linked together by peptide bonds. The terms "polypeptide" and "protein" are used interchangeably herein, although for the purposes for the present disclosure, a polypeptide may constitute a portion or the full length protein.

The term “expression” as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

The term “endogenously expressed” or “endogenous expression” as used herein, refers to the expression of a gene product at normal levels and under normal regulation for that cell type.

In the context of this specification, the term “activity” as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

The term “nucleic acid” or “oligonucleotide” or “polynucleotide” used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term “statistically significant” or “significantly” refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term “standard deviation” is a measure of the dispersion of a set of data from its mean. The more spread apart the data, the higher the deviation. Standard deviation is calculated as the square root of variance and can be calculated by one of ordinary skill in the art.

The term “cell culture medium” (also referred to herein as a “culture medium” or “medium”) as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. The appropriate cell culture media, for a particular cell type, is known to those skilled in the art.

The term “contacting” or “contact” as used herein as in connection with contacting a population of pluripotent stem cells, or iPSC or T/NK progenitor cells as disclosed herein, can be in vitro, for example, in conditioned media or exogenously added agent or growth factor.

As used herein, the terms “administering,” and “introducing” are used interchangeably, and refer to the placement of a population of iT cells and/or iNK cells as defined herein into a subject by a method or route which results in at least partial localization of the population of iT cells and/or iNK cells at a desired site, such as, e.g. the blood or a tumor site. A population of iT cells and/or iNK cells as defined herein can be administered by any appropriate route which results in an effective treatment in the subject.

The term “transplantation” as used herein refers to introduction of new cells (e.g. a population of iT cells and/or iNK cells as defined herein), tissues, or organs into a host (i.e. transplant recipient or transplant subject)

The term “genetically modified” cell, e.g. a genetically modified population of pluripotent stem cells, or iPSC as disclosed herein as used herein refers to a population of pluripotent stem cells, such as ES cells or iPSC as disclosed herein into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (e.g., sequences naturally found in the cells) but in a non-naturally occurring arrangement (e.g., a coding region linked to a promoter from a different gene), or altered versions of native sequences, etc., e.g., a modified version of the NICD1 gene etc. The process of transferring the nucleic into the cell is referred to as “transducing a cell” and can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term “transduction” as used herein refers to the use of viral particles to introduce new genetic material into a cell The term “transfection” as used herein refers the use of chemical methods, most often lipid containing vesicles, to introduce new genetic material into a cell The term “transformation” as used herein refers to when a cell becomes functionally abnormal in the process of malignancy, often obtaining a new capacity to multiply indefinitely or under new circumstances.

The term “mutant” refers to any change in the genetic material of an organism, in particular a change (i.e., deletion, substitution, addition, or alteration) in a wild-type polynucleotide sequence or any change in a wild-type protein sequence. The term “variant” is used interchangeably with “mutant”. Although it is often assumed that a change in the genetic material results in a change of the function of the protein, the terms “mutant” and “variant” refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The phrases “parenteral administration” and “administered parenterally” as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases “systemic administration,” “administered systemically”, “peripheral administration” and “administered peripherally” as used herein mean the administration of a population of iT cells or iNK cells and/or compound and/or other material other than directly into the pulmonary system, e.g., lungs or airways, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising: nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising: mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within the cell.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

A "reporter gene" as used herein encompasses any gene that is genetically introduced into a cell that adds to the phenotype of the stem cell. Reporter genes as disclosed in this invention are intended to encompass fluorescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, e.g., "selective conditions". To ensure an effective selection, a population of cells can be maintained under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 30%, or about 20%, more preferably fewer than about 15%, 10%, 8%, 7%, most preferably fewer than about 5%, 4%, 3%, 2%, 1%, or less than 1%, of cells that are not T/NK progenitor cells as disclosed herein.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

By an "increase" in the expression or activity of a gene or protein is meant a positive change in protein or polypeptide or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

As used herein the term "comprising" or "comprises" is used in reference to compositions, methods, and respective component(s) thereof, that are essential to the disclosure, yet open to the inclusion of unspecified elements, whether essential or not. Accordingly, compositions or methods "comprising" one or more recited elements may include other elements not specifically recited. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Thus, the use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%. The present disclosure is further explained in detail by the following, including the Examples, but the scope of the disclosure should not be limited thereto.

Although any known methods, devices, and materials may be used in the practice or testing of the invention, the methods, devices, and materials in this regard are disclosed herein.

In some embodiments, the present application may be defined in any of the following paragraphs:

1. A method of generating a population of hemogenic endothelium cells or T/NK primordial cells, comprising:
   a. obtaining a population of pluripotent stem cells,
   b. activating Notch signaling before the onset of endogenous Notch signaling in the population of pluripotent stem cells,
   c. collecting the population of cells from step b, wherein the cells express Notch target genes.
2. The method of paragraph 1, wherein the iPSC do not express any one or more of: Notch receptors (e.g., Notch1, Notch2, Notch3, notch4) or Notch ligands (e.g., DLL1, DLL2, DLL3, DLL4, JAG1, JAG2).
3. The method of any of paragraphs 1 or 2, wherein activating notch signaling before onset of endogenous Notch signaling is by expression of NICD1 or a Notch intracellular domain (NICD) protein in the pluripotent stem cell.
4. The method of any of paragraphs 1-3, wherein the Notch target genes are selected from any one or more of LM02, T (brachyury) TAL1, HES1 or HEY5.
5. The method of any of paragraphs 1-4, wherein activating the notch signaling pathway is between d0-d2, or before the onset of endogenous Notch signaling in the pluripotent stem cell.
6. The method of any of paragraphs 1-5, wherein activating the notch signaling pathway is by expression of a NICD1 gene.
7. The method of any of paragraphs 1-6, wherein the expression of NICD1 gene is by transient transfection with an expression vector or viral vector, or modified RNA, wherein the vector, viral vector or modified RNA comprises a nucleic acid sequence encoding a NICD protein.
8. The method of any of paragraphs 1-7, wherein the population of pluripotent stem cells comprise a nucleic acid sequence encoding an NICD1 gene, operatively linked to an inducible promoter.
9. The method of any of paragraphs 1-8, wherein the expression of NICD1 gene is induced by contacting the cells with an agent to induce expression from the inducible promoter.
10. The method of any of paragraphs 1-9, wherein the cells express $KDR^{high}$, $CD34^{+}$, VE-$cadherin^{+}$ at day 4 (D4) in culture.
11. The method of any of paragraphs 1-10, wherein the population of pluripotent stem cells is a population of induced pluripotent stem cell (iPSC) or a population of embryonic stem (ES) cells.
12. The method of any of paragraphs 1-11, wherein the population of induced pluripotent stem cell (iPSC) is human iPSCs.
13. The method of any of paragraphs 1-12, further comprising culturing the cells from step c at day 6 in iT media, wherein the iT media does not comprise erythropoietin (EPO) or angiotensin.
14. The method of any of paragraphs 1-13, further comprising culturing the cells according to an iT protocol.
15. The method of any of paragraphs 1-14, wherein the population of cells collected in step c comprise at least 30% CD+7 T/NK progenitor cells.
16. The method of any of paragraphs 1-15, wherein the population of cells collected in step c comprise between 30-60% CD+7 T/NK progenitor cells.
17. The method of any of paragraphs 1-16, wherein the population of cells collected in step c comprise greater than 60% CD+7 T/NK progenitor cells.
18. The method of any of paragraphs 1-17, further comprising plating the cells from step c in a co-culture comprising stromal cell feeder layer, wherein the stromal cell feeder layer expresses a notch ligand.
19. The method of any of paragraphs 1-18, wherein the cells from step c are plated at a density of about <5,000 cells/ml or about >20,000 cells/ml in the co-culture comprising stromal cell feeder layer, expressing a notch ligand.
20. The method of any of paragraphs 1-19, wherein collecting the population of cells in step c is performed without cell sorting, or a positive cell selection step, or a negative cell selection step, or both.
21. A method of obtaining a population of T-cells or a population of NK cells, comprising
   a. obtaining a population of T/NK progenitor cells having a phenotype of CD7+,
   b. culturing the population of T/NK progenitor cells at a low density on a stromal cell feeder layer, or culturing the population of T/NK progenitor cells at a high density on a stromal cell feeder layer, wherein the stromal cell feeder layer expresses a notch ligand,
   c. collecting the population of cells cultured at low density, wherein the collected cells are T-cells that are double positive for CD8+/CD4+, or collecting the population of cells cultured at high density, wherein the collected cells are NK cells that express CD56.
22. The method of paragraph 21, wherein the stromal cell feeder layer is OP9-DLL4 cells, or a stromal cell line expressing a notch ligand selected from any of DLL1, DLL2, DLL3, DLL4, JAG1, JAG2).
23. The method of paragraph 21 or 22, wherein the cells cultured at low density is at a density of less than about 50,000 cells/10 cm plate or less than about 5,000 cells/ml.
24. The method of any of paragraphs 21-23, wherein the cells cultured at high density is at density of greater than about 200,000/10 cm plate or greater than about 20,000 cells/ml.
25. The method of any of paragraphs 21-23, wherein the T/NK progenitor cells are obtained according to the method of any of paragraphs 1-20.
26. An isolated T/NK progenitor cell obtained from a pluripotent stem cell by a process of inducing notch signaling before the onset of endogenous Notch signaling in the pluripotent stem cell, wherein the T/NK progenitor cell is CD7+.
27. The isolated population of T/NK progenitors of paragraph 26, wherein the process of inducing notch signaling before the onset of endogenous notch signaling in the pluripotent stem cell is by inducible expression of a NICD gene at d0-d2 of differentiation.
28. The isolated population of T/NK progenitors of any of paragraphs 26-27, wherein inducing notch signaling before the onset of endogenous notch signaling results in the expression of notch target genes before onset of notch target genes.

29. The isolated population of T/NK progenitors any of paragraphs 26-27, wherein the notch target genes are selected from any one or more of: LM02, T (brachyury) TAL1, HES1 or HEY5
30. The isolated population of T/NK progenitors any of paragraphs 26-29, wherein the pluripotent stem cell is an induced pluripotent stem cell (iPSC).
31. The isolated population of T/NK progenitors of any of paragraphs 26-30, wherein the iPSC is a human iPSC.
32. The isolated population of T/NK progenitors of any of paragraphs 26-31, wherein the isolated population comprises at least 50% CD7+ T/NK cells.
33. The isolated population of T/NK progenitors of any of paragraphs 26-32, wherein the isolated population comprises between 50%-80% CD7+ T/NK cells.
34. An isolated T/NK progenitor cell population obtained by the method of any of paragraphs 1-20.
35. A substantially pure population of T/NK progenitor cells comprising at least 50% CD7+ T/NK cells.
36. A substantially pure population of T cells obtained from the method of any of paragraphs 1-25.
37. A substantially pure population of NK cells obtained from the method any of paragraphs 1-25.
38. An engineered iPSC, comprising a nucleic acid construct, the nucleic acid construct comprising a sequence encoding an NICD gene and an inducible promoter, wherein the sequence encoding an NICD gene is operatively linked to the inducible promoter.
39. The engineered iPSC of paragraph 38 for use in the generation of a population of T/NK progenitor cells.
40. The engineered iPSC of paragraph 38 or 39, wherein the NICD gene encodes NICD1, NICD2, NICD3 or NICD4.
41. The engineered iPSC of any of paragraphs 38-40, wherein the NICD gene encodes a NICD1 protein having the amino acid sequence of SEQ ID NO: 5, or a protein having at least 80% sequence identity to amino acid of SEQ ID NO: 5.
42. The engineered iPSC of any of paragraphs 38-41, wherein the NICD1 gene has a nucleic acid sequence of SEQ ID NO: 1, or a nucleic acid sequence having at least 80% sequence identity to SEQ ID NO: 1.
43. The engineered iPSC of any of paragraphs 38-42, wherein the NICD gene is operatively linked to a Tet:ON inducible promoter.
44. The engineered iPSC of any of paragraphs 38-43, wherein the nucleic acid construct is inserted into a genomic safe harbor (GSH) gene.
45. The engineered iPSC of any of paragraphs 38-44, wherein the genomic safe harbor (GSH) gene is selected from any of: AAVS1, albumin gene, hROSA26 or CCR5 gene.
46. The engineered iPSC of any of paragraphs 38-45, wherein the nucleic acid construct further comprises at least one nucleic acid insulator sequence located 5' and 3' of the sequence encoding the NICD gene and inducible promoter.
47. The engineered iPSC of any of paragraphs 38-46, wherein the engineered iPSC is further modified to knock out MHC I expression.
48. The engineered iPSC of any of paragraphs 38-47, wherein the engineered iPSC does not express beta-2-microglobin (B2M).
49. The engineered iPSC of any of paragraphs 38-48, wherein the iPSC further comprises a non-functional beta-2-microglobin (B2M) gene.
50. The engineered iPSC of any of paragraphs 38-49, wherein the endogenous beta-2-microglobin (B2M) gene is insertionally inactivated.
51. The engineered iPSC of any of paragraphs 38-50, wherein the endogenous beta-2-microglobin (B2M) gene comprises an exogenous nucleic acid sequence located in the beta-2-microglobin (B2M) locus.
52. The engineered iPSC of any of paragraphs 38-51, wherein the exogenous nucleic acid sequence encodes HLA-E.
53. The engineered iPSC of any of paragraphs 38-52, wherein the engineered iPSC is further modified to knock out MHC II expression.
54. The engineered iPSC of any of paragraphs 38-53, wherein the engineered iPSC does not express CIITA regulator transcription factor.
55. The engineered iPSC of any of paragraphs 38-54, wherein the iPSC further comprises a non-functional CIITA gene.
56. The engineered iPSC of any of paragraphs 38-55, wherein the endogenous CIITA gene is insertionally inactivated.
57. The engineered iPSC of any of paragraphs 38-56, wherein the endogenous CIITA gene comprises an exogenous nucleic acid sequence located in the CITA locus.
58. The engineered iPSC of any of paragraphs 38-57, wherein the exogenous nucleic acid sequence encodes CD47.
59. The engineered iPSC of any of paragraphs 38-58, wherein the nucleic acid sequence encoding CD47 is operatively linked to a promoter.
60. The engineered iPSC of any of paragraphs 38-59, wherein the promoter is an inducible promoter, or a high expressing promoter.
61. The engineered iPSC of any of paragraphs 38-60, wherein the high expressing promoter is EF1α promoter.
62. The use of the engineered iPSC of any of claims 38-61 for use in any of the methods of paragraphs 1-25.
63. An isolated T/NK progenitor cell population obtained by use of the engineered iPSC of any paragraphs 38-61 in the method according to any of paragraphs 1-20.
64. A substantially pure population of T/NK progenitor cells comprising at least 50% CD7+ T/NK cells, wherein the population of T/NK progenitor cells are obtained by use of the engineered iPSC of any paragraphs 38-61.
65. A substantially pure population of recombinant T cells obtained from the method of any of paragraphs 1-20, using the using the engineered iPSC of any of claims 38-61.
66. A substantially pure population of recombinant NK cells obtained from the method of any of paragraphs 1-20, using the using the engineered iPSC of any of claims 38-61.
67. A pharmaceutical composition comprising a substantially pure population of cells of paragraph 26-37 or 63-66.
68. A cryopreserved population of cells comprising a substantially pure population of cells of paragraph 26-37 or 38-52 or 63-66, and media suitable for cryopreservation.
69. A kit for generating an engineered iPSC, the kit comprising at least one of:
    a. a nucleic acid construct comprising a 5' Homology Arm (HA-L), an inducible promoter, a sequence encoding an NICD gene and a 3' homology arm (HA-R), wherein the sequence encoding an NICD gene is operatively linked to the inducible promoter, and wherein the 5' and 3' homology arm allows insertion of the sequence encoding an NICD gene which is operatively linked to the inducible promoter to be inserted into a genomic safe harbor gene;

b. a nucleic acid construct designed for targeting inactivation of the beta-2 microglobulin (B2M) gene, wherein optionally, exon 1 of beta-2 microglobulin (B2M) gene is targeted, and wherein optionally, the nucleic acid construct allows insertion of a HLA-E gene into the beta-2 microglobulin (B2M) gene;

c. a nucleic acid construct designed for targeting inactivation of the CIITA gene, wherein optionally, the nucleic acid construct allows insertion of a CD47 gene into CIITA gene.

It is understood that the foregoing detailed description and the following examples are illustrative only and are not to be taken as limitations upon the scope of the disclosure. Various changes and modifications to the disclosed embodiments, which will be apparent to those of skill in the art, may be made without departing from the spirit and scope of the present disclosure. Further, all patents, patent applications, and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the disclosure. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The disclosure can be understood more fully by reference to the following detailed description and illustrative examples, that are intended to exemplify non-limiting embodiments of the disclosure.

EXAMPLES

The examples presented herein relate to methods and compositions to produce a population of T/NK CD7+ progenitor cells from pluripotent stem cells, such as, but not limited to iPSC. The technology also describes maturation of the T/NK CD7+ progenitor population into mature T cells and NK cells. Also encompassed are compositions of an engineered iPSC line comprising an exogenous NICD gene under an inducible promoter for activation of the notch pathway before onset of endogenous notch signaling the cells. The engineered iPSC line can further also comprise modifications for MHC I KO and/or MHC II KO generated according the methods described herein. Throughout this application, various publications are referenced. The disclosures of all of the publications and those references cited within those publications in their entireties are hereby incorporated by reference into this application in order to more fully describe the state of the art to which this disclosure pertains. The following examples are not intended to limit the scope of the claims to the disclosure, but are rather intended to be exemplary of certain embodiments. Any variations in the exemplified methods that occur to the skilled artisan are intended to fall within the scope of the present disclosure.

Materials and Methods

Experimental Model and Subject Details

OP9 cells (Mouse, ATCC CRL-2749) were maintained in alpha MEM supplemented with 20% FBS, lx glutamax, 1-thioglycerol, and primocin at 37° C., 5% $CO_2$ in standard incubators. Cells were passaged using 0.05% trypsin every 3-4 days. 293T cells were maintained as above but using DMEM with 10% FBS, lx glutamax, and primocin. Human iPSC lines were maintained in tissue-culture treated 6-well plates coated with hESC-qualified matrigel in mTeSR™1 media with added primocin. Media was changed every day except for weekends, when one day was skipped and the cells fed twice the normal volume. Cells were split weekly using RELESR™ following the manufacturer's protocol. Cells were grown at 37° C., 5% $CO_2$ in standard incubators. Specific iPSC lines used in this study were bBU1c2 (XY, EF1α-hSTEMCCA4 loxp lentiviral infection, Cre-excised), BU2-15-Cr10 (XY, EF1a-hSTEMCCA4 loxp lentiviral infection, Cre-excised), BU3-10-Cr1 (XY, EF1a-hSTEMCCA4 loxp lentiviral infection, Cre-excised), BU8.3 (XX, Sendai virus-based infection), and BU6 (XY, EF1a-hSTEMCCA4 loxp lentiviral infection). Anonymized pediatric human thymus samples were obtained under IRB exemption through Boston Children's Hospital Cardiac Surgery Service.

Method Details

Creating OP9-Dll4:MHCII Cell Line

Human DLL4 coding sequence was amplified from oligo-dT generated cDNA (SUPERSCRIPT III First Strand Synthesis™) from human iPSC-derived hemogenic endothelium using DLL4 F and DLL4 R primers and Herculase II fusion enzyme. This amplicon was cloned into our PHAGE 2 lentiviral vector using NotI/BamHI and T4 ligase. The expression cassette placed DLL4 under the control of an EF1α promoter followed by and IRES:ZsGreen element to aid visualization. Successful transformants were verified by restriction digest and Sanger sequencing (GENEWIZ®). Human MHCII is a complex protein consisting of an alpha-beta dimer stabilized by the chaperone CD74. For this reason, the inventors created a polycistronic lentiviral vector containing EF1α HLA-DPα2A_DPβ:IRES:CD74_2A_ZsGreen. CD74, HLA DP α, and β were amplified from oligo-dT generated cDNA derived from human iPSC-derived dendritic cells using primers DPA1 NOT1 F/DPA1 WITH STOP R, DPB1 F/DPB1 BAMHI R, CD74 NDE1 F/CD74 PLAIN R. ZsGreen was amplified from the PHAGE 2 vector using ZSGRN P2A F/ZSGRN CLA1 R. 2A peptides were added to these amplicons where necessary using DPA1 T2A R, DPB1 T2A F, and CD74 P2A R, and two separate inserts were created using overlapping PCR: DPα_T2A_DPβ and CD74_P2A_ZsGreen. There were inserted into the PHAGE 2 lentiviral vector on either side on an IRES element using NotI/BamHI and NdeI/ClaI respectively to create an EF1α DPα_T2A_DPβ:IRES:CD74_P2A_ZsGreen expression construct. On sequencing, a small mutation lead to the addition of a 3 amino acid proline tag to the C-terminal of DPβ, which was considered inconsequential as the C-terminus does not participate in antigen binding. These two plasmid backbones were packaged into VSV-G pseudotyped lentiviral particles using a 5-plasmid co-transfection of 293T cells. Briefly, 80% confluent 15 cm plates of 293T cells grown in DMEM+10% FBS were transfected with 5 plasmids at a ratio of 24:1:1:1:2 (backbone:tat:rev:gag/pol:vsv-g, weight-based) in Trans-IT 293 reagent. Supernatant collections were begun after 48 hrs, with a total of 4-5 collections per plate. The resulting supernatant was filtered (40 uM) and concentrated by spinning for 90 minutes at 16.5K (48960 g on Beckman SW28 rotor). Resulting concentrated virus was aliquoted and stored at −80° C. To create the OP9-Dll4:MHCII cell line, OP9 cells were treated with polybrene at 5 ug/ml in αMEM+20% FBS and infected with both packaged lentiviruses at a high MOI (exact MOI was not calculated). A day later the polybrene was removed. After a minimum of 72 hrs, OP9 cells were dissociated and FACS sorted for DLL4/MHCII double positive cells using PE anti-DLL4 and AF647 anti-MHCII. These cells were expanded and confirmatory flow cytometry showed >95% double positive cells.

Creating iPSC TetOn:NICD1 Lines

Control of Notch activation in iPSCs was pursued by creating a TetOn:NICD1 construct inserted into the AAVS1 safe harbor locus using zinc finger nucleases. PZ P 4X(cHS4) TetON-3XFLAG-tdT CAGG-m2rtTA v2, an optimized targeting vector for the AAVS1 locus was obtained as the kind gift of Laura Ordovas (Ordovas et al., 2015). This vector has the addition of two cHS4 insulators on either side of the transgene to reduce the potential for silencing. In addition, the construct contains an m2rtTA under the control of a CAG promoter and a T2A puromycin resistance gene that should only be active when inserted near a coding sequence, improving the selection specificity. NICD1 cDNA was amplified from plasmid TetO-FUW-NICD, a gift from Rudolf Jaenisch (Addgene plasmid #61540) using primers NOTCH 1 NICD F (+RS)/NOTCH1 NICD R (+RS). This was inserted into the PZ plasmid using MluI and EcoRV. Correct insertion was verified using Sanger sequencing as before. In preparation for nucleofection, target iPSCs were treated with 10 υM Y27632 (Rho-associated kinase (ROCK) inhibitor) for at least 2 hours. Cells were then dissociated using a 10 minute incubation with ReLeSR™ followed by mechanical dissociation in mTeSR™+Rock inhibitor with the P1000 micropipette. Cells were counted using the LUNA-II™ Automated Cell Counter (Logos Biosystems, Inc.) and $2\times10^6$ live cells were resuspended in AMAXA™ P3 primary cell nucleofection solution containing 1 μg/$10^6$ cells of the TetOn:NICD1 plasmid and the left and right zinc finger plasmids. The cells were then nucleofected using the hES cell, H9 standard program on the LONZA 4D-NUCLEOFECTOR™. The cells were then resuspended in mTeSR™ with 10 uM Y27632 and plated on a 10 cm hESC-matrigel coated plate. Rock inhibitor was removed the following day. Cells were selected using puromycin at 500-700 ng/ml starting a minimum of 96 hrs after nucleofection. Selection was maintained for 7-10 days as the resistant colonies emerged and grew. Successful colonies were manually picked into 24-well hESC matrigel coated plates in mTeSR™ with rock inhibitor. Genomic DNA from each clone was extracted using the DNEASY BLOOD AND TISSUE™ KIT (Qiagen) and were screened for insertion using primers Z-AV-4 (binds in the AAVS1 locus outside the donor arm)/T2A R. Positive clones were expanded, re-selected with puromycin and frozen, and a single clone for each line was carried forward. For assessing Notch activation, cells were treated with doxycycline ranging from 100-500 ng/ml for 72 hrs in triplicate wells of a 12-well plate. Qualitative real-time PCR was used to assess the expression of Notch target genes HES5 and HEY1 on resulting cDNA using ACTB as a housekeeping gene.

Differentiation Protocols

For differentiation to hematopoietic progenitors, iPSCs were plated at low confluency (~30-50×$10^3$/well) on matrigel (corning cat #354234) coated 6-well plates in mTeSR™. Two days later, differentiations were begun by removing the mTeSR™ completely and adding the differentiation media for day 0. The primary protocols used in this paper to generate hematopoietic progenitors are outlined in detail below. Progenitor identity was checked by flow cytometry for CD34, CD45, and CD235a. Higher percentages of CD34/45 double positive cells negative for CD235a were considered optimal. T cell differentiation was accomplished using the OP9-dll4:MHCII feeder layer as described above. Co-cultures were initiated in 10 cm plates in T cell differentiation media containing αMEM, 20% FBS, glutamax, aMTG, ascorbic acid, 5 ng/ml IL-7, 5 ng/ml FLT3L, and 50 ng/ml SCF. Cultures were passaged onto new feeder cells every 7 days. After the first 7 days, SCF was removed and 10 υM dexamethasone was added. For passaging, the OP9-dll4:MHCII feeder layer was rinsed with existing media several times, and then the entire monolayer was broken up using the 10 ml serological pipette. The resulting suspension was passed through a 40 υM cell strainer, centrifuged, and resuspended in new T cell media over a new feeder layer. Progress of T cell differentiations were followed by weekly flow cytometry checking CD7, CD4, CD8, and CD5 with additional markers as needed (including CD3, CD1a, CD56, and others).

The three different differentiation protocols, HSPC, HSPC-HE ("HE" protocol) and iT protocol are shown in Table 6 below, with the day of differentiation in the first row.

TABLE 6

| Day 0 | 1 | 2 | 3 | 4 | 5 | 6 | 7 | 8 | 9 | 10 | 11 | 12 |
|---|---|---|---|---|---|---|---|---|---|---|---|---|
| HSPC | | | | | | | | | | | | |
| RPMI + KSR + primocin + aMTG + AA + glutamax (d0-d2) | | | StemPro 34 + glutamax + primocin + aMTG + Ascorbic Acid (d3-d12) | | | | | | | | | |
| Normoxia (d0-d12) | | | | | | | | | | | | |
| BMP4 5 ng/ml; VEGF 50 ng/ml; Wnt3a 25 ng/ml; (d0-d1) | | BMP4 5 ng/ml; VEGF 50 ng/ml; bFGF 20 ng/ml; Chir 3 uM (d2) | BMP4 5 ng/ml; VEGF 50 ng/ml; bFGF 20 ng/ml (d3) | VEGF 15 ng/ml; bFGF 5 ng/ml; CH223191 10 uM (d4-d5) | | VEGF 50 ng/ml; bFGF 100 ng/ml; SCF 200 ng/ml; FLT3L 100 ng/ml; TPO 100 ng/ml; IL-6 100 ng/ml (d6-d12) 2 ml media/well 6 well plate on day 6, 0.5 ml/well every day afterward. Sometimes longer to day 14. | | | | | | |
| HSPC-HE protocol (HE protocol) | | | | | | | | | | | | |
| RPMI + KSR + primocin + aMTG + AA + glutamax (d0-d2) | | | StemPro 34 + glutamax + primocin + aMTG + Ascorbic Acid (d3-d12) | | | | | | | | | |
| Normoxia (d0-d12) | | | | | | | | | | | | |
| BMP4 5 ng/ml; VEGF 50 ng/ml; Wnt3a 25 ng/ml; (d0-d1) | | BMP4 5 ng/ml; VEGF 50 ng/ml; bFGF 20 ng/ml; Chir 3 uM (d2) | BMP4 5 ng/ml; VEGF 50 ng/ml; bFGF 20 ng/ml (d3) | VEGF 15 ng/ml; bFGF 5 ng/ml; CH223191 10 uM (d4-d5) | | BMP4 10 ng/ml; VEGF 5 ng/ml; bFGF 5 ng/ml; SCF 100 ng/ml; FLT3L 10 ng/ml; TPO 30 ng/ml; IL3 30 ng/ml; IL6 10 ng/ml; IL11 5 ng/ml; IFG1 25 ng/ml; SHH 20 ng/ml; Transferrin 150 ug/ml. (d6-d12) 2ml media/well 6 well plate on day 6, 0.5 ml/well every day afterward. Sometimes longer to day 14. | | | | | | |
| iT Protocol | | | | | | | | | | | | |
| StemPro 34 + glutamax + primocin + aMTG + Ascorbic Acid (d0-d12) | | | | | | | | | | | | |
| Hypoxia (5% O2) (d0-d7) | | | | | | Normoxia (d8-d12) | | | | | | |
| BMP4 5 ng/mL; VEGF 50 ng/mL; CHIR99021 2 uM (d0-d1) | | BMP4 5 ng/mL; VEGF 50 ng/mL; bFGF 20 ng/mL (d2-d3) | | VEGF 15 ng/mL; bFGF 5 ng/mL (d4-d5) | | BMP4 10 ng/ml; VEGF 5 ng/ml; bFGF 5 ng/ml; SCF 100 ng/ml; FLT3L 10 ng/ml; TPO 30 ng/ml; IL3 30 ng/ml; IL6 10 ng/ml; IL11 5 ng/ml; IFG1 25 ng/ml; SHH 20 ng/ml; Transferrin 150 ug/ml. (d6-d12) 2 ml/well 6 well plate on day 6, spin cells down to replace media every 2 days. | | | | | | |
| DOX 100-500 ng/ml (d0-d2) | | | No DOX (d3-d12) | | | | | | | | | |

Cell Isolation

Cell sorting was carried out through the flow cytometry core facility at Boston University Medical Center using a MoFlo Astrios instrument (Beckman Coulter Life Sciences, Indianapolis, Ind.). For sorting at day 4 (see FIG. 2A-2F), adherent cells were rinsed in PBS and dissociated using TrpLE Select reagent for 5 minutes. Dissociation was stopped using full media. Cells were then rinsed in PBS and stained for VE-Cadherin-FITC, CD34-BV421, and KDR-APC for 30 minutes at room temperature. Populations sorted were KDR−, KDR+/CD34−/VE-Cadherin−, and KDR+/CD34+/VE-Cadherin+. Resulting cells were plated in 12-well matrigel-coated plates at $2\times10^5$ cells/well and cultured per the "iT protocol" starting at day 5. For CD7+ sorting at day 45, suspension cells were harvested from the co-culture dish and passed through a 40 uM cell strainer. Cells were stained with calcein blue per the manufacturer's protocol and then stained with hCD7-APC for 30 minutes at room temperature. Live, CD7+ cells were sorted for RNA extraction. For single cell RNA sequencing experiment, suspension cells were stained with FVS780 per manufacturer's protocol and then stained with hCD45-PE for 30 minutes at room temperature. Live, CD45+ cells were sorted, re-suspended at a minimum of $8\times10^4$ cells/ml and transported on ice to the Harvard Single Cell Core.

Realtime PCR: Gene expression analysis by real-time PCR was pursued during the first eight days of differentiation between tetOn-NICD1 lines and their parental counterparts and at day 45 CD7 FACS-sorted cells. For early gene-expression analysis, 4 tetOn-NICD1 lines and 4 parental iPSC lines were differentiated using the "iT protocol" above (all treated with doxycycline) and wells were collected at day 1, 2, 3, 4, 5, and 8. RNA extraction was accomplished using RNEASY MINIKIT™ (Qiagen). Complementary DNA was made using the superscript III first strand synthesis system (Invitrogen) using random hexamers and an input of 500 ng total RNA per sample. Real-time PCR for targets BACT, ETV2, HES5, HEY1, KDR, LMO2, MESP1, PDGFRA, T, and TAL1 was carried out using commercially available primers from IDT DNA using POWERSYBR GREEN PCR MASTER MIX™ (Applied Biosystems) using standard cycling protocol (60° C. Tm, 40 cycles, followed by melt curve). Data was normalized to BACT and analyzed in HTqPCR using the delta-delta Ct method for gene expression analysis. Comparisons analyzed were day1-day1 etc. between transgenic and control lines, and day1-2, 1-3, etc. within the transgenic lines. Significance was assigned at a p≤0.05. For day 45 CD7+ cell gene expression analysis, two separate differentiations with bBU1c2 N1 and BU3 N1 were carried to day 45. Cells were FACS sorted for live, CD7+ cells as above and RNA extracted using the RNEASY MICROKIT™ (Qiagen). First strand synthesis was done as above with RNA normalized to 26 ng/reaction.

Single cell analysis: Cells were differentiated per the "iT protocol," above with and without doxycycline at day 0-2.

Cells were taken for single cell analysis at day 12 (dox treated and untreated), day 13, 16, 20, 42 (after day 12, only dox treated samples), and freshly isolated human thymocytes. Cells were sorted for live, CD45+ cells as outlined above and single cell isolation and library preparation was done using the inDrops method at the Harvard Single Cell Core followed by library sequencing at the Boston University Medical Center Microarray and Sequencing core. The resulting sequencing data was demultiplexed using the inDrops pipeline (see world wide web at address:github.com/indrops/indrops). Reads were filtered to remove those with low quality or low complexity and subsequently mapped to the repeat-masked primary assembly of the human genome (GRCh38, ENSEMBL) using Bowtie v.1.1.1. Downstream analyses were done using Seurat (Butler et al., 2018). Briefly, the count matrices were further filtered to remove degraded cells (>15% of mitochondrial content) and multiplets (using the rates determined by Chromium 10× guidelines). Next, the inventors performed linear dimensionality reduction using PCA, which was then used as input for the Louvain clustering algorithm and non-linear dimensionality reduction with UMAP. Cell cycle stage was scored and classified using the strategy described in (Tirosh et al., 2016). The inventors tested differential gene expression for each cluster using hurdle models for sparse single-cell expression data implemented in MAST (Finak et al., 2015). The markers resulting from such analysis were used to annotate the identity of each cluster. Transcriptome data and metadata was finally imported into SPRING (Weinreb et al., 2018) for interactive analysis and visualization. All SPRING plots (k-NN graphs rendered using a force-directed layout) were generated in the SPRING upload server: https://kleintools.hms.harvard.edu/tools/spring.html using the default parameters. The analysis above were done both for the individual libraries and for the combination of all samples. All in all, 22,832 cells passed filtering with a read depth of approximately 40 k reads/cell.

Quantification and Statistical Analysis

Data and Code Availability

TABLE 7

Key Resources

| REAGENT or RESOURCE | SOURCE | IDENTIFIER |
|---|---|---|
| **Antibodies** | | |
| BV421 Mouse Anti-Human CD34 | BD Bioscience | Cat#562577; RRID: |
| PE Mouse Anti-Human CD235a | BD Bioscience | Cat#555570 |
| PE Mouse Anti-Human CD45 | BD Bioscience | Cat#555483 |
| AF647 Mouse Anti-Human CD309(KDR) | BD Bioscience | Cat#560495 |
| FITC Mouse Anti-Human CD144(VE-Cadherin) | BD Bioscience | Cat#560411 |
| PE Mouse Anti-Human CD4 | BD Bioscience | Cat#555347 |
| BB515 Mouse Anti-Human CD314 (NKG2D) | BD Bioscience | Cat#564566 |
| PE Mouse Anti-Human Delta-Like Protein 4 | BD Bioscience | Cat#564412 |
| BV421 Mouse Anti-Human CD335 (NKp46) | BD Bioscience | Cat#564065 |
| PE Mouse Anti-Human CD56 | Biolegend | Cat#304605 |
| BV605 Mouse Anti-Human CD5 | BD Bioscience | Cat#563945 |
| BB515 Mouse Anti-Human NKp44 | BD Bioscience | Cat#565099 |
| AF647 Mouse Anti-Human HLA-DR, DP, DQ | BD Bioscience | Cat#563591 |
| BV421 Mouse Anti-Human CD1a | BD Bioscience | Cat#563939 |
| BB515 Mouse Anti-Human CD4 | BD Bioscience | Cat#564500 |
| APC Mouse Anti-Human CD7 | BD Bioscience | Cat#561604 |
| FITC Mouse Anti-Human CD16 | BD Bioscience | Cat#561308 |
| APC Mouse Anti-Human CD69 | BD Bioscience | Cat#560967 |
| BV421 Mouse Anti-Human CD14 | BD Bioscience | Cat#565283 |
| BV421 Mouse Anti-Human CD8 | BD Bioscience | Cat#562428 |
| FITC Mouse Anti-Human CD235a | BD Bioscience | Cat#559943 |
| AF488 Mouse Anti-Human CD3 | BD Bioscience | Cat#557694 |
| APC Mouse Anti-Human CD45 | BD Bioscience | Cat#555485 |
| PE Mouse Anti-Human DLL4 | BD Bioscience | Cat# 564412 |
| **Bacterial and Virus Strains** | | |
| One Shot MAX Efficiency DH5a T1 Chemically Competent Cells (*E. coli*) | Life Technology | Cat#12297016 |
| MHCII lentivirus | This lab | N/A |
| DLL4 lentivirus | This lab | N/A |
| **Biological Samples** | | |
| Anonymized pediatric human thymus | Boston Children's Hospital | N/A |
| **Chemicals, Peptides, and Recombinant Proteins** | | |
| Recombinant Human BMP-4 Protein | R&D Systems | Cat# 314-BP |
| Recombinant Human VEGF 165 Protein | R&D Systems | Cat#293-VE |
| Recombinant Human Wnt-3a Protein | R&D Systems | Cat#5036-WN |
| Recombinant Human FGF basic/FGF2 (146 aa) Protein | R&D Systems | Cat#233-FB |
| CHIR99021 | Reprocell | Cat#04-0004 |
| CH223191 | Tocris | Cat#3858 |
| Recombinant Human SCF Protein | R&D Systems | Cat#255-SC |
| Recombinant Human Sonic Hedgehog (Shh) | Peprotech | Cat#100-45 |
| Recombinant Human FLT3L | Bio X Cell | No longer made |
| Recombinant Human TPO | R&D Systems | Cat#288-TP |
| Recombinant Human IL-6 Protein, CF | R&D Systems | Cat#206-IL CF |
| Recombinant Human IL-3 Protein | R&D Systems | Cat#203-IL |

TABLE 7-continued

| REAGENT or RESOURCE | SOURCE | IDENTIFIER |
| --- | --- | --- |
| Key Resources | | |
| Recombinant Human IL-11 | Peprotech | Cat#200-11 |
| Recombinant Human IGF-I/IGF-1 Protein, CF | R&D Systems | Cat#291-G1 |
| Human Transferrin | Sigma-Aldrich | Cat#10652202001 |
| Recombinant Human IL-7 Protein | R&D Systems | Cat#207-IL |
| Angiotensin II human | SIGMA-ALDRICH | Cat#A9525 |
| Losartan potassium | Fisher | Cat#3798 |
| DEXAMETHASONE BIOREAGENT | Sigma | Cat#D4902 |
| Herculase II Fusion enzyme | Agilent Technologies | Cat#600679 |
| TransIT 293 | Mirus | Cat#MIR2700 |
| SuperScript III First Strand Synthesis | Invitrogen | Cat#18080-051 |
| PowerSYBR Green PCR Master Mix | Applied Biosystems | Cat#4367659 |
| hESC Matrigel Matrix | Corning | Cat#354277 |
| Matrigel Matrix | Corning | Cat#354234 |
| Stemolecule Y27632 | Reprocell | Cat#04-0012-02 |
| Ascorbic Acid | Sigma | Cat#A4544 |
| mTeSR™1 Media | StemCell | Cat#85850 |
| MEM Alpha | Gibco | Cat#12571-063 |
| StemPro®-34 SFM | Gibco | Cat#10640-019 |
| GlutaMax™ (100x) | Gibco | Cat#35050-061 |
| 1-thioglycerol | Sigma | Cat#M6145 |
| TrypLE™ Select | Gibco | Cat#12563-011 |
| ReLeSR™ | StemCell | Cat#05873 |
| Primocin | InvivoGen | Ant-pm-2 |
| Puromycin | Old stock, unknown | N/A |
| Hyclone Characterized Fetal Bovine Serum | GEHealthcare Life Sciences | Cat# SH30071 |
| Doxycycline | Sigma | Cat# D3072 |
| Trypsin | | |
| DMEM | | |
| NotI | New England Biolabs | Cat# R0189S |
| BamHI | New England Biolabs | Cat# R0136S |
| T4 DNA ligase | New England Biolabs | Cat# M0202S |
| NdeI | New England Biolabs | Cat# R0111S |
| ClaI | New England Biolabs | Cat# R0197S |
| polybrene | | |
| MluI | New England Biolabs | Cat# R0198S |
| Calcein blue | BD Biosciences | Cat# 564060 |
| FVS780 | BD Biosciences | Cat# 565388 |
| EcoRV | New England Biolabs | Cat# R0195S |
| Critical Commercial Assays | | |
| Amaxa™ P3 Primary Cell Kit | Lonza | Cat#V4XP-3024 |
| RNeasy minikit | | |
| RNeasy microkit | | |
| Deposited Data | | |
| Experimental Models: Cell Lines | | |
| OP9 | ATCC | CRL-2749 |
| 293T | | |
| bBU1c2 iPSC (Plus TetOn:NICD1 version) | This lab | N/A |
| BU6 iPSC | This lab | N/A |
| BU8 iPSC (Plus TetOn:NICD1 version) | This lab | N/A |
| BU3 iPSC (Plus TetOn:NICD1 version) | This lab | N/A |
| BU2 iPSC (Plus TetOn:NICD1 version) | This lab | N/A |
| Experimental Models: Organisms/Strains | | |
| Oligonucleotides | | |
| Hes5 | Integrated DNA Technologies | Hs.PT.58.14966721.gs |
| Hey1 | Integrated DNA Technologies | Hs.PT.58.4299267 |
| Etv2 | Integrated DNA Technologies | Hs.PT.58.4291149 |
| Kdr | Integrated DNA Technologies | Hs.PT.58.39954597 |
| Pdgfra | Integrated DNA Technologies | Hs.PT.58.25123874 |
| Mesp1 | Integrated DNA Technologies | Hs.PT.58.38974490.g |
| Scl/Tal1 | Integrated DNA Technologies | Hs.PT.58.975520 |
| Lmo2 | Integrated DNA Technologies | Hs.PT.58.27100749 |
| Bcl11b | Integrated DNA Technologies | Hs.PT.58.27217530 |

TABLE 7-continued

| Key Resources | | |
|---|---|---|
| REAGENT or RESOURCE | SOURCE | IDENTIFIER |
| CD247 | Integrated DNA Technologies | Hs.PT.56a.21399083.g |
| Lck | Integrated DNA Technologies | Hs.PT.58.40262054 |
| Ptcra | Integrated DNA Technologies | Hs.PT.58.22840650 |
| Rag1 | Integrated DNA Technologies | Hs.PT.58.22734140 |
| Rag2 | Integrated DNA Technologies | Hs.PT.58.1807593 |
| Runx3 | Integrated DNA Technologies | Hs.PT.56a.40098776 |
| Spi1 | Integrated DNA Technologies | Hs.PT.58.19735554 |
| Actb | Integrated DNA Technologies | Hs.PT.39a.22214847 |
| Zap70 | Integrated DNA Technologies | Hs.PT.58.3371269 |
| DLL4 F (ttctGCGGCCGCCATGGCGGCAGCGTCCCGGAGC (SEQ ID NO: 15)) | This lab | N/A |
| DLL4 R (atttggatccTTATACCTCCGTGGCAATGACAC (SEQ ID NO: 16)) | This lab | N/A |
| DPA1 NOT1 F (TGCTTGCGGCCGCCATGCGCCCTGAAGACAGAATG (SEQ ID NO: 17)) | This lab | N/A |
| DPA1 WITH STOP R (CCTTTACAGTATTTCACAGGGTCC (SEQ ID NO: 18)) | This lab | N/A |
| DPA1 T2A R (tcctccacgtccccgcatgttagtagacttcccctgccctcgccggagccCAGGGTCCCCTGGGCCCGGG (SEQ ID NO: 19)) | This lab | N/A |
| DPB1 F (GCCATCCTTTTCCAGCTCCA (SEQ ID NO: 20)) | This lab | N/A |
| DPB1 T2A F (caggggaagtctactaacatgcggggacgtggaggaaaatcccggcccaATGATGGTTCTGCAGGTTTCTGCGGC (SEQ ID NO: 21)) | This lab | N/A |
| DPB1 BAMHI R (tttttGGATCCTTATGCAGATCCTCGTTGAACTTTCTTG (SEQ ID NO: 22)) | This lab | N/A |
| DPB1 R (TCAGTGAGCTCAGGAACCCT (SEQ ID NO: 23)) | This lab | N/A |
| CD74 NDE1 F (attattCATATGatgcacaggaggagaagcaggagct (SEQ ID NO: 24)) | This lab | N/A |
| CD74 PLAIN R (CAGGATGTTGAAGACCGCCT (SEQ ID NO: 25)) | This lab | N/A |
| CD74 P2A R (ttctcttcgacatcccctgcttgtttcaacagggagaagttagtggctccgcttccggacatggggactgggcccagatcctgcttggt (SEQ ID NO: 26)) | This lab | N/A |
| ZSGRN P2A F (gccactaacttctccctgttgaaacaagcaggggatgtcgaagagaatcccgggccaatggcccagtccaagcacggcctgaccaag (SEQ ID NO: 27)) | This lab | N/A |
| ZSGRN CLA1 R (ggatctatcgatttagggcaaggcggagccgg (SEQ ID NO: 28)) | This lab | N/A |
| NOTCH 1 NICD F (+RS) (agatacGATATCatgcggeggcagcatggccagct (SEQ ID NO: 29)) | This lab | N/A |

TABLE 7-continued

| Key Resources | | |
|---|---|---|
| REAGENT or RESOURCE | SOURCE | IDENTIFIER |
| NOTCH 1 NICD R (+RS) (ctagcaACGCGTttacttgaacgcctccggga (SEQ ID NO: 30)) | This lab | N/A |
| Z-AV-4 (gccggaactctgccctctaacgct (SEQ ID NO: 31)) | This lab | N/A |
| T2A R (GATTCTCCTCCACGTCACCGC (SEQ ID NO: 32)) | This lab | N/A |
| Recombinant DNA | | |
| PZ P 4X(cHS4) TetON-3XFLAG-tdT CAGG-m2rtTA v2 | (Ordovas et al., 2015) | N/A |
| Phage-2 lentiviral vectors<br>AAVS1 Zinc Finger R<br>AAVS1 Zinc Finger L | This lab | N/A |
| TetO-FUW-NICD | Addgene | Cat#61540<br>RRID: Addgene_615v |
| Software and Algorithms | | |
| inDrops pipeline | GitHub, Inc. | (see world wide web at address: github.com/indrops/indrops). |
| Seurat | (Butler et al., 2018) | N/A |
| MAST | (Finak et al., 2015) | N/A |
| SPRING | (Weinreb et al., 2018) | N/A |
| Other | | |

Example 1

Defining the Best Conditions for Mesodermal to Hematopoietic Transition for Inducing T Competence of iPSC-Derived Hematopoietic Progenitors.

Figure 1C:
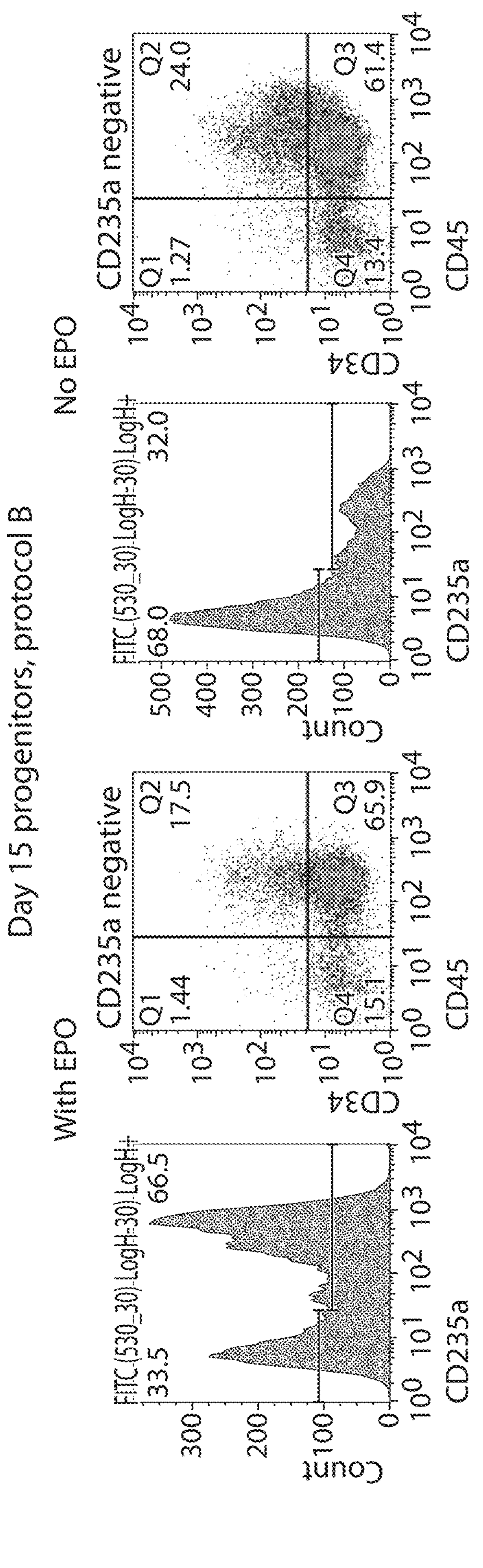

Starting with an established 2-D hematopoietic differentiation protocol for the production of erythrocytes and megakaryocytes (Leung et al., 2018), the inventors developed a method to improve the T/NK-lineage capable progenitor yield. This "HSPC" protocol has two main phases, a mesoderm to hemogenic endothelium phase (day 0-5) followed by a hematopoietic cell production phase (day 6-15) (FIG. 1A). To assess T/NK lineage capacity, the resulting progenitors at day 15 were co-cultured with an engineered OP9-hdll4:hMHCII feeder layer (FIG. 3B) and assessed for CD7 positive cells after 7 days of co-culture. Surprisingly, few if any CD7+ positive cells were observed with this protocol (FIG. 1B). The inventors discovered there were surprisingly important and critical differences between the HSPC protocol and previously published protocols that produce some T-capable progenitors such as the embryoid-body based differentiation (Ditadi and Sturgeon, 2016). Three main differences the inventors discovered were as follows: the use of embryoid bodies, the sorting for hemogenic endothelium at day 8 (based on $CD34^+$, $CD43^-$, $CD73^-$, $CD184^-$), and the alternative day 6 media ("HE" media). The inventors discovered that the HE media was the most significant factor in improving T/NK-capable progenitor yield and not the use of embryoid bodies or a sorting step (FIG. 1A, 1B). Surprisingly, the inventors also discovered that use of iT media between d6-d12, where the iT media is a modified HE media where erythropoietin and angiotensin are removed from the normal HE media, significantly reduced the $CD235^+$ cell population without sacrificing overall cell yield (FIG. 1C).

Example 2

Early application of a GSK-3β inhibitor (Chir) combined with hypoxia robustly improves hematopoietic progenitor output by increasing the $KDR^{high}$, $CD34^+$, VE-$Cadherin^+$ population at day 4.

Figure 2E:
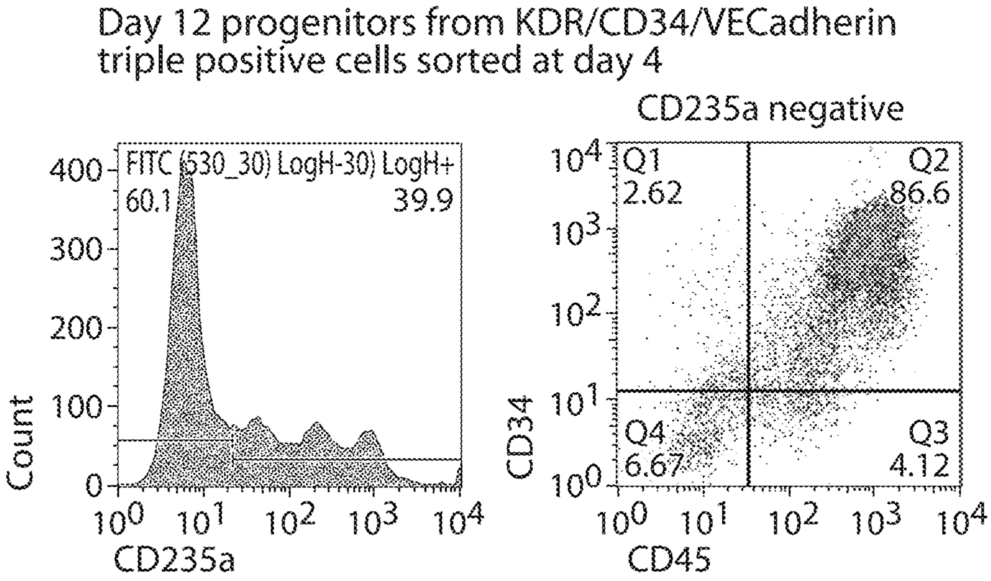
Figure 2F:
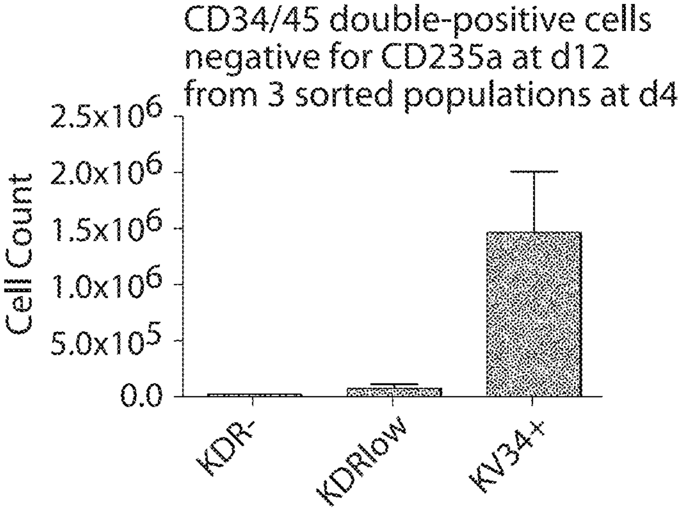

It has been previously reported that the use a GSK3β inhibitor (CHIR 99021, 3 uM) at day 2 can be used to improve the output and differentiation of more definitive hematopoietic cells (Leung et al., 2018; Sturgeon, 2014). However, the use of CHIR earlier has also been reported to boost mesodermal commitment (D'Souza et al., 2016; Galat et al., 2018; Takata et al., 2017). To explore the impact of earlier application of CHIR, the inventors assessed the HSPC-HE protocol with an alternative protocol involving CHIR from day 0-1 (2 uM) with hypoxia (5% $O_2$) (Takata et al., 2017) followed by use of iT media, where EPO and angiotensin are absent (FIG. 2A). The inventors discovered that earlier application of CHIR consistently resulted in a larger population of $KDR^{high}$, $CD34^+$, $VECadherin^+$ cells at day 4 of differentiation (marking putative hemogenic endothelium (Choi et al., 2012; Fraser et al., 2002; Gritz and Hirschi, 2016)) (FIG. 2D) and a higher efficiency of hematopoietic progenitor production by day 12 (FIG. 2C). To test whether the increase in efficiency was due to the larger $KDR^{high}$ population, cells were sorted by FACS for $KDR^-$, $KDR^+/CD34^-/VECadherin^-$, and $KDR^+/CD34^+/VECadherin^+$ at day 4 of differentiation. These three populations were cultured until day 12 and assessed by floating cell output and flow cytometry of both floating and stromal compartments. The majority of hematopoietic potential was in the $KDR^+/CD34^+/VECadherin^+$ population (FIG. 2E-2F). Based on these results, the inventors adopted a mesodermal commitment step defined by early GSK3β inhibition and hypoxia, followed by culturing in an iT media where EPO and angiotensin is absent, which is referred to herein as the "iT" protocol. Surprisingly, this "iT" protocol consistently produced a large population of CD45 positive hematopoietic cells, much more consistently and robustly than any previously reported protocol. For instance, the were 65.1%, 61.5%, 67% and 44.4% CD7+ cells at day 19 in each of the iPSC cell lines assessed after early Notch induction (Dox d0-d2) as compared to in the absence of Dox. This is a major significant improvement in yield of CD7+ cells compared to previously established protocols. When bulk floating cells were plated on OP9-hdll4:hMHCII feeder cells, T/NK cell lineage commitment based on CD7 staining at 1 week of co-culture hovered around 10% (See FIG. 5E, no dox conditions).

Example 3

Notch Activation During Mesoderm Induction Robustly Improves Access to the T/NK Cell Lineage by Stimulating Notch Target Genes Prior to the Onset of Endogenous Notch Signaling.

Figure 6A:
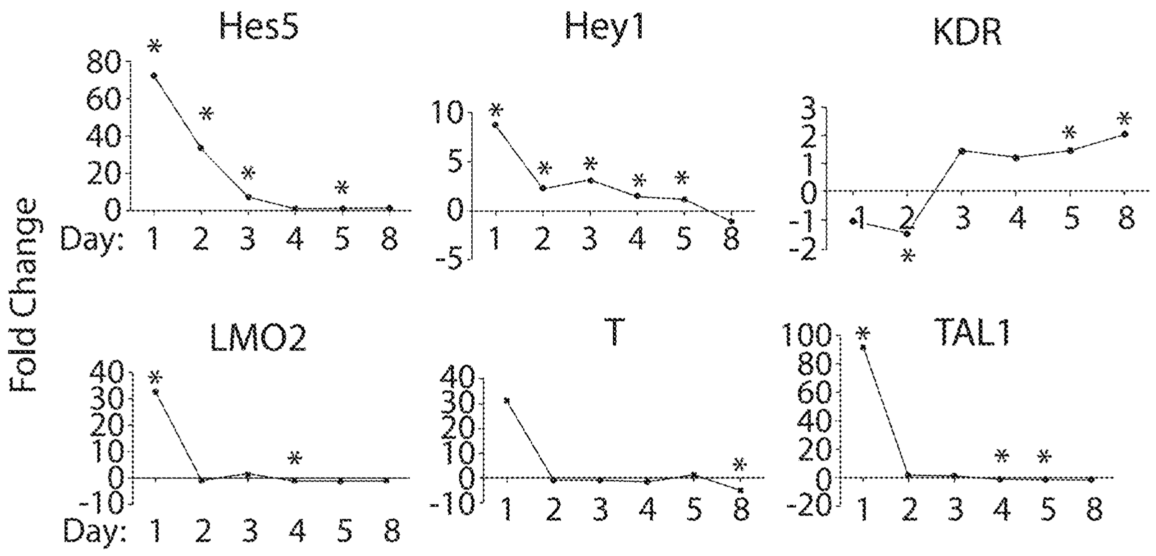
FIGS. 6A-6E show Notch activation is required for T/NK lineage competence in a time dependent manner.
Figure 6B:
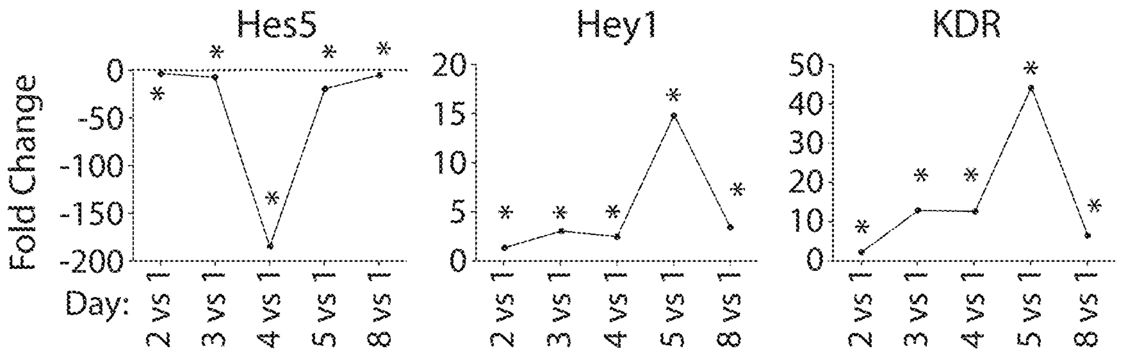
Figure 6D:
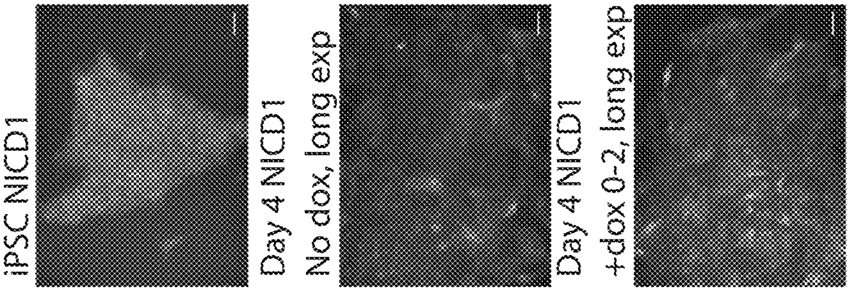
Figure 6C:
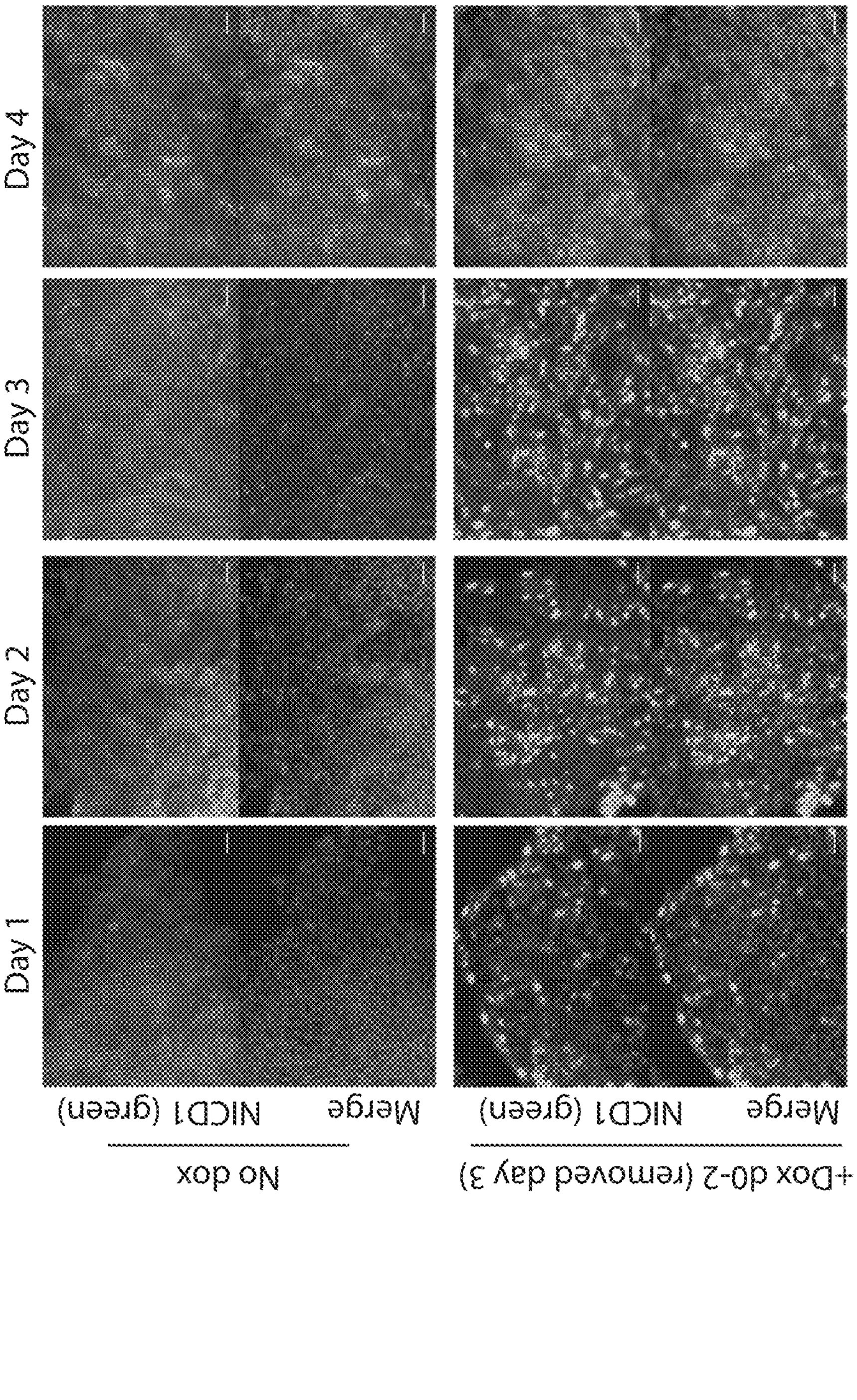
Figure 6E:
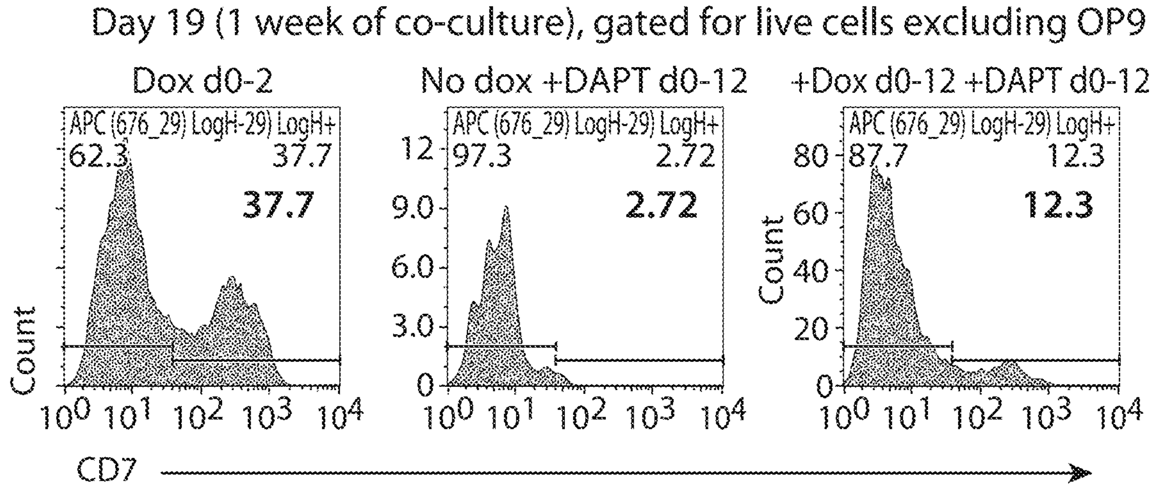

To gain autonomous or independent control of Notch1 activation, a Tet-On:NICD1 construct was inserted into the AAVS1 locus of four iPSC lines using zinc-finger nucleases and an optimized targeting vector for the AAVS1 locus ((Ordovas et al., 2015)) (FIG. 5A). Positive clones were isolated by puromycin selection and screened by PCR. New lines were induced with doxycycline and Notch activation assessed by qRT-PCR for Notch target genes HES5 and HEY1 (FIG. 5B, 5C). Doxycycline stimulation from day 0-2 of differentiation yielded an increase in $CD34^{high}$ cells and a decrease of $CD235a^{+}$ cells at day 12 and a robust increase in $CD7^{+}$ cells after 1 week of co-culture (FIG. 5E). Notch stimulation after day 2 or for a longer period of time did not improve the outcome. Unexpectedly, a narrow window of effect was observed for Notch stimulation, with too little yielding no improvement and too much abrogating hematopoietic progenitor production (data not shown), therefore demonstrating the inventors had discovered both the critical nature of the timing and amount of Notch activation for robust increase in CD7+ cells. To assess the kinetics of Notch activation during differentiation, the inventors sought to specifically define the gene expression profile of the four NICD1 lines compared to their parental iPSC lines at days 1, 2, 3, 4, 5, and 8 of differentiation. All lines were treated with doxycycline from day 0-2 to rule out any effect of DMSO or doxycycline in the measured response. Differential gene expression was measured using qRT-PCR (data not shown, with genes assessed HES5, HEY1, ETV2, SCL/Tal1, LMO2, KDR, PDGFA, T, MESP1) see also FIG. 6A-6B. Comparisons between NICD1 and parental lines for each day showed a strong up-regulation of Notch target genes by day 1; the difference between Notch target gene expression in NICD1 and parental lines decreased with time even before doxycycline was removed, suggesting that endogenous Notch signaling had taken over and supporting the data that showed that later Notch stimulation had no effect on hematopoietic differentiation. The lateral plate mesoderm marker KDR showed a significant increase in NICD1 lines by day 5. LMO2, T (brachyury), and TAL1 all show a marked increase at day 1 that dropped to parental levels by day 2, suggesting a coordinated function with early Notch activation (FIG. 6A). A second analysis comparing each day to day 1 in the NICD1 lines showed the expected drop in HES5 expression one day after dox withdrawal, and then a re-bound to pre-withdrawal levels consistent with endogenous Notch activation. Mesoderm and early hematopoietic genes KDR, PDGFRA, LMO2, and TAL1 slowly increase over time, while T decreases (FIG. 6B).

Example 4

Progenitor Plating Density Governs T Vs NK Choice

In multiple co-cultures after day 19, the developing hematopoietic cells lysed the OP9-hdll4:hMHCII feeder cells. Further exploration of these cells showed strong staining for CD56 consistent with the emergence of NK cells. These cells also stained positive for other NK cell markers such as NKp44, NKG2D, and NKp46 and continued to lyse the feeder cell layer for several passages (FIG. 7B). To elucidate the optimal culture conditions promoting the development of T rather than NK cells, the inventors tested several modifications including modulating Notch signal intensity, serum concentrations, IL-7 concentration, day of progenitor harvest, progenitor plating density, and sorting for CD4+ cells. The inventors surprisingly determined that only variable that demonstrated a consistent and strong influence on T cell emergence was the plating density of hematopoietic progenitors into the co-culture environment. Importantly, the inventors demonstrate that low progenitor density favored T cells emergence and higher density favored NK cell emergence (FIG. 7A.

Example 5 iPSC-Derived T Cells Mature into CD3/CD8 SP Cells Despite hMHCII Expressed on OP9:Dll4 Feeder Cells.

Figure 3A:
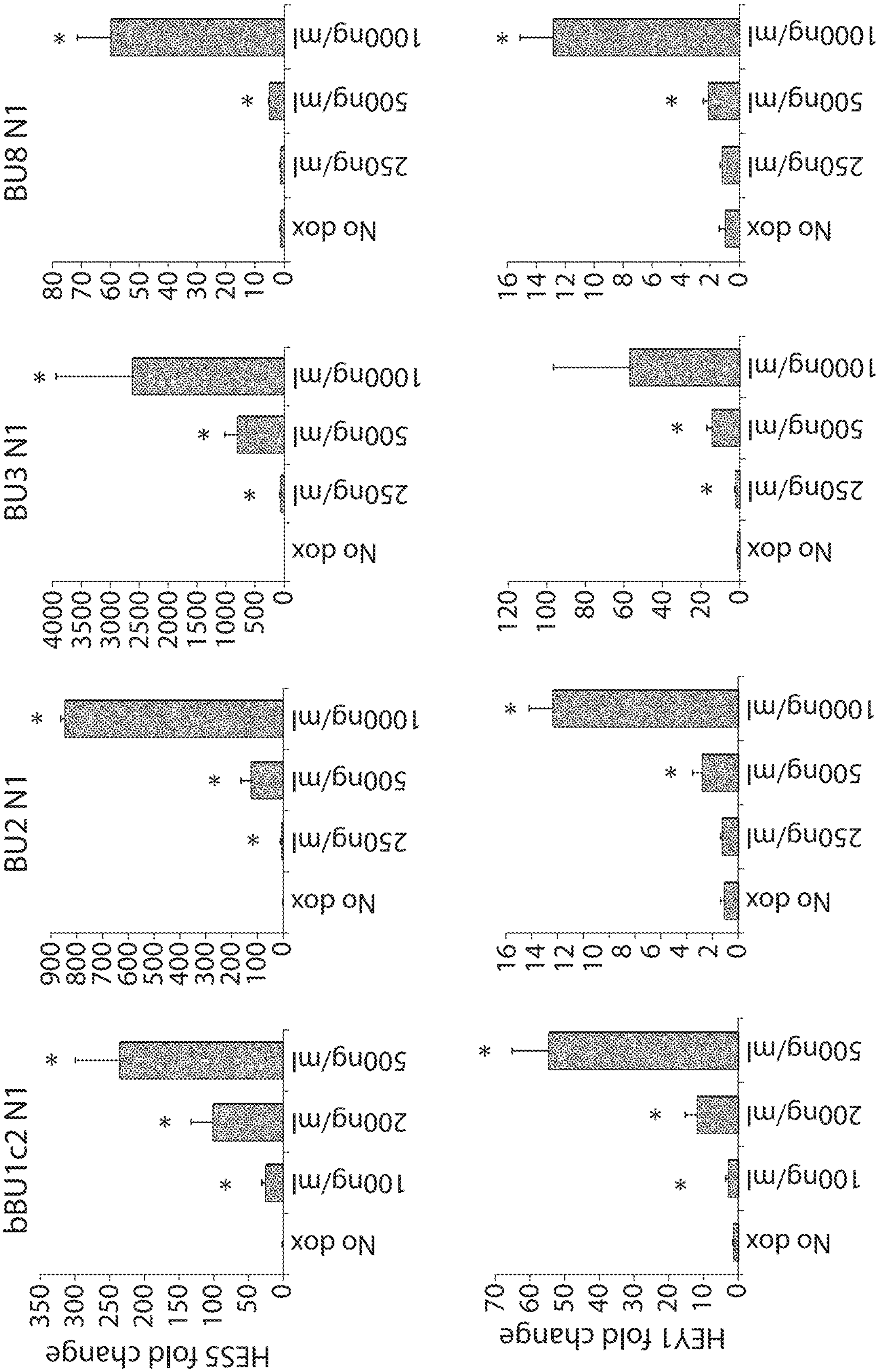
FIG. 3A-3B shows Notch target gene expression in four independent NICD1 lines when treated with doxycycline.
Figure 3B:
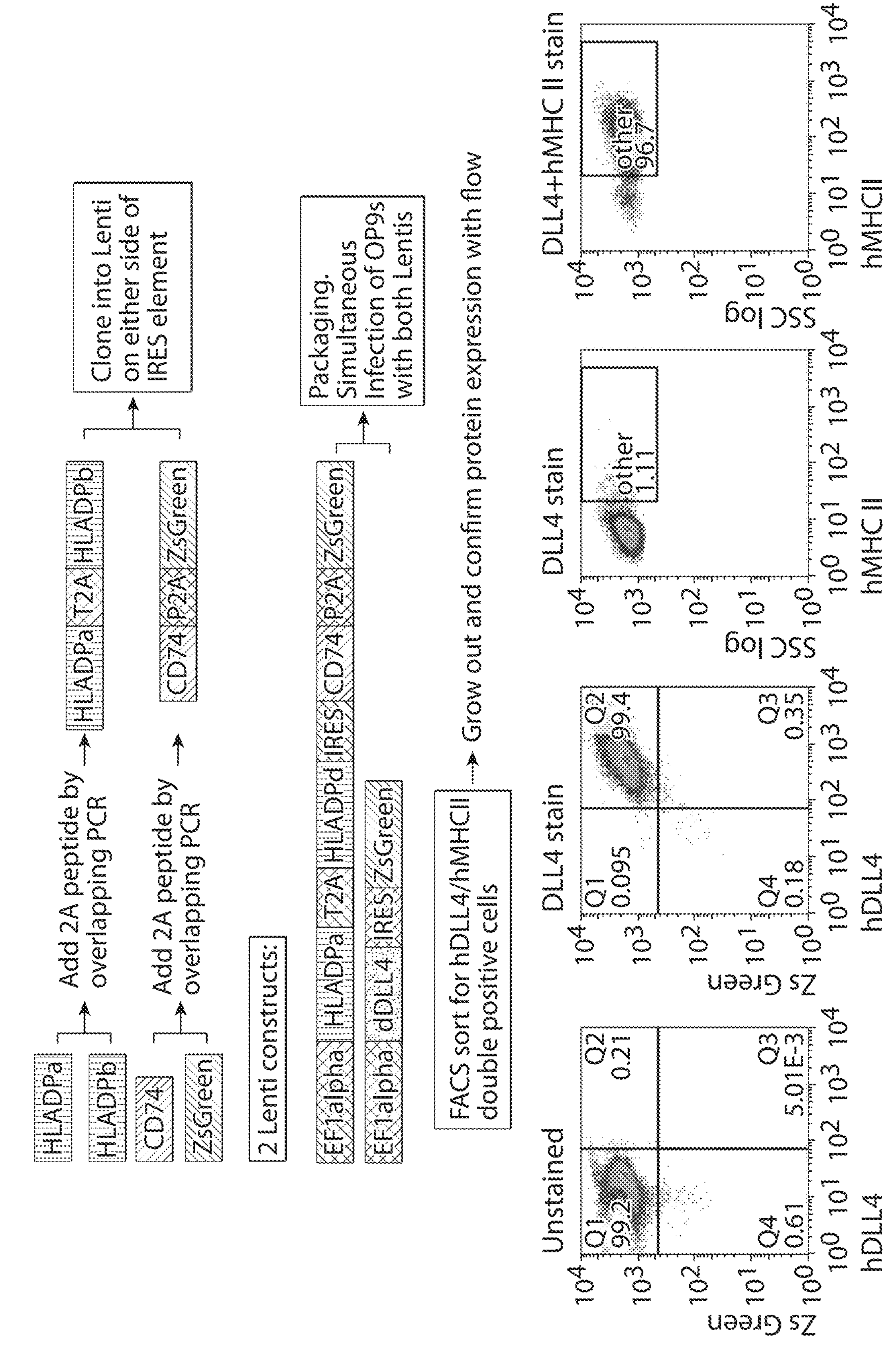
Figure 4A:
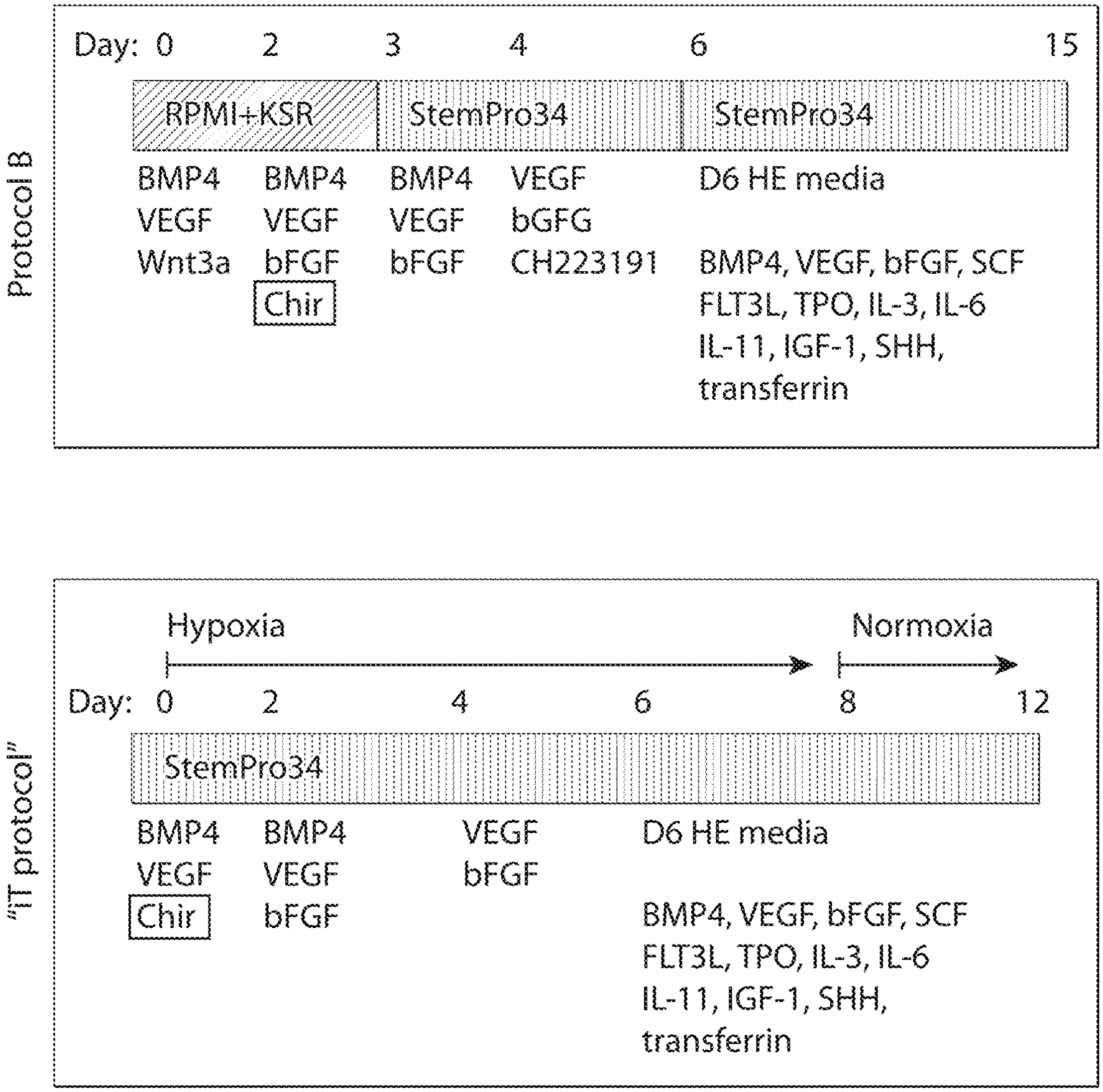
FIG. 4A-4D shows that Dox treatment from day 0-2 of the iT protocol has the most robust impact on CD7+ cell numbers at day 19 (1 week of co-culture).
Figure 4B:
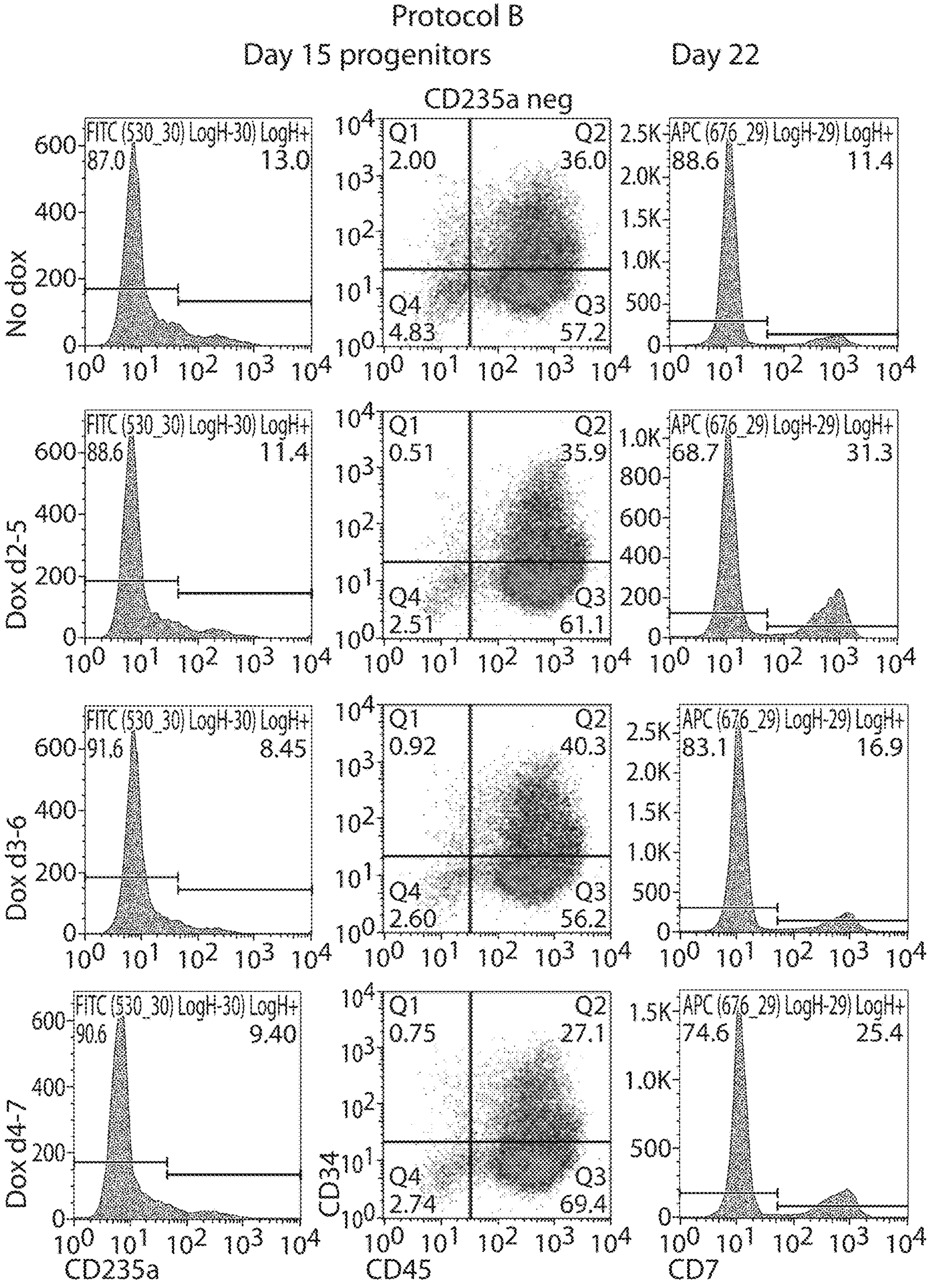
Figure 4C:
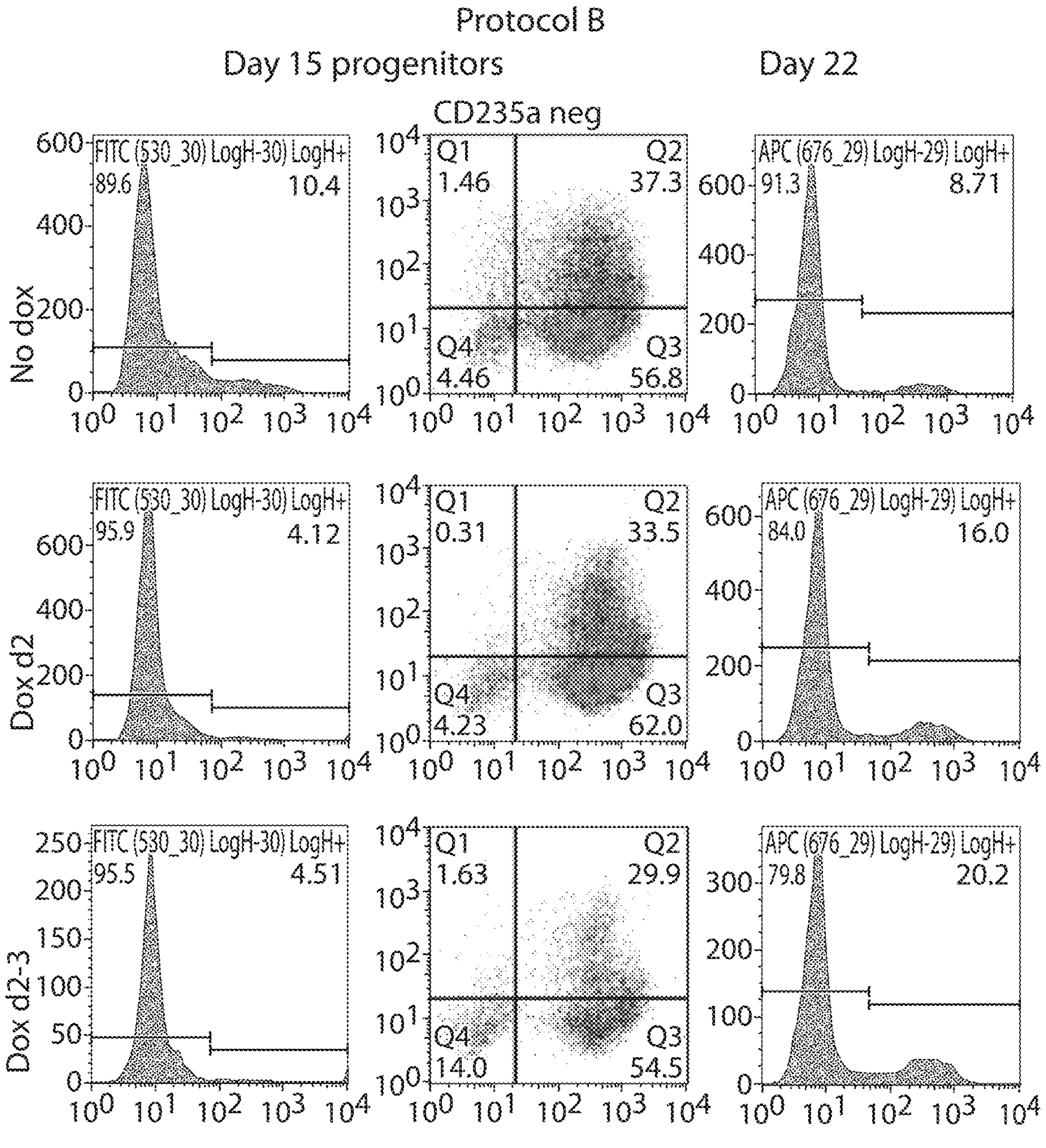
Figure 4C:
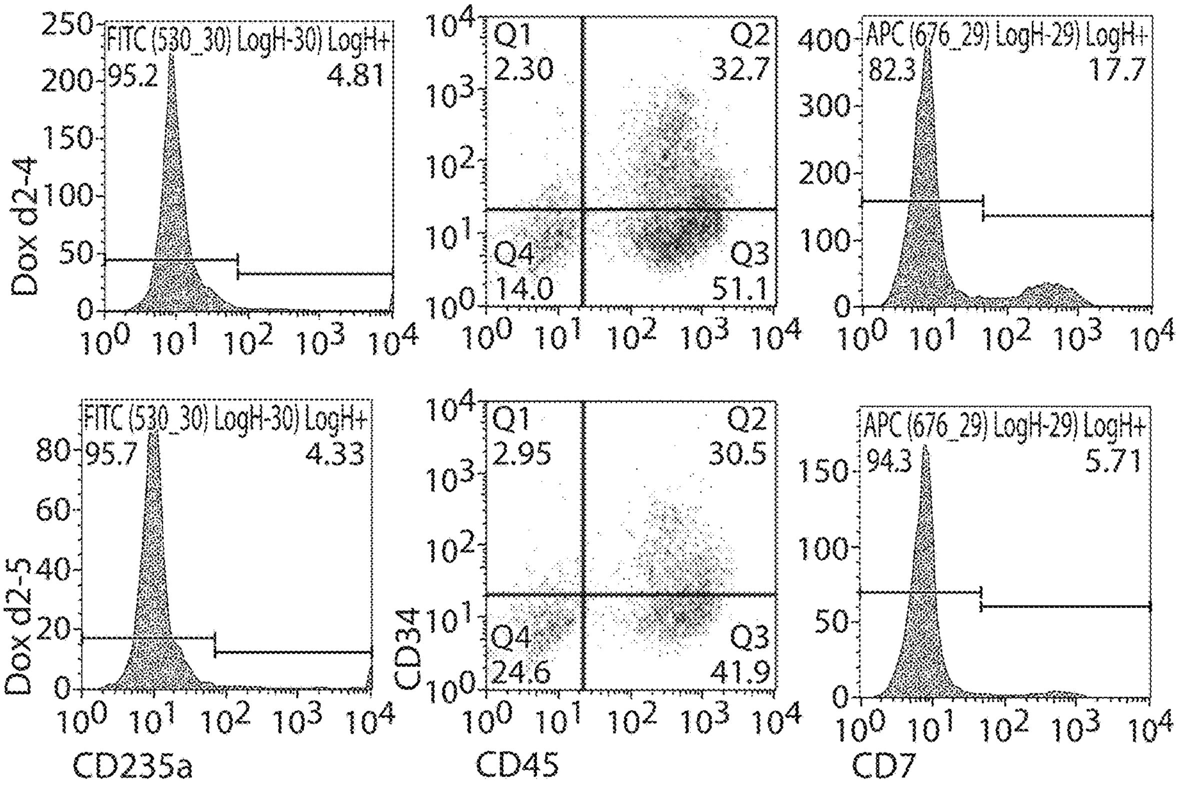
Figure 4D:
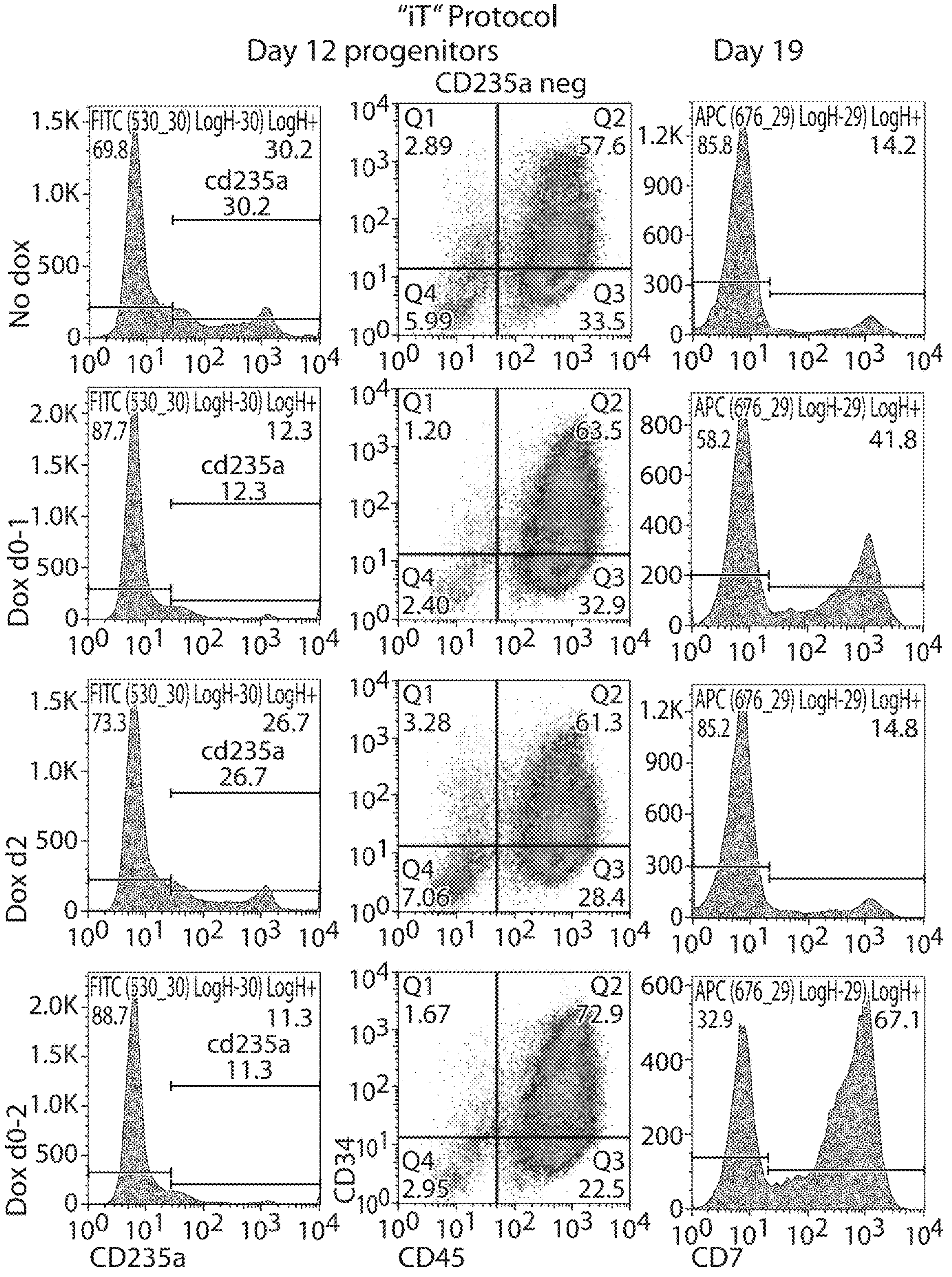
Figure 8B:
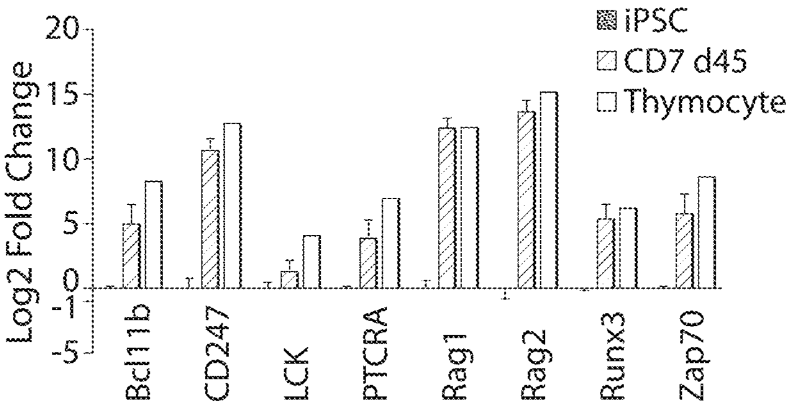
Figure 8C:
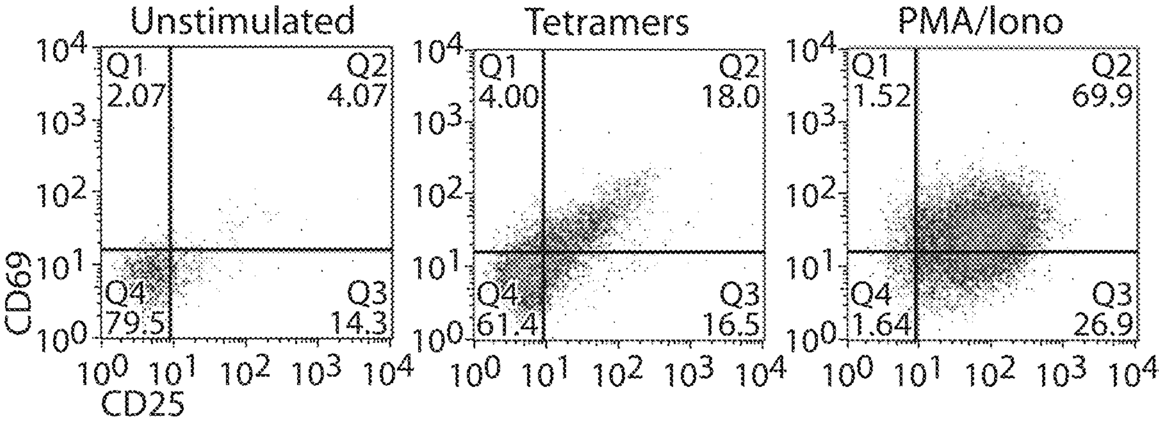
Figure 8D:
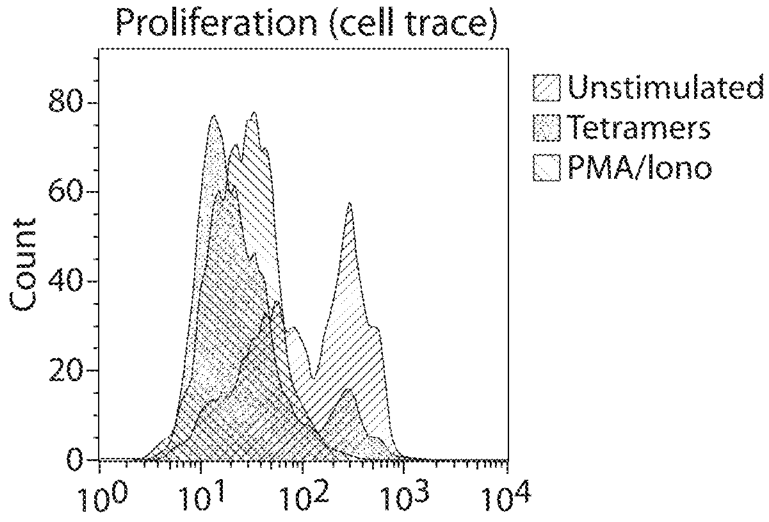
Figure 8E:
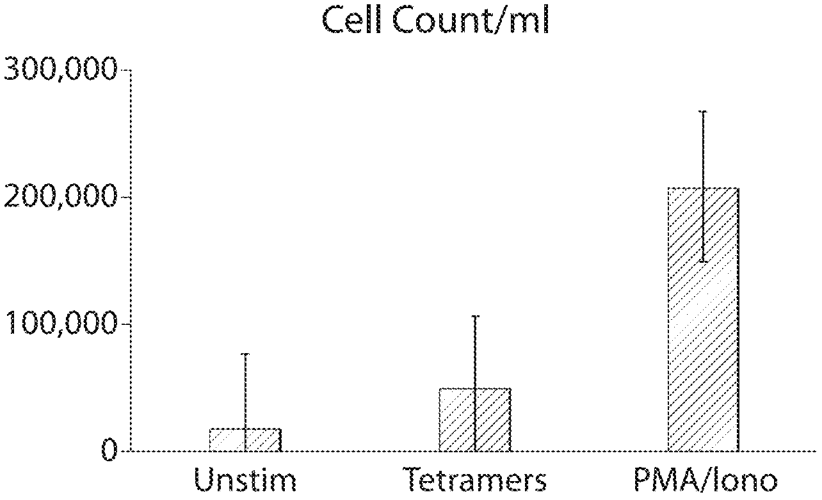
Figure 9A:
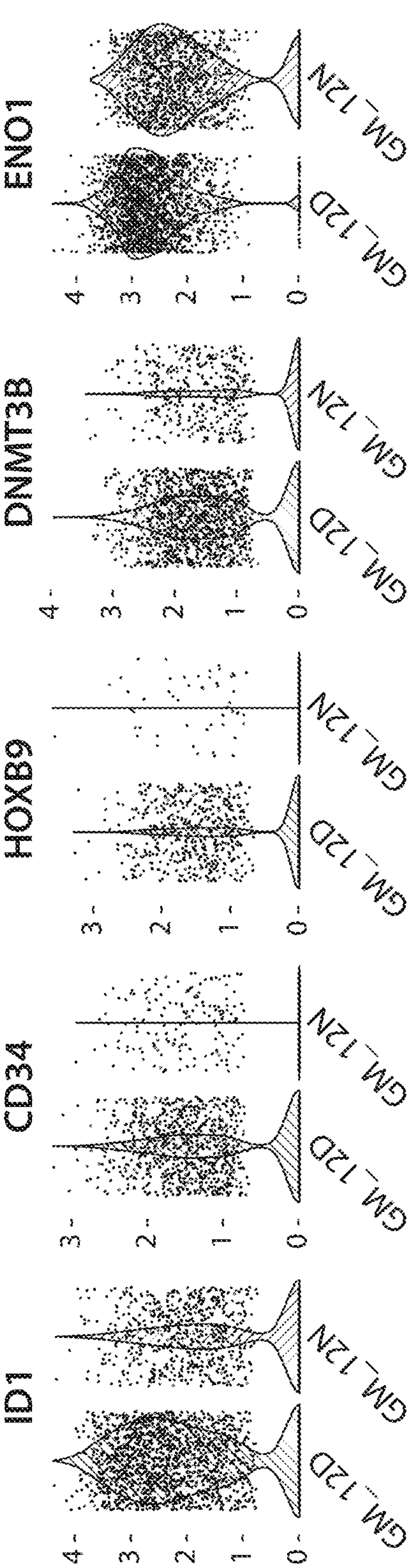
FIGS. 9A-9H shows early notch activation induces a 6-fold increase in multipotent progenitors. Single-cell RNA sequencing of day 12 progenitors from dox treated (day 0-2) and untreated cultures (GM_12D and GM_12N respectively).
Figure 9B:
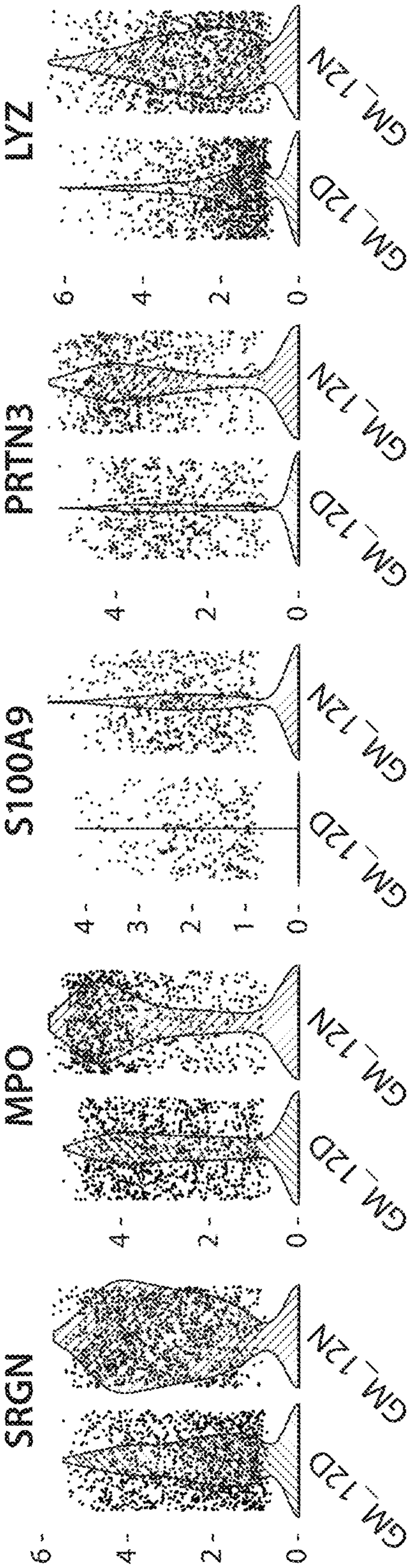
Figure 9C:
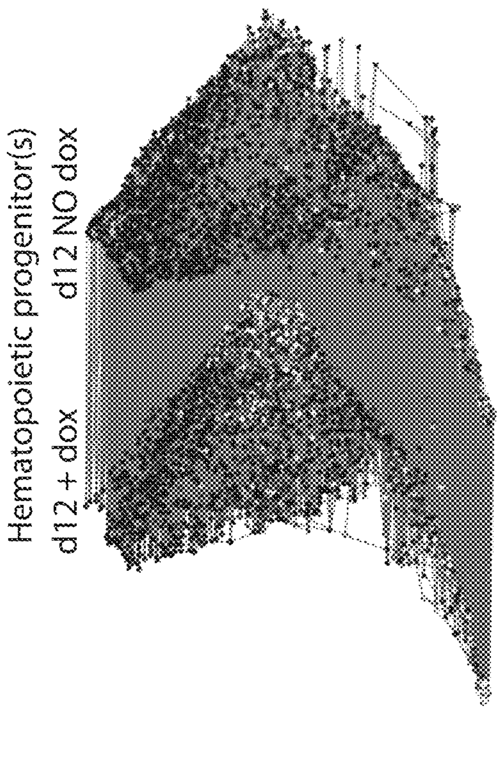
Figure 9D:
Figure 9E:
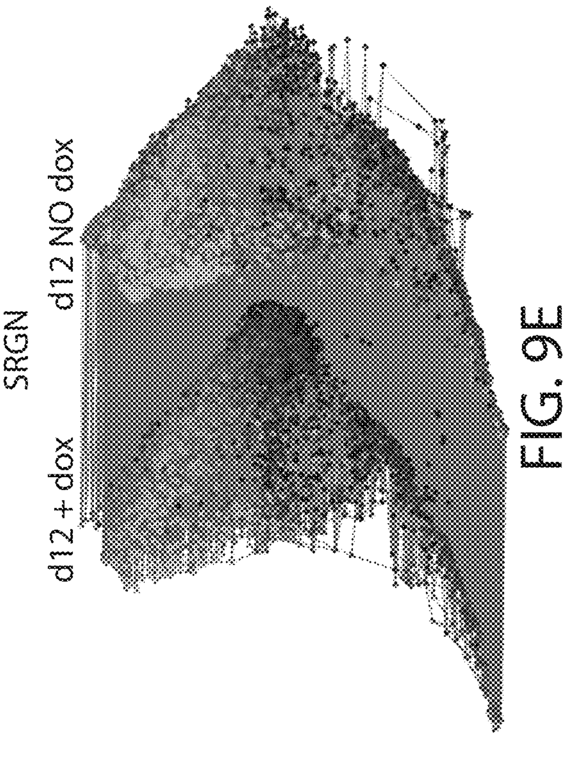
Figure 9F:
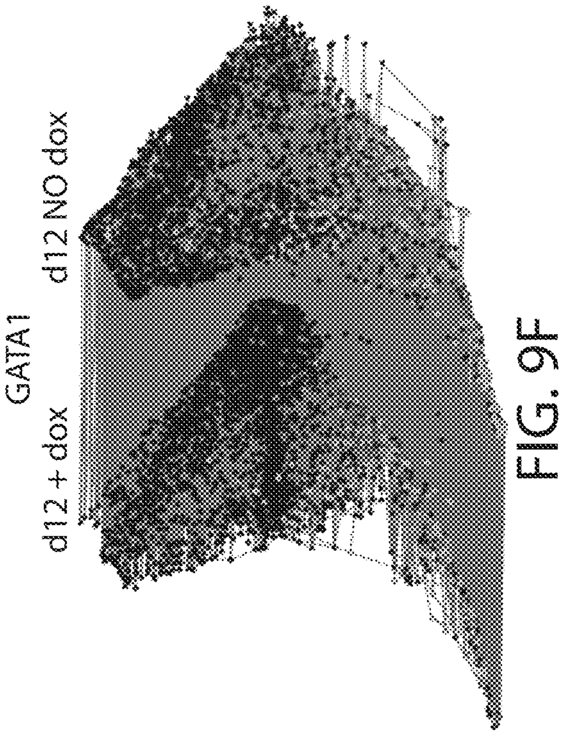
Figure 9G:
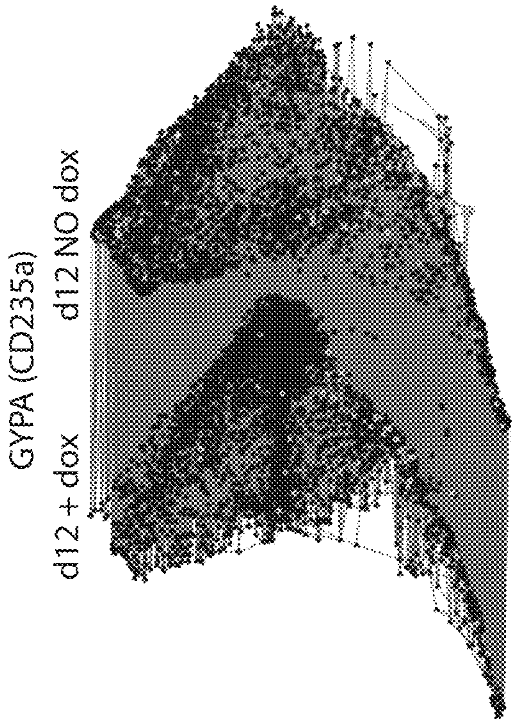
Figure 9H:
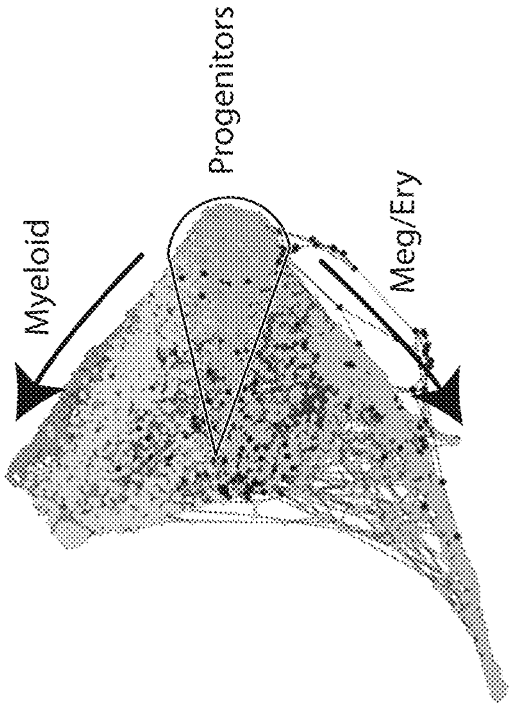

The inventors demonstrated that T cell maturation in OP9-hdll4:hMHCII co-culture was primarily a function of time, with strong double-positive cells beginning to appear around day 30 and coalescing toward CD3/CD8 positive cells around day 50 (FIG. 8A). The strong CD8 single positive T cell bias occurred despite the presence of human MHC class II (DPα, DPβ, and CD74 from an EF1α-driven polycistronic lentiviral construct) on the surface of the OP9 feeder cells (FIG. 3B). To further verify cell identity, CD7+ cells were isolated from three separate differentiations at day 30 and gene expression measured by qRT-PCR compared to day 15 progenitors. The inventors demonstrated that the CD7+ cells showed strong upregulation of T-cell related genes BCL11b, CD247, LCK, PTCRA, Rag1/2, RUNX3, and ZAP70, and downregulation of the myeloid marker Spi1 (FIG. 8B).

Example 6

Single Cell Analysis Showed the Developmental Progression Toward T Cells and Doxycycline Treatment (Notch Activation) Produced a More Definitive Progenitor Cell.

To further assess the impact of Notch stimulation on iPSC-derived hematopoietic progenitors, the inventors used single-cell RNAseq across the differentiation process. Single cells were analyzed at day 12 (progenitors) in unstimulated and doxycycline stimulated cultures, and at day 13 (1 day of co-culture), 16, 20, and 42 in dox stimulated cultures. These were compared to freshly isolated pediatric thymocytes obtained from anonymized cardiac surgical operations at Boston Children's Hospital. Cells were first sorted by FACS for live human CD45+ cells and then isolated using InDrops technology offered through the Harvard University Single Cell Core Facility and libraries sequenced using an Illumina NextSeq 500. The results were visualized using spring (Weinreb et al., 2018). Overall, 22,832 cells passed quality control and were included in the analysis. Initial clustering did not show cell cycle as a major driver of the resulting visualization. The inventors demonstrate that at day 12, a clear difference in clustering between the doxycycline stimulated and unstimulated cells is evident. In particular, the inventors demonstrate that the stimulated cells cluster much more tightly, showing they are more homogeneous. In addition, this clustering overlaps the area of highest expression of a list of hematopoietic progenitor genes supplied a priori to the analysis (see Table 5 for gene list), demonstrating that these cells represent a more definitive progenitor.

TABLE 5

Gene lists comprising classical transcripts for T cell development, NK cells, Notch Signaling, and hematopoietic progenitors where compiled and provide to the scRNAseq analysis.

| T cell development | | NK cell | Notch | hematopoietic progenitor |
|---|---|---|---|---|
| IL7R | CD7 | ID2 | Hes1 | CD34 |
| BCL11B | CD5 | 1L15R | Hes2 | CDHS |
| ThPOK | CD1a | CD56 | Hes3 | Runx1 |
| Runx3 | TESPA | NKp46 | Hes4 | hoxA9 |
| Rag1 | THEMIS | KLRC1 | Hes5 | cMYB |
| Rag2 | PTPRC | KLRK1 | Hes6 | CD41 |
| PTCRA | AIRE | KLRD1 | Hes7 | CD235a |
| CD3g | EOMES | CD161 | Hey1 | APLN |
| CD3d | TBX21 | NCR2 | RBPJ | ITGA6 |
| CD3e | GATA3 | NCR1 | Notch1 | CD90 |
| CD247 | Foxp3 | GZMB | dll4 | CD133 |
| Zap70 | RORC | PRF1 | Notch3 | CD201 |
| LCK | Lef1 | IL15 | Notch2 | CD38 |
| CD4 | Ets2 | NFIL3 | Notch4 | HKF |
| CD8 | TCF1 | | MIB1 | MEIS1 |
| | | | NRARP | KIT |
| | | | MAML | LMO2 |
| | | | | TAL1 |

Figure 10A:
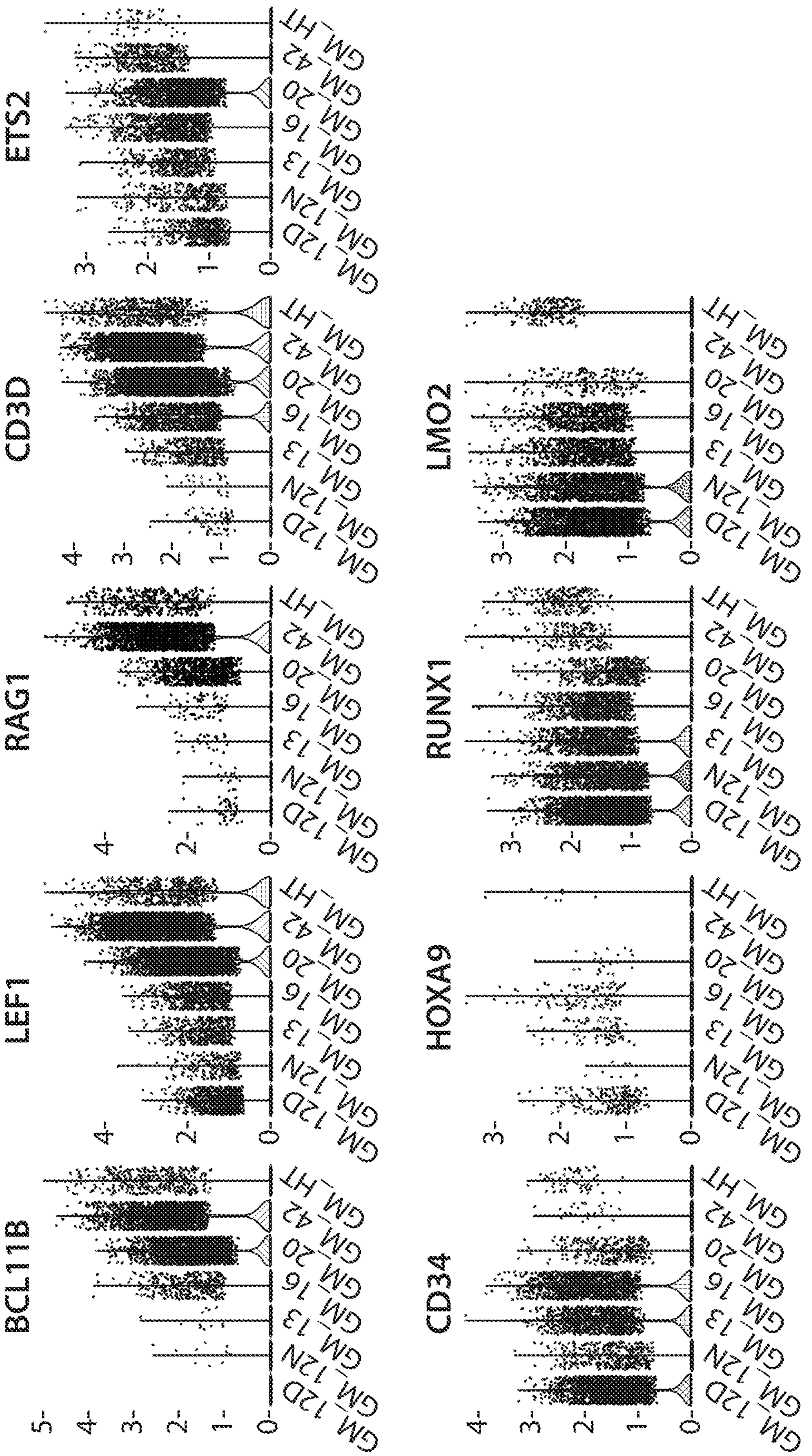
FIG. 10A-10E shows development of trajectory towards T cells using single cell analysis. Single cell RNA sequencing of developing T cells from day 12 progenitors to day 42 T cells (12D=day 12 dox treated; 12N=day 12 untreated; 13, 16, 20, and 42 refer to the day of culture in dox treated cultures; HT=human thymus). All samples received dox from day 0-2 except the untreated day 12 sample.
Figure 10B:
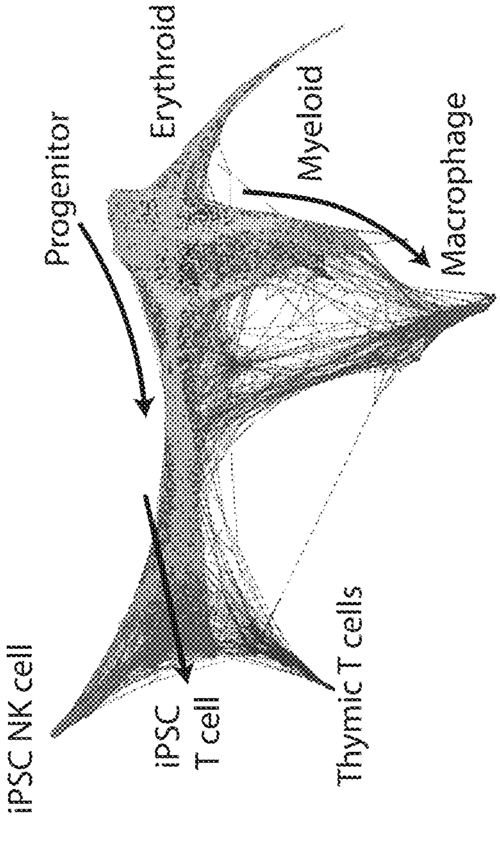
Figure 10C:
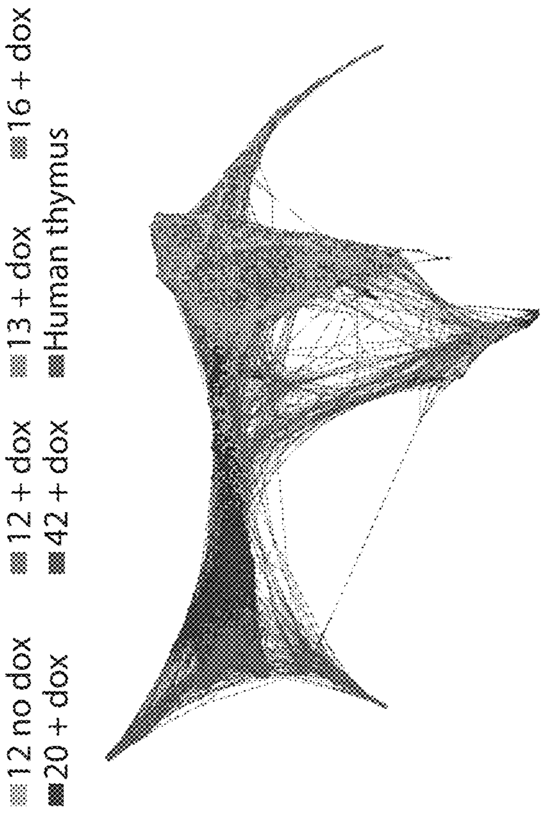
Figure 10D:
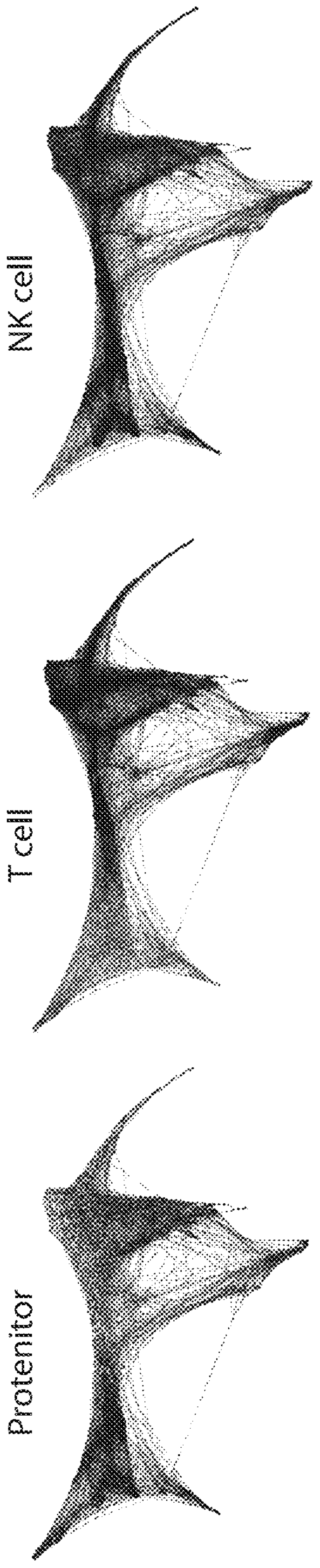
Figure 10E:
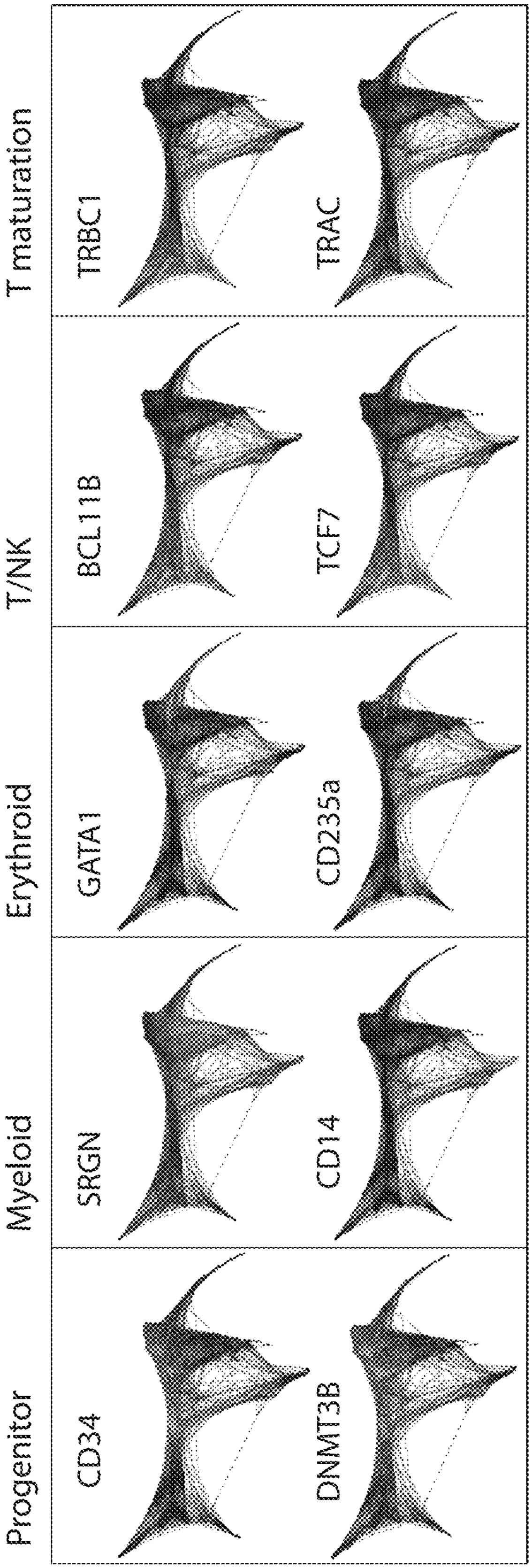

Day 13 cells represent two main groups, one that maintains the progenitor identity and another that acquired more myeloid markers. Day 16 cells showed strong separation of macrophage, granulocyte, and progenitor clusters. However, by day 20 there is a clear progression of the progenitor cluster to express many T cell markers, while the macrophage cluster is greatly reduced, correlating well with the FACS analysis of day 27 bulk cultures showing >90% of the cells are CD7+(FIG. 7A-7C, 8A-8B). The inventors demonstrate that by day 42, no macrophage cells were identified, but two distinct clusters emerged that express either markers of T cells or NK cells. The human thymic cells clustered in two discreet populations, one within the progenitor zone near day 12 iPSC-derived cells, and the other near but separate from the day 42 T cell cluster (FIG. 10C). Several gene lists were supplied to the analysis before the spring visualization was done. These included a hematopoietic progenitor, Notch signaling, NK cell, and T cell gene list. The cells expressing these gene lists could be visualized and nicely supported the expected developmental trajectory of the cells (FIG. 10D). To further analyze the full data set, the clustering data derived from the analysis was used to visualize cell clusters at 0.25 resolution in spring (FIG. 10B). The cells in these clusters were selected and the top 50 enriched genes in each cluster were submitted to Enrichr (Chen et al., 2013; Kuleshov et al., 2016). The top five significant (adjusted p<0.05) terms for Human Gene Atlas, ARCHS4 Tissues, GO Biological Process, and TRRUST Transcription factors were tabulated for each cluster, along with the top 10 enriched genes in each cluster (Table 3 and 4). This identified an erythroid cluster defined by terms "whole blood" and "erythroblast" as well as platelet degranulation and coagulation. The dox progenitor cluster has no hematopoietic-specific terms but instead expresses genes related to cholesterol biosynthesis. There is a known link between HSC cycling and cholesterol, but it is unclear the developmental role this may have (Oguro, 2019). Interestingly, the progenitor cluster (excluding the myeloid clusters) did not express T-cell specific genes until day 20, with ontology terms at day 13 and 16 more consistent with hematopoietic progenitor cells. This suggests the co-culture system may be prolonging the progenitor state. At day 20, clear T-cell genes are expressed including components of the CD3 complex and ontology terms identify "thymus," "T lymphocyte," and "antigen-receptor mediated signaling" The day 40 T cell cluster is similar but highlights T cell activation terms and genes such as CD8B; the NK cell cluster expresses granzymes, perforins, and CD94. The human thymus T cell cluster identified similar ontology terms to the iPSC-T cells but the top 10 genes expressed were different with well-known T cell genes such as CD1a, TRAC, and TCF7. The topology of this analysis showed an early exploration of myeloid and erythroid fates that rapidly fades toward a single T/NK cell developmental trajectory. The doxycycline-induced Notch activation from day 0-2 clearly produced a more definitive population of progenitors in this analysis.

TABLE 3

Gene ontology terms from Enrichr for the top 50 enriched genes in each cluster derived from Spring at 0.25 resolution. The top 5 significant terms for the four categories selected (Human gene atlas, ARCHS4 Tissues, GO biological process, and TRRUST transcription factors) based on adjusted P value <0.05. In some cases, there were fewer than 5 significant terms, in these cases only the significant terms (if any) are shown.

| | HUMAN GENE ATLAS | ARCHS4 TISSUES | GO BIOLOGICAL PROCESS | TRRUST TRANSCRIPTION FACTORS |
|---|---|---|---|---|
| Erythroid Progenitor | WholeBlood | ERYTHROBLAST | platelet degranulation (GO:0002576) | GATA1_human |
| | CD71 + Early Erythroid | CORD BLOOD | regulated exocytosis (GO:0045055) | FLI1_human |
| | Placenta | PERIPHERAL BLOOD | positive regulation of blood coagulation (GO:0030194) | HOXA10_mouse |
| | | SPLEEN (BULK TISSUE) | platelet aggregation (GO:0070527) | |
| | | MYOFIBROBLAST | homotypic cell-cell adhesion (GO:0034109) | |
| Dox Pregnitor Cluster | | HUMAN EMBRYO | cholesterol biosynthetic process (GO:0006695) | SP3_human |
| | | MIDBRAIN | secondary alcohol biosynthetic process (GO:1902653) | SREBF1_human |
| | | RENAL CORTEX | sterol biosynthetic process (GO:0016126) | ZNF148_human |
| | | FORESKIN FIBROBLAST | cholesterol metabolic process (GO:0008203) | HOXA9_human |
| | | LIVER (BULK TISSUE) | regulation of alcohol biosynthetic process (GO:1902930) | ZNF382_human |
| | | HUMAN EMBRYO | cholesterol biosynthetic process (GO:0006695) | SP3_human |
| Day 13 Myeloid | CD33+_Myeloid | CORD BLOOD | neutrophil degranulation (GO:0043312) | SPI1_human |
| | WholeBlood | DENDRITIC CELL | neutrophil activation involved in immune response (GO:0002283) | RBMX_human |
| | CD14+_Monocytes | NEUTROPHIL | neutrophil mediated immunity (GO:0002446) | GLI1_human |
| | Bonemarrow | MACROPHAGE | cellular response to cytokine stimulus (GO:0071345) | SP1_human |
| | | PERIPHERAL BLOOD | inflammatory response (GO:0006954) | STAT3_human |
| Day 13 | 721_B_lymphoblasts | KIDNEY (BULK TISSUE) | | |
| | CD34+ | HUMAN EMBRYO | | |
| | Leukemia_chronicMyelogenousK-562 | CD34 + CELL | | |
| Day 16 | CD34+ | CD34 + CELL | | TAL1_human |
| | | BONE MARROW (BULK TISSUE) | | HOXA9_mouse |
| | | CORD BLOOD | | |
| Day 20 | Leukemialymphoblastic (MOLT-4) | REGULATORY T CELLS | antigen receptor-mediated sig. pathway (GO:0050851) | |
| | Thymus | THYMUS (BULK TISSUE) | T cell receptor signaling pathway (GO:0050852) | |
| | CD8+_Tcells | TLYMPHOCYTE | positive reg. of intracellular signal transduction (GO:1902533) | |
| | CD4+_Tcells | CD4 + T CELL | | |
| | | BLOOD PBMC | | |
| Macrophage cluster | CD14+_Monocytes | MACROPHAGE | antigen proc. and pres. of exog. peptide ant. (GO:0002478) | RFXANK_human |
| | CD33+_Myeloid | ALVEOLAR MACROPHAGE | antigen proc. and pres. of exog. Pep. ant. via MHCII (GO:0019886) | RFXAP_human |
| | Lung | SPLEEN (BULK TISSUE) | antigen proc. and pres. of pep. ant. via MHCII (GO:0002495) | RFX5_human |
| | BDCA4+_DendriticCells | DENDRITIC CELL | regulation of interferon-gamma production (GO:0032649) | CIITA_human |
| | CD19+_BCells(neg._sel.) | LUNG (BULK TISSUE) | interferon-gamma-mediated sig. pathway (GO:0060333) | RFX1_human |
| iPSC-T cell cluster | Thymus | THYMUS (BULK TISSUE) | viral process (GO:0016032) | |
| | CD4+_Tcells | TLYMPHOCYTE | T cell activation (GO:0042110) | |
| | Leukemialymphoblastic (MOLT-4) | REGULATORY T CELLS | SRP-dependent cotranslational protein targeting to membrane (GO:0006614) | |
| | Lymphoma_burkitts(Raji) | BLOOD PBMC | cotranslational protein targeting to membrane (GO:0006613) | |
| | CD8+_Tcells | BONE MARROW (BULK TISSUE) | protein targeting to ER (GO:0045047) | |

TABLE 3-continued

Gene ontology terms from Enrichr for the top 50 enriched genes in each cluster derived from Spring at 0.25 resolution. The top 5 significant terms for the four categories selected (Human gene atlas, ARCHS4 Tissues, GO biological process, and TRRUST transcription factors) based on adjusted P value <0.05. In some cases, there were fewer than 5 significant terms, in these cases only the significant terms (if any) are shown.

| | HUMAN GENE ATLAS | ARCHS4 TISSUES | GO BIOLOGICAL PROCESS | TRRUST TRANSCRIPTION FACTORS |
|---|---|---|---|---|
| iPSC-NK cell | CD56+_NKCells | TLYMPHOCYTE | regulation of natural killer cell chemotaxis (GO:2000501) | |
| cluster | CD8+_Tcells | NATURAL KILLER CELLS | response to interferon-gamma (GO:0034341) | |
| | | CD4 + T CELL | cytokine-mediated signaling pathway (GO:0019221) | |
| | | REGULATORY T CELLS | eosinophil migration (GO:0072677) | |
| | | PERIPHERAL BLOOD | eosinophil chemotaxis (GO:0048245) | |
| Human thymus T cell | Thymus | DENDRITIC CELL | SRP-dependent cotranslational protein targeting to membrane (GO:0006614) | |
| cluster | Leukemialymphoblastic (MOLT-4) | BONE MARROW (BULK TISSUE) | cotranslational protein targeting to membrane (GO:0006613) | |
| | CD8+_Tcells | CD34 + CELL | protein targeting to ER (GO:0045047) | |
| | | CORD BLOOD | viral gene expression (GO:0019080) | |
| | | BLOOD | nuclear-transcribed mRNA catabolic | |
| | | DENDRITIC CELLS | process, nonsense-mediated decay (GO):0000184) | |

TABLE 4

Top 10 enriched genes from each cluster identified in Spring at 0.25 resolution.

| Erythroid Progenitor | Dox prog. cluster | Day 13 Myeloid | Day 13 | Day 16 | Day 20 | Macrophage cluster | iPSC-T cell cluster | iPSC-NK cell cluster | Human thymus T cell cluster |
|---|---|---|---|---|---|---|---|---|---|
| THBS1 | ID1 | LYZ | DNMT3B | CD34 | CD247 | HLA-DRA | CD8B | GNLY | CHCHD2 |
| LTBP1 | HOXB9 | S100A8 | PABPC4 | ACY3 | GATA3 | C1QB | CD99 | GZMK | DNTT |
| TIMP3 | CD24 | S100A9 | YBX3 | SMIM24 | IGLL1 | C1QC | MAL | CTSW | CD1A |
| LGALSL | MDK | FCN1 | SUPT16H | SPINK2 | EXD3 | C1QA | CD1E | PRF1 | TRBC2 |
| GMPR | FASN | MNDA | FABP5 | IGLL1 | LTB | HLA-DRB1 | LEF1 | GZMA | TRAC |
| C6orf25 | LAPTM4B | RP11-1143G9.4 | ILF2 | SELL | EFEMP1 | CD74 | CD79A | GZMB | SATB1 |
| TUBB1 | SOX18 | FOS | RANBP1 | SOX4 | OSM | MRC1 | RAG1 | IL2RB | TRBC1 |
| MMRN1 | HMGCS1 | DUSP1 | COTL1 | CD82 | GPR183 | HLA-DPA1 | CD7 | XCL2 | TCF7 |
| ITGA2B | YBX3 | NCF2 | ZMIZ1 | MYCN | ITM2A | LGMN | PTP4A2 | IL32 | RPS27 |
| PF4 | SCD | CSTA | B3GNT7 | ITM2A | CD3G | CD14 | STMN1 | KLRD1 | RPLP2 |

Example 7

Here, the inventors have demonstrated a novel platform based on a 2-D differentiation protocol for the efficient production of more definitive hematopoietic progenitors in defined serum-free media conditions. These iPSC-derived hematopoietic progenitors were able to reach the T/NK cell lineage, with robust production of CD7+ cells at 1 week of co-culture in four independent iPSC lines. This protocol has advantages over alternative methods as it does not rely on feeder cells (Minagawa et al., 2018; Vizcardo et al., 2018), EB formation (Ditadi and Sturgeon, 2016; Themeli et al., 2013), or extensive sorting or selection steps (Ditadi and Sturgeon, 2016; Montel-Hagen et al., 2019), making it efficient and easy to employ. Improved induction of mesodermal and endodermal fates following GSK-3β inhibition is thought to occur through formation of a primitive-streak like cell population (Tan et al., 2013) that is pushed toward mesoderm by the addition of BMP4. This is supported by the results herein demonstrating improved access to a $KDR^{high}$, $CD34^{+}$, VE-$Cadherin^{+}$ population at day 4 of differentiation. The use of hypoxia during hematopoietic differentiation has been widely reported (Ditadi and Sturgeon, 2016; Takata et al., 2017) and is supported by the developmental physiology present in the embryo at the time of HSC formation as well as reported interactions between hematopoietic transcription factor RUNX1 and hypoxia inducible factor 1α (Peng et al., 2008), but its specific effects during differentiation were not assessed in this work. The use of iT media (i.e., a modified HE media that lacks EPO or angiotensin) at day 6-d12, rather than the previously published HSPC day 6 (D6) media significantly improved access to the T/NK cell lineage. This was not pursued other than the functional output of CD7+ cells at 1 week of co-culture, however it demonstrates the composition of the hematopoietic cell production media exerts a patterning effect on the developing progenitor cells, an effect that could likely be further optimized toward the T/NK lineage. Together, this work demonstrates that improved differentiation toward a $KDR^{high}$, $CD34^{+}$, VE-$Cadherin^{+}$ population at day 4 underlies a significant increase in the efficiency of progenitor production, while the day 6 iT media improves access to the T/NK cell lineage. The GSK-3β inhibition from day 0-1 is analogous to its use at day 2 (Ditadi and Sturgeon, 2016; Leung et al., 2018) in terms of promoting more definitive fates in the developing hematopoietic progenitors (i.e., T potential).

Most importantly, the inventors have identified a critical 72 hr window during early mesoderm induction and before the onset of endogenous notch signaling when artificial activation of the notch pathway induces a profound increase in the T/NK potential of the resulting progenitors. Using the tet-on:NICD1 system allowed activation of the Notch pathway prior to the expression of Notch receptors and without disturbance of the developing cell layer in completely defined media. This is in contrast to the use of feeder cells expressing notch ligands or the use of dll4-fc fusion proteins (Schmitt et al., 2004; Uenishi et al., 2018). Despite the artificial nature of this tet-on system, it identifies a missing signal in hematopoietic mesodermal differentiation that allows more robust and consistent access to the lymphoid lineage. The interplay of Notch and WNT pathways in early HSC development has been reported in zebrafish models (Clements et al., 2011) and support for the dual activation as discovered herein by the inventors as part of the physiologic developmental pathway of the HSC.

Herein, the inventors have demonstrated that the density of hematopoietic progenitors introduced into the co-culture system had a major impact on the T vs NK lineage choice. This could be due to the increased access of developing T cells to Notch ligands when plated at low density, suggesting that NK cell differentiation proceeds vigorously under slightly lower intensity Notch activation than T cells. In support of this idea, NK differentiation proceeded even in the presence of low concentration gamma-secretase inhibitor (data not shown).

The inventors also demonstrate that the iPSC-derived T cells were not blocked at the CD4+/CD8+ double-positive stage, but progress even without stimulation to a CD3+/CD8+ T cell, with a very small population of apparently CD4 SP cells. This strong bias toward CD8 SP occurred even though the feeder cells were engineered to express human MHC class II (DPα, DPβ, and CD74 from an EF1α-driven polycistronic lentiviral construct). The strong CD8 SP bias of iPSC-derived T cells is a general outcome in most if not all previously reported T cell differentiation protocols (Awong et al., 2011; Minagawa et al., 2018; Montel-Hagen et al., 2019), however it has been unclear what cells participate in antigen presentation for positive selection. The strong CD8 bias present in OP9-hdll4:hMHCII co-culture demonstrates that the OP9 feeder cells are not participating as APCs in a meaningful way. Rather, the inventors demonstrate that exposing the progenitors to the MHC-II expressing OP9 cells must occur at a specific time in T cell development to help the selection of CD4 SP cells.

Single-cell analysis demonstrated that early activation of the notch pathway results in a homogenous population of more definitive progenitors that develop into T/NK and macrophage lineage cells, with the macrophage lineage dying out in culture shortly after day 16 (4 days of co-culture). The inventors demonstrated that this protocol lead to a clear separation of T and NK cells at day 40, with the T cell group clustering close to primary thymocytes. The separation of thymocytes and iPSC-derived T cells is based on the CD8 SP bias of iPSC-derived T cells, and represents the gene-expression signature of the aberrant selective process active in in vitro T cell cultures. In support of this, the most enriched gene in the inventors iPSC-derived T cells is CD8b, while the thymocytes represent a broader T cell picture with CD1a, TRBC2, and TRAC among the top 10 enriched genes. Nevertheless, these genes are also expressed in the iPSC-derived T cell cluster at lower intensity. In addition, the inventors demonstrate that there are clear T-cell specific genes such as BCL11B, TCF7, and RAG1/2 expressed in iPSC-derived T cells, demonstrating their T cell identity.

Here, the inventors discovered that notch activation during early mesodermal differentiation produced a robust population of T/NK capable hematopoietic progenitors. Single-cell analysis demonstrated that early Notch activation renders a population of progenitors that are potentially more definitive than those without early notch activation. Furthermore, the inventors discovered that introducing T-capable progenitors at low density into OP9-hdll4:hMHCII co-culture strongly favored T cell maturation, whereas culturing at high density cultures differentiated the progenitors into NK-like cells. Importantly, single-cell analysis demonstrated that the inventors have developed a protocol that reliably and robustly gives rise to cells that follow an elegant developmental pathway toward the T/NK lineage with robust emergence of the T cell identity beginning by day 20 that clearly recapitulates a primary human T cell signature upon maturation.

Example 8

MHC Class I Knock-Out

Removing native expression of beta-2 microglobulin will abrogate the expression of MHC class I alleles, making it difficult for the immune system to recognize these cells as allogeneic. However, certain NK cells can target cells lacking MHC I expression. The inventors have inserted a beta-2 microglobulin_HLA-E fusion protein into the beta-2 microglobulin locus, effectively blocking MHC I expression and instead over-expressing HLA-E, and inhibitory MHC I molecule to block NK cell recognition.

A cDNA corresponding to beta-2 microglobulin_(G4S)4_HLA-E*103_bGH poly(A) will be synthesized with 400 bp homology arms targeting the first exon of beta-2 microglobulin. This synthesized donor will be cloned into the pJET1.2 vector. CRISPR guides for the beginning of the first exon of beta-2 microglobulin will be designed using Broad Institute GPP and ChopChop using SpCas9 PAM NGG. Three guides will be selected and cloned into add gene plasmid 48138 (SpCas9_2A_GFP). IPSCs will be nucleofected with individual guides and the donor plasmid with 1 μg each plasmid/$10^6$ cells. After 48 hrs, they will be sorted for GFP positive cells and plated at low density on 10 cm plates to allow grow-out of clonal populations. Individual clones will be screened for bi-allelic insertion of the donor template using PCR.

As an alternative donor strategy, the stop codon of beta-2 microglobulin is targeted and a donor cassette inserted into the locus, where the cassette comprises: (G4S)4 linker_HLA-E*103_stop. This would mean the cell would express beta-2 microglobulin as usual but it would be a fusion with HLA-E. This would make the donor considerably shorter by avoiding the beta-2 microglobulin cDNA sequence and could also admit the bGH poly A since polyA signal for beta-2 microglobulin remains.

Example 9

MHC Class II Knock-Out

Removing expression of MHC II from the surface of the cell would reduce recognition of these cells as allogeneic by the immune system. CIITA is the master-regulator transcription factor for MHC II expression, and creating CIITA −/− iPSCs would block all MHC II expression. CD47 is a molecule expressed by many cell types to block phagocytosis by macrophages.

To block expression of MHC II, interruption of the expression of CIITA is done by inserting a DNA construct for the expression of CD47 from this locus. However, where the baseline expression of CIITA is low, and a promoter or regulatory element operatively linked to CD47 will promote high expression of CD47 to benefit from its capacity to improve immune-evasion. This is done by inserting a cDNA consisting of human EF1-alpha promoter_CD47_bGH poly (A) into the CIITA locus. This construct is synthesized with 400 bp homology arms targeting the first exon of CIITA and cloned in pJET1.2 vector. CRISPR guides for the beginning of the first exon of CIITA are readily designed using Broad Institute GPP and ChopChop using SpCas9 PAM NGG. Three guides are then selected and cloned into add gene plasmid 48138 (SpCas9_2A_GFP). IPSCs are nucleofected with individual guides and the donor plasmid with 1 μg each plasmid/$10^6$ cells. After 48 hrs, the cells are sorted for GFP positive cells and plated at low density on 10 cm plates to allow grow-out of clonal populations. Individual clones are screened and selected for bi-allelic insertion of the donor template using PCR.

In summary, the inventors teach herein a method and compositions for a highly reproducible, and efficient method of producing a T/NK progenitor cell from iPSC, which can mature to produce T cells or NK cells. The iPSC-NICD cell line disclosed herein can be further modified to be a "universal iPSC" for generation of universal T/NK progenitor cells which can be differentiated into mature T cells or NK cells according to the methods disclosed herein.

REFERENCES

The references cited herein and throughout the specification are incorporated herein in their entirety by reference.

Awong, G., Herer, E., La Motte-Mohs, R. N., and Zuniga-Pflucker, J. C. (2011). Human CD8 T cells generated in vitro from hematopoietic stem cells are functionally mature. BMC Immunol 12, 22.

Butler, A., Hoffman, P., Smibert, P., Papalexi, E., and Satija, R. (2018). Integrating single-cell transcriptomic data across different conditions, technologies, and species. Nature biotechnology 36, 411-420.

Chen, E. Y., Tan, C. M., Kou, Y., Duan, Q., Wang, Z., Meirelles, G. V., Clark, N. R., and Ma'ayan, A. (2013). Enrichr: interactive and collaborative HTML5 gene list enrichment analysis tool. BMC Bioinformatics 14, 128.

Choi, K. D., Vodyanik, M. A., Togarrati, P. P., Suknuntha, K., Kumar, A., Samarjeet, F., Probasco, M. D., Tian, S., Stewart, R., Thomson, J. A., et al. (2012). Identification of the hemogenic endothelial progenitor and its direct precursor in human pluripotent stem cell differentiation cultures. Cell reports 2, 553-567.

Clements, W. K., Kim, A. D., Ong, K. G., Moore, J. C., Lawson, N. D., and Traver, D. (2011). A somitic Wnt16/Notch pathway specifies haematopoietic stem cells. Nature 474, 220-224.

D'Souza, S. S., Maufort, J., Kumar, A., Zhang, J., Smuga-Otto, K., Thomson, J. A., and Slukvin, II (2016). GSK3beta Inhibition Promotes Efficient Myeloid and Lymphoid Hematopoiesis from Non-human Primate-Induced Pluripotent Stem Cells. Stem Cell Reports 6, 243-256.

Dallas, M. H., Varnum-Finney, B., Delaney, C., Kato, K., and Bernstein, I. D. (2005). Density of the Notch ligand Delta1 determines generation of B and T cell precursors from hematopoietic stem cells. The Journal of experimental medicine 201, 1361-1366.

Ditadi, A., and Sturgeon, C. M. (2016). Directed differentiation of definitive hemogenic endothelium and hematopoietic progenitors from human pluripotent stem cells. Methods 101, 65-72.

Finak, G., McDavid, A., Yajima, M., Deng, J., Gersuk, V., Shalek, A. K., Slichter, C. K., Miller, H. W., McElrath, M. J., Prlic, M., et al. (2015). MAST: a flexible statistical framework for assessing transcriptional changes and characterizing heterogeneity in single-cell RNA sequencing data. Genome Biol 16, 278.

Fraser, S. T., Ogawa, M., Yu, R. T., Nishikawa, S., Yoder, M. C., and Nishikawa, S. (2002). Definitive hematopoietic commitment within the embryonic vascular endothelial-cadherin(+) population. Experimental hematology 30, 1070-1078.

Galat, Y., Elcheva, I., Dambaeva, S., Katukurundage, D., Beaman, K., Iannaccone, P. M., and Galat, V. (2018). Application of small molecule CHIR99021 leads to the loss of hemangioblast progenitor and increased hematopoiesis of human pluripotent stem cells. Experimental hematology 65, 38-48 e31.

Gordon, W. R., Zimmerman, B., He, L., Miles, L. J., Huang, J., Tiyanont, K., McArthur, D. G., Aster, J. C., Perrimon, N., Loparo, J. J., et al. (2015). Mechanical Allostery: Evidence for a Force Requirement in the Proteolytic Activation of Notch. Dev Cell 33, 729-736.

Gritz, E., and Hirschi, K. K. (2016). Specification and function of hemogenic endothelium during embryogenesis. Cell Mol Life Sci 73, 1547-1567.

Kuleshov, M. V., Jones, M. R., Rouillard, A. D., Fernandez, N. F., Duan, Q., Wang, Z., Koplev, S., Jenkins, S. L., Jagodnik, K. M., Lachmann, A., et al. (2016). Enrichr: a comprehensive gene set enrichment analysis web server 2016 update. Nucleic Acids Res 44, W90-97.

Kumano, K., Chiba, S., Kunisato, A., Sata, M., Saito, T., Nakagami-Yamaguchi, E., Yamaguchi, T., Masuda, S., Shimizu, K., Takahashi, T., et al. (2003). Notch1 but not Notch2 is essential for generating hematopoietic stem cells from endothelial cells. Immunity 18, 699-711.

Leung, A., Zulick, E., Skvir, N., Vanuytsel, K., Morrison, T. A., Naing, Z. H., Wang, Z., Dai, Y., Chui, D. H. K., Steinberg, M. H., et al. (2018). Notch and Aryl Hydrocarbon Receptor Signaling Impact Definitive Hematopoiesis from Human Pluripotent Stem Cells. Stem Cells 36, 1004-1019.

Matsuno, Y., Kiwamoto, T., Morishima, Y., Ishii, Y., Hizawa, N., and Hogaboam, C. M. (2018). Notch signaling regulates cell density-dependent apoptosis of NIH 3T3 through an IL-6/STAT3 dependent mechanism. Eur J Cell Biol 97, 512-522.

Minagawa, A., Yoshikawa, T., Yasukawa, M., Hotta, A., Kunitomo, M., Iriguchi, S., Takiguchi, M., Kassai, Y., Imai, E., Yasui, Y., et al. (2018). Enhancing T Cell Receptor Stability in Rejuvenated iPSC-Derived T Cells Improves Their Use in Cancer Immunotherapy. Cell Stem Cell 23, 850-858 e854.

Montel-Hagen, A., Seet, C. S., Li, S., Chick, B., Zhu, Y., Chang, P., Tsai, S., Sun, V., Lopez, S., Chen, H. C., et al. (2019). Organoid-Induced Differentiation of Conventional T Cells from Human Pluripotent Stem Cells. Cell Stem Cell 24, 376-389 e378.

Oguro, H. (2019). The Roles of Cholesterol and Its Metabolites in Normal and Malignant Hematopoiesis. Front Endocrinol (Lausanne) 10, 204.

Ordovas, L., Boon, R., Pistoni, M., Chen, Y., Wolfs, E., Guo, W., Sambathkumar, R., Bobis-Wozowicz, S., Helsen, N., Vanhove, J., et al. (2015). Efficient Recombinase-Mediated Cassette Exchange in hPSCs to Study the Hepatocyte Lineage Reveals AAVS1 Locus-Mediated Transgene Inhibition. Stem Cell Reports 5, 918-931.

Peng, Z. G., Zhou, MX., Huang, Y., Qiu, J. H., Wang, L. S., Liao, S. H., Dong, S., and Chen, G. Q. (2008). Physical and functional interaction of Runt-related protein 1 with hypoxia-inducible factor-1alpha. Oncogene 27, 839-847.

Robert-Moreno, A., Guiu, J., Ruiz-Herguido, C., Lopez, M. E., Ingles-Esteve, J., Riera, L., Tipping, A., Enver, T., Dzierzak, E., Gridley, T., et al. (2008). Impaired embryonic haematopoiesis yet normal arterial development in the absence of the Notch ligand Jagged1. EMBO J 27, 1886-1895.

Schmitt, T. M., de Pooter, R. F., Gronski, M. A., Cho, S. K., Ohashi, P. S., and Zuniga-Pflucker, J. C. (2004). Induction of T cell development and establishment of T cell competence from embryonic stem cells differentiated in vitro. Nat Immunol 5, 410-417.

Schmitt, T. M., and Zuniga-Pflucker, J. C. (2002). Induction of T cell development from hematopoietic progenitor cells by delta-like-1 in vitro. Immunity 17, 749-756.

Shaya, O., Binshtok, U., Hersch, M., Rivkin, D., Weinreb, S., Amir-Zilberstein, L., Khamaisi, B., Oppenheim, O., Desai, R. A., Goodyear, R. J., et al. (2017). Cell-Cell Contact Area Affects Notch Signaling and Notch-Dependent Patterning. Dev Cell 40, 505-511 e506.

Souilhol, C., Lendinez, J. G., Rybtsov, S., Murphy, F., Wilson, H., Hills, D., Batsivari, A., Binagui-Casas, A., McGarvey, A. C., MacDonald, H. R., et al. (2016). Developing HSCs become Notch independent by the end of maturation in the AGM region. Blood 128, 1567-1577.

Sturgeon, C. M., Ditadi, A., Awong, G., Kennedy, M., Keller, G. (2014). Wnt signaling controls the specification of definitive and primitive hematopoiesis from human pluripotent stem cells. Nature biotechnology 32, 554-561.

Takata, K., Kozaki, T., Lee, C. Z. W., Thion, M. S., Otsuka, M., Lim, S., Utami, K. H., Fidan, K., Park, D. S., Malleret, B., et al. (2017). Induced-Pluripotent-Stem-Cell-Derived Primitive Macrophages Provide a Platform for Modeling Tissue-Resident Macrophage Differentiation and Function. Immunity 47, 183-198 e186.

Tan, J. Y., Sriram, G., Rufaihah, A. J., Neoh, K. G., and Cao, T. (2013). Efficient derivation of lateral plate and paraxial mesoderm subtypes from human embryonic stem cells through GSKi-mediated differentiation. Stem Cells Dev 22, 1893-1906.

Themeli, M., Kloss, C. C., Ciriello, G., Fedorov, V. D., Perna, F., Gonen, M., and Sadelain, M. (2013). Generation of tumor-targeted human T lymphocytes from induced pluripotent stem cells for cancer therapy. Nature biotechnology 31, 928-933.

Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016). Dissecting the multicellular ecosystem of metastatic melanoma by single-cell RNA-seq. Science 352, 189-196.

Uenishi, G. I., Jung, H. S., Kumar, A., Park, M. A., Hadland, B. K., McLeod, E., Raymond, M., Moskvin, O., Zimmerman, C. E., Theisen, D. J., et al. (2018). NOTCH signaling specifies arterial-type definitive hemogenic endothelium from human pluripotent stem cells. Nat Commun 9, 1828.

Vizcardo, R., Klemen, N. D., Islam, S. M. R., Gurusamy, D., Tamaoki, N., Yamada, D., Koseki, H., Kidder, B. L., Yu, Z., Jia, L., et al. (2018). Generation of Tumor Antigen-Specific iPSC-Derived Thymic Emigrants Using a 3D Thymic Culture System. Cell reports 22, 3175-3190.

Weinreb, C., Wolock, S., and Klein, A. M. (2018). SPRING: a kinetic interface for visualizing high dimensional single-cell expression data. Bioinformatics 34, 1246-1248.

The invention claimed is:

1. A method of obtaining a population of CD7+ T/NK progenitor cells, comprising the steps of, in order of:

(a) obtaining a population of pluripotent stem cells, (b) expressing a Notch intracellular domain (NICD) in the population of pluripotent stem cells between day 0 (d0) and day 2 (d2) to activate Notch signaling in the population of pluripotent stem cells before onset of endogenous Notch signaling (c) after expressing NICD in the population of cells in step (b), culturing the population of cells for at least 9 days in the absence of an agent that induces the expression of a NICD protein, then co-culturing the population of cells in the presence of a stromal cell feeder layer which expresses a notch ligand for between 9 and 17 days or until the cells express $CD7^+$, wherein after the co-culturing a proportion of the cells are a population of CD7+ T/NK progenitor cells that express $CD7^+$ and one or more Notch target genes, and (d) collecting the population of CD7+ T/NK progenitor cells.

2. The method of claim 1, wherein expression of the Notch intracellular domain (NICD) is expression of a NICD1 protein in the pluripotent stem cell.

3. The method of claim 1, wherein the Notch target genes are selected from any one or more of LM02, T (brachyury) TAL1, HES1 or HEY5.

4. The method of claim 1, wherein the expression of NICD is by transient transfection with an expression vector or viral vector, or modified RNA (modRNA), wherein the vector, viral vector or modified RNA comprises a nucleic acid sequence encoding a NICD protein.

5. The method of claim 1, wherein the population of pluripotent stem cells comprise a nucleic acid sequence encoding an NICD1 protein, operatively linked to an inducible promoter, and wherein the expression of the NICD1 protein is induced by contacting the cells with an agent to induce the expression from the inducible promoter.

6. The method of claim 1, wherein the population of pluripotent stem cells is a population of human induced pluripotent stem cell (iPSC) or a population of human embryonic stem (ES) cells or an engineered iPSC comprising an exogenous nucleic acid construct, the exogenous nucleic acid construct comprising a sequence encoding an NICD gene and an inducible promoter, wherein the sequence encoding an NICD gene is operatively linked to the inducible promoter.

7. The method of claim 1, wherein culturing the population of cells in step c comprises culturing the cells in any one or more of the conditions:

with a GSK-3b inhibitor at d0-d1, in hypoxia conditions at d0-d7;

in normoxia conditions from d8;

in the absence of erythropoietin (EPO) from d6.

8. The method of claim 1, wherein the collected population of cells in step (d) comprise at least 30% $CD7^+$ T/NK progenitor cells.

9. The method of claim 1, further comprising, after step (de), plating the cells collected from step (de) at a density of about <5,000 cells/ml or about >20,000 cells/ml in the co-culture comprising stromal cell feeder layer, wherein the stromal cell feeder layer expresses a notch ligand.

10. An isolated population of T/NK progenitor cells obtained by the method of claim 1, wherein the pluripotent stem cell population is a human induced pluripotent stem cell (iPSC) population, wherein the iPSC population is an engineered iPSC population comprising an exogenous nucleic acid construct, the exogenous nucleic acid construct comprising a sequence encoding an NICD gene and an inducible promoter, wherein the sequence encoding an NICD gene is operably linked to the inducible promoter.

11. The isolated population of T/NK progenitors of claim 10, wherein the isolated population comprises at least 50% CD7+ T/NK cells.

12. The isolated population of T/NK progenitors of claim 10, wherein the isolated population are present in a media suitable for cryopreservation.

13. The method of claim 1, wherein the CD7+ T/NK progenitor cells are also $CD34^+$, E-$Cadherin^+$, and $KDR^+$.

14. The method of claim 1, wherein the population of $CD7^+$ T/NK progenitor cells are collected without cell sorting or positive or negative cell selection methods.

15. The method of claim 8, wherein the collected population of cells in step (d) comprise between 70% and 95% $CD7^+$ T/NK progenitor cells.

* * * * *

SEQUENCE LISTING

```
<160> NUMBER OF SEQ ID NOS: 32

<210> SEQ ID NO 1
<211> LENGTH: 2391
<212> TYPE: DNA
<213> ORGANISM: Homo sapiens

<400> SEQUENCE: 1

atgcggcggc agcatggcca gctctggttc cctgagggct tcaaagtgtc tgaggccagc      60

aagaagaagc ggcgggagcc cctcggcgag gactccgtgg gcctcaagcc cctgaagaac     120

gcttcagacg gtgccctcat ggacgacaac cagaatgagt gggggggacga ggacctggag     180

accaagaagt tccggttcga ggagcccgtg gttctgcctg acctggacga ccagacagac     240

caccggcagt ggactcagca gcacctggat gccgctgacc tgcgcatgtc tgccatggcc     300

cccacaccgc cccagggtga ggttgacgcc gactgcatgg acgtcaatgt ccgcgggcct     360

gatggcttca ccccgctcat gatcgcctcc tgcagcgggg gcggcctgga gacgggcaac     420

agcgaggaag aggaggacgc gccggccgtc atctccgact tcatctacca gggcgccagc     480
```

-continued

```
ctgcacaacc agacagaccg cacgggcgag accgccttgc acctggccgc ccgctactca    540

cgctctgatt ccgccaagcg cctgctggag gccagcgcag atgccaacat ccaggacaac    600

atgggccgca ccccgctgca tgcggctgtg tctgccgacg cacaaggtgt cttccagatc    660

ctgatccgga accgagccac agacctggat gcccgcatgc atgatggcac gacgccactg    720

atcctggctg cccgcctggc cgtggagggc atgctggagg acctcatcaa ctcacacgcc    780

gacgtcaacg ccgtagatga cctgggcaag tccgccctgc actgggccgc cgccgtgaac    840

aatgtggatg ccgcagttgt gctcctgaag aacggggcta acaaagatat gcagaacaac    900

agggaggaga cacccctgtt tctggccgcc cgggagggca gctacgagac cgccaaggtg    960

ctgctggacc actttgccaa ccgggacatc acggatcata tggaccgcct gccgcgcgac   1020

atcgcacagg agcgcatgca tcacgacatc gtgaggctgc tggacgagta caacctggtg   1080

cgcagcccgc agctgcacgg agccccgctg gggggcacgc ccaccctgtc gccccgctc    1140

tgctcgccca acggctacct gggcagcctc aagcccggcg tgcagggcaa gaaggtccgc   1200

aagcccagca gcaaaggcct ggcctgtgga agcaaggagg ccaaggacct caaggcacgg   1260

aggaagaagt cccaggacgg caagggctgc ctgctggaca gctccggcat gctctcgccc   1320

gtggactccc tggagtcacc ccatggctac ctgtcagacg tggcctcgcc gccactgctg   1380

ccctccccgt tccagcagtc tccgtccgtg cccctcaacc acctgcctgg gatgcccgac   1440

acccacctgg gcatcgggca cctgaacgtg gcggccaagc ccgagatggc ggcgctgggt   1500

gggggcggcc ggctggcctt tgagactggc ccacctcgtc tctcccacct gcctgtggcc   1560

tctggcacca gcaccgtcct gggctccagc agcggagggg ccctgaattt cactgtgggc   1620

gggtccacca gtttgaatgg tcaatgcgag tggctgtccc ggctgcagag cggcatggtg   1680

ccgaaccaat acaaccctct gcgggggagt gtggcaccag gccccctgag cacacaggcc   1740

ccctccctgc agcatggcat ggtaggcccg ctgcacagta gccttgctgc cagcgccctg   1800

tcccagatga tgagctacca gggcctgccc agcacccggc tggccaccca gcctcacctg   1860

gtgcagaccc agcaggtgca gccacaaaac ttacagatgc agcagcagaa cctgcagcca   1920

gcaaacatcc agcagcagca aagcctgcag ccgccaccac caccaccaca gccgcacctt   1980

ggcgtgagct cagcagccag cggccacctg ggccggagct tcctgagtgg agagccgagc   2040

caggcagacg tgcagccact gggccccagc agcctggcgg tgcacactat tctgccccag   2100

gagagccccg ccctgcccac gtcgctgcca tcctcgctgg tcccacccgt gaccgcagcc   2160

cagttcctga cgccccccctc gcagcacagc tactcctcgc ctgtggacaa cacccccagc   2220

caccagctac aggtgcctga gcacccccttc ctcaccccgt cccctgagtc ccctgaccag   2280

tggtccagct cgtccccgca ttccaacgtc tccgactggt ccgagggcgt ctccagccct   2340

cccaccagca tgcagtccca gatcgcccgc atcccggagg cgttcaagta a            2391
```

<210> SEQ ID NO 2
<211> LENGTH: 2322
<212> TYPE: DNA
<213> ORGANISM: Homo sapiens

<400> SEQUENCE: 2

```
atggcaaaac gaaagcgtaa gcatggctct ctctggctgc ctgaaggttt cactcttcgc     60

cgagatgcaa gcaatcacaa gcgtcgtgag ccagtgggac aggatgctgt ggggctgaaa    120

aatctctcag tgcaagtctc agaagctaac ctaattggta ctggaacaag tgaacactgg    180

gtcgatgatg aagggcccca gccaaagaaa gtaaaggctg aagatgaggc cttactctca    240
```

```
gaagaagatg accccattga tcgacggcca tggacacagc agcaccttga agctgcagac    300
atccgtagga caccatcgct ggctctcacc cctcctcagg cagagcagga ggtggatgtg    360
ttagatgtga atgtccgtgg cccagatggc tgcaccccat tgatgttggc ttctctccga    420
ggaggcagct cagatttgag tgatgaagat gaagatgcag aggactcttc tgctaacatc    480
atcacagact tggtctacca gggtgccagc ctccaggccc agacagaccg gactggtgag    540
atggccctgc accttgcagc ccgctactca cgggctgatg ctgccaagcg tctcctggat    600
gcaggtgcag atgccaatgc ccaggacaac atgggccgct gtccactcca tgctgcagtg    660
gcagctgatg cccaaggtgt cttccagatt ctgattcgca accgagtaac tgatctagat    720
gccaggatga atgatggtac tacacccctg atcctggctg cccgcctggc tgtggaggga    780
atggtggcag aactgatcaa ctgccaagcg gatgtgaatg cagtggatga ccatggaaaa    840
tctgctcttc actgggcagc tgctgtcaat aatgtggagg caactctttt gttgttgaaa    900
aatggggcca accgagacat gcaggacaac aaggaagaga cacctctgtt tcttgctgcc    960
cgggagggga gctatgaagc agccaagatc ctgttagacc attttgccaa tcgagacatc   1020
acagaccata tggatcgtct tccccgggat gtggctcggg atcgcatgca ccatgacatt   1080
gtgcgccttc tggatgaata caatgtgacc ccaagccctc caggcaccgt gttgacttct   1140
gctctctcac ctgtcatctg tgggcccaac agatctttcc tcagcctgaa gcacacccca   1200
atgggcaaga agtctagacg gcccagtgcc aagagtacca tgcctactag cctccctaac   1260
cttgccaagg aggcaaagga tgccaagggt agtaggagga agaagtctct gagtgagaag   1320
gtccaactgt ctgagagttc agtaacttta tcccctgttg attccctaga atctcctcac   1380
acgtatgttt ccgacaccac atcctctcca atgattacat cccctgggat cttacaggcc   1440
tcacccaacc ctatgttggc cactgccgcc cctcctgccc cagtccatgc ccagcatgca   1500
ctatcttttt ctaaccttca tgaaatgcag cctttggcac atggggccag cactgtgctt   1560
ccctcagtga gccagttgct atcccaccac cacattgtgt ctccaggcag tggcagtgct   1620
ggaagcttga gtaggctcca tccagtccca gtcccagcag attggatgaa ccgcatggag   1680
gtgaatgaga cccagtacaa tgagatgttt ggtatggtcc tggctccagc tgagggcacc   1740
catcctggca tagctcccca gagcaggcca cctgaaggga agcacataac cacccctcgg   1800
gagcccttgc cccccattgt gactttccag ctcatcccta aaggcagtat tgcccaacca   1860
gcgggggctc cccagcctca gtccacctgc cctccagctg ttgcgggccc cctgccccacc  1920
atgtaccaga ttccagaaat ggcccgtttg cccagtgtgg ctttccccac tgccatgatg   1980
ccccagcagg acgggcaggt agctcagacc attctcccag cctatcatcc tttcccagcc   2040
tctgtgggca agtaccccac acccccttca cagcacagtt atgcttcctc aaatgctgct   2100
gagcgaacac ccagtcacag tggtcacctc cagggtgagc atccctacct gacaccatcc   2160
ccagagtctc ctgaccagtg gtcaagttca tcacccccact ctgcttctga ctggtcagat  2220
gtgaccacca gccctacccc tgggggtgct ggaggaggtc agcggggacc tgggacacac   2280
atgtctgagc caccacacaa caacatgcag gtttatgcgt ga                      2322
```

<210> SEQ ID NO 3
<211> LENGTH: 1977
<212> TYPE: DNA
<213> ORGANISM: Homo sapiens

<400> SEQUENCE: 3

-continued

```
atggcccggc gcaagcgcga gcacagcacc ctctggttcc ctgagggctt ctcactgcac     60
aaggacgtgg cctctggtca caagggccgg cgggaacccg tgggccagga cgcgctgggc    120
atgaagaaca tggccaaggg tgagagcctg atgggggagg tggccacaga ctggatggac    180
acagagtgcc cagaggccaa gcggctaaag gtagaggagc caggcatggg ggctgaggag    240
gctgtggatt gccgtcagtg gactcaacac catctggttg ctgctgacat ccgcgtggca    300
ccagccatgg cactgacacc accacagggc gacgcagatg ctgatggcat ggatgtcaat    360
gtgcgtggcc cagatggctt caccccgcta atgctggctt ccttctgtgg gggggctctg    420
gagccaatgc caactgaaga ggatgaggca gatgacacat cagctagcat catctccgac    480
ctgatctgcc agggggctca gcttggggca cggactgacc gtactggcga gactgctttg    540
cacctggctg cccgttatgc ccgtgctgat gcagccaagc ggctgctgga tgctggggca    600
gacaccaatg cccaggacca ctcaggccgc actcccctgc acacagctgt cacagccgat    660
gcccagggtg tcttccagat tctcatccga aaccgctcta cagacttgga tgcccgcatg    720
gcagatggct caacggcact gatcctggcg gcccgcctgg cagtagaggg catggtggaa    780
gagctcatcg ccagccatgc tgatgtcaat gctgtggatg agcttgggaa atcagcctta    840
cactgggctg cggctgtgaa caacgtggaa gccactttgg ccctgctcaa aaatggagcc    900
aataaggaca tgcaggatag caaggaggag accccccctat tcctggccgc ccgcgagggc    960
agctatgagg ctgccaagct gctgttggac cactttgcca accgtgagat caccgaccac   1020
ctggacaggc tgccgcggga cgtagcccag gagagactgc accaggacat cgtgcgcttg   1080
ctggatcaac ccagtgggcc ccgcagcccc cccggtcccc acggcctggg gcctctgctc   1140
tgtcctccag ggccttcct ccctggcctc aaagcggcac agtcggggtc caagaagagc   1200
aggaggcccc ccgggaaggc ggggctgggg ccgcaggggc cccgggggcg gggcaagaag   1260
ctgacgctgg cctgcccggg ccccctggct gacagctcgg tcacgctgtc gcccgtggac   1320
tcgctggact ccccgcggcc tttcggtggg ccccctgctt cccctggtgg cttccccctt   1380
gaggggccct atgcagctgc cactgccact gcagtgtctc tggcacagct tggtggccca   1440
ggccgggcgg gtctagggcg ccagcccccct ggaggatgtg tactcagcct gggcctgctg   1500
aaccctgtgg ctgtgcccct cgattgggcc cggctgcccc cacctgcccc tccaggcccc   1560
tcgttcctgc tgccactggc gccgggaccc cagctgctca acccagggac cccccgtctcc   1620
ccgcaggagc ggcccccgcc ttacctggca gtcccaggac atggcgagga gtacccggcg   1680
gctggggcac acagcagccc cccaaaggcc cgcttcctgc gggttcccag tgagcaccct   1740
tacctgaccc catcccccga atcccctgag cactgggcca gcccctcacc tccctccctc   1800
tcagactggt ccgaatccac gcctagccca gccactgcca ctggggccat ggccaccacc   1860
actggggcac tgcctgccca gccacttccc ttgtctgttc ccagctccct tgctcaggcc   1920
cagacccagc tggggcccca gccggaagtt acccccaaga ggcaagtgtt ggcctga       1977
```

<210> SEQ ID NO 4
<211> LENGTH: 1611
<212> TYPE: DNA
<213> ORGANISM: Homo sapiens

<400> SEQUENCE: 4

```
atgcagctca tccggcgtcg acgccgagag catggagctc tctggctgcc ccctggtttc     60
actcgacggc ctcggactca gtcagctccc caccgacgcc ggcccccact aggcgaggac    120
agcattggtc tcaaggcact gaagccaaag gcagaagttg atgaggatgg agttgtgatg    180
```

```
tgctcaggcc ctgaggaggg agaggaggtg ggccaggctg aagaaacagg cccaccctcc    240
acgtgccagc tctggtctct gagtggtggc tgtggggcgc tccctcaggc agccatgcta    300
actcctcccc aggaatctga gatggaagcc cctgacctgg acacccgtgg acctgatggg    360
gtgacacccc tgatgtcagc agtttgctgt ggggaagtac agtccgggac cttccaaggg    420
gcatggttgg gatgtcctga gccctgggaa cctctgctgg atggaggggc ctgtccccag    480
gctcacaccg tgggcactgg ggagaccccc ctgcacctgg ctgcccgatt ctcccggcca    540
accgctgccc gccgcctcct tgaggctgga gccaacccca accagccaga ccgggcaggg    600
cgcacacccc ttcatgctgc tgtggctgct gatgctcggg aggtctgcca gcttctgctc    660
cgtagcagac aaactgcagt ggacgctcgc acagaggacg ggaccacacc cttgatgctg    720
gctgccaggc tggcggtgga agacctggtt gaagaactga ttgcagccca agcagacgtg    780
ggggccagag ataaatgggg gaaaactgcg ctgcactggg ctgctgccgt gaacaacgcc    840
cgagccgccc gctcgcttct ccaggccgga gccgataaag atgcccagga caacagggag    900
cagacgccgc tattcctggc ggcgcgggaa ggagcggtgg aagtagccca gctactgctg    960
gggctggggg cagcccgaga gctgcgggac caggctgggc tagcgccggc ggacgtcgct   1020
caccaacgta accactggga tctgctgacg ctgctggaag ggctgggcc accagaggcc   1080
cgtcacaaag ccacgccggg ccgcgaggct gggcccttcc cgcgcgcacg gacggtgtca   1140
gtaagcgtgc ccccgcatgg gggcggggct ctgccgcgct gccggacgct gtcagccgga   1200
gcaggccctc gtgggggcgg agcttgtctg caggctcgga cttggtccgt agacttggct   1260
gcgcgggggg gcggggccta ttctcattgc cggagcctct cgggagtagg agcaggagga   1320
ggcccgaccc ctcgcggccg taggttttct gcaggcatgc gcgggcctcg gcccaaccct   1380
gcgataatgc gaggaagata cggagtggct gccgggcgcg gaggcagggt ctcaacggat   1440
gactggccct gtgattgggt ggccctggga gcttgcggtt ctgcctccaa cattccgatc   1500
ccgcctcctt gccttactcc gtccccggag cggggatcac ctcaacttga ctgtggtccc   1560
ccagccctcc aagaaatgcc cataaaccaa ggaggagagg gtaaaaaata g            1611
```

<210> SEQ ID NO 5
<211> LENGTH: 796
<212> TYPE: PRT
<213> ORGANISM: Homo sapiens

<400> SEQUENCE: 5

```
Met Arg Arg Gln His Gly Gln Leu Trp Phe Pro Glu Gly Phe Lys Val
1               5                   10                  15

Ser Glu Ala Ser Lys Lys Lys Arg Arg Glu Pro Leu Gly Glu Asp Ser
            20                  25                  30

Val Gly Leu Lys Pro Leu Lys Asn Ala Ser Asp Gly Ala Leu Met Asp
        35                  40                  45

Asp Asn Gln Asn Glu Trp Gly Asp Glu Asp Leu Glu Thr Lys Lys Phe
    50                  55                  60

Arg Phe Glu Glu Pro Val Val Leu Pro Asp Leu Asp Asp Gln Thr Asp
65                  70                  75                  80

His Arg Gln Trp Thr Gln Gln His Leu Asp Ala Ala Asp Leu Arg Met
                85                  90                  95

Ser Ala Met Ala Pro Thr Pro Pro Gln Gly Glu Val Asp Ala Asp Cys
            100                 105                 110

Met Asp Val Asn Val Arg Gly Pro Asp Gly Phe Thr Pro Leu Met Ile
```

```
        115                 120                 125

Ala Ser Cys Ser Gly Gly Gly Leu Glu Thr Gly Asn Ser Glu Glu Glu
    130                 135                 140

Glu Asp Ala Pro Ala Val Ile Ser Asp Phe Ile Tyr Gln Gly Ala Ser
145                 150                 155                 160

Leu His Asn Gln Thr Asp Arg Thr Gly Glu Thr Ala Leu His Leu Ala
                165                 170                 175

Ala Arg Tyr Ser Arg Ser Asp Ser Ala Lys Arg Leu Leu Glu Ala Ser
            180                 185                 190

Ala Asp Ala Asn Ile Gln Asp Asn Met Gly Arg Thr Pro Leu His Ala
        195                 200                 205

Ala Val Ser Ala Asp Ala Gln Gly Val Phe Gln Ile Leu Ile Arg Asn
    210                 215                 220

Arg Ala Thr Asp Leu Asp Ala Arg Met His Asp Gly Thr Thr Pro Leu
225                 230                 235                 240

Ile Leu Ala Ala Arg Leu Ala Val Glu Gly Met Leu Glu Asp Leu Ile
                245                 250                 255

Asn Ser His Ala Asp Val Asn Ala Val Asp Asp Leu Gly Lys Ser Ala
            260                 265                 270

Leu His Trp Ala Ala Ala Val Asn Asn Val Asp Ala Ala Val Val Leu
        275                 280                 285

Leu Lys Asn Gly Ala Asn Lys Asp Met Gln Asn Asn Arg Glu Glu Thr
    290                 295                 300

Pro Leu Phe Leu Ala Ala Arg Glu Gly Ser Tyr Glu Thr Ala Lys Val
305                 310                 315                 320

Leu Leu Asp His Phe Ala Asn Arg Asp Ile Thr Asp His Met Asp Arg
                325                 330                 335

Leu Pro Arg Asp Ile Ala Gln Glu Arg Met His His Asp Ile Val Arg
            340                 345                 350

Leu Leu Asp Glu Tyr Asn Leu Val Arg Ser Pro Gln Leu His Gly Ala
        355                 360                 365

Pro Leu Gly Gly Thr Pro Thr Leu Ser Pro Pro Leu Cys Ser Pro Asn
    370                 375                 380

Gly Tyr Leu Gly Ser Leu Lys Pro Gly Val Gln Gly Lys Lys Val Arg
385                 390                 395                 400

Lys Pro Ser Ser Lys Gly Leu Ala Cys Gly Ser Lys Glu Ala Lys Asp
                405                 410                 415

Leu Lys Ala Arg Arg Lys Lys Ser Gln Asp Gly Lys Gly Cys Leu Leu
            420                 425                 430

Asp Ser Ser Gly Met Leu Ser Pro Val Asp Ser Leu Glu Ser Pro His
        435                 440                 445

Gly Tyr Leu Ser Asp Val Ala Ser Pro Pro Leu Leu Pro Ser Pro Phe
    450                 455                 460

Gln Gln Ser Pro Ser Val Pro Leu Asn His Leu Pro Gly Met Pro Asp
465                 470                 475                 480

Thr His Leu Gly Ile Gly His Leu Asn Val Ala Ala Lys Pro Glu Met
                485                 490                 495

Ala Ala Leu Gly Gly Gly Gly Arg Leu Ala Phe Glu Thr Gly Pro Pro
            500                 505                 510

Arg Leu Ser His Leu Pro Val Ala Ser Gly Thr Ser Thr Val Leu Gly
        515                 520                 525

Ser Ser Ser Gly Gly Ala Leu Asn Phe Thr Val Gly Gly Ser Thr Ser
    530                 535                 540
```

Leu Asn Gly Gln Cys Glu Trp Leu Ser Arg Leu Gln Ser Gly Met Val
545 550 555 560

Pro Asn Gln Tyr Asn Pro Leu Arg Gly Ser Val Ala Pro Gly Pro Leu
565 570 575

Ser Thr Gln Ala Pro Ser Leu Gln His Gly Met Val Gly Pro Leu His
580 585 590

Ser Ser Leu Ala Ala Ser Ala Leu Ser Gln Met Met Ser Tyr Gln Gly
595 600 605

Leu Pro Ser Thr Arg Leu Ala Thr Gln Pro His Leu Val Gln Thr Gln
610 615 620

Gln Val Gln Pro Gln Asn Leu Gln Met Gln Gln Gln Asn Leu Gln Pro
625 630 635 640

Ala Asn Ile Gln Gln Gln Gln Ser Leu Gln Pro Pro Pro Pro Pro Pro
645 650 655

Gln Pro His Leu Gly Val Ser Ser Ala Ala Ser Gly His Leu Gly Arg
660 665 670

Ser Phe Leu Ser Gly Glu Pro Ser Gln Ala Asp Val Gln Pro Leu Gly
675 680 685

Pro Ser Ser Leu Ala Val His Thr Ile Leu Pro Gln Glu Ser Pro Ala
690 695 700

Leu Pro Thr Ser Leu Pro Ser Ser Leu Val Pro Pro Val Thr Ala Ala
705 710 715 720

Gln Phe Leu Thr Pro Pro Ser Gln His Ser Tyr Ser Ser Pro Val Asp
725 730 735

Asn Thr Pro Ser His Gln Leu Gln Val Pro Glu His Pro Phe Leu Thr
740 745 750

Pro Ser Pro Glu Ser Pro Asp Gln Trp Ser Ser Ser Ser Pro His Ser
755 760 765

Asn Val Ser Asp Trp Ser Glu Gly Val Ser Ser Pro Pro Thr Ser Met
770 775 780

Gln Ser Gln Ile Ala Arg Ile Pro Glu Ala Phe Lys
785 790 795

<210> SEQ ID NO 6
<211> LENGTH: 773
<212> TYPE: PRT
<213> ORGANISM: Homo sapiens

<400> SEQUENCE: 6

Met Ala Lys Arg Lys Arg Lys His Gly Ser Leu Trp Leu Pro Glu Gly
1 5 10 15

Phe Thr Leu Arg Arg Asp Ala Ser Asn His Lys Arg Arg Glu Pro Val
20 25 30

Gly Gln Asp Ala Val Gly Leu Lys Asn Leu Ser Val Gln Val Ser Glu
35 40 45

Ala Asn Leu Ile Gly Thr Gly Thr Ser Glu His Trp Val Asp Asp Glu
50 55 60

Gly Pro Gln Pro Lys Lys Val Lys Ala Glu Asp Glu Ala Leu Leu Ser
65 70 75 80

Glu Glu Asp Asp Pro Ile Asp Arg Arg Pro Trp Thr Gln Gln His Leu
85 90 95

Glu Ala Ala Asp Ile Arg Arg Thr Pro Ser Leu Ala Leu Thr Pro Pro
100 105 110

Gln Ala Glu Gln Glu Val Asp Val Leu Asp Val Asn Val Arg Gly Pro

-continued

```
        115                 120                 125

Asp Gly Cys Thr Pro Leu Met Leu Ala Ser Leu Arg Gly Gly Ser Ser
    130                 135                 140

Asp Leu Ser Asp Glu Asp Glu Asp Ala Glu Asp Ser Ser Ala Asn Ile
145                 150                 155                 160

Ile Thr Asp Leu Val Tyr Gln Gly Ala Ser Leu Gln Ala Gln Thr Asp
                165                 170                 175

Arg Thr Gly Glu Met Ala Leu His Leu Ala Ala Arg Tyr Ser Arg Ala
            180                 185                 190

Asp Ala Ala Lys Arg Leu Leu Asp Ala Gly Ala Asp Ala Asn Ala Gln
        195                 200                 205

Asp Asn Met Gly Arg Cys Pro Leu His Ala Ala Val Ala Ala Asp Ala
    210                 215                 220

Gln Gly Val Phe Gln Ile Leu Ile Arg Asn Arg Val Thr Asp Leu Asp
225                 230                 235                 240

Ala Arg Met Asn Asp Gly Thr Thr Pro Leu Ile Leu Ala Ala Arg Leu
                245                 250                 255

Ala Val Glu Gly Met Val Ala Glu Leu Ile Asn Cys Gln Ala Asp Val
            260                 265                 270

Asn Ala Val Asp Asp His Gly Lys Ser Ala Leu His Trp Ala Ala Ala
        275                 280                 285

Val Asn Asn Val Glu Ala Thr Leu Leu Leu Leu Lys Asn Gly Ala Asn
    290                 295                 300

Arg Asp Met Gln Asp Asn Lys Glu Glu Thr Pro Leu Phe Leu Ala Ala
305                 310                 315                 320

Arg Glu Gly Ser Tyr Glu Ala Ala Lys Ile Leu Leu Asp His Phe Ala
                325                 330                 335

Asn Arg Cys His Thr Asp His Met Asp Arg Leu Pro Arg Asp Val Ala
            340                 345                 350

Arg Asp Arg Met His His Asp Ile Val Arg Leu Leu Asp Glu Tyr Asn
        355                 360                 365

Val Thr Pro Ser Pro Pro Gly Thr Val Leu Thr Ser Ala Leu Ser Pro
    370                 375                 380

Val Ile Cys Gly Pro Asn Arg Ser Phe Leu Ser Leu Lys His Thr Pro
385                 390                 395                 400

Met Gly Lys Lys Ser Arg Arg Pro Ser Ala Lys Ser Thr Met Pro Thr
                405                 410                 415

Ser Leu Pro Asn Leu Ala Lys Glu Ala Lys Asp Ala Lys Gly Ser Arg
            420                 425                 430

Arg Lys Lys Ser Leu Ser Glu Lys Val Gln Leu Ser Glu Ser Ser Val
        435                 440                 445

Thr Leu Ser Pro Val Asp Ser Leu Glu Ser Pro His Thr Tyr Val Ser
    450                 455                 460

Asp Thr Thr Ser Ser Pro Met Ile Thr Ser Pro Gly Ile Leu Gln Ala
465                 470                 475                 480

Ser Pro Asn Pro Met Leu Ala Thr Ala Ala Pro Pro Ala Pro Val His
                485                 490                 495

Ala Gln His Ala Leu Ser Phe Ser Asn Leu His Glu Met Gln Pro Leu
            500                 505                 510

Ala His Gly Ala Ser Thr Val Leu Pro Ser Val Ser Gln Leu Leu Ser
        515                 520                 525

His His His Ile Val Ser Pro Gly Ser Gly Ser Ala Gly Ser Leu Ser
    530                 535                 540
```

```
Arg Leu His Pro Val Pro Val Pro Ala Asp Trp Met Asn Arg Met Glu
545                 550                 555                 560

Val Asn Glu Thr Gln Tyr Asn Glu Met Phe Gly Met Val Leu Ala Pro
                565                 570                 575

Ala Glu Gly Thr His Pro Gly Ile Ala Pro Gln Ser Arg Pro Pro Glu
            580                 585                 590

Gly Lys His Ile Thr Thr Pro Arg Glu Pro Leu Pro Pro Ile Val Thr
        595                 600                 605

Phe Gln Leu Ile Pro Lys Gly Ser Ile Ala Gln Pro Ala Gly Ala Pro
    610                 615                 620

Gln Pro Gln Ser Thr Cys Pro Pro Ala Val Ala Gly Pro Leu Pro Thr
625                 630                 635                 640

Met Tyr Gln Ile Pro Glu Met Ala Arg Leu Pro Ser Val Ala Phe Pro
                645                 650                 655

Thr Ala Met Met Pro Gln Gln Asp Gly Gln Val Ala Gln Thr Ile Leu
            660                 665                 670

Pro Ala Tyr His Pro Phe Pro Ala Ser Val Gly Lys Tyr Pro Thr Pro
        675                 680                 685

Pro Ser Gln His Ser Tyr Ala Ser Ser Asn Ala Ala Glu Arg Thr Pro
    690                 695                 700

Ser His Ser Gly His Leu Gln Gly Glu His Pro Tyr Leu Thr Pro Ser
705                 710                 715                 720

Pro Glu Ser Pro Asp Gln Trp Ser Ser Ser Ser Pro His Ser Ala Ser
                725                 730                 735

Asp Trp Ser Asp Val Thr Thr Ser Pro Thr Pro Gly Gly Ala Gly Gly
            740                 745                 750

Gly Gln Arg Gly Pro Gly Thr His Met Ser Glu Pro Pro His Asn Asn
        755                 760                 765

Met Gln Val Tyr Ala
    770
```

<210> SEQ ID NO 7
<211> LENGTH: 658
<212> TYPE: PRT
<213> ORGANISM: Homo sapiens

<400> SEQUENCE: 7

```
Met Ala Arg Arg Lys Arg Glu His Ser Thr Leu Trp Phe Pro Glu Gly
1               5                   10                  15

Phe Ser Leu His Lys Asp Val Ala Ser Gly His Lys Gly Arg Arg Glu
            20                  25                  30

Pro Val Gly Gln Asp Ala Leu Gly Met Lys Asn Met Ala Lys Gly Glu
        35                  40                  45

Ser Leu Met Gly Glu Val Ala Thr Asp Trp Met Asp Thr Glu Cys Pro
    50                  55                  60

Glu Ala Lys Arg Leu Lys Val Glu Glu Pro Gly Met Gly Ala Glu Glu
65                  70                  75                  80

Ala Val Asp Cys Arg Gln Trp Thr Gln His His Leu Val Ala Ala Asp
                85                  90                  95

Ile Arg Val Ala Pro Ala Met Ala Leu Thr Pro Pro Gln Gly Asp Ala
            100                 105                 110

Asp Ala Asp Gly Met Asp Val Asn Val Arg Gly Pro Asp Gly Phe Thr
        115                 120                 125

Pro Leu Met Leu Ala Ser Phe Cys Gly Gly Ala Leu Glu Pro Met Pro
```

```
    130                 135                 140

Thr Glu Glu Asp Glu Ala Asp Asp Thr Ser Ala Ser Ile Ile Ser Asp
145                 150                 155                 160

Leu Ile Cys Gln Gly Ala Gln Leu Gly Ala Arg Thr Asp Arg Thr Gly
                165                 170                 175

Glu Thr Ala Leu His Leu Ala Ala Arg Tyr Ala Arg Ala Asp Ala Ala
            180                 185                 190

Lys Arg Leu Leu Asp Ala Gly Ala Asp Thr Asn Ala Gln Asp His Ser
        195                 200                 205

Gly Arg Thr Pro Leu His Thr Ala Val Thr Ala Asp Ala Gln Gly Val
    210                 215                 220

Phe Gln Ile Leu Ile Arg Asn Arg Ser Thr Asp Leu Asp Ala Arg Met
225                 230                 235                 240

Ala Asp Gly Ser Thr Ala Leu Ile Leu Ala Ala Arg Leu Ala Val Glu
                245                 250                 255

Gly Met Val Glu Glu Leu Ile Ala Ser His Ala Asp Val Asn Ala Val
            260                 265                 270

Asp Glu Leu Gly Lys Ser Ala Leu His Trp Ala Ala Ala Val Asn Asn
        275                 280                 285

Val Glu Ala Thr Leu Ala Leu Leu Lys Asn Gly Ala Asn Lys Asp Met
    290                 295                 300

Gln Asp Ser Lys Glu Glu Thr Pro Leu Phe Leu Ala Ala Arg Glu Gly
305                 310                 315                 320

Ser Tyr Glu Ala Ala Lys Leu Leu Leu Asp His Phe Ala Asn Arg Glu
                325                 330                 335

Ile Thr Asp His Leu Asp Arg Leu Pro Arg Asp Val Ala Gln Glu Arg
            340                 345                 350

Leu His Gln Asp Ile Val Arg Leu Leu Asp Gln Pro Ser Gly Pro Arg
        355                 360                 365

Ser Pro Pro Gly Pro His Gly Leu Gly Pro Leu Leu Cys Pro Pro Gly
    370                 375                 380

Ala Phe Leu Pro Gly Leu Lys Ala Ala Gln Ser Gly Ser Lys Lys Ser
385                 390                 395                 400

Arg Arg Pro Pro Gly Lys Ala Gly Leu Gly Pro Gln Gly Pro Arg Gly
                405                 410                 415

Arg Gly Lys Lys Leu Thr Leu Ala Cys Pro Gly Pro Leu Ala Asp Ser
            420                 425                 430

Ser Val Thr Leu Ser Pro Val Asp Ser Leu Asp Ser Pro Arg Pro Phe
        435                 440                 445

Gly Gly Pro Pro Ala Ser Pro Gly Gly Phe Pro Leu Glu Gly Pro Tyr
    450                 455                 460

Ala Ala Ala Thr Ala Thr Ala Val Ser Leu Ala Gln Leu Gly Gly Pro
465                 470                 475                 480

Gly Arg Ala Gly Leu Gly Arg Gln Pro Pro Gly Gly Cys Val Leu Ser
                485                 490                 495

Leu Gly Leu Leu Asn Pro Val Ala Val Pro Leu Asp Trp Ala Arg Leu
            500                 505                 510

Pro Pro Pro Ala Pro Pro Gly Pro Ser Phe Leu Leu Pro Leu Ala Pro
        515                 520                 525

Gly Pro Gln Leu Leu Asn Pro Gly Thr Pro Val Ser Pro Gln Glu Arg
    530                 535                 540

Pro Pro Pro Tyr Leu Ala Val Pro Gly His Gly Glu Glu Tyr Pro Ala
545                 550                 555                 560
```

```
Ala Gly Ala His Ser Ser Pro Pro Lys Ala Arg Phe Leu Arg Val Pro
                565                 570                 575

Ser Glu His Pro Tyr Leu Thr Pro Ser Pro Glu Ser Pro Glu His Trp
            580                 585                 590

Ala Ser Pro Ser Pro Pro Ser Leu Ser Asp Trp Ser Glu Ser Thr Pro
        595                 600                 605

Ser Pro Ala Thr Ala Thr Gly Ala Met Ala Thr Thr Thr Gly Ala Leu
    610                 615                 620

Pro Ala Gln Pro Leu Pro Leu Ser Val Pro Ser Ser Leu Ala Gln Ala
625                 630                 635                 640

Gln Thr Gln Leu Gly Pro Gln Pro Glu Val Thr Pro Lys Arg Gln Val
                645                 650                 655

Leu Ala


<210> SEQ ID NO 8
<211> LENGTH: 536
<212> TYPE: PRT
<213> ORGANISM: Homo sapiens

<400> SEQUENCE: 8

Met Gln Leu Ile Arg Arg Arg Arg Arg Glu His Gly Ala Leu Trp Leu
1               5                   10                  15

Pro Pro Gly Phe Thr Arg Arg Pro Arg Thr Gln Ser Ala Pro His Arg
            20                  25                  30

Arg Arg Pro Pro Leu Gly Glu Asp Ser Ile Gly Leu Lys Ala Leu Lys
        35                  40                  45

Pro Lys Ala Glu Val Asp Glu Asp Gly Val Val Met Cys Ser Gly Pro
    50                  55                  60

Glu Glu Gly Glu Glu Val Gly Gln Ala Glu Glu Thr Gly Pro Pro Ser
65                  70                  75                  80

Thr Cys Gln Leu Trp Ser Leu Ser Gly Gly Cys Gly Ala Leu Pro Gln
                85                  90                  95

Ala Ala Met Leu Thr Pro Pro Gln Glu Ser Glu Met Glu Ala Pro Asp
            100                 105                 110

Leu Asp Thr Arg Gly Pro Asp Gly Val Thr Pro Leu Met Ser Ala Val
        115                 120                 125

Cys Cys Gly Glu Val Gln Ser Gly Thr Phe Gln Gly Ala Trp Leu Gly
    130                 135                 140

Cys Pro Glu Pro Trp Glu Pro Leu Leu Asp Gly Gly Ala Cys Pro Gln
145                 150                 155                 160

Ala His Thr Val Gly Thr Gly Glu Thr Pro Leu His Leu Ala Ala Arg
                165                 170                 175

Phe Ser Arg Pro Thr Ala Ala Arg Arg Leu Leu Glu Ala Gly Ala Asn
            180                 185                 190

Pro Asn Gln Pro Asp Arg Ala Gly Arg Thr Pro Leu His Ala Ala Val
        195                 200                 205

Ala Ala Asp Ala Arg Glu Val Cys Gln Leu Leu Leu Arg Ser Arg Gln
    210                 215                 220

Thr Ala Val Asp Ala Arg Thr Glu Asp Gly Thr Thr Pro Leu Met Leu
225                 230                 235                 240

Ala Ala Arg Leu Ala Val Glu Asp Leu Val Glu Glu Leu Ile Ala Ala
                245                 250                 255

Gln Ala Asp Val Gly Ala Arg Asp Lys Trp Gly Lys Thr Ala Leu His
            260                 265                 270
```

```
Trp Ala Ala Ala Val Asn Asn Ala Arg Ala Ala Arg Ser Leu Leu Gln
        275                 280                 285

Ala Gly Ala Asp Lys Asp Ala Gln Asp Asn Arg Glu Gln Thr Pro Leu
    290                 295                 300

Phe Leu Ala Ala Arg Glu Gly Ala Val Glu Val Ala Gln Leu Leu Leu
305                 310                 315                 320

Gly Leu Gly Ala Ala Arg Glu Leu Arg Asp Gln Ala Gly Leu Ala Pro
                325                 330                 335

Ala Asp Val Ala His Gln Arg Asn His Trp Asp Leu Leu Thr Leu Leu
            340                 345                 350

Glu Gly Ala Gly Pro Pro Glu Ala Arg His Lys Ala Thr Pro Gly Arg
        355                 360                 365

Glu Ala Gly Pro Phe Pro Arg Ala Arg Thr Val Ser Val Ser Val Pro
    370                 375                 380

Pro His Gly Gly Gly Ala Leu Pro Arg Cys Arg Thr Leu Ser Ala Gly
385                 390                 395                 400

Ala Gly Pro Arg Gly Gly Gly Ala Cys Leu Gln Ala Arg Thr Trp Ser
                405                 410                 415

Val Asp Leu Ala Ala Arg Gly Gly Gly Ala Tyr Ser His Cys Arg Ser
            420                 425                 430

Leu Ser Gly Val Gly Ala Gly Gly Gly Pro Thr Pro Arg Gly Arg Arg
        435                 440                 445

Phe Ser Ala Gly Met Arg Gly Pro Arg Pro Asn Pro Ala Ile Met Arg
    450                 455                 460

Gly Arg Tyr Gly Val Ala Ala Gly Arg Gly Gly Arg Val Ser Thr Asp
465                 470                 475                 480

Asp Trp Pro Cys Asp Trp Val Ala Leu Gly Ala Cys Gly Ser Ala Ser
                485                 490                 495

Asn Ile Pro Ile Pro Pro Pro Cys Leu Thr Pro Ser Pro Glu Arg Gly
            500                 505                 510

Ser Pro Gln Leu Asp Cys Gly Pro Pro Ala Leu Gln Glu Met Pro Ile
        515                 520                 525

Asn Gln Gly Gly Glu Gly Lys Lys
    530                 535
```

<210> SEQ ID NO 9
<211> LENGTH: 14187
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480
```

-continued

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtacctg    660
ctttctctga ccagcattct ctcccctggg cctgtgccgc tttctgtctg cagcttgtgg    720
cctgggtcac ctctacggct ggcccagatc cttccctgcc gcctccttca ggttccgtct    780
tcctccactc cctcttcccc ttgctctctg ctgtgttgct gcccaaggat gctctttccg    840
gagcacttcc ttctcggcgc tgcaccacgt gatgtcctct gagcggatcc tccccgtgtc    900
tgggtcctct ccgggcatct ctcctccctc acccaacccc atgccgtctt cactcgctgg    960
gttccctttt ccttctcctt ctggggcctg tgccatctct cgtttcttag gatggccttc   1020
tccgacggat gtctcccttg cgtcccgcct ccccttcttg taggcctgca tcatcaccgt   1080
ttttctggac aaccccaaag taccccgtct ccctggcttt agccacctct ccatcctctt   1140
gctttctttg cctggacacc ccgttctcct gtggattcgg gtcacctctc actcctttca   1200
tttgggcagc tcccctaccc cccttacctc tctagtctgt gctagctctt ccagcccccct   1260
gtcatggcat cttccagggg tccgagagct cagctagtct tcttcctcca acccgggccc   1320
ctatgtccac ttcaggacag catgtttgct gcctccaggg atcctgtgtc cccgagctgg   1380
gaccaccttta tattcccagg gccggttaat gtggctctgg ttctgggtac ttttatctgt   1440
cccctccacc ccacagtggg gcaagcttga agttcctatt cttcaaatag tataggaact   1500
tcggcctgac ctcttctctt cctcccacag ggcctcagat ctggcagcgg agagggcaga   1560
ggaagtcttc taacatgcgg tgacgtggag gagaatcccg gccctaggct cgaaatgacc   1620
gagtacaagc ccacggtgcg cctcgccacc cgcgacgacg tcccccgggc cgtacgcacc   1680
ctcgccgccg cgttcgccga ctaccccgcc acgcgccaca ccgtcgaccc ggaccgccac   1740
atcgagcggg tcaccgagct gcaagaactc ttcctcacgc gcgtcgggct cgacatcggc   1800
aaggtgtggg tcgcggacga cggcgccgcg gtggcggtct ggaccacgcc ggagagcgtc   1860
gaagcggggg cggtgttcgc cgagatcggc ccgcgcatgg ccgagttgag cggttcccgg   1920
ctggccgcgc agcaacagat ggaaggcctc ctggcgccgc accggcccaa ggagcccgcg   1980
tggttcctgg ccaccgtcgg cgtctcgccc gaccaccagg gcaagggtct gggcagcgcc   2040
gtcgtgctcc ccggagtgga ggcggccgag cgcgccgggg tgcccgcctt cctggagacc   2100
tccgcgcccc gcaacctccc cttctacgag cggctcggct tcaccgtcac cgccgacgtc   2160
gaggtgcccg aaggaccgcg cacctggtgc atgacccgca agcccggtgc ctgacgcccg   2220
ccccacgacc cgcagcgccc gaccgaaagg agcgcacgac cccatggctc cgaccgaagc   2280
cacccggggc ggccccgccg accccgcacc cgcccccgag gcccaccgac tctagagggc   2340
ccgtttaaac ccgctgatca gcctcgactg tgccttctag ttgccagcca tctgttgttt   2400
gcccctcccc cgtgccttcc ttgaccctgg aaggtgccac tcccactgtc ctttcctaat   2460
aaaatgagga aattgcatcg cattgtctga gtaggtgtca ttctattctg gggggtgggg   2520
tggggcagga cagcaagggg gaggattggg aagacaatag cactcgacac tagtaagcgt   2580
atcgatacgg ggacagcccc cccccaaagc ccccagggat gtaattacgt ccctcccccg   2640
ctagggggca gcagcgagcc gcccggggct ccgctccggt ccggcgctcc ccccgcatcc   2700
ccgagccggc agcgtgcggg gacagcccgg gcacggggaa ggtggcacgg gatcgctttc   2760
ctctgaacgc ttctcgctgc tctttgagcc tgcagacacc tggggggata cggggaaaaa   2820
gctttaggct tgtgtctgag cctgcatgtt tgatggtgtc tggatgcaag cagaaggggt   2880
```

```
ggaagagctt gcctggagag atacagctgg gtcagtagga ctgggacagg cagctggaga   2940
attgccatgt agatgttcat acaatcgtca aatcatgaag gctggaaaag ccctccaaga   3000
tccccaagac caaccccaac ccacccaccg tgcccactgg ccatgtccct cagtgccaca   3060
tccccacagt tcttcatcac ctccagggac ggtgaccccc ccacctccgt gggcagctgt   3120
gccactgcag caccgctctt tggagaaggt aaatcttgct aaatccagcc cgaccctccc   3180
ctggcacaac gtaaggccat tatctctcat ccaactccag gacggagtca gtgagatgca   3240
tacggggaca gccccccccc aaagccccca gggatgtaat tacgtccctc ccccgctagg   3300
gggcagcagc gagccgcccg gggctccgct ccggtccggc gctccccccg catccccgag   3360
ccggcagcgt gcggggacag cccgggcacg gggaaggtgg cacgggatcg ctttcctctg   3420
aacgcttctc gctgctcttt gagcctgcag acacctgggg ggatacgggg aaaaagcttt   3480
aggcttgtgt ctgagcctgc atgtttgatg gtgtctggat gcaagcagaa ggggtggaag   3540
agcttgcctg gagagataca gctgggtcag taggactggg acaggcagct ggagaattgc   3600
catgtagatg ttcatacaat cgtcaaatca tgaaggctgg aaaagccctc caagatcccc   3660
aagaccaacc ccaacccacc caccgtgccc actggccatg tccctcagtg ccacatcccc   3720
acagttcttc atcacctcca gggacggtga cccccccacc tccgtgggca gctgtgccac   3780
tgcagcaccg ctctttggag aaggtaaatc ttgctaaatc cagcccgacc ctcccctggc   3840
acaacgtaag gccattatct ctcatccaac tccaggacgg agtcagtgag atcgatcaaa   3900
tgcgcttcga tctcgagcta tggcagggcc tgccgccccg acgttggctg cgagccctgg   3960
gccttcaccc gaacttgggg ggtggggtgg ggaaaaggaa gaaacgcggg cgtattggcc   4020
ccaatggggt ctcggtgggg tatcgacaga gtgccagccc tgggaccgaa ccccgcgttt   4080
atgaacaaac gacccaacac cgtgcgtttt attctgtctt tttattgccg tcatagcgcg   4140
ggttccttcc ggtattgtct ccttccgtgt ttcagttagc ctcccccacg cgtttacttg   4200
aacgcctccg ggatgcgggc gatctgggac tgcatgctgg tgggagggct ggagacgccc   4260
tcggaccagt cggagacgtt ggaatgcggg gacgagctgg accactggtc aggggactca   4320
ggggacgggg tgaggaaggg gtgctcaggc acctgtagct ggtggctggg ggtgttgtcc   4380
acaggcgagg agtagctgtg ctgcgagggg ggcgtcagga actgggctgc ggtcacgggt   4440
gggaccagcg aggatggcag cgacgtgggc agggcggggc tctcctgggg cagaatagtg   4500
tgcaccgcca ggctgctggg gcccagtggc tgcacgtctg cctggctcgg ctctccactc   4560
aggaagctcc ggcccaggtg gccgctggct gctgagctca cgccaaggtg cggctgtggt   4620
ggtggtggtg gcggctgcag gctttgctgc tgctggatgt ttgctggctg caggttctgc   4680
tgctgcatct gtaagttttg tggctgcacc tgctgggtct gcaccaggtg aggctgggtg   4740
gccagccggg tgctgggcag gccctggtag ctcatcatct gggacagggc gctggcagca   4800
aggctactgt gcagcgggcc taccatgcca tgctgcaggg agggggcctg tgtgctcagg   4860
gggcctggtg ccacactccc ccgcagaggg ttgtattggt tcggcaccat gccgctctgc   4920
agccgggaca gccactcgca ttgaccattc aaactggtgg acccgcccac agtgaaattc   4980
agggcccctc cgctgctgga gcccaggacg gtgctggtgc cagaggccac aggcaggtgg   5040
gagagacgag gtgggccagt ctcaaaggcc agccggccgc ccccacccag cgccgccatc   5100
tcgggcttgg ccgccacgtt caggtgcccg atgcccaggt gggtgtcggg catcccaggc   5160
aggtggttga ggggcacgga cggagactgc tggaacgggg agggcagcag tggcggcgag   5220
```

-continued

```
gccacgtctg acaggtagcc atggggtgac tccagggagt ccacgggcga gagcatgccg   5280
gagctgtcca gcaggcagcc cttgccgtcc tgggacttct tcctccgtgc cttgaggtcc   5340
ttggcctcct tgcttccaca ggccaggcct ttgctgctgg gcttgcggac cttcttgccc   5400
tgcacgccgg gcttgaggct gcccaggtag ccgttgggcg agcagagcgg gggcgacagg   5460
gtgggcgtgc cccccagcgg ggctccgtgc agctgcgggc tgcgcaccag gttgtactcg   5520
tccagcagcc tcacgatgtc gtgatgcatg cgctcctgtg cgatgtcgcg cggcaggcgg   5580
tccatatgat ccgtgatgtc ccggttggca aagtggtcca gcagcacctt ggcggtctcg   5640
tagctgccct cccgggcggc cagaaacagg ggtgtctcct ccctgttgtt ctgcatatct   5700
ttgttagccc cgttcttcag gagcacaact gcggcatcca cattgttcac ggcggcggcc   5760
cagtgcaggg cggacttgcc caggtcatct acggcgttga cgtcggcgtg tgagttgatg   5820
aggtcctcca gcatgccctc cacggccagg cgggcagcca ggatcagtgg cgtcgtgcca   5880
tcatgcatgc gggcatccag gtctgtggct cggttccgga tcaggatctg gaagacacct   5940
tgtgcgtcgg cagacacagc cgcatgcagc ggggtgcggc ccatgttgtc ctggatgttg   6000
gcatctgcgc tggcctccag caggcgcttg gcggaatcag agcgtgagta gcgggcggcc   6060
aggtgcaagg cggtctcgcc cgtgcggtct gtctggttgt gcaggctggc gccctggtag   6120
atgaagtcgg agatgacggc cggcgcgtcc tcctcttcct cgctgttgcc cgtctccagg   6180
ccgcccccgc tgcaggaggc gatcatgagc ggggtgaagc catcaggccc gcggacattg   6240
acgtccatgc agtcggcgtc aacctcaccc tggggcggtg tgggggccat ggcagacatg   6300
cgcaggtcag cggcatccag gtgctgctga gtccactgcc ggtggtctgt ctggtcgtcc   6360
aggtcaggca gaaccacggg ctcctcgaac cggaacttct tggtctccag gtcctcgtcc   6420
ccccactcat tctggttgtc gtccatgagg gcaccgtctg aagcgttctt caggggcttg   6480
aggcccacgg agtcctcgcc gaggggctcc cgccgcttct tcttgctggc ctcagacact   6540
ttgaagccct cagggaacca gagctggcca tgctgccgcc gcatgatatc tccaccggtc   6600
gtcatcgtca tccttgtaat caatatcatg atctttataa tcaccgtcat ggtctttgta   6660
gtccatggtg gccttaagcg atctgacggt tcactaaacg agctctgctt atataggcct   6720
cccaccgtac acgcctacct cgacatacgt tctctatcac tgatagggag taaactcgac   6780
atacgttctc tatcactgat agggataaac tcgacatacg ttctctatca ctgataggga   6840
gtaaactcga catacgttct ctatcactga tagggagtaa actcgacata cgttctctat   6900
cactgatagg gagtaaactc gacatcgttc tctatcactg atagggagta aactcgtcta   6960
gaacctcgga ccttcgaaaa aagtttcgag tgtacagcat catcgtcgac attgattatt   7020
gactagctag ttattaatag taatcaatta cggggtcatt agttcatagc ccatatatgg   7080
agttccgcgt tacataactt acggtaaatg gcccgcctgg ctgaccgccc aacgaccccc   7140
gcccattgac gtcaataatg acgtatgttc ccatagtaac gccaataggg actttccatt   7200
gacgtcaatg ggtggagtat ttacggtaaa ctgcccactt ggcagtacat caagtgtatc   7260
atatgccaag tacgccccct attgacgtca atgacggtaa atggcccgcc tggcattatg   7320
cccagtacat gaccttatgg gactttccta cttggcagta catctacgta ttagtcatcg   7380
ctattaccat gatggtcgag gtgagcccca cgttctgctt cactctcccc atctcccccc   7440
cctccccacc cccaattttg tatttattta ttttttaatt attttgtgca gcgatggggg   7500
cggggggggg gggggggcgc gcgccaggcg gggcggggcg gggcgagggg cggggcgggg   7560
cgaggcggag aggtgcggcg gcagccaatc agagcggcgc gctccgaaag tttcctttta   7620
```

-continued

```
tggcgaggcg gcggcggcgg cggccctata aaaagcgaag cgcgcggcgg gcgggagtcg   7680
ctgcgcgctg ccttcgcccc gtgccccgct ccgccgccgc ctcgcgccgc ccgccccggc   7740
tctgactgac cgcgttactc ccacaggtga gcgggcggga cggcccttct cctccgggct   7800
gtaattagcg cttggtttaa tgacggcttg tttcttttct gtggctgcgt gaaagccttg   7860
aggggctccg ggagggccct ttgtgcgggg ggagcggctc ggggggtgcg tgcgtgtgtg   7920
tgtgcgtggg gagcgccgcg tgcggctccg cgctgcccgg cggctgtgag cgctgcgggc   7980
gcggcgcggg gctttgtgcg ctccgcagtg tgcgcgaggg gagcgcggcc gggggcggtg   8040
ccccgcggtg cggggggggc tgcgagggga acaaaggctg cgtgcggggt gtgtgcgtgg   8100
gggggtgagc agggggtgtg ggcgcgtcgg tcgggctgca acccccccctg cacccccctc   8160
cccgagttgc tgagcacggc ccggcttcgg gtgcggggct ccgtacgggg cgtggcgcgg   8220
ggctcgccgt gccgggcggg gggtggcggc aggtgggggt gccgggcggg gcggggccgc   8280
ctcgggccgg ggagggctcg gggggagggc gcggcggccc ccggagcgcc ggcggctgtc   8340
gaggcgcggc gagccgcagc cattgccttt tatggtaatc gtgcgagagg gcgcagggac   8400
ttcctttgtc ccaaatctgt gcggagccga aatctgggag gcgccgccgc acccccctcta   8460
gcgggcgcgg ggcgaagcgg tgcggcgccg gcaggaagga aatgggcggg gagggccttc   8520
gtgcgtcgcc gcgccgccgt ccccttctcc ctctccagcc tcggggctgt ccgcgggggg   8580
acggctgcct tcggggggga cggggcaggg cggggttcgg cttctggcgt gtgaccggcg   8640
gctctagagc ctctgctaac catgttcatg ccttcttctt tttcctacag ctcctgggca   8700
acgtgctggt tattgtgctg tctcatcatt ttggcaaaga attcatgtct agactggaca   8760
agagcaaagt cataaacggc gctctggaat tactcaatgg agtcggtatc gaaggcctga   8820
cgacaaggaa actcgctcaa aagctgggag ttgagcagcc taccctgtac tggcacgtga   8880
agaacaagcg ggccctgctc gatgccctgc caatcgagat gctggacagg catcataccc   8940
acttctgccc cctggaaggc gagtcatggc aagactttct gcggaacaac gccaagtcat   9000
tccgctgtgc tctcctctca catcgcgacg gggctaaagt gcatctcggc acccgcccaa   9060
cagagaaaca gtacgaaacc ctggaaaatc agctcgcgtt cctgtgtcag caaggcttct   9120
ccctggagaa cgcactgtac gctctgtccg ccgtgggcca ctttacactg ggctgcgtat   9180
tggaggaaca ggagcatcaa gtagcaaaag aggaaagaga gacacctacc accgattcta   9240
tgcccccact tctgagacaa gcaattgagc tgttcgaccg gcagggagcc gaacctgcct   9300
tccttttcgg cctggaacta atcatatgtg gcctggagaa acagctaaag tgcgaaagcg   9360
gcgggccggc cgacgccctt gacgattttg acttagacat gctcccagcc gatgcccttg   9420
acgactttga ccttgatatg ctgcctgctg acgctcttga cgattttgac cttgacatgc   9480
tccccgggta aactagtgcc tcgactgtgc cttctagttg ccagccatct gttgtttgcc   9540
cctcccccgt gccttccttg accctggaag gtgccactcc cactgtcctt tcctaataaa   9600
atgaggaaat tgcatcgcat tgtctgagta ggtgtcattc tattctgggg ggtggggtgg   9660
ggcaggacag caagggggag gattgggaag acaatagcag gcatgctggg gatgcggtgg   9720
gctctatggt tcgaactagt gtcgaggcgc atttgatcga tctcactgac tccgtcctgg   9780
agttggatga gagataatgg ccttacgttg tgccagggga gggtcgggct ggatttagca   9840
agatttacct tctccaaaga gcggtgctgc agtggcacag ctgcccacgg aggtgggggg   9900
gtcaccgtcc ctggaggtga tgaagaactg tggggatgtg gcactgaggg acatggccag   9960
```

-continued

```
tgggcacggt gggtgggttg gggttggtct tggggatctt ggagggcttt tccagccttc  10020
atgatttgac gattgtatga acatctacat ggcaattctc cagctgcctg tcccagtcct  10080
actgacccag ctgtatctct ccaggcaagc tcttccaccc cttctgcttg catccagaca  10140
ccatcaaaca tgcaggctca gacacaagcc taaagctttt tccccgtatc cccccaggtg  10200
tctgcaggct caaagagcag cgagaagcgt tcagaggaaa gcgatcccgt gccaccttcc  10260
ccgtgcccgg gctgtccccg cacgctgccg gctcggggat gcgggggggag cgccggaccg  10320
gagcggagcc ccgggcggct cgctgctgcc ccctagcggg ggagggacgt aattacatcc  10380
ctgggggctt tggggggggg ctgtccccgt atgcatctca ctgactccgt cctggagttg  10440
gatgagagat aatggcctta cgttgtgcca ggggagggtc gggctggatt tagcaagatt  10500
taccttctcc aaagagcggt gctgcagtgg cacagctgcc cacggaggtg ggggggtcac  10560
cgtccctgga ggtgatgaag aactgtgggg atgtggcact gagggacatg gccagtgggc  10620
acggtgggtg ggttggggtt ggtcttgggg atcttggagg gcttttccag ccttcatgat  10680
ttgacgattg tatgaacatc tacatggcaa ttctccagct gcctgtccca gtcctactga  10740
cccagctgta tctctccagg caagctcttc caccccttct gcttgcatcc agacaccatc  10800
aaacatgcag gctcagacac aagcctaaag ctttttcccc gtatcccccc aggtgtctgc  10860
aggctcaaag agcagcgaga agcgttcaga ggaaagcgat cccgtgccac cttccccgtg  10920
cccgggctgt ccccgcacgc tgccggctcg gggatgcggg gggagcgccg gaccggagcg  10980
gagccccggg cggctcgctg ctgcccccta gcgggggagg gacgtaatta catccctggg  11040
ggctttgggg gggggctgtc cccgtatcga tacgcttgtc gagatcgaag aagttcctat  11100
tctctagaaa gtataggaac ttcgcggccg ctactaggga caggattggt gacagaaaag  11160
ccccatcctt aggcctcctc cttcctagtc tcctgatatt gggtctaacc cccacctcct  11220
gttaggcaga ttccttatct ggtgacacac ccccatttcc tggagccatc tctctccttg  11280
ccagaacctc taaggtttgc ttacgatgga gccagagagg atcctgggag ggagagcttg  11340
gcagggggtg ggagggaagg gggggatgcg tgacctgccc ggttctcagt ggccaccctg  11400
cgctaccctc tcccagaacc tgagctgctc tgacgcggct gtctggtgcg tttcactgat  11460
cctggtgctg cagcttcctt acacttccca agaggagaag cagtttggaa aaacaaaatc  11520
agaataagtt ggtcctgagt tctaactttg gctcttcacc tttctagtcc ccaatttata  11580
ttgttcctcc gtgcgtcagt tttacctgtg agataaggcc agtagccagc cccgtcctgg  11640
cagggctgtg gtgaggaggg gggtgtccgt gtggaaaact ccctttgtga gaatggtgcg  11700
tcctaggtgt tcaccaggtc gtggccgcct ctactccctt tctctttctc catccttctt  11760
tccttaaaga gtccccagtg ctatctggga catattcctc cgcccagagc agggtcccgc  11820
ttccctaagg ccctgctctg ggcttctggg tttgagtcct tggcaagccc aggagaggcg  11880
ctcaggcttc cctgtccccc ttcctcgtcc accatctcat gcccctggct ctcctgcccc  11940
ttccctacag gggttcctgg ctctgctctc caccgcggtg gagctccagc ttttgttccc  12000
tttagtgagg gttaattgcg cgcttggcgt aatcatggtc atagctgttt cctgtgtgaa  12060
attgttatcc gctcacaatt ccacacaaca tacgagccgg aagcataaag tgtaaagcct  12120
ggggtgccta atgagtgagc taactcacat taattgcgtt gcgctcactg cccgctttcc  12180
agtcgggaaa cctgtcgtgc cagctgcatt aatgaatcgg ccaacgcgcg gggagaggcg  12240
gtttgcgtat tgggcgctct tccgcttcct cgctcactga ctcgctgcgc tcggtcgttc  12300
ggctgcggcg agcggtatca gctcactcaa aggcggtaat acggttatcc acagaatcag  12360
```

```
gggataacgc aggaaagaac atgtgagcaa aaggccagca aaaggccagg aaccgtaaaa  12420
aggccgcgtt gctggcgttt ttccataggc tccgcccccc tgacgagcat cacaaaaatc  12480
gacgctcaag tcagaggtgg cgaaacccga caggactata aagataccag gcgtttcccc  12540
ctggaagctc cctcgtgcgc tctcctgttc cgaccctgcc gcttaccgga tacctgtccg  12600
cctttctccc ttcgggaagc gtggcgcttt ctcatagctc acgctgtagg tatctcagtt  12660
cggtgtaggt cgttcgctcc aagctgggct gtgtgcacga accccccgtt cagcccgacc  12720
gctgcgcctt atccggtaac tatcgtcttg agtccaaccc ggtaagacac gacttatcgc  12780
cactggcagc agccactggt aacaggatta gcagagcgag gtatgtaggc ggtgctacag  12840
agttcttgaa gtggtggcct aactacggct acactagaag gacagtattt ggtatctgcg  12900
ctctgctgaa gccagttacc ttcggaaaaa gagttggtag ctcttgatcc ggcaaacaaa  12960
ccaccgctgg tagcggtggt ttttttgttt gcaagcagca gattacgcgc agaaaaaaag  13020
gatctcaaga agatcctttg atcttttcta cggggtctga cgctcagtgg aacgaaaact  13080
cacgttaagg gattttggtc atgagattat caaaaaggat cttcacctag atccttttaa  13140
attaaaaatg aagttttaaa tcaatctaaa gtatatatga gtaaacttgg tctgacagtt  13200
accaatgctt aatcagtgag gcacctatct cagcgatctg tctatttcgt tcatccatag  13260
ttgcctgact ccccgtcgtg tagataacta cgatacggga gggcttacca tctggcccca  13320
gtgctgcaat gataccgcga gacccacgct caccggctcc agatttatca gcaataaacc  13380
agccagccgg aagggccgag cgcagaagtg gtcctgcaac tttatccgcc tccatccagt  13440
ctattaattg ttgccgggaa gctagagtaa gtagttcgcc agttaatagt ttgcgcaacg  13500
ttgttgccat tgctacaggc atcgtggtgt cacgctcgtc gtttggtatg gcttcattca  13560
gctccggttc ccaacgatca aggcgagtta catgatcccc catgttgtgc aaaaaagcgg  13620
ttagctcctt cggtcctccg atcgttgtca gaagtaagtt ggccgcagtg ttatcactca  13680
tggttatggc agcactgcat aattctctta ctgtcatgcc atccgtaaga tgcttttctg  13740
tgactggtga gtactcaacc aagtcattct gagaatagtg tatgcggcga ccgagttgct  13800
cttgcccggc gtcaatacgg gataataccg cgccacatag cagaacttta aaagtgctca  13860
tcattggaaa acgttcttcg gggcgaaaac tctcaaggat cttaccgctg ttgagatcca  13920
gttcgatgta acccactcgt gcacccaact gatcttcagc atcttttact ttcaccagcg  13980
tttctgggtg agcaaaaaca ggaaggcaaa atgccgcaaa aaagggaata agggcgacac  14040
ggaaatgttg aatactcata ctcttccttt ttcaatatta ttgaagcatt tatcagggtt  14100
attgtctcat gagcggatac atatttgaat gtatttagaa aaataaacaa ataggggttc  14160
cgcgcacatt tccccgaaaa gtgccac                                     14187
```

<210> SEQ ID NO 10
<211> LENGTH: 2361
<212> TYPE: DNA
<213> ORGANISM: Mus musculus

<400> SEQUENCE: 10

```
atgtcccgca agcgccggcg gcagcatggc cagctctggt tccctgaggg tttcaaagtg     60
tcagaggcca gcaagaagaa gcggagagag cccctcggcg aggactcagt cggcctcaag    120
cccctgaaga atgcctcaga tggtgctctg atggacgaca atcagaacga gtggggagac    180
gaagacctgg agaccaagaa gttccggttt gaggagccag tagttctccc tgacctgagt    240
```

-continued

```
gatcagactg accacaggca gtggacccag cagcacctgg acgctgctga cctgcgcatg    300
tctgccatgg ccccaacacc gcctcagggg gaggtggatg ctgactgcat ggatgtcaat    360
gttcgaggac cagatggctt cacacccctc atgattgcct cctgcagtgg agggggcctt    420
gagacaggca acagtgaaga agaagaagat gcacctgctg tcatctctga cttcatctac    480
cagggcgcca gcttgcacaa ccagacagac cgcaccgggg agaccgcctt gcacttggct    540
gcccgatact ctcgttcaga tgctgcaaag cgcttgctgg aggccagtgc agatgccaac    600
atccaggaca acatgggccg tactccgtta catgcagcag tttctgcaga tgctcagggt    660
gtcttccaga tcctgctccg gaacagggcc acagatctgg atgcccgaat gcatgatggc    720
acaactccac tgatcctggc tgcgcgcctg gccgtggagg gcatgctgga ggacctcatc    780
aactcacatg ctgacgtcaa tgccgtggat gacctaggca agtcggcttt gcattgggcg    840
gccgcggtga acaatgtgga tgctgctgtt gtgctcctga agaacggagc caacaaggac    900
atgcagaaca acaaggagga gactcccctg ttcctggccg cccgtgaggg cagctatgag    960
actgccaaag tgttgctgga ccactttgcc aaccgggaca tcacggatca catggaccga   1020
ttgccgcggg acatcgcaca ggagcgtatg caccacgata tcgtgcggct tttggatgag   1080
tacaacctgg tgcgcagccc acagctgcat ggcactgccc tgggtggcac acccactctg   1140
tctcccacac tctgctcgcc caatggctac ctgggcaatc tcaagtctgc cacacagggc   1200
aagaaggccc gcaagcccag caccaaaggg ctggcttgtg gtagcaagga agctaaggac   1260
ctcaaggcac ggaggaagaa gtcccaggat ggcaagggct gcctgttgga cagctcgagc   1320
atgctgtcgc ctgtggactc cctcgagtca ccccatggct acttgtcaga tgtggcctcg   1380
ccaccccctcc tcccctccc attccagcag tctccatcca tgcctctcag ccacctgcct   1440
ggtatgcctg acactcacct gggcatcagc cacttgaatg tggcagccaa gcctgagatg   1500
gcagcactgg ctggaggtag ccggttggcc tttgagccac ccccgccacg cctctcccac   1560
ctgcctgtag cctccagtgc cagcacagtg ctgagtacca atggcacggg ggctatgaat   1620
ttcaccgtgg gtgcaccggc aagcttgaat ggccagtgtg agtggcttcc ccggctccag   1680
aatggcatgg tgcccagcca gtacaaccca ctacggccgg gtgtgacgcc gggcacactg   1740
agcacacagg cagctggcct ccagcatagc atgatggggc cactacacag cagcctctcc   1800
accaatacct tgtccccgat tatttaccag ggcctgccca acacacggct ggcaacacag   1860
cctcacctgg tgcagaccca gcaggtgcag ccacagaact tacagctcca gcctcagaac   1920
ctgcagccac catcacagcc acacctcagt gtgagctcgg cagccaatgg gcacctgggc   1980
cggagcttct tgagtgggga gcccagtcag gcagatgtac aaccgctggg ccccagcagt   2040
ctgcctgtgc acaccattct gccccaggaa agccaggccc tgcccacatc actgccatcc   2100
tccatggtcc cacccatgac cactacccag ttcctgaccc ctccttccca gcacagttac   2160
tcctcctccc ctgtggacaa cacccccagc caccagctgc aggtgccaga gcacccttc    2220
ctcaccccat cccctgagtc ccctgaccag tggtccagct cctccccgca ttccaacatc   2280
tctgattggt ccgagggcat ctccagcccg ccccaccacca tgccgtccca gatcacccac   2340
attccagagg catttaaata a                                              2361
```

<210> SEQ ID NO 11
<211> LENGTH: 785
<212> TYPE: PRT
<213> ORGANISM: Mus musculus

<400> SEQUENCE: 11

-continued

```
Met Ser Arg Lys Arg Arg Arg Gln His Gly Gln Leu Trp Phe Pro Glu
1               5                   10                  15

Gly Phe Lys Val Ser Glu Ala Ser Lys Lys Lys Arg Arg Glu Pro Leu
            20                  25                  30

Gly Glu Asp Ser Val Gly Leu Lys Pro Leu Lys Asn Ala Ser Asp Gly
        35                  40                  45

Ala Leu Met Asp Asp Asn Gln Asn Glu Trp Gly Asp Glu Asp Leu Glu
    50                  55                  60

Thr Lys Lys Phe Arg Phe Glu Glu Pro Val Val Leu Pro Asp Leu Ser
65                  70                  75                  80

Asp Gln Thr Asp His Arg Gln Trp Thr Gln Gln His Leu Asp Ala Ala
                85                  90                  95

Asp Leu Arg Met Ser Ala Met Ala Pro Thr Pro Pro Gln Gly Glu Val
            100                 105                 110

Asp Ala Asp Cys Met Asp Val Asn Val Arg Gly Pro Asp Gly Phe Thr
        115                 120                 125

Pro Leu Met Ile Ala Ser Cys Ser Gly Gly Gly Leu Glu Thr Gly Asn
    130                 135                 140

Ser Glu Glu Glu Glu Asp Ala Pro Ala Val Ile Ser Asp Phe Ile Tyr
145                 150                 155                 160

Gln Gly Ala Ser Leu His Asn Gln Thr Asp Arg Thr Gly Glu Thr Ala
                165                 170                 175

Leu His Leu Ala Ala Arg Tyr Ser Arg Ser Asp Ala Ala Lys Arg Leu
            180                 185                 190

Leu Glu Ala Ser Ala Asp Ala Asn Ile Gln Asp Asn Met Gly Arg Thr
        195                 200                 205

Pro Leu His Ala Ala Val Ser Ala Asp Ala Gln Gly Val Phe Gln Ile
    210                 215                 220

Leu Leu Arg Asn Arg Ala Thr Asp Leu Asp Ala Arg Met His Asp Gly
225                 230                 235                 240

Thr Thr Pro Leu Ile Leu Ala Ala Arg Leu Ala Val Glu Gly Met Leu
                245                 250                 255

Glu Asp Leu Ile Asn Ser His Ala Asp Val Asn Ala Val Asp Asp Leu
            260                 265                 270

Gly Lys Ser Ala Leu His Trp Ala Ala Ala Val Asn Asn Val Asp Ala
        275                 280                 285

Ala Val Val Leu Leu Lys Asn Gly Ala Asn Lys Asp Met Gln Asn Asn
    290                 295                 300

Lys Glu Glu Thr Pro Leu Phe Leu Ala Ala Arg Glu Gly Ser Tyr Glu
305                 310                 315                 320

Thr Ala Lys Val Leu Leu Asp His Phe Ala Asn Arg Asp Ile Thr Asp
                325                 330                 335

His Met Asp Arg Leu Pro Arg Asp Ile Ala Gln Glu Arg Met His His
            340                 345                 350

Asp Ile Val Leu Leu Asp Glu Tyr Asn Leu Val Arg Ser Pro Gln Leu
        355                 360                 365

His Gly Thr Ala Leu Gly Gly Thr Pro Thr Leu Ser Pro Thr Leu Cys
    370                 375                 380

Ser Pro Asn Gly Tyr Leu Gly Asn Leu Lys Ser Ala Thr Gln Gly Lys
385                 390                 395                 400

Lys Ala Arg Lys Pro Ser Thr Lys Gly Leu Ala Cys Gly Ser Lys Glu
                405                 410                 415
```

-continued

```
Ala Lys Asp Leu Lys Ala Arg Arg Lys Lys Ser Gln Asp Gly Lys Gly
            420                 425                 430

Cys Leu Leu Asp Ser Ser Ser Met Leu Ser Pro Val Asp Ser Leu Glu
        435                 440                 445

Ser Pro His Gly Tyr Leu Ser Asp Val Ala Ser Pro Pro Leu Leu Pro
    450                 455                 460

Ser Pro Phe Gln Gln Ser Pro Ser Met Pro Leu Ser His Leu Pro Gly
465                 470                 475                 480

Met Pro Asp Thr His Leu Gly Ile Ser His Leu Asn Val Ala Ala Lys
                485                 490                 495

Pro Glu Met Ala Ala Leu Ala Gly Gly Ser Arg Leu Ala Phe Glu Pro
            500                 505                 510

Pro Pro Pro Arg Leu Ser His Leu Pro Val Ala Ser Ser Ala Ser Thr
        515                 520                 525

Val Leu Ser Thr Asn Gly Thr Gly Ala Met Asn Phe Thr Val Gly Ala
    530                 535                 540

Pro Ala Ser His Ile Gly Gln Cys Glu Trp Leu Pro Arg Leu Gln Asn
545                 550                 555                 560

Gly Met Val Pro Ser Gln Tyr Asn Pro Leu Arg Pro Gly Val Thr Pro
                565                 570                 575

Gly Thr Leu Ser Thr Gln Ala Ala Gly Leu Gln His Ser Met Met Gly
            580                 585                 590

Pro Leu His Ser Ser Leu Ser Thr Asn Thr Leu Ser Pro Ile Ile Tyr
        595                 600                 605

Gln Gly Leu Pro Asn Thr Arg Leu Ala Thr Gln Pro His Leu Val Gln
    610                 615                 620

Thr Gln Gln Val Gln Pro Gln Asn Leu Gln Leu Gln Pro Gln Asn Leu
625                 630                 635                 640

Gln Pro Pro Ser Gln Pro His Leu Ser Val Ser Ser Ala Ala Asn Gly
                645                 650                 655

His Leu Gly Arg Ser Phe Leu Ser Gly Glu Pro Ser Gln Ala Asp Val
            660                 665                 670

Gln Pro Leu Gly Pro Ser Ser Leu Pro Val His Thr Ile Leu Pro Gln
        675                 680                 685

Glu Ser Gln Ala Leu Pro Thr Ser Leu Pro Ser Ser Met Val Pro Pro
    690                 695                 700

Met Thr Thr Thr Gln Phe Leu Thr Pro Pro Ser Gln His Ser Tyr Ser
705                 710                 715                 720

Ser Ser Pro Val Asp Asn Thr Pro Ser His Gln Leu Gln Val Pro Glu
                725                 730                 735

His Pro Phe Leu Thr Pro Ser Pro Glu Ser Pro Asp Gln Trp Ser Ser
            740                 745                 750

Ser Ser Pro His Ser Asn Ile Ser Asp Trp Ser Glu Gly Ile Ser Ser
        755                 760                 765

Pro Pro Thr Thr Met Pro Ser Gln Ile Thr His Ile Pro Glu Ala Phe
    770                 775                 780

Lys
785


<210> SEQ ID NO 12
<211> LENGTH: 2322
<212> TYPE: DNA
<213> ORGANISM: Mus musculus

<400> SEQUENCE: 12
```

```
atggccaagc ggaagcgcaa gcatggcttc ctctggctgc cggaagggtt caccctccgc     60
cgagactcta gcaatcacaa gcgccgtgaa cctgtgggac aggatgccgt ggggctgaaa    120
aatctctccg tgcaagtgtc agaggctaac ctgattggtt ctgggacaag tgaacattgg    180
gttgatgatg aaggacccca gccaaagaaa gccaaggctg aggatgaggc tttgctgtcg    240
gaagatgacc ccatcgatcg acggccctgg acacagcagc accttgaagc tgcagacatc    300
cgccacactc catccctggc actcactcct cctcaggcag aacaggaggt ggacgtgctg    360
gacgtgaatg tccgaggccc agatgggtgt actccactga tgctggcttc tctccgagga    420
ggcagctcag acctgagtga tgaagacgaa gatgctgagg actcttctgc caacatcatc    480
acagacttgg tctaccaagg tgccagcctt caagcacaga cagaccgcac tggcgagatg    540
gccctgcacc ttgcagcccg ctattcgaga gctgatgctg ccaaacgcct cctggatgct    600
ggtgcggatg caaatgccca ggacaacatg ggccgatgtc ctcttcacgc tgcggtggca    660
gcagacgccc aaggtgtctt tcagattctg atccgcaacc gtgtaaccga tctggatgcc    720
agaatgaacg atggtactac cccccctgatc ctggctgccc gcctggctgt ggaaggaatg    780
gtggcagagt tgatcaattg ccaagcagat gtcaatgcag tggatgacca tggaaaatct    840
gccctccact gggcagctgc tgtcaataat gtggaggcga ctcttctgct gttgaagaat    900
ggggccaaca gagatatgca ggacaataag gaagagacac ctttgtttct tgctgcccga    960
gagggaagtt atgaagcggc caaaatcctg ttagaccatt ttgccaaccg ggacatcact   1020
gaccacatgg accgccttcc ccgggatgtg gctcgggacc gcatgcacca tgacatcgtt   1080
cgcctcctgg acgagtataa cgtgactccc agccctccgg gaacggtctt gacttctgcg   1140
ctctcacctg tcctctgtgg gcccaacagg tctttcctca gtctgaagca caccccaatg   1200
ggtaagaagg ctaggcggcc caacaccaag agcaccatgc ccacgagcct gcctaacctt   1260
gccaaggagg ccaaggatgc caagggcagc aggaggaaga agtgtctgaa cgagaaggtc   1320
cagctgtccg agagctcagt gactctatcc cccgtcgatt cgctcgagtc tcctcacacg   1380
tatgtctccg atgccacatc ctctcccatg atcacatccc ctggaatctt acaggcctcg   1440
cccaccccccc tgctggctgc tgccgccccg gctgccccag tgcacacaca gcatgcgctg   1500
tctttctcta accttcatga catgcagcct ttggctcctg gagccagcac cgtgctcccc   1560
tcggtcagcc agctgctatc ccaccaccac atcgcgcccc caggtagtag cagtgcagga   1620
agcttgggca ggttacatcc agttcctgtc ccagcagact ggatgaaccg tgtggagatg   1680
aacgagaccc agtacagtga aatgtttggc atggtcctgg ctcctgcaga gggagcccac   1740
cctggcatag cagctcccca gagcagacct ccggaaggga agcacatgtc cacccagcgg   1800
gagcccttgc ctcccatcgt gactttccag cttatcccaa aaggcagcat tgcccaggca   1860
gccggagctc cccagacgca gtccagttgc cctccagctg ttgcaggccc cttgccctct   1920
atgtaccaga tcccagagat gccccgtttg cccagtgtgg ctttcccacc taccatgatg   1980
ccccagcagg aggggcaggt agctcagacc attgtgccaa cctatcatcc tttcccagcc   2040
tctgtgggca agtaccccac accccccttcc caacacagtt acgcctcctc aaatgctgct   2100
gagcgaaccc ccagtcatgg tggtcacctc cagggcgagc acccatacct gacaccatcc   2160
ccagagtctc ctgaccaatg gtcaagctct tcaccacact ctgcatctga ctggtcagat   2220
gtgaccacca gcccaactcc tggaggtggt ggaggcggtc agcggggacc cggaacacac   2280
atgtccgagc caccacacag caacatgcag gtgtatgcat ga                      2322
```

<210> SEQ ID NO 13
<211> LENGTH: 773
<212> TYPE: PRT
<213> ORGANISM: Mus musculus

<400> SEQUENCE: 13

```
Met Ala Lys Arg Lys Arg Lys His Gly Phe Leu Trp Leu Pro Glu Gly
1               5                   10                  15

Phe Thr Leu Arg Arg Asp Ser Ser Asn His Lys Arg Arg Glu Pro Val
            20                  25                  30

Gly Gln Asp Ala Val Gly Leu Lys Asn Leu Ser Val Gln Val Ser Glu
        35                  40                  45

Ala Asn Leu Ile Gly Ser Gly Thr Ser Glu His Trp Val Asp Asp Glu
    50                  55                  60

Gly Pro Gln Pro Lys Lys Ala Lys Ala Glu Asp Glu Ala Leu Leu Ser
65                  70                  75                  80

Glu Asp Asp Pro Ile Asp Arg Arg Pro Trp Thr Gln Gln His Leu Glu
                85                  90                  95

Ala Ala Asp Ile Arg His Thr Pro Ser Leu Ala Leu Thr Pro Pro Gln
            100                 105                 110

Ala Glu Gln Glu Val Asp Val Leu Asp Val Asn Val Arg Gly Pro Asp
        115                 120                 125

Gly Cys Thr Pro Leu Met Leu Ala Ser Leu Arg Gly Gly Ser Ser Asp
    130                 135                 140

Leu Ser Asp Glu Asp Glu Asp Ala Glu Asp Ser Ser Ala Asn Ile Ile
145                 150                 155                 160

Thr Asp Leu Val Tyr Gln Gly Ala Ser Leu Gln Ala Gln Thr Asp Arg
                165                 170                 175

Thr Gly Glu Met Ala Leu His Leu Ala Ala Arg Tyr Ser Arg Ala Asp
            180                 185                 190

Ala Ala Lys Arg Leu Leu Asp Ala Gly Ala Asp Ala Asn Ala Gln Asp
        195                 200                 205

Asn Met Gly Arg Cys Pro Leu His Ala Ala Val Ala Ala Asp Ala Gln
    210                 215                 220

Gly Val Phe Gln Ile Leu Ile Arg Asn Arg Val Thr Asp Leu Asp Ala
225                 230                 235                 240

Arg Met Asn Asp Gly Thr Thr Pro Leu Ile Leu Ala Ala Arg Leu Ala
                245                 250                 255

Val Glu Gly Met Val Ala Glu Leu Asn Ile Cys Gln Ala Asp Val Asn
            260                 265                 270

Ala Val Asp Asp His Gly Lys Ser Ala Leu His Trp Ala Ala Ala Val
        275                 280                 285

Asn Asn Val Glu Ala Thr Leu Leu Leu Leu Lys Asn Gly Ala Asn Arg
    290                 295                 300

Asp Met Gln Asp Asn Lys Glu Glu Thr Pro Leu Phe Leu Ala Ala Arg
305                 310                 315                 320

Glu Gly Ser Tyr Glu Ala Ala Lys Ile Leu Leu Asp His Phe Ala Asn
                325                 330                 335

Arg Asp Ile Thr Asp His Met Asp Arg Leu Pro Arg Asp Val Ala Arg
            340                 345                 350

Asp Arg Met His His Asp Ile Val Arg Leu Leu Asp Glu Tyr Asn Val
        355                 360                 365

Thr Pro Ser Pro Pro Gly Thr Val Leu Thr Ser Ala Leu Ser Pro Val
    370                 375                 380
```

```
Leu Cys Gly Pro Asn Arg Ser Phe Leu Ser Leu Lys His Thr Pro Met
385                 390                 395                 400

Gly Lys Lys Ala Arg Arg Pro Asn Thr Lys Ser Thr Met Pro Thr Ser
                405                 410                 415

Leu Pro Asn Leu Ala Lys Glu Ala Lys Asp Ala Lys Gly Ser Arg Arg
            420                 425                 430

Lys Lys Cys Leu Asn Glu Lys Val Gln Leu Ser Glu Ser Ser Val Thr
        435                 440                 445

Leu Ser Pro Val Asp Ser Leu Glu Ser Pro His Thr Tyr Val Ser Asp
    450                 455                 460

Ala Thr Ser Ser Pro Met Ile Thr Ser Pro Gly Ile Leu Gln Ala Ser
465                 470                 475                 480

Pro Thr Pro Leu Leu Ala Ala Ala Ala Pro Ala Ala Pro Val His Thr
                485                 490                 495

Gln His Ala Leu Ser Phe Ser Asn Leu His Asp Met Gln Pro Leu Ala
            500                 505                 510

Pro Gly Ala Ser Thr Val Leu Pro Ser Val Ser Gln Leu Leu Ser His
        515                 520                 525

His His Ile Ala Pro Pro Gly Ser Ser Ser Ala Gly Ser Leu Gly Arg
    530                 535                 540

Leu His Pro Val Pro Val Pro Ala Asp Trp Met Asn Arg Val Glu Met
545                 550                 555                 560

Asn Glu Thr Gln Tyr Ser Glu Met Phe Gly Met Val Leu Ala Pro Ala
                565                 570                 575

Glu Gly Ala His Pro Gly Ile Ala Ala Pro Gln Ser Arg Pro Pro Glu
            580                 585                 590

Gly Lys His Met Ser Thr Gln Arg Glu Pro Leu Pro Pro Ile Val Thr
        595                 600                 605

Phe Gln Leu Ile Pro Lys Gly Ser Ile Ala Gln Ala Ala Gly Ala Pro
    610                 615                 620

Gln Thr Gln Ser Ser Cys Pro Pro Ala Val Ala Gly Pro Leu Pro Ser
625                 630                 635                 640

Met Tyr Gln Ile Pro Glu Met Pro Arg Leu Pro Ser Val Ala Phe Pro
                645                 650                 655

Pro Thr Met Met Pro Gln Gln Glu Gly Gln Val Ala Gln Leu Ile Val
            660                 665                 670

Pro Thr Tyr His Pro Phe Pro Ala Ser Val Gly Lys Tyr Pro Thr Pro
        675                 680                 685

Pro Ser Gln His Ser Tyr Ala Ser Ser Asn Ala Ala Glu Arg Thr Pro
    690                 695                 700

Ser His Gly Gly His Leu Gln Gly Glu His Pro Tyr Leu Thr Pro Ser
705                 710                 715                 720

Pro Glu Ser Pro Asp Gln Trp Ser Ser Ser Ser Pro His Ser Ala Ser
                725                 730                 735

Asp Trp Ser Asp Val Thr Thr Ser Pro Thr Pro Gly Gly Gly Gly Gly
            740                 745                 750

Gly Gln Arg Gly Pro Gly Thr His Met Ser Glu Pro Pro His Ser Asn
        755                 760                 765

Met Gln Val Tyr Ala
    770
```

<210> SEQ ID NO 14
<211> LENGTH: 1611

<212> TYPE: DNA
<213> ORGANISM: Homo sapiens

<400> SEQUENCE: 14
atgcagctca tccggcgtcg acgccgagag catggagctc tctggctgcc ccctggtttc 60
actcgacggc ctcggactca gtcagctccc caccgacgcc ggcccccact aggcgaggac 120
agcattggtc tcaaggcact gaagccaaag gcagaagttg atgaggatgg agttgtgatg 180
tgctcaggcc ctgaggaggg agaggaggtg ggccaggctg aagaaacagg cccaccctcc 240
acgtgccagc tctggtctct gagtggtggc tgtggggcgc tccctcaggc agccatgcta 300
actcctcccc aggaatctga gatggaagcc cctgacctgg acacccgtgg acctgatggg 360
gtgacacccc tgatgtcagc agtttgctgt ggggaagtac agtccgggac cttccaaggg 420
gcatggttgg gatgtcctga gccctgggaa cctctgctgg atggaggggc ctgtccccag 480
gctcacaccg tgggcactgg ggagaccccc ctgcacctgg ctgcccgatt ctcccggcca 540
accgctgccc gccgcctcct tgaggctgga gccaacccca accagccaga ccgggcaggg 600
cgcacacccc ttcatgctgc tgtggctgct gatgctcggg aggtctgcca gcttctgctc 660
cgtagcagac aaactgcagt ggacgctcgc acagaggacg ggaccacacc cttgatgctg 720
gctgccaggc tggcggtgga agacctggtt gaagaactga ttgcagccca agcagacgtg 780
ggggccagag ataaatgggg gaaaactgcg ctgcactggg ctgctgccgt gaacaacgcc 840
cgagccgccc gctcgcttct ccaggccgga gccgataaag atgcccagga caacagggag 900
cagacgccgc tattcctggc ggcgcgggaa ggagcggtgg aagtagccca gctactgctg 960
gggctggggg cagcccgaga gctgcgggac caggctgggc tagcgccggc ggacgtcgct 1020
caccaacgta accactggga tctgctgacg ctgctggaag ggctgggcc accagaggcc 1080 cgtcacaaag ccacgccggg ccgcgaggct gggcccttcc cgcgcgcacg gacggtgtca 1140
gtaagcgtgc ccccgcatgg gggcggggct ctgccgcgct gccggacgct gtcagccgga 1200
gcaggccctc gtgggggcgg agcttgtctg caggctcgga cttggtccgt agacttggct 1260
gcgcgggggg gcggggccta ttctcattgc cggagcctct cgggagtagg agcaggagga 1320
ggcccgaccc ctcgcggccg taggttttct gcaggcatgc gcgggcctcg gcccaaccct 1380
gcgataatgc gaggaagata cggagtggct gccgggcgcg gaggcagggt ctcaacggat 1440
gactggccct gtgattgggt ggccctggga gcttgcggtt ctgcctccaa cattccgatc 1500
ccgcctcctt gccttactcc gtccccggag cggggatcac ctcaacttga ctgtggtccc 1560
ccagccctcc aagaaatgcc cataaaccaa ggaggagagg gtaaaaaata g 1611

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
ttctgcggcc gccatggcgg cagcgtcccg gagc 34

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
atttggatcc ttatacctcc gtggcaatga cac 33

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
tgcttgcggc cgccatgcgc cctgaagaca gaatg 35

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
cctttacagt atttcacagg gtcc 24

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
tcctccacgt ccccgcatgt tagtagactt cccctgccct cgccggagcc cagggtcccc 60
tgggcccggg 70

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
gccatccttt tccagctcca 20

<210> SEQ ID NO 21
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
caggggaagt ctactaacat gcggggacgt ggaggaaaat cccggcccaa tgatggttct 60
gcaggtttct gcggc 75

<210> SEQ ID NO 22
<211> LENGTH: 39
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 22
tttttggatc cttatgcaga tcctcgttga actttcttg 39

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tcagtgagct caggaaccct 20

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
attattcata tgatgcacag gaggagaagc aggagct 37

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
caggatgttg aagaccgcct 20

<210> SEQ ID NO 26
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ttctcttcga catcccctgc ttgtttcaac agggagaagt tagtggctcc gcttccggac 60
atggggactg ggcccagatc ctgcttggt 89

<210> SEQ ID NO 27
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gccactaact tctccctgtt gaaacaagca ggggatgtcg aagagaatcc cgggccaatg 60
gcccagtcca agcacggcct gaccaag 87

-continued

```
<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

ggatctatcg atttagggca aggcggagcc gg                                32


<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

agatacgata tcatgcggcg gcagcatggc cagct                             35


<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

ctagcaacgc gtttacttga acgcctccgg ga                                32


<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

gccggaactc tgccctctaa cgct                                         24


<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

gattctcctc cacgtcaccg c                                            21
```